United States Patent
Chai et al.

(10) Patent No.: US 9,682,971 B2
(45) Date of Patent: *Jun. 20, 2017

(54) 1,2,5-SUBSTITUTED BENZIMIDAZOLES AS FLAP MODULATORS

(71) Applicant: JANSSEN PHARMACEUTICA NV, Beerse (BE)

(72) Inventors: Wenying Chai, San Diego, CA (US); Charlotte Deckhut, San Diego, CA (US); Curt A. Dvorak, Poway, CA (US); Wendy Eccles, San Diego, CA (US); James P. Edwards, San Diego, CA (US); Steven D. Goldberg, Encinitas, CA (US); Paul J. Krawczuk, San Diego, CA (US); Alec D. Lebsack, Ladera Ranch, CA (US); Jing Liu, San Diego, CA (US); Virginia M. Tanis, Carlsbad, CA (US); Kyle T. Tarantino, Princeton, NJ (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,481

(22) PCT Filed: Mar. 13, 2014

(86) PCT No.: PCT/US2014/025582
§ 371 (c)(1),
(2) Date: Sep. 15, 2015

(87) PCT Pub. No.: WO2014/151367
PCT Pub. Date: Sep. 25, 2014

(65) Prior Publication Data
US 2016/0046600 A1    Feb. 18, 2016

Related U.S. Application Data

(60) Provisional application No. 61/799,660, filed on Mar. 15, 2013.

(51) Int. Cl.
| | | |
|---|---|---|
| C07D 417/14 | (2006.01) | |
| C07D 401/12 | (2006.01) | |
| C07D 413/14 | (2006.01) | |
| C07D 401/14 | (2006.01) | |
| C07D 417/12 | (2006.01) | |
| C07D 405/14 | (2006.01) | |
| A61K 31/428 | (2006.01) | |
| A61K 31/4709 | (2006.01) | |
| A61K 31/4725 | (2006.01) | |
| A61K 31/506 | (2006.01) | |
| A61K 31/5377 | (2006.01) | |

(52) U.S. Cl.
CPC .......... *C07D 417/14* (2013.01); *A61K 31/428* (2013.01); *A61K 31/4709* (2013.01); *A61K 31/4725* (2013.01); *A61K 31/506* (2013.01); *A61K 31/5377* (2013.01); *C07D 401/12* (2013.01); *C07D 401/14* (2013.01); *C07D 405/14* (2013.01); *C07D 413/14* (2013.01); *C07D 417/12* (2013.01)

(58) Field of Classification Search
CPC .................................................... C07D 417/14
See application file for complete search history.

(56) References Cited

U.S. PATENT DOCUMENTS

| 5,021,443 A | 6/1991 | Bru-Maginez |
|---|---|---|
| 5,124,336 A | 6/1992 | Bru-Maginez |
| 5,128,359 A | 7/1992 | Bru-Maginez |
| 8,952,177 B2 | 2/2015 | Chai et al. |
| 9,067,917 B2 | 6/2015 | Chai et al. |
| 9,089,569 B2 | 7/2015 | Chai et al. |
| 9,265,770 B2 | 2/2016 | Chai et al. |

(Continued)

FOREIGN PATENT DOCUMENTS

| EP | 1878724 A1 | 1/2008 |
|---|---|---|
| WO | WO 0157020 A1 | 8/2001 |

(Continued)

OTHER PUBLICATIONS

Abramovitz et al, "5-lipoxygenase-activating protein stimulates the utilization of arachidonic acid by 5-lipoxygenase," *Eur. J. Biochem.*, 1993, 215:105-111.
Avis et al, editors, *Pharmaceutical Dosage Forms: Parenteral Medications*, 2nd Edition, vol. 1, published by Marcel Dekker, Inc., 1992, Table of Contents and Index.
Avis et al, editors, *Pharmaceutical Dosage Forms: Parenteral Medications*, vol. 2, published by Marcel Dekker, Inc., 1993, Table of Contents and Index.
Banoglu, E., et al., "Identification of Novel Benzimidazole Derivatives as Inhibitors of Leukotriene Biosynthesis by Virtual Screening, Targeting 5-Lipoxygenase-Activating Protein (FLAPP")," vol. 20, No. 12, pp. 3728-3741 (2012).
Berge et al, "Pharmaceutical Salts," *Journal of Pharmaceutical Sciences*, 1977, 66(1):1-19.
Bundgaard, editor, *Design of Prodrugs*, published by Elsevier, 1985, Table of Contents.
Chi et al, "Interaction between ALOX5AP and CYP3A5 gene variants significantly increases the risk for cerebral infarctions in Chinese," *NeuroReport.*, 2014, 25(7):452-457.
Chu et al, "Involvement of 5-lipoxygenase activating protein in the amyloidotic phenotype of an Alzheimer's disease mouse model," *Journal of Neuroinflammation*, 2012, 9:127.

(Continued)

Primary Examiner — Joseph Kosack
Assistant Examiner — Karen Cheng

(57) ABSTRACT

The present invention relates to compounds of Formula (I),

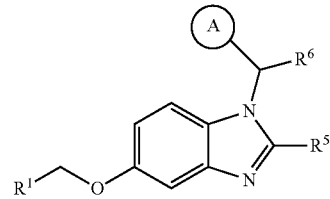

(I)

and solvates, hydrates, and pharmaceutically acceptable salts thereof, wherein ring A, $R^1$, $R^5$ and $R^6$ are as defined herein, useful as FLAP modulators. The invention also relates to pharmaceutical compositions comprising compounds of Formula (I). Methods of making and using the compounds of Formula (I) are also within the scope of the invention.

13 Claims, No Drawings

(56) References Cited

U.S. PATENT DOCUMENTS

| | | |
|---|---|---|
| 2005/0101647 A1 | 5/2005 | Oda |
| 2007/0244128 A1 | 10/2007 | Hutchinson et al. |
| 2011/0190343 A1 | 8/2011 | Gochin |
| 2012/0214762 A1 | 8/2012 | Staben |
| 2014/0275028 A1 | 9/2014 | Chai et al. |
| 2014/0275029 A1 | 9/2014 | Chai et al. |
| 2015/0119382 A1 | 4/2015 | Chai et al. |
| 2015/0246052 A1 | 9/2015 | Chai et al. |
| 2016/0039790 A1 | 2/2016 | Chai et al. |
| 2016/0046600 A1 | 2/2016 | Chai et al. |
| 2016/0108028 A1 | 4/2016 | Chai et al. |

FOREIGN PATENT DOCUMENTS

| | | |
|---|---|---|
| WO | WO 03018061 A1 | 3/2003 |
| WO | WO 2004108686 A2 | 12/2004 |
| WO | WO 2005018672 A1 | 3/2005 |
| WO | WO 2008153129 A1 | 12/2008 |
| WO | WO 2009000413 A1 | 12/2008 |
| WO | WO 2010/001869 A1 | 1/2010 |
| WO | WO 2011109254 A1 | 9/2011 |

OTHER PUBLICATIONS

Chwiesko-Minarowska et al, "The role of leukotrienes in the pathogenesis of systemic sclerosis," *Folia Histochemica et Cytobiologica*, 2012, 50(2), 180-85.

Gould, "Salt selection for basic drugs," *International Journal of Pharmaceutics*, 1986, 33:201-217.

Greene et al, editors, *Protective Groups in Organic Synthesis*, 3rd Edition, published by John Wiley & Sons, 1999, Index.

Griffiths et al, "Collagen-induced Arthritis Is Reduced in 5-Lipoxygenase-activating Protein-deficient Mice," *J. Exp. Med.*, 1997, 185(6):1123-29).

Haeggström et al, "Lipoxygenase and Leukotriene Pathways: Biochemistry, Biology, and Roles in Disease," *Chemical Reviews*, 2011, 111(10):5866-98.

Helgadottir et al, "The gene encoding 5-lipoxygenase activating protein confers risk of myocardial infarction, atherosclerosis and stroke," *Nature Genetics*, Mar. 2004, 36(3):233-39.

Holloway et al, "The role of LTA4H and ALOX5AP polymorphism in asthma and allergy susceptibility," *Allergy*, 2008, 63(8):1046-53.

Ji et al, "Genetic Variants in the Promoter Region of the ALOX5AP Gene and Susceptibility of Ischemic Stroke," *Cerebrovascular Diseases*, 2011, 32(3), 261-68.

Krawiec et al, "Leukotriene inhibitors and non-steroidal therapies in the treatment of asthma," *Expert Opinion on Pharmacotherapy*, 2001, 2(1), 47-65.

Lieberman et al, editors, *Pharmaceutical Dosage Forms: Tablets*, Second Edition, vol. 1, published by Marcel Dekker, Inc., 1989, Table of Contents and Index.

Lieberman et al, editors, *Pharmaceutical Dosage Forms: Tablets*, Second Edition, vols. 2-3, published by Marcel Dekker, Inc., 1990, Table of Contents and Index.

Lieberman et al, editors, *Pharmaceutical Dosage Forms: Disperse Systems*, vols. 1-2, published by Marcel Dekker, Inc., 1996, Table of Contents and Index.

Loell et al, "Activated LTB4 pathway in muscle tissue of patients with polymyositis or dermatomyositis," *Ann. Rheum. Dis.*, 2013, 72(2):293-99.

Mcomie, editor, *Protective Groups in Organic Chemistry*, published Plenum Press, 1973, Index and Table of Contents.

Nair et al, "Expression Analysis of Leukotriene-Inflammatory Gene Interaction Network in Patients with Coronary Artery Disease," *Journal of Atherosclerosis and Thrombosis*, 2013, 20:000-000.

Reicin et al, "Montelukast, a Leukotriene Receptor Antagonist, in Combination with Loratadine, a Histamine Receptor Antagonist, in the Treatment of Chronic Asthma," *Arch. Intern. Med.*, 2000, 160(16):2418-88.

Rosnowska et al, "Leukotrienes C4 and B4 in cerebrospinal fluid of patients with multiple sclerosis," *Polski Merkuriusz Lekarski*, 1997, 2:254-55. (English Abstract).

Rowe et al, editors, *The Handbook of Pharmaceutical Excipients*, 5th Edition, published by the American Pharmaceutical Association and the Pharmaceutical Society of Great Britain, 2006, Table of Contents and Index.

Samuelsson, "Leukotrienes: Mediators of Immediate Hypersensitivity Reactions and Inflammation," *Science*, 1983, 220:568-75).

Sanada et al, "The effectiveness of montelukast for the treatment of anti-histamine-resistant chronic urticaria," *Arch. Dermatol. Res.*, 2005, 297(3):134-138.

Strid et al, "Distinct parts of leukotriene C(4) synthase interact with 5-lipoxygenase and 5-lipoxygenase activating protein," *Biochemical and Biophysical Research Communications*, 2009, 381(4):518-22.

Tulah et al, "The role of ALOX5AP, LTA4H and LTB4R polymorphisms in determining baseline lung function and COPD susceptibility in UK smokers," *BMC Medical Genetucs*, 2011, 29(12), 173.

Wang et al, "Eicosanoids and cancer," *Nature Reviews—Cancer*, 2010, 10(3), 181-93.

Yu et al, "Disruption of the 5-lipoxygenase pathway attenuates atherogenesis consequent to COX-2 deletion in mice," *Proc. Natl. Acad. Sci. (PNAS)*, 2012, 109(17):6727-32.

Yu et al, "Myeloid Cell 5-Lipoxygenase Activating Protein.Modulates the Response to Vascular Injury," *Circulation Research*, 2013, 112:432-440.

International Search Report mailed Jul. 17, 2014 for Application No. PCT/US2014/025609.

International Search Report mailed Jul. 29, 2014 for Application No. PCT/US2014/025582.

U.S. Appl. No. 61/799,660, filed Mar. 15, 2013, Expired, Chai et al.

U.S. Appl. No. 61/799,901, filed Mar. 15, 2013, Expired, Chai et al.

1,2,5-SUBSTITUTED BENZIMIDAZOLES AS FLAP MODULATORS

CROSS REFERENCE TO RELATED APPLICATIONS

This application is a 35 U.S.C. §371 nationalization of PCT application PCT/US2014/025582 filed Mar. 13, 2014, which claims priority to Provisional Application 61/799,660, filed Mar. 15, 2013.

FIELD OF THE INVENTION

The present invention relates to substituted compounds useful as 5-lipoxygenase-activating protein (FLAP) modulators, pharmaceutical compositions of such compounds, methods of preparation and use thereof. More particularly, FLAP modulators are useful for preventing, treating or ameliorating FLAP-mediated diseases and/or disorders, including those inflammation diseases and/or disorders associated with dermatological and respiratory disorders, allergic disorders, autoimmunity, cancer, cardiovascular and metabolic disorders.

BACKGROUND OF THE INVENTION

FLAP is a key initiator of the leukotriene synthesis pathway that binds and then transfers arachidonic acid to 5-lipoxygenase (M. Abramovitz et al., "5-lipoxygenase-activating protein stimulates the utilization of arachidonic acid by 5-lipoxygenase," *Eur. J. Biochem.*, 1993, 215, 105-11). FLAP has been demonstrated to interact with $LTC_4$ synthase, and could putatively modulate the production of $LTC_4$ (T. Strid et al., "Distinct parts of leukotriene C(4) synthase interact with 5-lipoxygenase and 5-lipoxygenase activating protein," *Biochem. Biophys. Res. Comm.*, 2009, 381(4), 518-22). Modulation (including without limitation inhibition) or genetic deletion of FLAP blocks leukotriene production, specifically $LTB_4$, the cysteinyl leukotrienes ($LTC_4$, $LTD_4$ and $LTE_4$) as well as 5-oxo-ETE (J. Z. Haeggström et al., "Lipoxygenase and leukotriene pathways: biochemistry, biology, and roles in disease," *Chem Rev.*, 2011, 111(10), 5866-98).

Leukotrienes are immune-modulating lipids formed from arachidonic acid (reviewed in B. Samuelsson, "Leukotrienes: mediators of immediate hypersensitivity reactions and inflammation," *Science*, 1983, 220, 568-75). They are synthesized primarily by eosinophils, neutrophils, mast cells, basophils, dendritic cells, macrophages and monocytes. Leukotrienes mediate multiple biological effects including, by way of example only, smooth muscle contraction, leukocyte recruitment and activation, cytokine secretion, fibrosis, mucous secretion, and vascular function (J. Z. Haeggström, at 5866-98).

FLAP-deficient mice are healthy and reproduce normally. They do not produce leukotrienes and have decreased susceptibility in mouse models of arthritis (R. J. Griffiths et al., "Collagen-induced arthritis is reduced in 5-lipoxygenase-activating protein-deficient mice," *J. Exp. Med.*, 1997, 185, 1123-29). In humans, FLAP itself has been linked by genetic studies to respiratory disorders and cardiovascular disease, including myocardial infarction, atherosclerosis, cerebral infarctions, coronary artery disease and stroke (A. Helgadottir et al., "The gene encoding 5-lipoxygenase activating protein confers risk of myocardial infarction, atherosclerosis and stroke," *Nat. Genet.*, 2004, 36, 233-39; A. S. Tulah et al., "The role of ALOX5AP, LTA4H and LTB4R polymorphisms in determining baseline lung function and COPD susceptibility in UK smokers," *BMC Med. Genet.*, 2011, 29(12), 173; R. Ji et al., "Genetic variants in the promoter region of the ALOX5AP gene and susceptibility of ischemic stroke," *Cerebrovasc. Dis.*, 2011, 32(3), 261-68; J. W. Holloway et al., "The role of LTA4H and ALOX5AP polymorphism in asthma and allergy susceptibility," *Allergy*, 2008, 63(8), 1046-53; J. Nair et al., "Expression analysis of leukotriene-inflammatory gene interaction network in patients with coronary artery disease," *J Atheroscler. Thromb.*, 2013; L. F. Chi et al., "Interaction between ALOX5AP and CYP3A5 gene variants significantly increases the risk for cerebral infarctions in Chinese," *Neuroreport.*, 2013). In addition, studies using animal models support a causative role for leukotrienes in aortic aneurisms, pulmonary arterial hypertension, myocardial infarction, atherosclerosis, and stroke (reviewed in J. Z. Haeggström, at 5866-98).

Leukotrienes also play a role in autoimmune disorders such as rheumatoid arthritis, inflammatory bowel disease, nephritis, spondyloarthritis, polymyositis, dermatomyositis, gouty effusions, systemic lupus erythematosus, systemic sclerosis, Alzheimer's disease and multiple sclerosis (S. Chwieśko-Minarowska et al., "The role of leukotrienes in the pathogenesis of systemic sclerosis," *Folia Histochem. Cytobiol.*, 2012, 50(2), 180-85; M. Rosnowska et al., "Leukotrienes C4 and B4 in cerebrospinal fluid of patients with multiple sclerosis," *Pol. Merkuriusz Lek.*, 1997, 2, 254-55; and reviewed in J. Z. Haeggström, at 5866-98; I. Loell et al., "Activated LTB4 pathway in muscle tissue of patients with polymyositis or dermatomyositis," *Ann. Rheum. Dis.*, 2013, 72(2), 293-99; J. Chu et al., "Involvement of 5-lipoxygenase activating protein in the amyloidotic phenotype of an Alzheimer's disease mouse model," *J. Neuroinflammation*, 2012, 9, 127). Leukotrienes have also been implicated in several aspects of carcinogenesis including tumor cell proliferation, differentiation, apoptosis, tumor-associated angiogenesis, as well as the migration and invasion of carcinoma cells (D. Wang and R. N. Dubois, "Eicosanoids and cancer," *Nat. Rev. Cancer*, 2010, 10(3), 181-93).

Leukotrienes play a key role in allergic disorders such as allergic rhinitis, allergic dermatitis and asthma, as well as respiratory disorders such as exacerbations, non-allergic asthma, aspirin exacerbated respiratory disease, fibrotic lung diseases, acute respiratory distress syndrome and chronic obstructive pulmonary disease (reviewed in J. Z. Haeggström at 5866-98). Approved antagonists of the $LTC_4$ receptor and leukotriene synthesis modulators such as zileuton have shown clinical efficacy in a variety of respiratory disorders (reviewed in M. E. Krawiec and S. E. Wenzel, "Leukotriene modulators and non-steroidal therapies in the treatment of asthma," *Expert. Opin. Pharmacotherapy*, 2001, 2(1), 47-65).

All the above evidence supports a key role of leukotrienes in a variety of human diseases and/or disorders, and FLAP modulation would be effective for the prevention, treatment, or amelioration of these immune-mediated inflammatory diseases and/or disorders. Furthermore, there still remains a need for FLAP modulator compounds that have pharmacokinetic and pharmacodynamic properties suitable for use as human pharmaceuticals.

SUMMARY OF THE INVENTION

In its many embodiments, the present invention provides novel compounds useful as, for example, FLAP modulators (including without limitation novel compounds that inhibit FLAP), methods of preparing such compounds, pharmaceutical compositions comprising one or more such compounds, methods of preparing pharmaceutical compositions comprising one or more such compounds, and methods of prophylaxis, treatment, amelioration, including without limitation inhibition, of one or more diseases and/or disorders associated with FLAP using such compounds or pharmaceutical compositions.

One aspect of the present invention is directed to compounds, methods, and compositions for the treatment or prophylaxis or amelioration of a variety of diseases and/or disorders that are mediated or sustained through the activity of leukotrienes, including pulmonary, allergic, fibrotic, neurological, inflammatory, autoimmune and cardiovascular diseases and cancer or associated symptoms or complications thereof. More specifically, this invention is directed to a method of treating exacerbations, non-allergic asthma, fibrotic lung diseases, acute respiratory distress syndrome and chronic obstructive pulmonary disease, or associated symptoms or complications thereof, in a subject afflicted with such a disease and/or disorder, wherein the method comprises administering a FLAP modulator.

Another aspect of the present invention is directed to compounds, methods, and compositions for the treatment or prophylaxis or amelioration of cardiac and cardiovascular diseases and/or disorders, or associated symptoms or complications thereof, that include but are not limited to myocardial infarction, atheroschlerosis, atherosclerosis and stroke aortic aneurisms, or associated symptoms or complications thereof, in a subject afflicted with such a disease and/or disorder, wherein the method comprises administering a FLAP modulator.

Yet another aspect of the present invention is directed to compounds, methods, and compositions for the prophylaxis, treatment, or amelioration of autoimmune diseases and/or disorders, or associated symptoms or complications thereof, that include but are not limited to rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis or allergic disorders that include but are not limited to allergic rhinitis, allergic dermatitis and asthma, or associated symptoms or complications thereof, in a subject afflicted with such a disease and/or disorder, wherein the method comprises administering a FLAP modulator.

Finally, one aspect of the present invention is directed to compounds, methods, and compositions for the prophylaxis, treatment, or amelioration of carcinogenesis including but not limited to tumor cell proliferation, differentiation, apoptosis, tumor-associated angiogenesis, as well as the migration and invasion of carcinoma cells, or associated symptoms or complications thereof, in a subject afflicted with such a disease and/or disorder, wherein the method comprises administering a FLAP modulator.

Another aspect of the present invention features a compound of Formula (I)

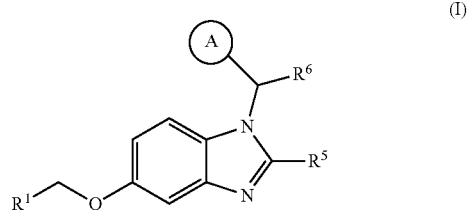

wherein:

$R^1$ is

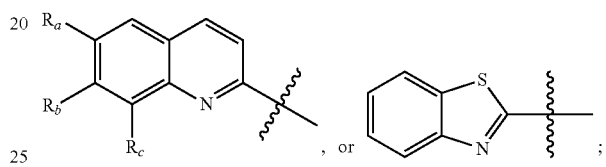

$R_a$ is H, F, or Cl;
$R_b$ is H, F, or Cl;
$R_c$ is H, or F;

is a ring selected from the group consisting of

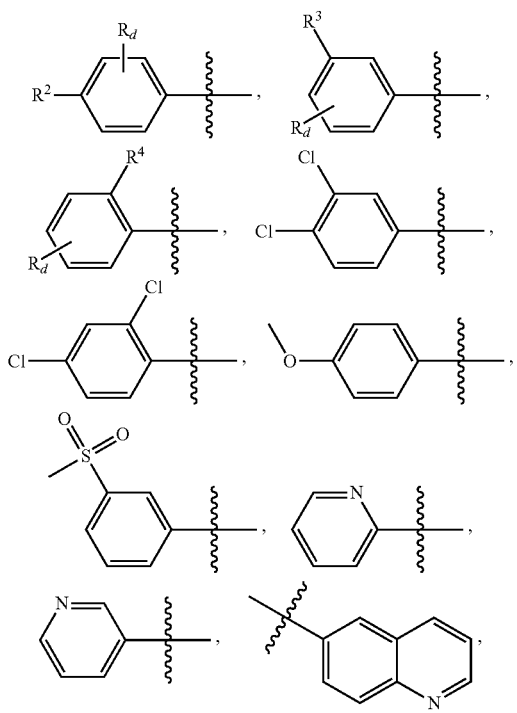

-continued

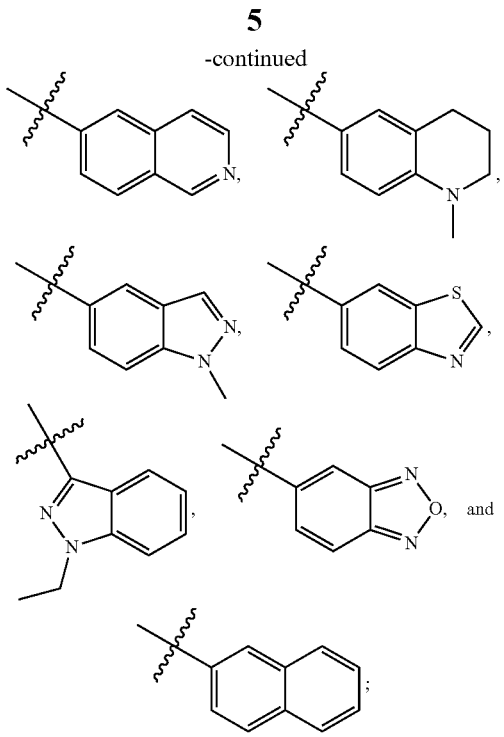

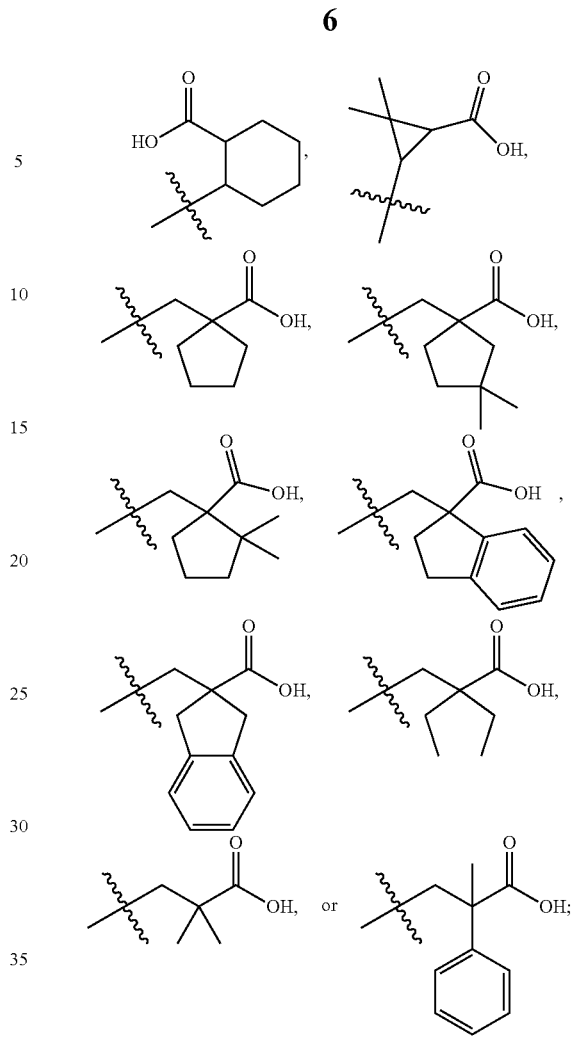

R² is H, Br, Cl, F, —CN, —CH₂CN, OCF₃, CF₃, CH₃, pyrrolyl, pyridyl, pyrazolyl, pyrimidyl, pyridyl, thiazolyl, isoxazolyl, 1,2,3-triazolyl, furanyl, 3,5-dimethylisoxazol-4-yl, 5-methyl-1,2,4-oxadiazol-3-yl, —CH₂-(3,3-difluoropiperidin-1-yl), azetidin-1-yl, 3,3-difluoroazetidin-1-yl, pyrrolidinyl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluorophen-4-yl or phenyl, wherein said phenyl is optionally substituted with one substituent selected from the group consisting of F, CH₃, CF₃, CH(CH₃)₂, —CN, CH₃SO₂—, CH₃SO₂NH—, NH₂SO₂—, NH₂C(O)—, CH₃C(O)NH, and CH₃O—; and said pyrazolyl is optionally substituted with methyl, and said pyrimidyl and said pyridyl are optionally substituted with one or two substituents selected from the group consisting of —OC₍₁₋₂₎alkyl, —N(CH₃)₂, and CF₃;

R³ is H, Br, Cl, F, —CN, —CH₂CN, OCF₃, CF₃, CH₃, pyrrolyl, pyridyl, pyrazolyl, pyrimidyl, pyridyl, thiazolyl, isoxazolyl, 1,2,3-triazolyl, furanyl, 3,5-dimethylisoxazol-4-yl, 5-methyl-1,2,4-oxadiazol-3-yl, —CH₂-(3,3-difluoropiperidin-1-yl), azetidin-1-yl, 3,3-difluoroazetidin-1-yl, pyrrolidinyl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluorophen-4-yl or phenyl, wherein said phenyl is optionally substituted with one substituent selected from the group consisting of F, CH₃, CF₃, CH(CH₃)₂, —CN, CH₃SO₂—, CH₃SO₂NH—, NH₂SO₂—, NH₂C(O)—, CH₃C(O)NH, and CH₃O—; and said pyrazolyl is optionally substituted with methyl, and said pyrimidyl and said pyridyl are optionally substituted with one or two substituents selected from the group consisting of —OC₍₁₋₂₎alkyl, —N(CH₃)₂, and CF₃;

R⁴ is H, F, CF₃, OCF₃, Cl, Br, —CN, HO₂C-phen-3-yl, 2-trifluoromethyl-pyrid-5-yl, 2-methoxy-pyrid-5-yl, or CH₃;

R_d is H, or F;

R⁵ is

R⁶ is H, CH₃, or CH₂CH₃;

and solvates, hydrates, and pharmaceutically acceptable salts thereof.

Another aspect of the present invention features a pharmaceutical composition comprising a therapeutically effective amount of at least one compound of Formula (I) and at least one pharmaceutically acceptable carrier. The invention is also directed towards providing a process for formulating a pharmaceutical composition, comprising formulating a pharmaceutical composition of a therapeutically effective amount of at least one compound of Formula (I) and at least one pharmaceutically acceptable carrier. The present invention further relates to a process for making a pharmaceutical composition comprising mixing any of the compounds according to Formula (I) and a pharmaceutically acceptable carrier.

The present invention also features a method of treating a subject suffering from or diagnosed with a disease and/or disorder mediated by FLAP activity, comprising administering to the subject a therapeutically effective amount of at least one compound of Formula (I). Such a disease and/or disorder can include, but is not limited to respiratory disorders, cardiac and cardiovascular diseases, autoimmune disorders, carcinogenesis or associated symptoms or complications. More specifically, this invention is directed to a method of treating exacerbations, non-allergic asthma, fibrotic lung diseases, acute respiratory distress syndrome, chronic obstructive pulmonary disease myocardial infarction, atherosclerosis, atherosclerosis and stroke aortic aneurisms, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, tumor cell proliferation, differentiation, apoptosis, tumor-associated angiogenesis, as well as the migration and invasion of carcinoma cells, or associated symptoms or complications thereof, in a subject afflicted with such a disease and/or disorder, or associated symptoms or complications thereof, wherein the method comprises administering a FLAP modulator to a subject in need thereof, a therapeutically effective amount of at least one compound of Formula (I), preferably in a pharmaceutical composition comprising at least one compound of Formula (I).

Additional embodiments and advantages of the invention will become apparent from the detailed discussion, schemes, examples, and claims below.

DETAILED DESCRIPTION OF THE INVENTION

This invention relates to novel FLAP modulators and compositions thereof for the prophylaxis, treatment, or amelioration of numerous diseases and/or disorders, including but not limited to respiratory diseases and/or disorders, cardiac and cardiovascular diseases and/or disorders, autoimmune diseases and/or disorders, carcinogenesis, and associated symptoms or complications thereof.

Another aspect of the present invention features a compound of Formula (I)

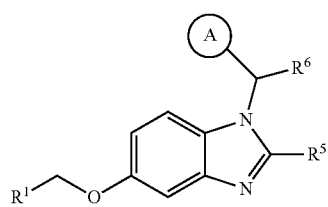

(I)

wherein:
$R^1$ is

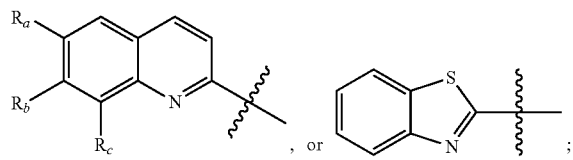

$R_a$ is H, F, or Cl;
$R_b$ is H, F, or Cl;
$R_c$ is H, or F;

is a ring selected from the group consisting of

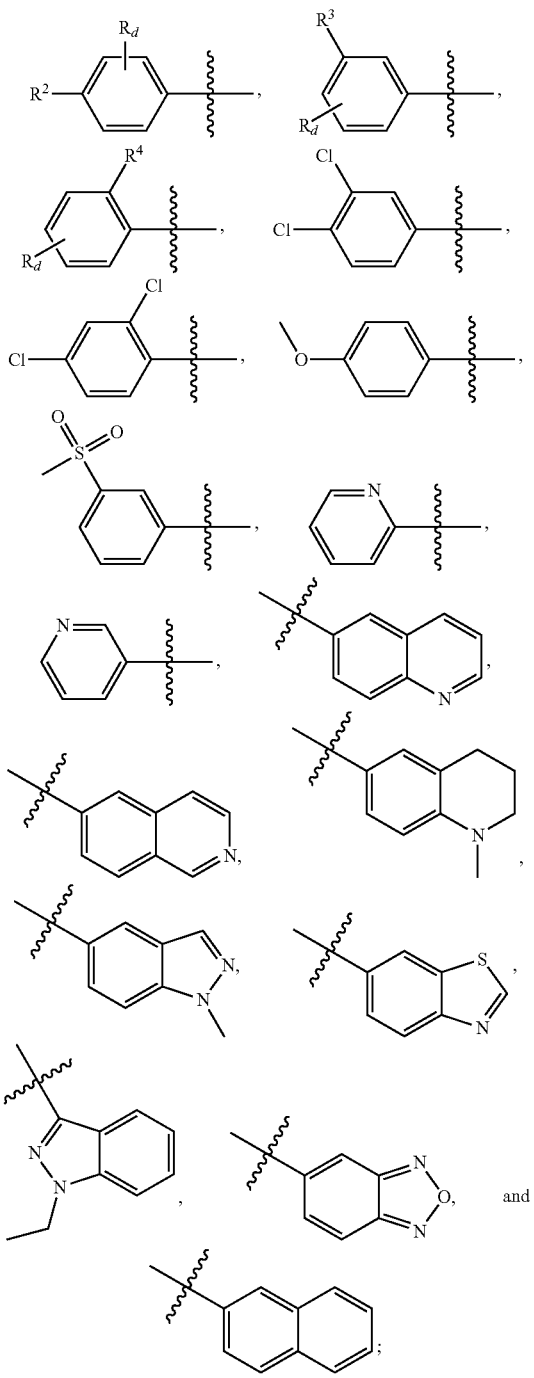

$R^2$ is H, Br, Cl, F, —CN, —CH$_2$CN, OCF$_3$, CF$_3$, CH$_3$, pyrrolyl, pyridyl, pyrazolyl, pyrimidyl, pyridyl, thiazolyl, isoxazolyl, 1,2,3-triazolyl, furanyl, 3,5-dimethylisoxazol-4-yl, 5-methyl-1,2,4-oxadiazol-3-yl, —CH$_2$-(3,3-difluoropiperidin-1-yl), azetidin-1-yl, 3,3-difluoroazetidin-1-yl, pyrrolidinyl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluorophen-4-yl or phenyl, wherein said phenyl is optionally substituted with one substituent selected from the group consisting of F, CH$_3$, CF$_3$, CH(CH$_3$)$_2$, —CN, CH$_3$SO$_2$—, CH$_3$SO$_2$NH—, NH$_2$SO$_2$—, NH$_2$C(O)—, CH$_3$C(O)NH, and CH$_3$O—; and said pyrazolyl is optionally substituted with methyl, and said pyrimidyl and said pyridyl are optionally substituted with one or two substituents selected from the group consisting of —OC$_{(1-2)}$alkyl, —N(CH$_3$)$_2$, and CF$_3$;

R$^3$ is H, Br, Cl, F, —CN, —CH$_2$CN, OCF$_3$, CF$_3$, CH$_3$, pyrrolyl, pyridyl, pyrazolyl, pyrimidyl, pyridyl, thiazolyl, isoxazolyl, 1,2,3-triazolyl, furanyl, 3,5-dimethylisoxazol-4-yl, 5-methyl-1,2,4-oxadiazol-3-yl, —CH$_2$-(3,3-difluoropiperidin-1-yl), azetidin-1-yl, 3,3-difluoroazetidin-1-yl, pyrrolidinyl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluorophen-4-yl or phenyl, wherein said phenyl is optionally substituted with one substituent selected from the group consisting of F, CH$_3$, CF$_3$, CH(CH$_3$)$_2$, —CN, CH$_3$SO$_2$—, CH$_3$SO$_2$NH—, NH$_2$SO$_2$—, NH$_2$C(O)—, CH$_3$C(O)NH, and CH$_3$O—; and said pyrazolyl is optionally substituted with methyl, and said pyrimidyl and said pyridyl are optionally substituted with one or two substituents selected from the group consisting of —OC$_{(1-2)}$alkyl, —N(CH$_3$)$_2$, and CF$_3$;

R$^4$ is H, F, CF$_3$, OCF$_3$, Cl, Br, —CN, HO$_2$C-phen-3-yl, 2-trifluoromethyl-pyrid-5-yl, 2-methoxy-pyrid-5-yl, or CH$_3$;

R$_d$ is H, or F;

R$^5$ is

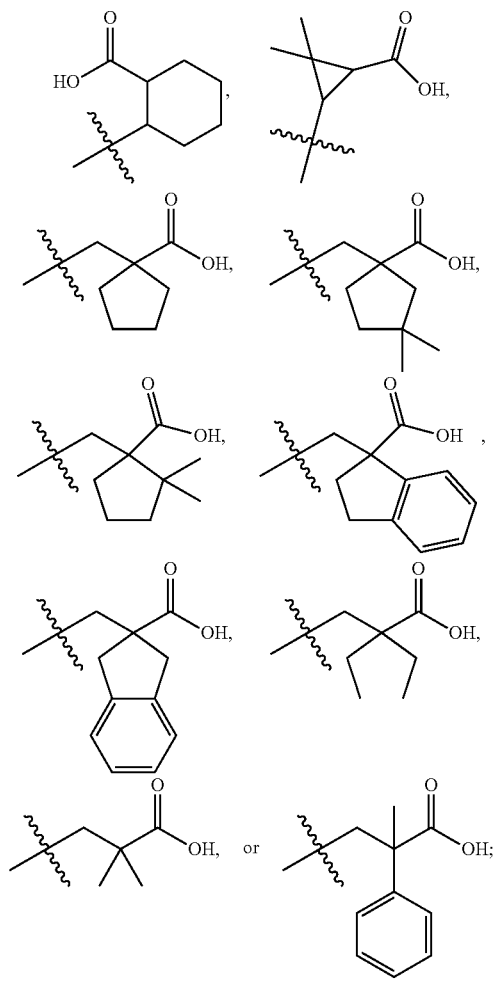

R$^6$ is H, CH$_3$, or CH$_2$CH$_3$;

and solvates, hydrates, and pharmaceutically acceptable salts thereof.

Another aspect of the present invention features R$^1$ is

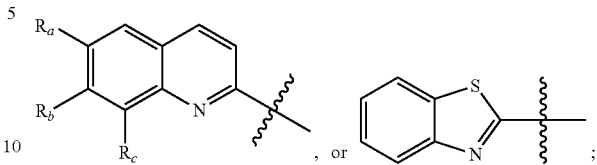

R$_a$ is H, F, or Cl;
R$_b$ is H, F, or Cl;
R$_c$ is H, or F;

is a ring selected from the group consisting of

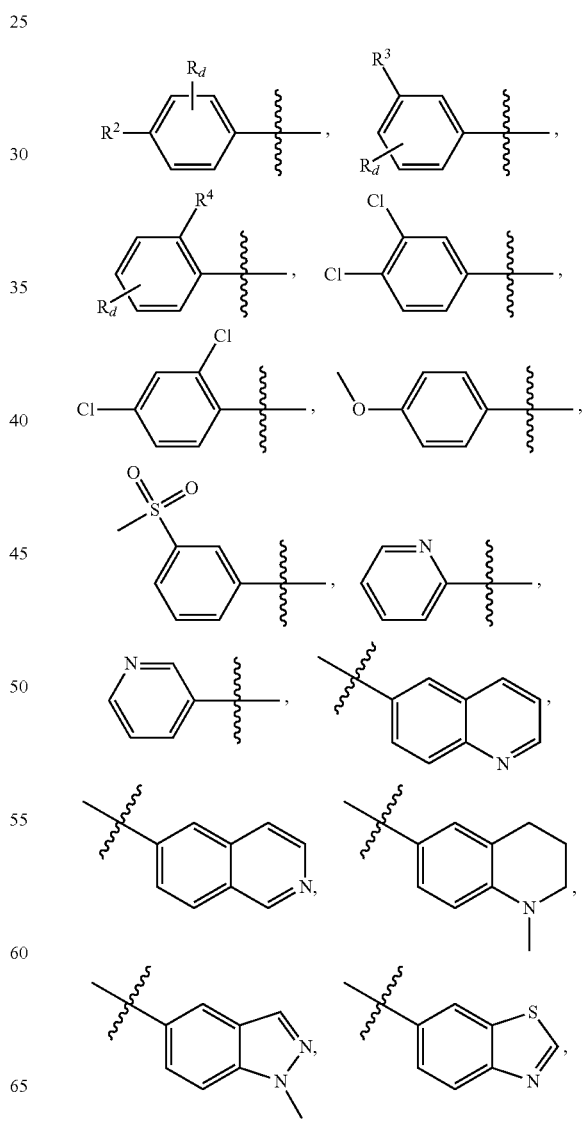

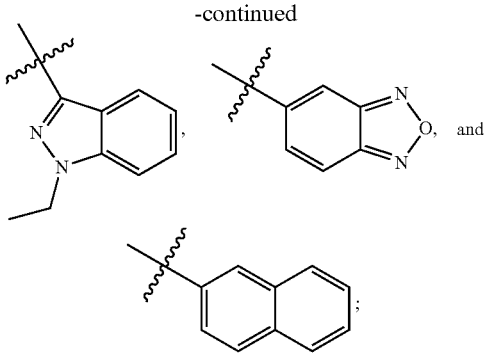

R² is H, Br, Cl, F, —CN, —CH₂CN, OCF₃, CF₃, CH₃, pyrrol-2-yl, pyrid-3-yl, pyrid-2-yl, pyrimid-2-yl, pyrimid-5-yl, 2-methoxy pyrimid-5-yl, 2-dimethylamino-pyrimid-5-yl, 2-methoxy-pyrid-5-yl, 2-methoxy-3-trifluoromethyl-pyrid-5-yl, 2-ethoxy pyrid-5-yl, 2-trifluoromethyl-pyrid-5-yl, 2-dimethylamino-pyrid-5-yl, pyrazol-1-yl, 1-methyl-pyrazol-4-yl, 1-methyl pyrazol-5-yl, 1-H-pyrazol-4-yl, thiazolyl, isoxazol-4yl, 1,2,3-triazol-1-yl, 1,2,3-triazol-2-yl, furan-3-yl, 3,5-dimethylisoxazol-4-yl, 5-methyl-1,2,4-oxadiazol-3-yl, —CH₂-(3,3-difluoropiperidin-1-yl), azetidin-1-yl, 3,3-difluoroazetidin-1-yl, pyrrolidin-2-yl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluoro-phen-4-yl or phenyl, wherein said phenyl is optionally substituted with one substituent selected from the group consisting of F, CH₃, CF₃, CH(CH₃)₂, —CN, CH₃SO₂—, CH₃SO₂NH—, NH₂SO₂—, NH₂C(O)—, CH₃C(O)NH, and CH₃O—;

R³ is H, Br, Cl, —CN, —CH₂CN, OCF₃, CF₃, CH₃, pyrrol-2-yl, thiazol-5-yl, thiazol-4-yl, 2-methoxy pyrid-5-yl, 2-trifluoromethyl-pyrid-5-yl, pyrimid-2-yl, 2-methoxy pyrimid-5-yl, 1-methyl-pyrazolyl, 1-H-pyrazol-5-yl, furan-3-yl, 3,5-dimethylisoxazol-4-yl, pyrrolidin-2-yl, 1,2-difluoro-phen-4-yl, or phenyl; wherein said phenyl is optionally substituted with one substituent selected from the group consisting of F, CF₃, NH₂SO₂—, CH₃SO₂NH—, and CH₃SO₂—;

R⁴ is H, F, CF₃, OCF₃, Cl, Br, —CN, HO₂C-phen-3-yl, 2-trifluoromethyl-pyrid-5-yl, 2-methoxy-pyrid-5-yl, or CH₃;

R$_d$ is H, or F;

R⁵ is

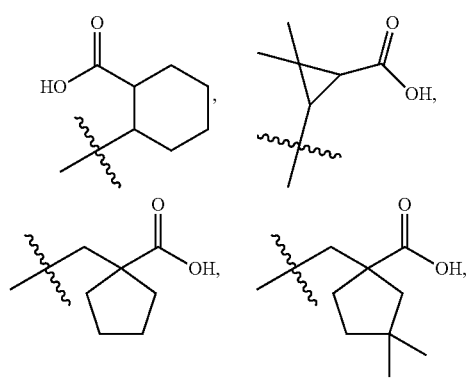

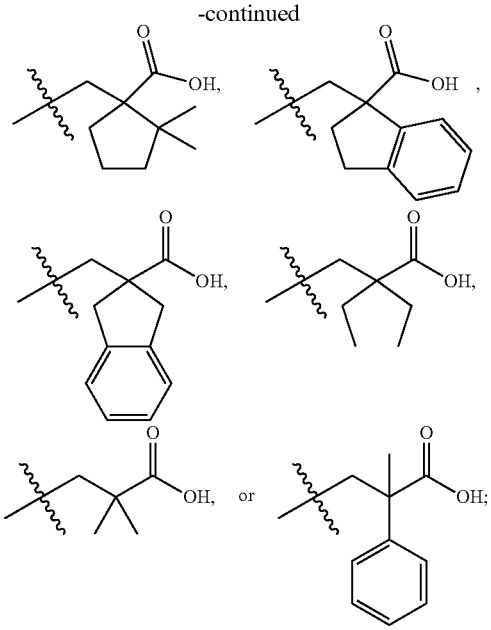

R⁶ is H, CH₃, or CH₂CH₃;

and solvates, hydrates, and pharmaceutically acceptable salts thereof.

Another aspect of the present invention features
R¹ is

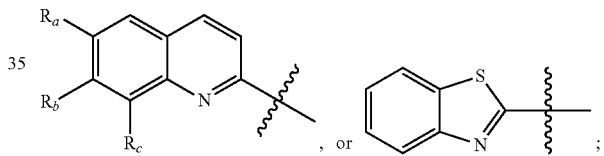

R$_a$ is H, F, or Cl;
R$_b$ is H, F, or Cl;
R$_c$ is H, or F;

is a ring selected from the group consisting of

R² is H, Br, Cl, F, —CN, —CH₂CN, OCF₃, CF₃, CH₃, pyrrol-2-yl, pyrid-3-yl, pyrid-2-yl, pyrimid-2-yl, pyrimid-5-yl, 2-methoxy pyrimid-5-yl, 2-dimethylamino-pyrimid-5-yl, 2-methoxy-pyrid-5-yl, 2-methoxy-3-trifluoromethyl-pyrid- 5-yl, 2-ethoxy pyrid-5-yl, 2-trifluoromethyl-pyrid-5-yl, 2-dimethylamino-pyrid-5-yl, pyrazol-1-yl, 1-methyl-pyrazol-4-yl, 1-methyl pyrazol-5-yl, 1-H-pyrazol-4-yl, thiazolyl, isoxazol-4yl, 1,2,3-triazol-1-yl, 1,2,3-triazol-2-yl, furan-3-yl, 3,5-dimethylisoxazol-4-yl, 5-methyl-1,2,4-oxadiazol-3-yl, —CH$_2$-(3,3-difluoropiperidin-1-yl), azetidin-1-yl, 3,3-difluoroazetidin-1-yl, pyrrolidin-2-yl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluoro-phen-4-yl or phenyl, wherein said phenyl is optionally substituted with one substituent selected from the group consisting of F, CH$_3$, CF$_3$, CH(CH$_3$)$_2$, —CN, CH$_3$SO$_2$—, CH$_3$SO$_2$NH—, NH$_2$SO$_2$—, NH$_2$C(O)—, CH$_3$C(O)NH, and CH$_3$O—;

R$^3$ is H, Br, Cl, —CN, —CH$_2$CN, OCF$_3$, CF$_3$, CH$_3$, pyrrol-2-yl, thiazol-5-yl, thiazol-4-yl, 2-methoxy pyrid-5-yl, 2-trifluoromethyl-pyrid-5-yl, pyrimid-2-yl, 2-methoxy pyrimid-5-yl, 1-methyl-pyrazolyl, 1-H-pyrazol-5-yl, furan-3-yl, 3,5-dimethylisoxazol-4-yl, pyrrolidin-2-yl, 1,2-difluoro-phen-4-yl, or phenyl; wherein said phenyl is optionally substituted with one substituent selected from the group consisting of F, CF$_3$, NH$_2$SO$_2$—, CH$_3$SO$_2$NH—, and CH$_3$SO$_2$—;

R$^4$ is H, F, CF$_3$, OCF$_3$, Cl, Br, —CN, HO$_2$C-phen-3-yl, 2-trifluoromethyl-pyrid-5-yl, 2-methoxy-pyrid-5-yl, or CH$_3$;

R$_d$ is H, or F;

R$^5$ is

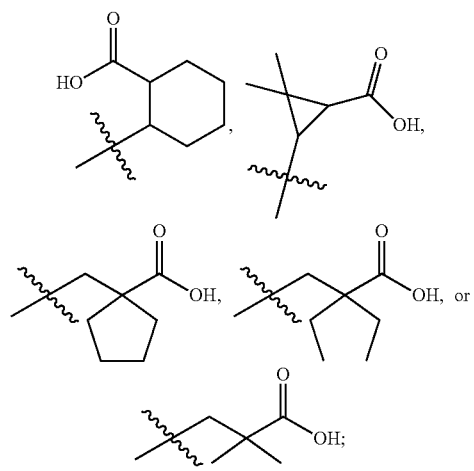

R$^6$ is H;

and solvates, hydrates, and pharmaceutically acceptable salts thereof.

Another aspect of the present invention features
R$^1$ is

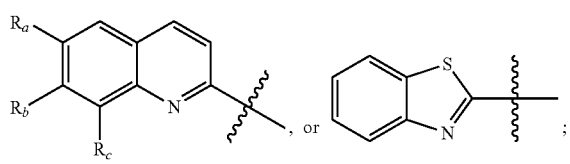

R$_a$ is H;
R$_b$ is H;
R$_c$ is H;

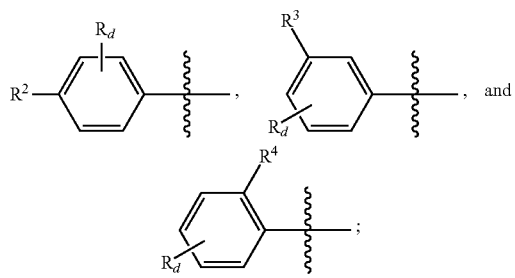

is a ring selected from the group consisting of

, and
;

R$^2$ is H, Br, Cl, F, —CN, —CH$_2$CN, OCF$_3$, CF$_3$, CH$_3$, pyrrol-2-yl, pyrid-3-yl, pyrid-2-yl, pyrimid-2-yl, pyrimid-5-yl, 2-methoxy pyrimid-5-yl, 2-dimethylamino-pyrimid-5-yl, 2-methoxy-pyrid-5-yl, 2-methoxy-3-trifluoromethyl-pyrid-5-yl, 2-ethoxy pyrid-5-yl, 2-trifluoromethyl-pyrid-5-yl, 2-dimethylamino-pyrid-5-yl, pyrazol-1-yl, 1-methyl-pyrazol-4-yl, 1-methyl pyrazol-5-yl, 1-H-pyrazol-4-yl, thiazolyl, isoxazol-4yl, 1,2,3-triazol-1-yl, 1,2,3-triazol-2-yl, furan-3-yl, 3,5-dimethylisoxazol-4-yl, 5-methyl-1,2,4-oxadiazol-3-yl, —CH$_2$-(3,3-difluoropiperidin-1-yl), azetidin-1-yl, 3,3-difluoroazetidin-1-yl, pyrrolidin-2-yl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluoro-phen-4-yl or phenyl, wherein said phenyl is optionally substituted with one substituent selected from the group consisting of F, CH$_3$, CF$_3$, CH(CH$_3$)$_2$, —CN, CH$_3$SO$_2$—, CH$_3$SO$_2$NH—, NH$_2$SO$_2$—, NH$_2$C(O)—, CH$_3$C(O)NH, and CH$_3$O—;

R$^3$ is H, Br, Cl, —CN, —CH$_2$CN, OCF$_3$, CF$_3$, CH$_3$, pyrrol-2-yl, thiazol-5-yl, thiazol-4-yl, 2-methoxy pyrid-5-yl, 2-trifluoromethyl-pyrid-5-yl, pyrimid-2-yl, 2-methoxy pyrimid-5-yl, 1-methyl-pyrazolyl, 1-H-pyrazol-5-yl, furan-3-yl, 3,5-dimethylisoxazol-4-yl, pyrrolidin-2-yl, 1,2-difluoro-phen-4-yl, or phenyl; wherein said phenyl is optionally substituted with one substituent selected from the group consisting of F, CF$_3$, NH$_2$SO$_2$—, CH$_3$SO$_2$NH—, and CH$_3$SO$_2$—;

R$^4$ is H, F, CF$_3$, OCF$_3$, Cl, Br, —CN, HO$_2$C-phen-3-yl, 2-trifluoromethyl-pyrid-5-yl, 2-methoxy-pyrid-5-yl, or CH$_3$;

R$_d$ is H, or F;

R$^5$ is

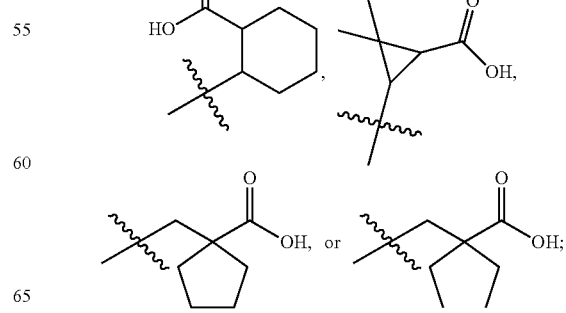

$R^6$ is H;

and solvates, hydrates, and pharmaceutically acceptable salts thereof.

The embodiments of the present invention also include the optical isomers, hydrates, metabolites, enantiomers, diastereomers, cis-trans isomers, racemates, prodrugs or pharmaceutically acceptable salts thereof.

It is an embodiment of the present invention to provide a compound selected from the compounds listed in Table 1.

TABLE 1 racemic cis-2-[1-(4-Bromobenzyl)-5-(quinolin-2-ylmethoxy)-1H-benzimidazol-2-yl]cyclohexanecarboxylic acid,
(1R*,2S*)-2-[1-(4-Bromobenzyl)-5-(quinolin-2-ylmethoxy)-1H-benzimidazol-2-yl]cyclohexanecarboxylic acid,
(1S*,2R*)-2-[1-(4-Bromobenzyl)-5-(quinolin-2-ylmethoxy)-1H-benzimidazol-2-yl]cyclohexanecarboxylic acid,
racemic cis-2-[1-(3-Bromobenzyl)-5-(quinolin-2-ylmethoxy)-1H-benzimidazol-2-yl]cyclohexanecarboxylic acid as the TFA salt,
2,2-Dimethyl-3-{5-(quinolin-2-ylmethoxy)-1-[3-(trifluoromethoxy) benzyl]-1H-benzimidazol-2-yl}propanoic acid,
2,2-Dimethyl-3-{5-(quinolin-2-ylmethoxy)-1-[2-(trifluoromethoxy)benzyl]-1H-benzimidazol-2-yl}propanoic acid,
2,2-Dimethyl-3-{5-(quinolin-2-ylmethoxy)-1-[4-(trifluoromethoxy)benzyl]-1H-benzimidazol-2-yl}propanoic acid,
racemic 1-{[1-(4-Bromobenzyl)-5-(quinolin-2-ylmethoxy)-1H-benzimidazol-2-yl]methyl}-2,2-dimethylcyclopentanecarboxylic acid,
3-[1-(4-Bromo-2-fluorobenzyl)-5-(quinolin-2-ylmethoxy)-1H-benzimidazol-2-yl]-2,2-dimethylpropanoic acid,
3-[1-(2,4-Difluorobenzyl)-5-(quinolin-2-ylmethoxy)-1H-benzimidazol-2-yl]-2,2-dimethylpropanoic acid,
racemic cis-3-[1-(2,4-Difluorobenzyl)-5-(quinolin-2-ylmethoxy)-1H-benzimidazol-2-yl]-2,2-dimethylcyclopropanecarboxylic acid,
3-[1-(2,4-Dichlorobenzyl)-5-(quinolin-2-ylmethoxy)-1H-benzimidazol-2-yl]-2,2-dimethylpropanoic acid,
racemic cis-3-[1-(2,4-Dichlorobenzyl)-5-(quinolin-2-ylmethoxy)-1H-benzimidazol-2-yl]-2,2-dimethylcyclopropanecarboxylic acid,
racemic cis-3-[1-(4-Bromo-2-fluorobenzyl)-5-(quinolin-2-ylmethoxy)-1H-benzimidazol-2-yl]-2,2-dimethylcyclopropanecarboxylic acid,
racemic cis-2-[1-(4-Bromo-2-fluorobenzyl)-5-(quinolin-2-ylmethoxy)-1H-benzimidazol-2-yl]cyclohexanecarboxylic acid,
racemic trans-2-[1-(4-Bromo-2-fluorobenzyl)-5-(quinolin-2-ylmethoxy)-1H-benzimidazol-2-yl]cyclohexanecarboxylic acid,
racemic 1-{[1-(4-Bromobenzyl)-5-(quinolin-2-ylmethoxy)-1H-benzimidazol-2-yl]methyl}-3,3-dimethylcyclopentanecarboxylic acid as the TFA salt,
racemic cis-2-(1-(4-(5-Methyl-1,2,4-oxadiazol-3-yl)benzyl)-5-(quinolin-2-ylmethoxy)-1H-benzo[d]imidazol-2-yl)cyclohexanecarboxylic acid as the TFA salt
2-Ethyl-2-({1-[4-(5-methyl-1,2,4-oxadiazol-3-yl)benzyl]-5-(quinolin-2-ylmethoxy)-1H-benzimidazol-2-yl}methyl)butanoic acid as the TFA salt,
1-({1-[4-(5-Methyl-1,2,4-oxadiazol-3-yl)benzyl]-5-(quinolin-2-ylmethoxy)-1H-benzimidazol-2-yl}methyl)cyclopentanecarboxylic acid as the TFA salt,
racemic trans-2-[1-(4-Bromobenzyl)-5-(quinolin-2-ylmethoxy)-1H-benzimidazol-2-yl]cyclohexanecarboxylic acid as the TFA salt,
racemic 1-{[1-(4-Bromobenzyl)-5-(quinolin-2-ylmethoxy)-1H-benzimidazol-2-yl]methyl}-2,3-dihydro-1H-indene-1-carboxylic acid as the TFA salt,
2-{[1-(4-Bromobenzyl)-5-(quinolin-2-ylmethoxy)-1H-benzimidazol-2-yl]methyl}-2-ethylbutanoic acid as theTFA salt,
2-{[1-(4-Bromobenzyl)-5-(quinolin-2-ylmethoxy)-1H-benzimidazol-2-yl]methyl}-2,3-dihydro-1H-indene-2-carboxylic acid as the TFA salt,
racemic cis-3-{1-[(1-Ethyl-1H-indazol-3-yl)methyl]-5-(quinolin-2-ylmethoxy)-1H-benzimidazol-2-yl}-2,2-dimethylcyclopropanecarboxylic acid,
3-[1-(4-Bromobenzyl)-5-(quinolin-2-ylmethoxy)-1H-benzimidazol-2-yl]-2,2-dimethylpropanoic acid,
3-{1-(4-Bromobenzyl)-5-[(6-fluoroquinolin-2-yl)methoxy]-1H-benzimidazol-2-yl}-2,2-dimethylpropanoic acid,
3-[5-(1,3-Benzothiazol-2-ylmethoxy)-1-(4-bromobenzyl)-1H-benzimidazol-2-yl]-2,2-dimethylpropanoic acid,
1-{[1-(4-Bromobenzyl)-5-(quinolin-2-ylmethoxy)-1H-benzimidazol-2-yl]methyl}cyclopentanecarboxylic acid as the TFA salt,
racemic 3-[1-(4-Bromobenzyl)-5-(quinolin-2-ylmethoxy)-1H-benzimidazol-2-yl]-2-methyl-2-phenylpropanoic acid as the TFA salt,
racemic cis-3-[1-(4-Bromobenzyl)-5-(quinolin-2-ylmethoxy)-1H-benzimidazol-2-yl]-2,2-dimethylcyclopropanecarboxylic acid as the TFA salt,
racemic trans-3-[1-(4-Bromobenzyl)-5-(quinolin-2-ylmethoxy)-1H-benzimidazol-2-yl]-2,2-dimethylcyclopropanecarboxylic acid as the TFA salt,
3-[1-(2-Bromobenzyl)-5-(quinolin-2-ylmethoxy)-1H-benzimidazol-2-yl]-2,2-dimethylpropanoic acid,
3-[1-(3-Bromobenzyl)-5-(quinolin-2-ylmethoxy)-1H-benzimidazol-2-yl]-2,2-dimethylpropanoic acid,

TABLE 1-continued racemic cis-2-[1-(4-Cyanobenzyl)-5-(quinolin-2-ylmethoxy)-1H-benzimidazol-2-yl]cyclohexanecarboxylic acid as a hydrochloride salt,
racemic cis-2-[1-Benzyl-5-(quinolin-2-ylmethoxy)-1H-benzimidazol-2-yl]cyclohexanecarboxylic acid as the hydrochloride salt,
racemic cis-2-{5-(Quinolin-2-ylmethoxy)-1-[2-(trifluoromethoxy)benzyl]-1H-benzimidazol-2-yl}cyclohexanecarboxylic acid as the hydrochloride salt,
racemic cis-2-[1-(2-Methylbenzyl)-5-(quinolin-2-ylmethoxy)-1H-benzimidazol-2-yl]cyclohexanecarboxylic acid as the hydrochloride salt,
racemic cis-2-{5-(Quinolin-2-ylmethoxy)-1-[2-(trifluoromethyl)benzyl]-1H-benzimidazol-2-yl}cyclohexanecarboxylic acid as the hydrochloride salt,
racemic cis-2-{1-[3-Fluoro-4-(trifluoromethoxy)benzyl]-5-(quinolin-2-ylmethoxy)-1H-benzimidazol-2-yl}cyclohexanecarboxylic acid as the hydrochloride salt,
racemic cis-2-{1-[2-Fluoro-4-(trifluoromethoxy)benzyl]-5-(quinolin-2-ylmethoxy)-1H-benzimidazol-2-yl}cyclohexanecarboxylic acid as the hydrochloride salt,
(1R*,2S*)-2-{1-[2-Fluoro-4-(trifluoromethoxy)benzyl]-5-(quinolin-2-ylmethoxy)-1H-benzimidazol-2-yl}cyclohexanecarboxylic acid,
(1S*,2R*)-2-{1-[2-Fluoro-4-(trifluoromethoxy)benzyl]-5-(quinolin-2-ylmethoxy)-1H-benzimidazol-2-yl}cyclohexanecarboxylic acid,
racemic cis-2-[1-(4-Methylbenzyl)-5-(quinolin-2-ylmethoxy)-1H-benzimidazol-2-yl]cyclohexanecarboxylic acid as the hydrochloride salt,
racemic cis-2-{5-(Quinolin-2-ylmethoxy)-1-[4-(trifluoromethoxy)benzyl]-1H-benzimidazol-2-yl}cyclohexanecarboxylic acid as the hydrochloride salt,
racemic cis-2-{5-(Quinolin-2-ylmethoxy)-1-[4-(trifluoromethyl)benzyl]-1H-benzimidazol-2-yl}cyclohexanecarboxylic acid as the hydrochloride salt,
racemic cis-2-[1-(3-Cyanobenzyl)-5-(quinolin-2-ylmethoxy)-1H-benzimidazol-2-yl]cyclohexanecarboxylic acid as the hydrochloride salt,
racemic cis-2-(5-(quinolin-2-ylmethoxy)-1-(3-(trifluoromethoxy)benzyl)-1H-benzo[d]imidazol-2-yl)cyclohexanecarboxylic acid as the hydrochloride salt,
racemic cis-2-[1-(3-Methylbenzyl)-5-(quinolin-2-ylmethoxy)-1H-benzimidazol-2-yl]cyclohexanecarboxylic acid as the hydrochloride salt,
racemic cis-2-(5-(quinolin-2-ylmethoxy)-1-(3-(trifluoromethyl)benzyl)-1H-benzo[d]imidazol-2-yl)cyclohexanecarboxylic acid as the hydrochloride salt,
racemic cis-2-[1-(2-Cyanobenzyl)-5-(quinolin-2-ylmethoxy)-1H-benzimidazol-2-yl]cyclohexanecarboxylic acid as the hydrochloride salt,
racemic cis-2-{1-(4-Bromobenzyl)-5-[(6-fluoroquinolin-2-yl)methoxy]-1H-benzimidazol-2-yl}cyclohexanecarboxylic acid as the formic acid salt,
racemic trans-2-{1-(4-Bromobenzyl)-5-[(8-fluoroquinolin-2-yl)methoxy]-1H-benzimidazol-2-yl}cyclohexanecarboxylic acid,
racemic cis-2-{1-(4-Bromobenzyl)-5-[(8-fluoroquinolin-2-yl)methoxy]-1H-benzimidazol-2-yl}cyclohexanecarboxylic acid as the formic acid salt,
racemic cis-2-{1-(4-Bromobenzyl)-5-[(7-chloroquinolin-2-yl)methoxy]-1H-benzimidazol-2-yl}cyclohexanecarboxylic acid as the formic acid salt,
racemic cis-2-{1-(4-Bromobenzyl)-5-[(6-chloroquinolin-2-yl)methoxy]-1H-benzimidazol-2-yl}cyclohexanecarboxylic acid,
1-({5-(Quinolin-2-ylmethoxy)-1-[4-(trifluoromethyl)benzyl]-1H-benzimidazol-2-yl}methyl)cyclopentanecarboxylic acid,
1-{[1-(4-Fluorobenzyl)-5-(quinolin-2-ylmethoxy)-1H-benzimidazol-2-yl]methyl}cyclopentanecarboxylic acid as the TFA salt,
1-({5-(Quinolin-2-ylmethoxy)-1-[4-methoxybenzyl]-1H-benzimidazol-2-yl}methyl)cyclopentanecarboxylic acid as the TFA salt,
1-({5-(Quinolin-2-ylmethoxy)-1-[4-(trifluoromethoxy)benzyl]-1H-benzimidazol-2-yl}methyl)cyclopentanecarboxylic acid as the TFA salt,
1-{[1-(Pyridin-2-ylmethyl)-5-(quinolin-2-ylmethoxy)-1H-benzimidazol-2-yl]methyl}cyclopentanecarboxylic acid,
1-{[1-(Pyridin-3-ylmethyl)-5-(quinolin-2-ylmethoxy)-1H-benzimidazol-2-yl]methyl}cyclopentanecarboxylic acid,
1-{[1-(4-Chlorobenzyl)-5-(quinolin-2-ylmethoxy)-1H-benzimidazol-2-yl]methyl}cyclopentanecarboxylic acid,
3-{1-[1-(4-Bromophenyl)propyl]-5-(quinolin-2-ylmethoxy)-1H-benzimidazol-2-yl}-2,2-dimethylpropanoic acid,
2,2-Dimethyl-3-[1-(4-methylbenzyl)-5-(quinolin-2-ylmethoxy)-1H-benzimidazol-2-yl]propanoic acid,
3-[1-(4-Fluorobenzyl)-5-(quinolin-2-ylmethoxy)-1H-benzimidazol-2-yl]-2,2-dimethylpropanoic acid,
3-[1-(3-Chlorobenzyl)-5-(quinolin-2-ylmethoxy)-1H-benzimidazol-2-yl]-2,2-dimethylpropanoic acid as the TFA acid salt,
2,2-Dimethyl-3-[1-(3-methylbenzyl)-5-(quinolin-2-ylmethoxy)-1H-benzimidazol-2-yl]propanoic acid,
3-[1-(2-Chlorobenzyl)-5-(quinolin-2-ylmethoxy)-1H-benzimidazol-2-yl]-2,2-dimethylpropanoic acid as the TFA salt,
3-[1-(4-Methoxybenzyl)-5-(quinolin-2-ylmethoxy)-1H-benzimidazol-2-yl]-2,2-dimethylpropanoic acid as the TFA salt,
2,2-Dimethyl-3-{5-(quinolin-2-ylmethoxy)-1-[4-(trifluoromethyl)benzyl]-1H-benzimidazol-2-yl}propanoic acid as the TFA salt,
3-{1-[1-(4-Bromophenyl)ethyl]-5-(quinolin-2-ylmethoxy)-1H-benzimidazol-2-yl}-2,2-dimethylpropanoic acid,
3-[1-(3,4-Dichlorobenzyl)-5-(quinolin-2-ylmethoxy)-1H-benzimidazol-2-yl]-2,2-dimethylpropanoic acid,
3-{1-[4-Fluoro-3-(trifluoromethyl)benzyl]-5-(quinolin-2-ylmethoxy)-1H-benzimidazol-2-yl}-2,2-dimethylpropanoic acid, TABLE 1-continued 3-[1-(3-Chloro-4-fluorobenzyl)-5-(quinolin-2-ylmethoxy)-1H-benzimidazol-2-yl]-2,2-dimethylpropanoic acid,
3-[1-Benzyl-5-(quinolin-2-ylmethoxy)-1H-benzimidazol-2-yl]-2,2-dimethylpropanoic acid,
3-[1-(4-Chlorobenzyl)-5-(quinolin-2-ylmethoxy)-1H-benzimidazol-2-yl]-2,2-dimethylpropanoic acid,
3-[1-{4-[(3,3-Difluoropiperidin-1-yl)methyl]benzyl}-5-(quinolin-2-ylmethoxy)-1H-benzimidazol-2-yl]-2,2-dimethylpropanoic acid as the hydrochloric acid salt,
2,2-Dimethyl-3-[1-(naphthalen-2-ylmethyl)-5-(quinolin-2-ylmethoxy)-1H-benzimidazol-2-yl]propanoic acid,
2,2-Dimethyl-3-[5-(quinolin-2-ylmethoxy)-1-(quinolin-6-ylmethyl)-1H-benzimidazol-2-yl]propanoic acid,
3-[1-(1,3-Benzothiazol-6-ylmethyl)-5-(quinolin-2-ylmethoxy)-1H-benzimidazol-2-yl]-2,2-dimethylpropanoic acid,
2,2-Dimethyl-3-{1-[(1-methyl-1,2,3,4-tetrahydroquinolin-6-yl)methyl]-5-(quinolin-2-ylmethoxy)-1H-benzimidazol-2-yl}propanoic acid,
2,2-Dimethyl-3-{1-[3-(methylsulfonyl)benzyl]-5-(quinolin-2-ylmethoxy)-1H-benzimidazol-2-yl}propanoic acid,
3-[1-(2,1,3-Benzoxadiazol-5-ylmethyl)-5-(quinolin-2-ylmethoxy)-1H-benzimidazol-2-yl]-2,2-dimethylpropanoic acid,
3-[1-(Isoquinolin-6-ylmethyl)-5-(quinolin-2-ylmethoxy)-1H-benzimidazol-2-yl]-2,2-dimethylpropanoic acid - Hydrochloric acid salt,
2,2-Dimethyl-3-{1-[(1-methyl-1H-indazol-5-yl)methyl]-5-(quinolin-2-ylmethoxy)-1H-benzimidazol-2-yl}propanoic acid as the hydrochloric acid salt,
racemic 3-[1-(4-Cyanobenzyl)-5-(quinolin-2-ylmethoxy)-1H-benzimidazol-2-yl]-2,2-dimethylcyclopropanecarboxylic acid,
1-{[1-(4-Cyanobenzyl)-5-(quinolin-2-ylmethoxy)-1H-benzimidazol-2-yl]methyl}cyclopentanecarboxylic acid,
1-{[1-(3-Bromobenzyl)-5-(quinolin-2-ylmethoxy)-1H-benzimidazol-2-yl]methyl}cyclopentanecarboxylic acid,
1-{[1-(3-Cyanobenzyl)-5-(quinolin-2-ylmethoxy)-1H-benzimidazol-2-yl]methyl}cyclopentanecarboxylic acid,
1-{[1-(Biphenyl-3-ylmethyl)-5-(quinolin-2-ylmethoxy)-1H-benzimidazol-2-yl]methyl}cyclopentanecarboxylic acid,
1-({1-[(4'-Fluorobiphenyl-3-yl)methyl]-5-(quinolin-2-ylmethoxy)-1H-benzimidazol-2-yl}methyl)cyclopentanecarboxylic acid,
1-{[1-{[4'-(Methylsulfonyl)biphenyl-3-yl]methyl}-5-(quinolin-2-ylmethoxy)-1H-benzimidazol-2-yl]methyl}cyclopentanecarboxylic acid,
1-({1-[3-(2-Methoxypyrimidin-5-yl)benzyl]-5-(quinolin-2-ylmethoxy)-1H-benzimidazol-2-yl}methyl)cyclopentanecarboxylic acid,
1-({1-[3-(6-Methoxypyridin-3-yl)benzyl]-5-(quinolin-2-ylmethoxy)-1H-benzimidazol-2-yl}methyl)cyclopentanecarboxylic acid,
1-({1-[(3',4'-Difluorobiphenyl-3-yl)methyl]-5-(quinolin-2-ylmethoxy)-1H-benzimidazol-2-yl}methyl)cyclopentanecarboxylic acid,
1-{[1-({4'-[(Methylsulfonyl)amino]biphenyl-3-yl}methyl)-5-(quinolin-2-ylmethoxy)-1H-benzimidazol-2-yl]methyl}cyclopentanecarboxylic acid,
1-({5-(Quinolin-2-ylmethoxy)-1-[3-(1,3-thiazol-4-yl)benzyl]-1H-benzimidazol-2-yl}methyl)cyclopentanecarboxylic acid,
1-({1-[3-(1-Methyl-1H-pyrazol-4-yl)benzyl]-5-(quinolin-2-ylmethoxy)-1H-benzimidazol-2-yl}methyl)cyclopentanecarboxylic acid,
1-{[1-(3-Furan-3-ylbenzyl)-5-(quinolin-2-ylmethoxy)-1H-benzimidazol-2-yl]methyl}cyclopentanecarboxylic acid,
1-({1-[3-(3,5-Dimethylisoxazol-4-yl)benzyl]-5-(quinolin-2-ylmethoxy)-1H-benzimidazol-2-yl}methyl)cyclopentanecarboxylic acid,
racemic cis-3-{1-[2-Fluoro-4-(6-methoxypyridin-3-yl)benzyl]-5-(quinolin-2-ylmethoxy)-1H-benzimidazol-2-yl}-2,2-dimethylcyclopropanecarboxylic acid,
racemic cis-3-{1-[(3,4'-Difluorobiphenyl-4-yl)methyl]-5-(quinolin-2-ylmethoxy)-1H-benzimidazol-2-yl}-2,2-dimethylcyclopropanecarboxylic acid,
racemic cis-2,2-Dimethyl-3-{5-(quinolin-2-ylmethoxy)-1-[(3,3',4'-trifluorobiphenyl-4-yl)methyl]-1H-benzimidazol-2-yl}cyclopropanecarboxylic acid,
1-({5-(Quinolin-2-ylmethoxy)-1-[4-(1,3-thiazol-4-yl)benzyl]-1H-benzimidazol-2-yl}methyl)cyclopentanecarboxylic acid,
racemic cis-2,2-Dimethyl-3-{5-(quinolin-2-ylmethoxy)-1-[3-(1,3-thiazol-4-yl)benzyl]-1H-benzimidazol-2-yl}cyclopropanecarboxylic acid,
1-({1-[4-(3,5-Dimethylisoxazol-4-yl)benzyl]-5-(quinolin-2-ylmethoxy)-1H-benzimidazol-2-yl}methyl)cyclopentanecarboxylic acid,
racemic cis-2,2-Dimethyl-3-{5-(quinolin-2-ylmethoxy)-1-[4-(1,3-thiazol-4-yl)benzyl]-1H-benzimidazol-2-yl}cyclopropanecarboxylic acid,
racemic cis-2-(5-((6-fluoroquinolin-2-yl)methoxy)-1-((4'-(trifluoromethyl)-[1,1'-biphenyl]-4-yl)methyl)-1H-benzo[d]imidazol-2-yl)cyclohexanecarboxylic acid,
1-{[1-(4-Furan-3-ylbenzyl)-5-(quinolin-2-ylmethoxy)-1H-benzimidazol-2-yl]methyl}cyclopentanecarboxylic acid,
1-({1-[4-(6-Methoxypyridin-3-yl)benzyl]-5-(quinolin-2-ylmethoxy)-1H-benzimidazol-2-yl}methyl)cyclopentanecarboxylic acid as the TFA salt,
1-{[5-(Quinolin-2-ylmethoxy)-1-{4-[6-(trifluoromethyl)pyridin-3-yl]benzyl}-1H-benzimidazol-2-yl]methyl}cyclopentanecarboxylic acid as the TFA salt,
1-({1-[(4'-Fluorobiphenyl-4-yl)methyl]-5-(quinolin-2-ylmethoxy)-1H-benzimidazol-2-yl}methyl)cyclopentanecarboxylic acid as the TFA salt,
1-({1-[4-(6-Ethoxypyridin-3-yl)benzyl]-5-(quinolin-2-ylmethoxy)-1H-benzimidazol-2-yl}methyl)cyclopentanecarboxylic acid as the TFA salt, TABLE 1-continued 1-{[1-{4-[6-(Dimethylamino)pyridin-3-yl]benzyl}-5-(quinolin-2-ylmethoxy)-1H-benzimidazol-2-yl]methyl}cyclopentanecarboxylic acid as the TFA salt,
1-({1-[(3',4'-Difluorobiphenyl-4-yl)methyl]-5-(quinolin-2-ylmethoxy)-1H-benzimidazol-2-yl}methyl)cyclopentanecarboxylic acid as the TFA salt,
1-{[1-{4-[2-(Dimethylamino)pyrimidin-5-yl]benzyl}-5-(quinolin-2-ylmethoxy)-1H-benzimidazol-2-yl]methyl}cyclopentanecarboxylic acid as the TFA salt,
1-{[1-(Biphenyl-4-ylmethyl)-5-(quinolin-2-ylmethoxy)-1H-benzimidazol-2-yl]methyl}cyclopentanecarboxylic acid as the TFA salt,
1-{[1-{[4'-(1-Methylethyl)biphenyl-4-yl]methyl}-5-(quinolin-2-ylmethoxy)-1H-benzimidazol-2-yl]methyl}cyclopentanecarboxylic acid as the TFA salt,
1-{[1-({3'-[(Methylsulfonyl)amino]biphenyl-4-yl}methyl)-5-(quinolin-2-ylmethoxy)-1H-benzimidazol-2-yl]methyl}cyclopentanecarboxylic acid as the TFA,
1-{[1-{4-[6-Methoxy-5-(trifluoromethyl)pyridin-3-yl]benzyl}-5-(quinolin-2-ylmethoxy)-1H-benzimidazol-2-yl]methyl}cyclopentanecarboxylic acid as the TFA salt,
1-{[1-{[4'-(Methylsulfonyl)biphenyl-4-yl]methyl}-5-(quinolin-2-ylmethoxy)-1H-benzimidazol-2-yl]methyl}cyclopentanecarboxylic acid,
1-({1-[4-(2-Methoxypyrimidin-5-yl)benzyl]-5-(quinolin-2-ylmethoxy)-1H-benzimidazol-2-yl}methyl)cyclopentanecarboxylic acid,
1-({1-[4-(1-Methyl-1H-pyrazol-4-yl)benzyl]-5-(quinolin-2-ylmethoxy)-1H-benzimidazol-2-yl}methyl)cyclopentanecarboxylic acid,
1-({1-[4-(1H-Pyrazol-4-yl)benzyl]-5-(quinolin-2-ylmethoxy)-1H-benzimidazol-2-yl}methyl)cyclopentanecarboxylic acid,
1-{[1-({4'-[(Methylsulfonyl)amino]biphenyl-4-yl}methyl)-5-(quinolin-2-ylmethoxy)-1H-benzimidazol-2-yl]methyl}cyclopentanecarboxylic acid,
racemic cis-3-{1-[4-(2-Methoxypyrimidin-5-yl)benzyl]-5-(quinolin-2-ylmethoxy)-1H-benzimidazol-2-yl}-2,2-dimethylcyclopropanecarboxylic acid,
racemic cis-3-{1-[3-(2-Methoxypyrimidin-5-yl)benzyl]-5-(quinolin-2-ylmethoxy)-1H-benzimidazol-2-yl}-2,2-dimethylcyclopropanecarboxylic acid,
racemic cis-3-{1-[(3',4'-Difluorobiphenyl-4-yl)methyl]-5-(quinolin-2-ylmethoxy)-1H-benzimidazol-2-yl}-2,2-dimethylcyclopropanecarboxylic acid,
racemic cis-3-{1-[(3',4'-Difluorobiphenyl-3-yl)methyl]-5-(quinolin-2-ylmethoxy)-1H-benzimidazol-2-yl}-2,2-dimethylcyclopropanecarboxylic acid,
racemic cis-3-{1-[(4'-Fluorobiphenyl-4-yl)methyl]-5-(quinolin-2-ylmethoxy)-1H-benzimidazol-2-yl}-2,2-dimethylcyclopropanecarboxylic acid,
racemic cis-3-{1-[(4'-Fluorobiphenyl-3-yl)methyl]-5-(quinolin-2-ylmethoxy)-1H-benzimidazol-2-yl}-2,2-dimethylcyclopropanecarboxylic acid,
racemic cis-2-{1-[4-(2-Methoxypyrimidin-5-yl)benzyl]-5-(quinolin-2-ylmethoxy)-1H-benzimidazol-2-yl}cyclohexanecarboxylic acid as the TFA salt,
racemic cis-2-[1-(4-Pyrimidin-5-ylbenzyl)-5-(quinolin-2-ylmethoxy)-1H-benzimidazol-2-yl]cyclohexanecarboxylic acid as the TFA salt,
racemic cis-2-[5-(Quinolin-2-ylmethoxy)-1-{4-[6-(trifluoromethyl)pyridin-3-yl]benzyl}-1H-benzimidazol-2-yl]cyclohexanecarboxylic acid as the TFA salt,
racemic cis-2-[1-({4'-[(Methylsulfonyl)amino]biphenyl-4-yl}methyl)-5-(quinolin-2-ylmethoxy)-1H-benzimidazol-2-yl]cyclohexanecarboxylic acid as the TFA salt,
racemic cis-2-[5-(Quinolin-2-ylmethoxy)-1-{3-[6-(trifluoromethyl)pyridin-3-yl]benzyl}-1H-benzimidazol-2-yl]cyclohexanecarboxylic acid as the TFA salt,
racemic cis-2-[1-({4'-[(Methylsulfonyl)amino]biphenyl-3-yl}methyl)-5-(quinolin-2-ylmethoxy)-1H-benzimidazol-2-yl]cyclohexanecarboxylic acid as the TFA salt,
racemic cis-2-[5-(Quinolin-2-ylmethoxy)-1-{[4'-(trifluoromethyl)biphenyl-4-yl]methyl}-1H-benzimidazol-2-yl]cyclohexanecarboxylic acid as the TFA salt,
racemic cis-2-[1-{[3-Fluoro-4'-(trifluoromethyl)biphenyl-4-yl]methyl}-5-(quinolin-2-ylmethoxy)-1H-benzimidazol-2-yl]cyclohexanecarboxylic acid as the TFA salt,
racemic cis-2-[5-(Quinolin-2-ylmethoxy)-1-{[4'-(trifluoromethyl)biphenyl-3-yl]methyl}-1H-benzimidazol-2-yl]cyclohexanecarboxylic acid as the TFA salt,
1-({1-[3-(1H-Pyrazol-5-yl)benzyl]-5-(quinolin-2-ylmethoxy)-1H-benzimidazol-2-yl}methyl)cyclopentanecarboxylic acid,
1-({1-[3-(Cyanomethyl)benzyl]-5-(quinolin-2-ylmethoxy)-1H-benzimidazol-2-yl}methyl)cyclopentanecarboxylic acid,
3-{1-[4-(6-Methoxypyridin-3-yl)benzyl]-5-(quinolin-2-ylmethoxy)-1H-benzimidazol-2-yl}-2,2-dimethylpropanoic acid as the TFA salt,
2,2-Dimethyl-3-[5-(quinolin-2-ylmethoxy)-1-{4-[6-(trifluoromethyl)pyridin-3-yl]benzyl}-1H-benzimidazol-2-yl]propanoic acid as the TFA salt,
3-{1-[4-(2-Methoxypyrimidin-5-yl)benzyl]-5-(quinolin-2-ylmethoxy)-1H-benzimidazol-2-yl}-2,2-dimethylpropanoic acid as the TFA salt,
3-{1-[3-(6-Methoxypyridin-3-yl)benzyl]-5-(quinolin-2-ylmethoxy)-1H-benzimidazol-2-yl}-2,2-dimethylpropanoic acid,
3-{1-[2-(6-Methoxypyridin-3-yl)benzyl]-5-(quinolin-2-ylmethoxy)-1H-benzimidazol-2-yl}-2,2-dimethylpropanoic acid,
2,2-Dimethyl-3-{1-[4-(1H-pyrrol-2-yl)benzyl]-5-(quinolin-2-ylmethoxy)-1H-benzimidazol-2-yl}propanoic acid,
2,2-Dimethyl-3-[1-({4'-[(methylsulfonyl)amino]biphenyl-4-yl}methyl)-5-(quinolin-2-ylmethoxy)-1H-benzimidazol-2-yl]propanoic acid,
2,2-Dimethyl-3-{1-[(3'-methylbiphenyl-4-yl)methyl]-5-(quinolin-2-ylmethoxy)-1H-benzimidazol-2-yl}propanoic acid,
2,2-Dimethyl-3-{1-[(4'-methylbiphenyl-4-yl)methyl]-5-(quinolin-2-ylmethoxy)-1H-benzimidazol-2-yl}propanoic acid,
2,2-Dimethyl-3-{1-[4-(1-methyl-1H-pyrazol-5-yl)benzyl]-5-(quinolin-2-ylmethoxy)-1H-benzimidazol-2-yl}propanoic acid,
2,2-Dimethyl-3-{5-(quinolin-2-ylmethoxy)-1-[(4'-sulfamoylbiphenyl-4-yl)methyl]-1H-benzimidazol-2-yl}propanoic acid, TABLE 1-continued 3-{1-[(2'-Fluorobiphenyl-4-yl)methyl]-5-(quinolin-2-ylmethoxy)-1H-benzimidazol-2-yl}-2,2-dimethylpropanoic acid,
3-{1-[(3'-Fluorobiphenyl-4-yl)methyl]-5-(quinolin-2-ylmethoxy)-1H-benzimidazol-2-yl}-2,2-dimethylpropanoic acid,
3-{1-[(4'-Fluorobiphenyl-4-yl)methyl]-5-(quinolin-2-ylmethoxy)-1H-benzimidazol-2-yl}-2,2-dimethylpropanoic acid,
2,2-Dimethyl-3-[5-(quinolin-2-ylmethoxy)-1-{3-[6-(trifluoromethyl)pyridin-3-yl]benzyl}-1H-benzimidazol-2-yl]propanoic acid,
2'-{[2-(2-Carboxy-2-methylpropyl)-5-(quinolin-2-ylmethoxy)-1H-benzimidazol-1-yl]methyl}biphenyl-3-carboxylic acid,
3-{1-[(3'-Cyanobiphenyl-4-yl)methyl]-5-(quinolin-2-ylmethoxy)-1H-benzimidazol-2-yl}-2,2-dimethylpropanoic acid,
3-{1-[(4'-Cyanobiphenyl-4-yl)methyl]-5-(quinolin-2-ylmethoxy)-1H-benzimidazol-2-yl}-2,2-dimethylpropanoic acid,
2,2-Dimethyl-3-[1-{[4'-(methylsulfonyl)biphenyl-4-yl]methyl}-5-(quinolin-2-ylmethoxy)-1H-benzimidazol-2-yl]propanoic acid,
2,2-Dimethyl-3-[1-(4-pyridin-3-ylbenzyl)-5-(quinolin-2-ylmethoxy)-1H-benzimidazol-2-yl]propanoic acid,
2,2-Dimethyl-3-[1-(4-pyridin-2-ylbenzyl)-5-(quinolin-2-ylmethoxy)-1H-benzimidazol-2-yl]propanoic acid,
2,2-Dimethyl-3-{5-(quinolin-2-ylmethoxy)-1-[(4'-sulfamoylbiphenyl-3-yl)methyl]-1H-benzimidazol-2-yl}propanoic acid,
2,2-Dimethyl-3-{1-[3-(1H-pyrrol-2-yl)benzyl]-5-(quinolin-2-ylmethoxy)-1H-benzimidazol-2-yl}propanoic acid,
2,2-Dimethyl-3-{5-(quinolin-2-ylmethoxy)-1-[3-(1,3-thiazol-5-yl)benzyl]-1H-benzimidazol-2-yl}propanoic acid,
2,2-Dimethyl-3-[1-({4'-[(methylsulfonyl)amino]biphenyl-3-yl}methyl)-5-(quinolin-2-ylmethoxy)-1H-benzimidazol-2-yl]propanoic acid,
2,2-Dimethyl-3-[1-{[4'-(methylsulfonyl)biphenyl-3-yl]methyl}-5-(quinolin-2-ylmethoxy)-1H-benzimidazol-2-yl]propanoic acid,
3-{1-[(4'-Methoxybiphenyl-4-yl)methyl]-5-(quinolin-2-ylmethoxy)-1H-benzimidazol-2-yl}-2,2-dimethylpropanoic acid,
2,2-Dimethyl-3-[1-({3'-[(methylsulfonyl)amino]biphenyl-4-yl}methyl)-5-(quinolin-2-ylmethoxy)-1H-benzimidazol-2-yl]propanoic acid,
2,2-Dimethyl-3-{5-(quinolin-2-ylmethoxy)-1-[(3'-sulfamoylbiphenyl-4-yl)methyl]-1H-benzimidazol-2-yl}propanoic acid,
3-{1-[(3'-Carbamoylbiphenyl-4-yl)methyl]-5-(quinolin-2-ylmethoxy)-1H-benzimidazol-2-yl}-2,2-dimethylpropanoic acid,
3-[1-{[3'-(Acetylamino)biphenyl-4-yl]methyl}-5-(quinolin-2-ylmethoxy)-1H-benzimidazol-2-yl]-2,2-dimethylpropanoic acid,
2,2-Dimethyl-3-[1-({2'-[(methylsulfonyl)amino]biphenyl-4-yl}methyl)-5-(quinolin-2-ylmethoxy)-1H-benzimidazol-2-yl]propanoic acid,
3-{1-[(2'-Carbamoylbiphenyl-4-yl)methyl]-5-(quinolin-2-ylmethoxy)-1H-benzimidazol-2-yl}-2,2-dimethylpropanoic acid,
2,2-Dimethyl-3-{5-(quinolin-2-ylmethoxy)-1-[4-(1,3-thiazol-2-yl)benzyl]-1H-benzimidazol-2-yl}propanoic acid,
2,2-Dimethyl-3-{1-[4-(1-methyl-1H-pyrazol-4-yl)benzyl]-5-(quinolin-2-ylmethoxy)-1H-benzimidazol-2-yl}propanoic acid,
2,2-Dimethyl-3-{1-[3-(1-methyl-1H-pyrazol-5-yl)benzyl]-5-(quinolin-2-ylmethoxy)-1H-benzimidazol-2-yl}propanoic acid,
2,2-Dimethyl-3-{1-[(2'-methylbiphenyl-4-yl)methyl]-5-(quinolin-2-ylmethoxy)-1H-benzimidazol-2-yl}propanoic acid,
2,2-Dimethyl-3-[5-(quinolin-2-ylmethoxy)-1-{2-[6-(trifluoromethyl)pyridin-3-yl]benzyl}-1H-benzimidazol-2-yl]propanoic acid,
3-{1-[(2'-Cyanobiphenyl-4-yl)methyl]-5-(quinolin-2-ylmethoxy)-1H-benzimidazol-2-yl}-2,2-dimethylpropanoic acid,
2,2-Dimethyl-3-[1-{[3'-(methylsulfonyl)biphenyl-4-yl]methyl}-5-(quinolin-2-ylmethoxy)-1H-benzimidazol-2-yl]propanoic acid,
2,2-Dimethyl-3-{1-[4-(1-methyl-1H-pyrazol-3-yl)benzyl]-5-(quinolin-2-ylmethoxy)-1H-benzimidazol-2-yl}propanoic acid,
3-[1-(4-Isoxazol-4-ylbenzyl)-5-(quinolin-2-ylmethoxy)-1H-benzimidazol-2-yl]-2,2-dimethylpropanoic acid,
2,2-Dimethyl-3-{5-(quinolin-2-ylmethoxy)-1-[4-(1,3-thiazol-5-yl)benzyl]-1H-benzimidazol-2-yl}propanoic acid,
2,2-Dimethyl-3-{5-(quinolin-2-ylmethoxy)-1-[4-(1,3-thiazol-4-yl)benzyl]-1H-benzimidazol-2-yl}propanoic acid,
racemic cis-2-[1-(4-Pyrimidin-2-ylbenzyl)-5-(quinolin-2-ylmethoxy)-1H-benzimidazol-2-yl]cyclohexanecarboxylic acid as the TFA salt,
racemic cis-2-[1-(3-Pyrimidin-2-ylbenzyl)-5-(quinolin-2-ylmethoxy)-1H-benzimidazol-2-yl]cyclohexanecarboxylic acid as the TFA salt,
racemic cis-2-[1-(4-Piperidin-1-ylbenzyl)-5-(quinolin-2-ylmethoxy)-1H-benzimidazol-2-yl]cyclohexanecarboxylic acid as the TFA salt,
racemic cis-2-{1-[4-(4,4-Difluoropiperidin-1-yl)-2-fluorobenzyl]-5-(quinolin-2-ylmethoxy)-1H-benzimidazol-2-yl}cyclohexanecarboxylic acid as the TFA salt,
racemic cis-2-{1-[4-(3,3-Difluoropiperidin-1-yl)-2-fluorobenzyl]-5-(quinolin-2-ylmethoxy)-1H-benzimidazol-2-yl}cyclohexanecarboxylic acid as the TFA salt,
racemic cis-2-{1-[4-(3,3-Difluoropyrrolidin-1-yl)-2-fluorobenzyl]-5-(quinolin-2-ylmethoxy)-1H-benzimidazol-2-yl}cyclohexanecarboxylic acid as the TFA salt,
racemic cis-2-{1-[4-(3,3-Difluoroazetidin-1-yl)-2-fluorobenzyl]-5-(quinolin-2-ylmethoxy)-1H-benzimidazol-2-yl}cyclohexanecarboxylic acid as the TFA salt,

TABLE 1-continued racemic cis-2-[1-{2-Fluoro-4-[4-(trifluoromethyl)piperidin-1-yl]benzyl}-5-(quinolin-2-ylmethoxy)-1H-benzimidazol-2-yl]cyclohexanecarboxylic acid as the TFA salt,
racemic cis-2-(5-((6-fluoroquinolin-2-yl)methoxy)-1-(4-(4-(trifluoromethyl)piperidin-1-yl)benzyl)-1H-benzo[d]imidazol-2-yl)cyclohexanecarboxylic acid,
1-{[1-(4-Morpholin-4-ylbenzyl)-5-(quinolin-2-ylmethoxy)-1H-benzimidazol-2-yl]methyl}cyclopentanecarboxylic acid,
1-{[1-(4-Piperidin-1-ylbenzyl)-5-(quinolin-2-ylmethoxy)-1H-benzimidazol-2-yl]methyl}cyclopentanecarboxylic acid - Trifluoroacetic acid salt,
1-{[1-(3-Pyrrolidin-1-ylbenzyl)-5-(quinolin-2-ylmethoxy)-1H-benzimidazol-2-yl]methyl}cyclopentanecarboxylic acid,
3-[1-(4-Azetidin-1-ylbenzyl)-5-(quinolin-2-ylmethoxy)-1H-benzimidazol-2-yl]-2,2-dimethylpropanoic acid,
3-{1-[4-(3,3-Difluoropiperidin-1-yl)benzyl]-5-(quinolin-2-ylmethoxy)-1H-benzimidazol-2-yl}-2,2-dimethylpropanoic acid,
2,2-Dimethyl-3-[1-(4-morpholin-4-ylbenzyl)-5-(quinolin-2-ylmethoxy)-1H-benzimidazol-2-yl]propanoic acid,
2,2-Dimethyl-3-[1-(4-piperidin-1-ylbenzyl)-5-(quinolin-2-ylmethoxy)-1H-benzimidazol-2-yl]propanoic acid,
2,2-Dimethyl-3-[1-(4-pyrrolidin-1-ylbenzyl)-5-(quinolin-2-ylmethoxy)-1H-benzimidazol-2-yl]propanoic acid,
2,2-Dimethyl-3-{1-[4-(1H-pyrazol-1-yl)benzyl]-5-(quinolin-2-ylmethoxy)-1H-benzimidazol-2-yl}propanoica cid,
2,2-Dimethyl-3-{5-(quinolin-2-ylmethoxy)-1-[4-(1H-1,2,3-triazol-1-yl)benzyl]-1H-benzimidazol-2-yl}propanoic acid,
2,2-Dimethyl-3-{5-(quinolin-2-ylmethoxy)-1-[4-(2H-1,2,3-triazol-2-yl)benzyl]-1H-benzimidazol-2-yl}propanoic acid,
racemic cis-2-(5-(Benzo[d]thiazol-2-ylmethoxy)-1-(4-bromobenzyl)-1H-benzo[d]imidazol-2-yl)cyclohexanecarboxylic acid,
(1R*,2S*)-2-(5-(benzo[d]thiazol-2-ylmethoxy)-1-(4-bromobenzyl)-1H-benzo[d]imidazol-2-yl)cyclohexanecarboxylic acid,
(1S*,2R*)-2-(5-(benzo[d]thiazol-2-ylmethoxy)-1-(4-bromobenzyl)-1H-benzo[d]imidazol-2-yl)cyclohexanecarboxylic acid,
racemic cis-3-(5-(Benzo[d]thiazol-2-ylmethoxy)-1-(4-bromobenzyl)-1H-benzo[d]imidazol-2-yl)-2,2-dimethylcyclopropanecarboxylic acid,
racemic trans-2-(5-(benzo[d]thiazol-2-ylmethoxy)-1-(4-bromobenzyl)-1H-benzo[d]imidazol-2-yl)cyclohexanecarboxylic acid,
2-((5-(Benzo[d]thiazol-2-ylmethoxy)-1-(4-bromobenzyl)-1H-benzo[d]imidazol-2-yl)methyl)-2-ethylbutanoic acid,
racemic 2-(5-(benzo[d]thiazol-2-ylmethoxy)-1-(4-(2-methoxypyrimidin-5-yl)benzyl)-1H-benzo[d]imidazol-2-yl)cyclohexanecarboxylic acid,
racemic cis-2-(5-(benzo[d]thiazol-2-ylmethoxy)-1-(4-(pyrimidin-5-yl)benzyl)-1H-benzo[d]imidazol-2-yl)cyclohexanecarboxylic acid,
racemic cis-2-(5-(Benzo[d]thiazol-2-ylmethoxy)-1-(4-(6-(trifluoromethyl)pyridin-3-yl)benzyl)-1H-benzo[d]imidazol-2-yl)cyclohexanecarboxylic acid,
racemic cis-2-(5-(Benzo[d]thiazol-2-ylmethoxy)-1-(4-(6-methoxypyridin-3-yl)benzyl)-1H-benzo[d]imidazol-2-yl)cyclohexanecarboxylic acid,
racemic cis-2-(5-(Benzo[d]thiazol-2-ylmethoxy)-1-(4-(pyrimidin-2-yl)benzyl)-1H-benzo[d]imidazol-2-yl)cyclohexanecarboxylic acid,
2-((5-(Benzo[d]thiazol-2-ylmethoxy)-1-(4-(pyrimidin-2-yl)benzyl)-1H-benzo[d]imidazol-2-yl)methyl)-2-ethylbutanoic acid, and
racemic cis-2-(5-(Benzo[d]thiazol-2-ylmethoxy)-1-(4-(piperidin-1-yl)benzyl)-1H-benzo[d]imidazol-2-yl)cyclohexanecarboxylic acid,
and solvates, hydrates, and pharmaceutically acceptable salts thereof.

Another embodiment of the invention is a compound selected from the group consisting of:
racemic cis-2-[1-(4-Bromobenzyl)-5-(quinolin-2-ylmethoxy)-1H-benzimidazol-2-yl]cyclohexanecarboxylic acid,
(1R*,2S*)-2-[1-(4-Bromobenzyl)-5-(quinolin-2-ylmethoxy)-1H-benzimidazol-2-yl]cyclohexanecarboxylic acid,
(1S*,2R*)-2-[1-(4-Bromobenzyl)-5-(quinolin-2-ylmethoxy)-1H-benzimidazol-2-yl]cyclohexanecarboxylic acid,
racemic cis-2-[1-(3-Bromobenzyl)-5-(quinolin-2-ylmethoxy)-1H-benzimidazol-2-yl]cyclohexanecarboxylic acid as the TFA salt,
racemic cis-3-[1-(2,4-Difluorobenzyl)-5-(quinolin-2-ylmethoxy)-1H-benzimidazol-2-yl]-2,2-dimethylcyclopropanecarboxylic acid,
racemic cis-3-[1-(2,4-Dichlorobenzyl)-5-(quinolin-2-ylmethoxy)-1H-benzimidazol-2-yl]-2,2-dimethylcyclopropanecarboxylic acid,
racemic cis-3-[1-(4-Bromo-2-fluorobenzyl)-5-(quinolin-2-ylmethoxy)-1H-benzimidazol-2-yl]-2,2-dimethylcyclopropane carboxylic acid,
racemic cis-2-[1-(4-Bromo-2-fluorobenzyl)-5-(quinolin-2-ylmethoxy)-1H-benzimidazol-2-yl]cyclohexanecarboxylic acid,
racemic cis-2-(1-(4-(5-Methyl-1,2,4-oxadiazol-3-yl)benzyl)-5-(quinolin-2-ylmethoxy)-1H-benzo[d]imidazol-2-yl)cyclohexanecarboxylic acid as the TFA salt,
racemic cis-3-{1-[(1-Ethyl-1H-indazol-3-yl)methyl]-5-(quinolin-2-ylmethoxy)-1H-benzimidazol-2-yl}-2,2-dimethylcyclopropanecarboxylic acid,
racemic cis-3-[1-(4-Bromobenzyl)-5-(quinolin-2-ylmethoxy)-1H-benzimidazol-2-yl]-2,2-dimethylcyclopropanecarboxylic acid as the TFA salt,
racemic cis-2-[1-(4-Cyanobenzyl)-5-(quinolin-2-ylmethoxy)-1H-benzimidazol-2-yl]cyclohexanecarboxylic acid as a hydrochloride salt,
racemic cis-2-[1-Benzyl-5-(quinolin-2-ylmethoxy)-1H-benzimidazol-2-yl]cyclohexanecarboxylic acid as the hydrochloride salt, racemic cis-2-{5-(Quinolin-2-ylmethoxy)-1-[2-(trifluoromethoxy)benzyl]-1H-benzimidazol-2-yl}cyclohexanecarboxylic acid as the hydrochloride salt,
racemic cis-2-[1-(2-Methylbenzyl)-5-(quinolin-2-ylmethoxy)-1H-benzimidazol-2-yl]cyclohexanecarboxylic acid as the hydrochloride salt,
racemic cis-2-{5-(Quinolin-2-ylmethoxy)-1-[2-(trifluoromethyl)benzyl]-1H-benzimidazol-2-yl}cyclohexanecarboxylic acid as the hydrochloride salt,
racemic cis-2-{1-[3-Fluoro-4-(trifluoromethoxy)benzyl]-5-(quinolin-2-ylmethoxy)-1H-benzimidazol-2-yl}cyclohexanecarboxylic acid as the hydrochloride salt,
racemic cis-2-{1-[2-Fluoro-4-(trifluoromethoxy)benzyl]-5-(quinolin-2-ylmethoxy)-1H-benzimidazol-2-yl}cyclohexanecarboxylic acid as the hydrochloride salt,
(1R*,2S*)-2-{1-[2-Fluoro-4-(trifluoromethoxy)benzyl]-5-(quinolin-2-ylmethoxy)-1H-benzimidazol-2-yl}cyclohexanecarboxylic acid,
(1S*,2R*)-2-{1-[2-Fluoro-4-(trifluoromethoxy)benzyl]-5-(quinolin-2-ylmethoxy)-1H-benzimidazol-2-yl}cyclohexanecarboxylic acid,
racemic cis-2-[1-(4-Methylbenzyl)-5-(quinolin-2-ylmethoxy)-1H-benzimidazol-2-yl]cyclohexanecarboxylic acid as the hydrochloride salt,
racemic cis-2-{5-(Quinolin-2-ylmethoxy)-1-[4-(trifluoromethoxy)benzyl]-1H-benzimidazol-2-yl}cyclohexanecarboxylic acid as the hydrochloride salt,
racemic cis-2-{5-(Quinolin-2-ylmethoxy)-1-[4-(trifluoromethyl)benzyl]-1H-benzimidazol-2-yl}cyclohexanecarboxylic acid as the hydrochloride salt,
racemic cis-2-[1-(3-Cyanobenzyl)-5-(quinolin-2-ylmethoxy)-1H-benzimidazol-2-yl]cyclohexanecarboxylic acid as the hydrochloride salt,
racemic cis-2-(5-(quinolin-2-ylmethoxy)-1-(3-(trifluoromethoxy)benzyl)-1H-benzo[d]imidazol-2-yl)cyclohexanecarboxylic acid as the hydrochloride salt,
racemic cis-2-[1-(3-Methylbenzyl)-5-(quinolin-2-ylmethoxy)-1H-benzimidazol-2-yl]cyclohexanecarboxylic acid as the hydrochloride salt,
racemic cis-2-(5-(quinolin-2-ylmethoxy)-1-(3-(trifluoromethyl)benzyl)-1H-benzo[d]imidazol-2-yl)cyclohexanecarboxylic acid as the hydrochloride salt,
racemic cis-2-[1-(2-Cyanobenzyl)-5-(quinolin-2-ylmethoxy)-1H-benzimidazol-2-yl]cyclohexanecarboxylic acid as the hydrochloride salt,
racemic cis-2-{1-(4-Bromobenzyl)-5-[(6-fluoroquinolin-2-yl)methoxy]-1H-benzimidazol-2-yl}cyclohexanecarboxylic acid as the formic acid salt,
racemic cis-2-{1-(4-Bromobenzyl)-5-[(8-fluoroquinolin-2-yl)methoxy]-1H-benzimidazol-2-yl}cyclohexanecarboxylic acid as the formic acid salt,
racemic cis-2-{1-(4-Bromobenzyl)-5-[(7-chloroquinolin-2-yl)methoxy]-1H-benzimidazol-2-yl}cyclohexanecarboxylic acid as the formic acid salt,
racemic cis-2-{1-(4-Bromobenzyl)-5-[(6-chloroquinolin-2-yl)methoxy]-1H-benzimidazol-2-yl}cyclohexanecarboxylic acid,
racemic 3-[1-(4-Cyanobenzyl)-5-(quinolin-2-ylmethoxy)-1H-benzimidazol-2-yl]-2,2-dimethylcyclopropanecarboxylic acid,
racemic cis-3-{1-[2-Fluoro-4-(6-methoxypyridin-3-yl)benzyl]-5-(quinolin-2-ylmethoxy)-1H-benzimidazol-2-yl}-2,2-dimethylcyclopropanecarboxylic acid,
racemic cis-3-{1-[(3,4'-Difluorobiphenyl-4-yl)methyl]-5-(quinolin-2-ylmethoxy)-1H-benzimidazol-2-yl}-2,2-dimethylcyclopropanecarboxylic acid,
racemic cis-2,2-Dimethyl-3-{5-(quinolin-2-ylmethoxy)-1-[(3,3',4'-trifluorobiphenyl-4-yl)methyl]-1H-benzimidazol-2-yl}cyclopropanecarboxylic acid,
racemic cis-2,2-Dimethyl-3-{5-(quinolin-2-ylmethoxy)-1-[3-(1,3-thiazol-4-yl)benzyl]-1H-benzimidazol-2-yl}cyclopropanecarboxylic acid,
racemic cis-2,2-Dimethyl-3-{5-(quinolin-2-ylmethoxy)-1-[4-(1,3-thiazol-4-yl)benzyl]-1H-benzimidazol-2-yl}cyclopropanecarboxylic acid,
racemic cis-2-(5-((6-fluoroquinolin-2-yl)methoxy)-1-((4'-(trifluoromethyl)-[1,1'-biphenyl]-4-yl)methyl)-1H-benzo[d]imidazol-2-yl)cyclohexanecarboxylic acid,
racemic cis-3-{1-[4-(2-Methoxypyrimidin-5-yl)benzyl]-5-(quinolin-2-ylmethoxy)-1H-benzimidazol-2-yl}-2,2-dimethylcyclopropanecarboxylic acid,
racemic cis-3-{1-[3-(2-Methoxypyrimidin-5-yl)benzyl]-5-(quinolin-2-ylmethoxy)-1H-benzimidazol-2-yl}-2,2-dimethylcyclopropanecarboxylic acid,
racemic cis-3-{1-[(3',4'-Difluorobiphenyl-4-yl)methyl]-5-(quinolin-2-ylmethoxy)-1H-benzimidazol-2-yl}-2,2-dimethylcyclopropanecarboxylic acid,
racemic cis-3-{1-[(3',4'-Difluorobiphenyl-3-yl)methyl]-5-(quinolin-2-ylmethoxy)-1H-benzimidazol-2-yl}-2,2-dimethylcyclopropanecarboxylic acid,
racemic cis-3-{1-[(4'-Fluorobiphenyl-4-yl)methyl]-5-(quinolin-2-ylmethoxy)-1H-benzimidazol-2-yl}-2,2-dimethylcyclopropanecarboxylic acid,
racemic cis-3-{1-[(4'-Fluorobiphenyl-3-yl)methyl]-5-(quinolin-2-ylmethoxy)-1H-benzimidazol-2-yl}-2,2-dimethylcyclopropanecarboxylic acid,
racemic cis-2-{1-[4-(2-Methoxypyrimidin-5-yl)benzyl]-5-(quinolin-2-ylmethoxy)-1H-benzimidazol-2-yl}cyclohexanecarboxylic acid as the TFA salt,
racemic cis-2-[1-(4-Pyrimidin-5-ylbenzyl)-5-(quinolin-2-ylmethoxy)-1H-benzimidazol-2-yl]cyclohexanecarboxylic acid as the TFA salt,
racemic cis-2-{5-(Quinolin-2-ylmethoxy)-1-{4-[6-(trifluoromethyl)pyridin-3-yl]benzyl}-1H-benzimidazol-2-yl]cyclohexanecarboxylic acid as the TFA salt,
racemic cis-2-[1-({4'-[(Methylsulfonyl)amino]biphenyl-4-yl}methyl)-5-(quinolin-2-ylmethoxy)-1H-benzimidazol-2-yl]cyclohexanecarboxylic acid as the TFA salt,
racemic cis-2-{5-(Quinolin-2-ylmethoxy)-1-{3-[6-(trifluoromethyl)pyridin-3-yl]benzyl}-1H-benzimidazol-2-yl]cyclohexanecarboxylic acid as the TFA salt,
racemic cis-2-[1-({4'-[(Methylsulfonyl)amino]biphenyl-3-yl}methyl)-5-(quinolin-2-ylmethoxy)-1H-benzimidazol-2-yl]cyclohexanecarboxylic acid as the TFA salt,
racemic cis-2-[5-(Quinolin-2-ylmethoxy)-1-{[4'-(trifluoromethyl)biphenyl-4-yl]methyl}-1H-benzimidazol-2-yl]cyclohexanecarboxylic acid as the TFA salt,
racemic cis-2-[1-{[3-Fluoro-4'-(trifluoromethyl)biphenyl-4-yl]methyl}-5-(quinolin-2-ylmethoxy)-1H-benzimidazol-2-yl]cyclohexanecarboxylic acid as the TFA salt,
racemic cis-2-[5-(Quinolin-2-ylmethoxy)-1-{[4'-(trifluoromethyl)biphenyl-3-yl]methyl}-1H-benzimidazol-2-yl]cyclohexanecarboxylic acid as the TFA salt,
racemic cis-2-[1-(4-Pyrimidin-2-ylbenzyl)-5-(quinolin-2-ylmethoxy)-1H-benzimidazol-2-yl]cyclohexanecarboxylic acid as the TFA salt,
racemic cis-2-[1-(3-Pyrimidin-2-ylbenzyl)-5-(quinolin-2-ylmethoxy)-1H-benzimidazol-2-yl]cyclohexanecarboxylic acid as the TFA salt,
racemic cis-2-[1-(4-Piperidin-1-ylbenzyl)-5-(quinolin-2-ylmethoxy)-1H-benzimidazol-2-yl]cyclohexanecarboxylic acid as the TFA salt, racemic cis-2-{1-[4-(4,4-Difluoropiperidin-1-yl)-2-fluorobenzyl]-5-(quinolin-2-ylmethoxy)-1H-benzimidazol-2-yl}cyclohexanecarboxylic acid as the TFA salt, racemic cis-2-{1-[4-(3,3-Difluoropiperidin-1-yl)-2-fluorobenzyl]-5-(quinolin-2-ylmethoxy)-1H-benzimidazol-2-yl}cyclohexanecarboxylic acid as the TFA salt, racemic cis-2-{1-[4-(3,3-Difluoropyrrolidin-1-yl)-2-fluorobenzyl]-5-(quinolin-2-ylmethoxy)-1H-benzimidazol-2-yl}cyclohexanecarboxylic acid as the TFA salt, racemic cis-2-{1-[4-(3,3-Difluoroazetidin-1-yl)-2-fluorobenzyl]-5-(quinolin-2-ylmethoxy)-1H-benzimidazol-2-yl}cyclohexanecarboxylic acid as the TFA salt, racemic cis-2-[1-{2-Fluoro-4-[4-(trifluoromethyl)piperidin-1-yl]benzyl}-5-(quinolin-2-ylmethoxy)-1H-benzimidazol-2-yl]cyclohexanecarboxylic acid as the TFA salt, racemic cis-2-(5-((6-fluoroquinolin-2-yl)methoxy)-1-(4-(4-(trifluoromethyl)piperidin-1-yl)benzyl)-1H-benzo[d]imidazol-2-yl)cyclohexanecarboxylic acid, racemic cis-2-(5-(Benzo[d]thiazol-2-ylmethoxy)-1-(4-bromobenzyl)-1H-benzo[d]imidazol-2-yl)cyclohexanecarboxylic acid, (1R*,2S*)-2-(5-(benzo[d]thiazol-2-ylmethoxy)-1-(4-bromobenzyl)-1H-benzo[d]imidazol-2-yl)cyclohexanecarboxylic acid, (1S*,2R*)-2-(5-(benzo[d]thiazol-2-ylmethoxy)-1-(4-bromobenzyl)-1H-benzo[d]imidazol-2-yl)cyclohexanecarboxylic acid, racemic cis-3-(5-(Benzo[d]thiazol-2-ylmethoxy)-1-(4-bromobenzyl)-1H-benzo[d]imidazol-2-yl)-2,2-dimethylcyclopropanecarboxylic acid, racemic 2-(5-(benzo[d]thiazol-2-ylmethoxy)-1-(4-(2-methoxypyrimidin-5-yl)benzyl)-1H-benzo[d]imidazol-2-yl)cyclohexanecarboxylic acid, racemic cis-2-(5-(benzo[d]thiazol-2-ylmethoxy)-1-(4-(pyrimidin-5-yl)benzyl)-1H-benzo[d]imidazol-2-yl)cyclohexanecarboxylic acid, racemic cis-2-(5-(Benzo[d]thiazol-2-ylmethoxy)-1-(4-(6-(trifluoromethyl)pyridin-3-yl)benzyl)-1H-benzo[d]imidazol-2-yl)cyclohexanecarboxylic acid, racemic cis-2-(5-(Benzo[d]thiazol-2-ylmethoxy)-1-(4-(6-methoxypyridin-3-yl)benzyl)-1H-benzo[d]imidazol-2-yl)cyclohexanecarboxylic acid, racemic cis-2-(5-(Benzo[d]thiazol-2-ylmethoxy)-1-(4-(pyrimidin-2-yl)benzyl)-1H-benzo[d]imidazol-2-yl)cyclohexanecarboxylic acid, and racemic cis-2-(5-(Benzo[d]thiazol-2-ylmethoxy)-1-(4-(piperidin-1-yl)benzyl)-1H-benzo[d]imidazol-2-yl)cyclohexanecarboxylic acid, and solvates, hydrates, and pharmaceutically acceptable salts thereof.

The invention is also directed to a pharmaceutical composition which include, without limitation, one or more of the disclosed compounds, and pharmaceutically acceptable carriers or excipients.

Another embodiment of the present invention is a pharmaceutical composition of the present invention that comprises at least a compound selected from the compounds listed in Table 1.

The present invention also features a method of treating a subject suffering from or diagnosed with a disease and/or disorder mediated by FLAP activity, comprising administering to the subject a therapeutically effective amount of at least one compound of Formula (I).

The present invention also features a method for preventing, treating, ameliorating, including without limitation inhibiting, the progression of an FLAP-mediated disease and/or disorder in a subject in need thereof, comprising administering to said subject a therapeutically effective amount of at least one compound of Formula (I). Such a disease and/or disorder includes, but is not limited to diabetes, respiratory disorders, and associated symptoms or complications thereof. More specifically, this invention is directed to a method of treating, but not limited to, exacerbations, non-allergic asthma, fibrotic lung diseases, acute respiratory distress syndrome and chronic obstructive pulmonary disease, and their associated symptoms or complications, in a subject afflicted with such a disease and/or disorder.

In another embodiment, the compounds of the present invention are useful for the amelioration of symptoms associated with and/or the treatment of the following cardiac and cardiovascular diseases and/or disorders: myocardial infarction, atherosclerosis, atherosclerosis and stroke aortic aneurisms, or associated symptoms or complications thereof, in a subject afflicted with such a disease and/or disorder.

In another embodiment, the compounds of the present invention are useful for the amelioration of symptoms associated with and/or the treatment of autoimmune or allergic diseases and/or disorders, wherein said autoimmune or allergic diseases and/or disorders include, but are not limited to, rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, or associated symptoms or complications thereof, in a subject afflicted with such a disease and/or disorder. In a further embodiment, the compounds of the present invention are useful for the amelioration of symptoms associated with and/or the prophylaxis or treatment of carcinogenesis, wherein said carcinogenesis include, but is not limited to, tumor cell proliferation, differentiation, apoptosis, tumor-associated angiogenesis, as well as the migration and invasion of carcinoma cells.

It is a further embodiment of the invention to provide a process for making a pharmaceutical composition comprising admixing any of the compounds according to Formula (I) and a pharmaceutically acceptable carrier.

In a further embodiment of the invention, a method for treating or ameliorating an FLAP-mediated disease and/or disorder in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose.

More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) TERMS

Some terms are defined below and by their usage throughout this disclosure.

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-n}$alkyl" means a saturated branched or straight-chain hydrocarbon radical having from 1 up to n carbon atoms, wherein n is 4 or 5, in a linear or branched arrangement. Examples include methyl, ethyl, 1-propyl, 2-propyl, isobutyl, tert-butyl, isopentyl, neopentyl, pentan-3-yl, and the like, and all that are exemplified in the below examples. An alkyl radical may be attached to a core molecule by any atom where allowed by available valences.

The term "aryl" means an unsaturated, aromatic monocyclic or polycyclic hydrocarbon ring system radical. Examples include phenyl and the like, and all that are exemplified in the below examples. An aryl radical may be attached to a core molecule by any ring atom where allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heteroaryl" means an unsaturated monocyclic, polycyclic aromatic "hetero" ring system radical, selected from the group consisting of pyrazolyl, oxadiazolyl, furanyl, imidazolyl, imidazolidinyl, triazolyl, pyridinyl, pyrimidinyl, pyridazinyl, pyrazinyl, benzimidazolyl, benzoxazolyl, quinoxalinyl, quinazolinyl, benzothiazolyl, isoxazolyl, thiazolyl, oxazolyl, and isoindolyl. Examples include 1H-pyrazol-1-yl, 1H-pyrazol-3-yl, 1H-pyrazol-5-yl, 1,2,4-oxadiazol-5-yl, 1,2,4-oxadiazol-3-yl, furan-2-yl, 1H-imidazol-1-yl, 1H-imidazol-2-yl, 1H-imidazol-4-yl, 1H-imidazol-5-yl, imidazolidin-1-yl, 1H-1,2,4-triazol-1-yl, 1H-1,2,4-triazol-2-yl, 1H-1,2,4-triazol-3-yl, 1H-1,2,4-triazol-4-yl, 1H-1,2,3-triazol-1-yl, 2H-1,2,3-triazol-2-yl, pyridin-3-yl, pyrimidin-1-yl, pyrimidin-2-yl, pyrimidin-4-yl, pyrimidin-5-yl, pyridazin-2-yl, pyridazin-3-yl, pyridazin-4-yl, pyrazin-1-yl, pyrazin-2-yl, pyrazin-3-yl, benzimidazol-1-yl, benzoxazol-2-yl, quinoxalin-2-yl, quinazolin-2-yl, benzothiazol-2-yl, isoxazol-3-yl, 1,3-thiazol-4-yl, 1,3-oxazol-2-yl, isoindol-1-yl, and the like, and all that are exemplified in the below examples. A heteroaryl radical may be attached to a core molecule by any ring atom where allowed by available valences.

The term "carboxy" means a radical of the formula: —C(O)OH.

The term "halogen" or "halo" means a radical selected from the group consisting of chloro, bromo, fluoro or iodo.

The term "oxo" means a radical of the formula: =O.

The term "substituted" refers to a radical in which one or more hydrogen atoms are each independently replaced with the same or different substituent(s). In a preferred embodiment, up to three hydrogen atoms are each independently replaced.

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

In general, IUPAC nomenclature rules are used herein.

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "composition" is intended to encompass a product comprising the specified ingredients in the specified amounts, as well as any product which results, directly or indirectly, from combinations of the specified ingredients in the specified amounts.

The term "subject" as used herein, refers to a patient, such as an animal, a mammal or a human, who has been the object of treatment, observation or experiment and is at risk of (or susceptible to) developing an FLAP-mediated disorder.

The term "administering" further means that the individual ingredients to be combined may be administered at the same time or at different times during the treatment period, either as one preparation or as different preparations. Accordingly, the invention should be so interpreted that it encompasses any and every administration mode at the same time or at different times. The range of the combination of the compound of the invention and the other therapeutic agent useful for the above-mentioned disorders encompasses, in principle, all combinations of the compound of the invention and any and every pharmaceutical agent useful for the above-mentioned disorders.

The term "treating" refers, without limitation, to facilitating the eradication of, preventing, ameliorating or otherwise inhibiting the progression of or promoting stasis of an FLAP-mediated disease and/or disorder, or associated symptoms or complications thereof.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions. Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a prodrug form of a compound of Formula (I) or a form thereof converted by in vivo metabolism or a metabolic process to a relatively less active functional derivative of said compound.

The term "medicament" or "medicine" refers to a product containing a compound of Formula (I) or a form thereof. The present invention includes use of such a medicament for treating an FLAP-mediated disorder.

The term "combination form" refers to the use of a combination product comprising a compound of Formula (I) or a form, pharmaceutical composition, medicine or medicament thereof and at least one therapeutic agent for treating an FLAP-mediated disorder.

Methods are known in the art for determining effective doses for therapeutic and prophylactic purposes for the disclosed pharmaceutical compositions or the disclosed drug combinations, whether or not formulated in the same composition.

For therapeutic purposes, the term "therapeutically effective amount" or "effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease and/or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together. The effective amount of said compound is from about 0.001 mg/kg/day to about 300 mg/kg/day.

Advantageously, the effective amount of a combination product for treating an FLAP-mediated disease and/or disorder, or associated symptoms or complications thereof, may be a reduced amount of either or both, the compound or therapeutic agent, compared to the effective amount of the compound or therapeutic agent otherwise recommended for treating the disease and/or disorder, or associated symptoms or complications thereof. Therefore, it is contemplated that the compound is administered to the subject before, during or after the time the agent is administered.

The term "pharmaceutically acceptable salt" refers to non-toxic pharmaceutically acceptable salts (*Ref. Int'l J. Pharm.*, 1986, 33: 201-217; *J. Pharm. Sci.*, 1997 (January), 66(1): 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic" means an equimolar mixture of two enantiomeric species, wherein each of the isolated species rotates the plane of polarized light in the opposite direction such that the mixture is devoid of optical activity.

The term "enantiomer" means an isomer having a non-superimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The symbols "R" and "S" are used in compound names and/or compound structures to describe a pure enantiomer, where the absolute stereochemistry of groups around a stereogenic carbon atom(s) is known.

The symbols "R*" and "S*" are used in compound names and/or compound structures to describe a pure enantiomer, where the relative stereochemistry of groups around a stereogenic carbon atom(s) is known, but where the absolute stereochemistry is unknown.

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to the Cahn-Ingold-Prelog priority rules. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

Substituent atoms (other than hydrogen) attached to a ring system may be in a "cis" or "trans" configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

B) SYNTHESIS

The invention provides methods of making the disclosed compounds according to traditional organic synthetic methods as well as matrix or combinatorial synthetic methods. Schemes A-D described suggested synthetic routes. Using the schemes, the guidelines below, and the examples, a person of skill in the a may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Representative compounds of the present invention can be synthesized in accordance with the general synthetic schemes described below and are illustrated more particularly in the specific synthetic examples that follow. The general schemes are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, New Jersey) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ESI) were recorded in the positive mode on a Hewlett Packard 59987A spectrometer. High resolution mass spectra (HRMS) were obtained on a Micromass Autospec. E spectrometer by fast atom bombardment (FAB) technique.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Schemes A-D, Intermediates A-T, and Examples 1-220. Compounds analogous to the target compounds of these examples can be made according to similar routes. The disclosed compounds are useful as pharmaceutical agents as described herein.

Abbreviations or acronyms useful herein include:

| Abbreviation | Meaning |
| --- | --- |
| ACN | acetonitrile |
| n-BuLi | n-butyl lithium |
| t-Bu | tert-butyl |
| calcd | calculated |
| $CDCl_3$ | deuterated chloroform |
| DCE | dichloroethane |
| DCM | dichloromethane |
| DIPEA | diisopropyl ethyl amine |
| DMA | N,N-dimethylacetamide |
| DMF | N,N-dimethylformamide |
| DME | dimethoxyethane |
| DMSO | dimethyl sulfoxide |
| ESI | Electrospray Ionization |
| Et | ethyl |
| $Et_2O$ | Diethyl ether |
| $Et_3N$ | triethylamine |
| EtOAc | ethyl acetate |
| FCC | flash column chromatography |
| h | hour(s) |
| HPLC | high pressure liquid chromatography |
| iPr | isopropyl |
| IPA | isopropyl alcohol |
| JohnPhos | (2-Biphenyl)di-tert-butylphosphine |
| LiHMDS | lithium hexamethyldisilylazide |
| MeOH | methanol |
| Me | methyl |
| min | minute(s) |
| Ms | mesyl |
| MS | mass spectroscopy |
| NMP | N-methyl-2-pyrrolidone |
| NMR | nuclear magnetic resonance spectroscopy |
| OAc | acetate |
| $Pd(dppf)Cl_2$ | (1,1'-Bis(diphenylphosphino)ferrocene)palladium(II) dichloride |
| Ph | phenyl |
| RuPhos/RuPhos precatalyst | 2-Dicyclohexylphosphino-2',6'-diisopropoxybiphenyl Chloro(2-dicyclohexylphosphino-2',6'-diisopropoxy-1,1'-biphenyl)[2-(2'-amino-1,1'-biphenyl)]palladium(II) |
| RT | room temperature |
| SFC | supercritical fluid chromatography |
| TBAF | tetrabutylammonium fluoride |
| TFA | trifluoroacetic acid |
| THF | tetrahydrofuran |
| TMS | trimethylsilyl |

General Guidance

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

Unless otherwise specified, reaction solutions were stirred at RT under a $N_{2(g)}$ or $Ar_{(g)}$ atmosphere. When solutions were "concentrated to dryness", they were concentrated using a rotary evaporator under reduced pressure, when solutions were dried, they are typically dried over a drying agent such as $MgSO_4$ or $Na_2SO_4$.

Normal phase flash column chromatography (FCC) was performed on silica gel with RediSep® silica gel columns using ethyl acetate (EtOAc)/hexanes, $CH_2Cl_2$/MeOH, $CH_2Cl_2$/10% 2 N $NH_3$ in MeOH, $CH_2Cl_2$/i-PrOH, and the like as eluent, unless otherwise indicated.

Reverse phase high performance liquid chromatography (HPLC) was performed under the following conditions: 1) Instrument, Shimadzu; Column, Waters XBridge C18 10 μM (250×50 mm), Phenomenex Gemini column 5 μm C18 (150×21.2 mm) or Waters Xterra RP18 OBD 5 μm (100×30 mm); Gradient, 95:5 to 0:100 water (0.05% trifluoroacetic acid (TFA))/$CH_3CN$ (0.05% TFA); Flow rate, 30-80 mL/min; Detection, UV at $\lambda$=220-254 nM; 2) Instrument, Gilson; Column, Phenomenex LUNA column 5 μm C18 (250×50 mm) or Waters XBridge Prep C18 OBD 5 μm (30×150 mm); Gradient, 95:5 to 0:100 water (0.05% TFA)/$CH_3CN$ (0.05% TFA); Flow rate, 30-80 mL/min; Detection, UV at $\lambda$=220-254 nM; 3) Instrument, Gilson/Shimadzu: Column, Inertsil ODS-3 column (30×100 mm) or Inertsil ODS-3 (30×50 mm, 5 μm); Gradient, water-acetonitrile with both phases with 0.05% by volume trifluoroacetic acid; 1 min hold at 5% ACN, then 6 min gradient to 99% ACN followed by a hold at that concentration for 3 min. Flow rate, 80 ml/min; heated column at 46° C. with detection of UV light at $\lambda$=254 nm; and 4) Instrument, Dionex: UVD 170U Diode array detector and ThermoFinnegan Surveyor MSQ plus mass spectrometer for data collection. Waters XBridge C18 5 μM OBD 50×100 mm prep column. All runs utilized water acetonitrile with 20 mM $NH_4OH$ added to the aqueous phase and a flow rate for all gradients was 80 mL/min using four possible gradients: 1) 5-60% MeCN over 12 min, then ramped to 100% MeCN and held for 6.3 min; 2) 30-70% MeCN over 12 min, then ramped to 100% MeCN and held for 6.3 min; 3) 50-80% MeCN over 12 min, then ramped to 100% MeCN and held for 6.3 min; and 4) 60-100% MeCN over 12 min, and then held for 6.3 min. The total run time for all gradient systems was 18.5 min.

Instances where solutions were filtered through a syringe filter, Pall 0.45 μM GHP membrane 13 mm and 25 mm diameter syringe filters were used.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone. Microwave reactions were carried out in either a CEM Discover® or a Biotage Initiator™ or Optimizer™ microwave at specified temperatures. Mass spectra were obtained on an Agilent series 1100 MSD using electrospray ionization (ESI) in positive mode unless otherwise indicated. Calculated mass corresponds to the exact mass. NMR spectra were obtained on either a Bruker model DPX400 (400 MHz), DPX500 (500 MHz), DRX600

(600 MHz) spectrometer. The format of the 1H NMR data below is: chemical shift in ppm down field of the tetramethylsilane reference (multiplicity, coupling constant J in Hz, integration).

Hydrochloride salts were obtained by treating the corresponding free bases with HCl (4 N in dioxane, 2 M in Et$_2$O, or 1.25 N in MeOH) at RT with mixtures and then either concentrated to obtain the HCl salt, or the resulting solid being isolated by filtration. Trifluoroacetic acid salts were obtained by purification of the crude reaction product by preparative reverse phase HPLC, whereby the final products were isolated as either mono-, di- or tri trifluoroacetic acid salts.

Chemical names were generated using ChemDraw Ultra 12.0 (CambridgeSoft Corp., Cambridge, Mass.) or ACD/Name Version 10.01 (Advanced Chemistry).

The compounds of Formula (I), wherein ring A, $R^1$, $R^5$ and $R^6$ are defined as in Formula (I), may be synthesized as outlined by the general synthetic route illustrated in Scheme A.

using known methods. $R^6$ may be hydrogen or one of various alkyl substituents. Diamines of formula (V) are obtained via alkylation of 4-fluoro-3-nitrophenol (II) with aryl or heteroaryl methylhalides. Preferably, 4-fluoro-3-nitrophenol (II) is treated with the desired halide in the presence of a base, such as $K_2CO_3$, $Cs_2CO_3$, or NaOH, with or without the presence of potassium iodide in a suitable polar solvent, such as $CH_3CN$, dimethyl formamide (DMF), dimethyl acetamide (DMA), tetrahydrofuran (THF), or a mixture thereof, at a temperature ranging from about 50° C. to about 180° C. using conventional heating or microwave irradiation. Nitroethers (III) are converted to compounds of Formulae (IV) via nucleophilic aromatic substitution ($S_NAr$) with aryl or heteroaryl-substituted methylene amines in the presence of a suitable base, such as DIPEA, Et$_3$N, or a mixture thereof, in a solvent, such as $CH_3CN$, DMF, DMA, N-methyl-2-pyrrolidone (NMP) or a mixture thereof, at a temperature ranging from about 50° C. to about 150° C. Diamines (V) are obtained by reduction of the nitro group using generally known methods, such as hydrogenation over

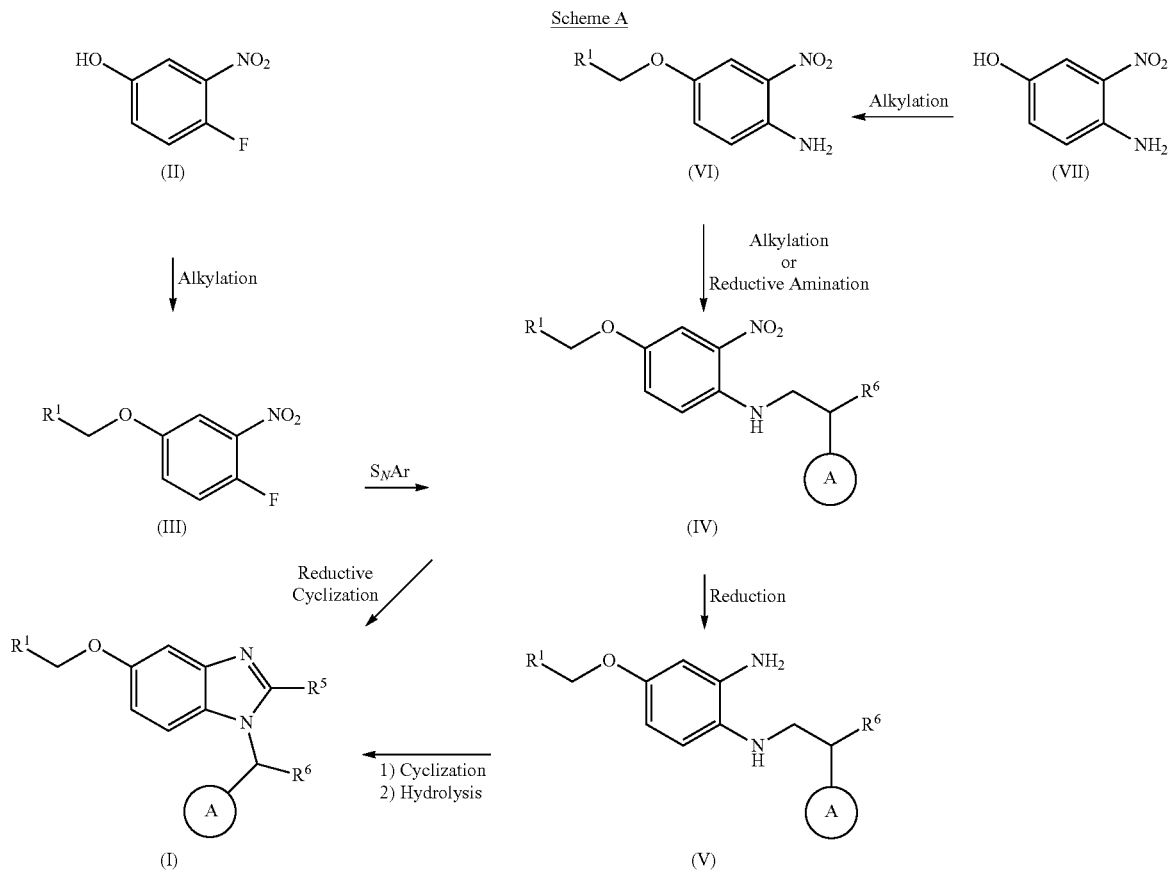

Scheme A

Referring to Scheme A, compounds of Formulae (I) are prepared from cyclization of diamines (V) with anhydrides, di-acids, or aldehyde containing acids where $R^1$ is an aryl or heteroaryl substituent and $R^5$ may contain substituents such as alkyl or cycloalkyl carboxylic acids. Ring A may represent or contain various substituents such as alkyls, cycloalkyls, halogens, amines, ethers, and aromatic or heteroaromatic rings. Various substituted anhydrides and diacids used in the preparation of compounds of Formulae (I) were obtained from commercial sources or were prepared a Pd or Pt catalyst using H$_2$, in solvents, such as THF, MeOH and EtOH, with or without the presence of DIPEA, or Et$_3$N. Alternatively, the nitro group can be reduced through the use of a heterogeneous stoichiometric reductant, such as Zn metal powder, in the presence of an acid, such as NH$_4$Cl or HOAc, in a solvent, such as MeOH, EtOH, acetone, or THF, at a temperature ranging from 0° C. to the reflux temperature of the solvent. Additionally, reduction can occur in the presence of a homogeneous stoichiometric reductant, such as SnCl$_2$.2H$_2$O, in solvents, such as EtOH, MeOH, and EtOAc, at temperatures ranging from 0° C. to the reflux temperature of the solvent. Formation of (I) can be achieved in a two-step process by first reacting diamine (V) with appropriate anhydrides in the presence of a base, such as DIPEA, in a solvent, such as CH₃CN, at a temperature performed using the appropriate aryl or heteroaryl aldehyde in the presence of a reductant, such as Na(OAc)$_3$BH or NaB(CN)H$_3$, in solvents, such as dichloromethane (DCM), dichloroethane (DCE), or THF or mixtures thereof.

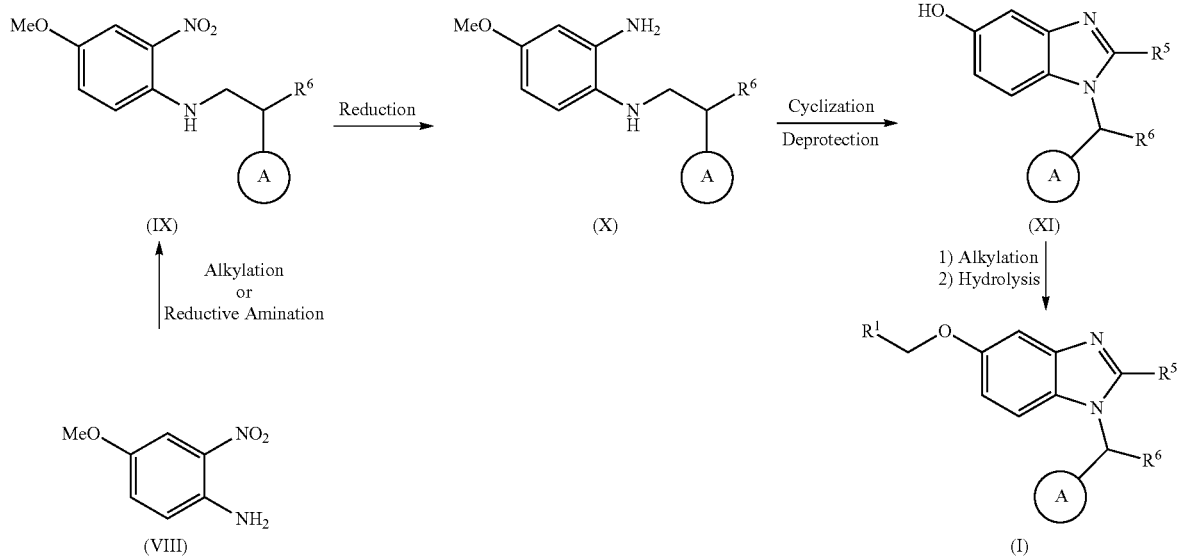

Scheme B ranging from about 50° C. to about 90° C. The product thus obtained is converted to (I) by subjecting it to further heating from 0° C. to the reflux temperature of the solvent, either conventionally or in a microwave reactor, in the presence of an acid, such as HCl, HOAc, or MsOH. Alternatively, formation of (I) can be achieved by heating diamine (V) and an appropriate organic diacid in the presence of a strong acid catalyst or Lewis acidic dehydrating agent, such as HCl or SnCl$_4$ respectively, at a temperature ranging from about 50° C. to about 90° C. In some instances, such as to ease purification, it is desirable to convert (I) to the corresponding alkyl ester by treating (I) with a strong acid, such as HCl, in the presence of an alcoholic solvent, such as EtOH or MeOH, at temperatures ranging from RT to 100° C. Methylesters of (I) can also be obtained using TMSCHN$_2$ in a mixture of toluene and MeOH. Benzimidazole (I) is then obtained by subsequent hydrolysis using known acidic or basic conditions. Preferably, hydrolysis is conducted using a base, such as LiOH, NaOH or KOH, in solvents, such as MeOH, THF, or a mixture thereof, at temperatures ranging from RT to about 80° C. Alternatively, compounds of Formulae (I) can synthesized directly via a reductive coupling from compounds of Formulae (IV) using the corresponding aldehyde or hemiacetal. This reaction is accomplished in the presence of a reducing agent, such as sodium dithionite, in a solvent, such as DMA.

Alternatively, compounds of Formulae (IV) could be obtained by alkylation of 4-amino-3-nitrophenol (VII) using analogous conditions stated above to provide (VI). Alkylation with suitable aryl or heteroaryl halomethanes in the presence of a base, such as (iPr)$_2$NEt or Et$_3$N, in a solvent, such as CH$_3$CN, at a temperature ranging from about 50° C. to about 150° C., provides compounds of Formulae (IV). Additionally, compounds of Formulae (IV) can be obtained via reductive amination of (VI). Reductive aminations are Referring to Scheme B, in alternative embodiments, benzimidazoles of Formulae (I) are obtained by alkylation and hydrolysis of phenol (XI). Phenols (XI) are prepared from an intermediate (VIII), wherein the phenol is protected with an appropriate protecting group, such as methyl, and the amino group alkylated, either by an S$_N$2 process or by reductive amination, using conditions described above to afford (IX). Reduction of the nitro group of (IX) to afford diamines (X) can be performed using conditions described above. Cyclization of (X) to afford (XI) can be performed using methods described above, The protecting group on the phenol of compounds of Formulae (X) may be removed using generally accepted methods. More specifically, when the protecting group is methyl, compounds of Formulae (XI) can be prepared using an appropriate reagent, such as BBr$_3$, in a solvent, such as DCM, at a temperature ranging from −78° C. to RT. Alkylation of (XI) and hydrolysis of the ester of R$^5$, if present, are performed using methods described in Scheme A.

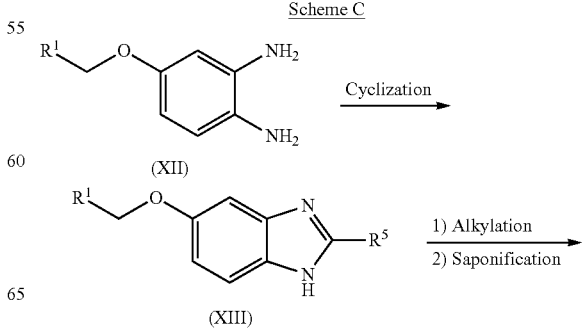

Scheme C

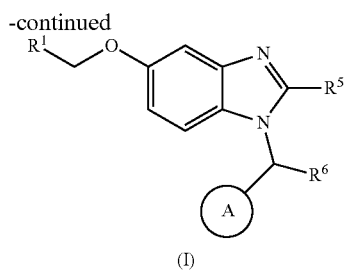

Referring to Scheme C, compounds of Formulae (I) can be obtained by N-alkylation of one of the benzimidazole (XIII) nitrogens followed by hydrolysis of the ester substituent of $R^5$. Benzimidazole (XIII) can be obtained from diamines XII using known procedures described in Scheme A. Reduction of the nitro group of (VI) using methods described above affords diamine (XII). Cyclization of (XII) to give (XIII) can be performed using conditions described above. Alkylation is performed with the desired aryl- or heteroaryl methylene halide in the presence of a base, such as $K_2CO_3$, $Cs_2CO_3$, or NaOH, a suitable polar solvent, such as $CH_3CN$, DMF, DMA, THF, or a mixture thereof, at a temperature ranging from about RT to about 180° C. Hydrolysis of the ester group $R^5$ can be performed using procedures described above.

MDS in 1,4-dioxane, toluene, or THF at temperatures ranging from about RT to the boiling point of the solvent. In instances where $R^5$ contains an alkyl ester, hydrolysis using methods described above provides (I).

C) EXAMPLES

The following examples are offered by way of illustration; the invention should not be construed as being limited by the chemical reactions and conditions expressed.

Intermediate A 2-((4-Fluoro-3-nitrophenoxy)methyl)quinolone

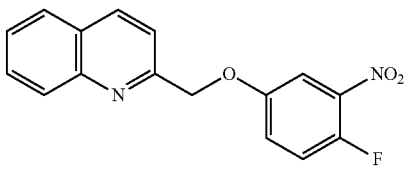 [SMILES: O=[N+]([O-])c1cc(OCc2ccc3ccccc3n2)ccc1F]

Scheme D

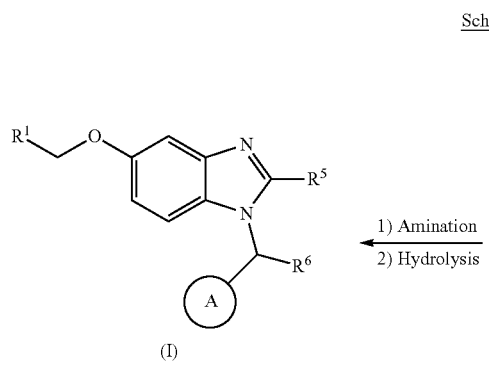

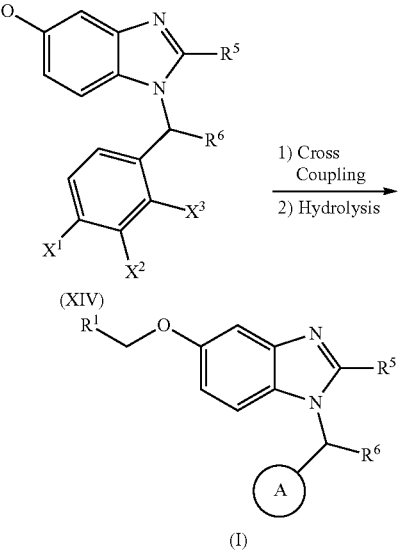

Referring to Scheme D, benzimidazoles (XIV), where $X^1$, $X^2$ or $X^3$ is an appropriate halogen, preferably Br, and substituent $R^5$ is protected as an ester, can be coupled with various amines, aryls, and heteroaryls using known organometallic cross coupling methods. Coupling of the aromatic halides (XIV) with various amines, boronic acids, boronic esters, and stannanes in the presence of a catalyst, such as $Pd(dppf)Cl_2 \cdot CH_2Cl_2$, $Pd(OAc)_2$, $Pd(PPh_3)_4$, or RuPhos/RuPhos pre-catalyst, in a solvent, such as THF, 1,4-dioxane, DMA, DMF, DME, or toluene, in the presence of a base, such as NaOt-Bu, LiHMDS, $Na_2CO_3$, $K_2CO_3$, $Cs_2CO_3$, or $K_3PO_4$, affords esters of benzamidazole (I). Preferred catalysts for amination include $Pd(dppf)Cl_2 \cdot CH_2Cl_2$ and RuPhos/RuPhos pre-catalyst with $K_3PO_4$, NaOt-Bu or LiH- To a mixture of 3-fluoro-4-nitrophenol (25 g, 159 mmol), 2-(chloromethyl)-quinoline hydrochloride (34 g, 159 mmol) and cesium carbonate (129 g, 398 mmol) was added DMF (530 mL) and the resulting suspension was allowed to stir at RT for 24 h. The reaction mixture was then poured into a large excess of water. The resulting solids were isolated by filtration and were dried to afford the title compound. MS (ESI): mass calcd. for $C_{16}H_{11}FN_2O_3$, 298.08; m/z found, 299.1 [M+H]$^+$. $^1$H NMR (500 MHz, CDCl$_3$) 8.22 (d, J=8.5, 1H), 8.09 (d, J=8.4, 1H), 7.84 (d, J=8.2, 1H), 7.79-7.72 (m, 2H), 7.61 (d, J=8.5, 1H), 7.58 (ddd, J=8.1, 6.9, 1.1, 1H), 7.29 (dt, J=9.2, 3.4, 1H), 7.20 (dd, J=10.1, 9.3, 1H), 5.41 (s, 2H).

Intermediate B racemic-cis-3-Hydroxyhexahydroisobenzofuran-1(3H)-one

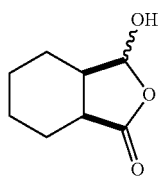

A solution of cis-hexahydroisobenzofuran-1,3-dione (96.5 g, 0.63 mol) and triethylamine (95 mL, 0.69 mol) in THF (2.5 L) was passed through a continuous-flow hydrogenation apparatus (H-Cube Midi®, manufactured by ThalesNano Nanotechnology Inc, Budapest, Hungary) under the following conditions: 10% Pd/C Midi-Cart® cartridge, 20 bar $H_2$ pressure, 50° C., 7.5 mL/min flow rate. The collected product solution was concentrated to dryness. The resulting residue was diluted with water (0.8 L), then the pH was adjusted to 2 using HCl (12 N). The mixture was extracted twice with methyl tert-butyl ether (0.8 L and 0.2 L). The combined organics were washed with saturated NaCl solution, dried over $Na_2SO_4$, filtered and then concentrated to dryness to afford title compound as a white solid (82 g, 84%). $^1$H NMR (400 MHz, $CDCl_3$) δ 5.49 (app br s, 1H), 3.07-2.80 (m, 1H), 2.50-2.31 (m, 1H), 2.21-1.93 (m, 1H), 1.92-1.74 (m, 1H), 1.72-1.35 (m, 3H), 1.32-0.91 (m, 3H).

Intermediate C

Ethyl 3-(5-methoxy-1H-benzo[d]imidazol-2-yl)-2,2-dimethylpropanoate

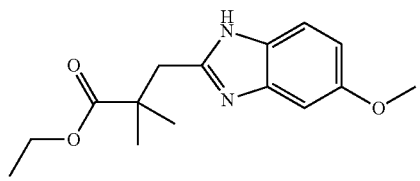 [SMILES: CCOC(=O)C(C)(C)Cc1nc2cc(OC)ccc2[nH]1]

To a 100 mL round-bottomed flask were added a stir bar, 4-methoxy-o-phenylenediamine bis-hydrochloride salt (2 g, 9.5 mmol), acetonitrile (20 mL), triethylamine (2.6 mL, 19 mmol), and 3,3-dimethyldihydrofuran-2,5-dione (1.2 g, 9.5 mmol). After 1 h, the mixture was concentrated to dryness and ethanol (50 mL) followed by HCl (1 mL, 12 N) was added to the residue. The reaction vessel was heated at 80° C. for 12 hours before cooling to RT. The reaction mixture was concentrated to dryness. The residue was diluted with water (50 mL) and neutralized with sat. $NaHCO_3$ until pH was 6.8-7. The aqueous was extracted with diethyl ether (3×100 mL), the combined extracts dried over sodium sulfate, filtered and concentrated to dryness. The residue was subjected to FCC to give the title compound (1.5 g, 57%). MS (ESI): mass calcd. for $C_{15}H_{20}N_2O_3$, 276.15; m/z found, 277.1 $[M+H]^+$. A mixture of two tautomers observed so peaks are listed for identification purposes only. $^1$H NMR (600 MHz, DMSO-$d_6$) δ 11.99-11.85 (m, 1H), 7.39 (d, J=8.7), 7.29 (d, J=8.6), 7.07 (d, J=2.4), 6.92 (d, J=2.4), 6.75 (dd, J=8.6, 2.4), 6.72 (dd, J=8.7, 2.4), 4.13-4.02 (m), 3.78-3.74 (m), 3.00-2.94 (m), 1.24-1.21 (m), 1.13 (t, J=7.1).

Intermediate D

Ethyl 3-(1-(4-bromobenzyl)-6-methoxy-1H-benzo[d]imidazol-2-yl)-2,2-dimethylpropanoate

Intermediate E

Ethyl 3-(1-(4-bromobenzyl)-5-methoxy-1H-benzo[d]imidazol-2-yl)-2,2-dimethylpropanoate

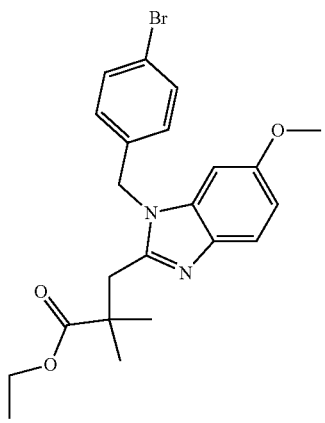

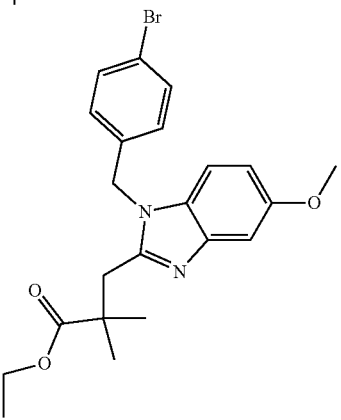

To a 100 mL round-bottomed flask were added a stir bar, ethyl 3-(5-methoxy-1H-benzo[d]imidazol-2-yl)-2,2-dimethylpropanoate (1.5 g, 5.4 mmol), DMF (19 mL), cesium carbonate (3.5 g, 11 mmol), and 4-bromobenzyl bromide (1.4 g, 5.4 mmol). After 12 h, the mixture was partitioned between water (100 mL) and EtOAc (50 mL). The aqueous layer was extracted with EtOAc (50 mL×3). The combined organic layers were dried with sodium sulfate, filtered, and concentrated to dryness. The residue was subjected to FCC to give ethyl 3-(1-(4-bromobenzyl)-6-methoxy-1H-benzo[d]imidazol-2-yl)-2,2-dimethylpropanoate (550 mg, 23%) and ethyl 3-(1-(4-bromobenzyl)-5-methoxy-1H-benzo[d]imidazol-2-yl)-2,2-dimethylpropanoate (620 mg, 26%).

Intermediate D: Ethyl 3-(1-(4-bromobenzyl)-6-methoxy-1H-benzo[d]imidazol-2-yl)-2,2-dimethylpropanoate. MS (ESI): mass calcd. for $C_{22}H_{25}BrN_2O_3$, 444.10; m/z found, 445.1 $[M+H]^+$. $^1$H NMR (500 MHz, DMSO-$d_6$) δ 7.55-7.52 (m, 2H), 7.44 (d, J=8.7, 1H), 7.05-7.00 (m, 3H), 6.77 (dd, J=8.7, 2.4, 1H), 5.46 (s, 2H), 4.02 (q, J=7.1, 2H), 3.73 (s, 3H), 3.00 (s, 2H), 1.27 (s, 6H), 1.06 (t, J=7.1, 3H).

Intermediate E: Ethyl 3-(1-(4-bromobenzyl)-5-methoxy-1H-benzo[d]imidazol-2-yl)-2,2-dimethylpropanoate. MS (ESI): mass calcd. for $C_{22}H_{25}BrN_2O_3$, 444.10; m/z found, 445.1 [M+H]$^+$. $^1$H NMR (500 MHz, DMSO-d$_6$) δ 7.54-7.50 (m, 2H), 7.29 (d, J=8.8, 1H), 7.10 (d, J=2.4, 1H), 7.00 (d, J=8.1, 2H), 6.79-6.75 (m, 1H), 5.44 (s, 2H), 4.07-4.00 (m, 2H), 3.76 (s, 3H), 3.04 (s, 2H), 1.28 (s, 6H), 1.08 (t, J=7.0, 3H).

Intermediate F

Ethyl 3-(1-(4-bromobenzyl)-5-hydroxy-1H-benzo[d]imidazol-2-yl)-2,2-dimethylpropanoate

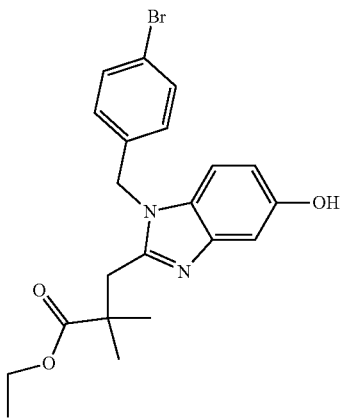 [SMILES: CCOC(=O)C(C)(C)Cc1nc2cc(O)ccc2n1Cc1ccc(Br)cc1]

A solution of boron tribromide (2.2 mL, 1 M in DCM) was added drop-wise to a 100 mL round bottomed flask containing ethyl 3-(1-(4-bromobenzyl)-5-methoxy-1H-benzo[d]imidazol-2-yl)-2,2-dimethylpropanoate (493 mg, 1.11 mmol) and DCM (20 mL) at −78° C. The resulting solution was allowed to warm to 5° C. over 3 h and partitioned with sat. NaHCO$_3$ (50 mL). The aqueous layer was extracted with DCM (25 mL×3). The combined organic layers were dried with sodium sulfate, filtered, and concentrated to dryness. The residue was subjected to FCC to give the title compound (370 mg, 77%). MS (ESI): mass calcd. for $C_{21}H_{23}BrN_2O_3$, 430.08; m/z found, 431.1 [M+H]$^+$. $^1$H NMR (500 MHz, CDCl$_3$) δ 7.43-7.39 (m, 2H), 7.25 (d, J=2.3, 1H), 6.94 (d, J=8.6, 1H), 6.88-6.84 (m, 2H), 6.77 (dd, J=8.7, 2.3, 1H), 5.32 (s, 2H), 4.07 (q, J=7.1, 2H), 3.05 (s, 2H), 1.35 (s, 6H), 1.16 (t, J=7.1, 3H).

Intermediate G

Ethyl 3-(1-(4-bromobenzyl)-5-(quinolin-2-ylmethoxy)-1H-benzo[d]imidazol-2-yl)-2,2-dimethylpropanoate

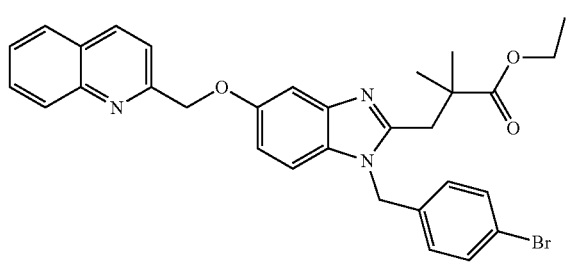 [SMILES: CCOC(=O)C(C)(C)Cc1nc2cc(OCc3ccc4ccccc4n3)ccc2n1Cc1ccc(Br)cc1]

To a 10 mL round-bottomed flask were added a stir bar, ethyl 3-(1-(4-bromobenzyl)-5-hydroxy-1H-benzo[d]imidazol-2-yl)-2,2-dimethylpropanoate (75 mg, 0.17 mmol), cesium carbonate (169 mg, 0.52 mmol), DMF (2 mL), and 2-(chloromethyl)quinolone hydrochloride salt (37 mg, 0.17 mmol). After 12 h, the mixture was partitioned between water (50 mL) and EtOAc (20 mL). The organic layer was separated and the aqueous layer was further extracted with EtOAc (20 mL×2). The combine organic layers were dried with sodium sulfate, filtered, and concentrated to dryness. The residue was subjected to FCC to give the title compound (60 mg, 99%). MS (ESI): mass calcd. for $C_{31}H_{30}BrN_3O_3$, 571.12; m/z found, 572.0 [M+H]$^+$. $^1$H NMR (500 MHz, CDCl$_3$) δ 8.18 (d, J=8.5, 1H), 8.09 (d, J=8.4, 1H), 7.84-7.80 (m, 1H), 7.76-7.69 (m, 2H), 7.57-7.51 (m, 1H), 7.44-7.39 (m, 2H), 7.34 (d, J=2.3, 1H), 7.02 (d, J=8.8, 1H), 6.97 (dd, J=8.8, 2.4, 1H), 6.88-6.84 (m, 2H), 5.42 (s, 2H), 5.31 (s, 2H), 4.08 (q, J=7.1, 2H), 3.02 (s, 2H), 1.36 (s, 6H), 1.16 (t, J=7.1, 3H).

Intermediate H

Ethyl 3-(5-(benzo[d]thiazol-2-ylmethoxy)-1-(4-bromobenzyl)-1H-benzo[d]imidazol-2-yl)-2,2-dimethylpropanoate

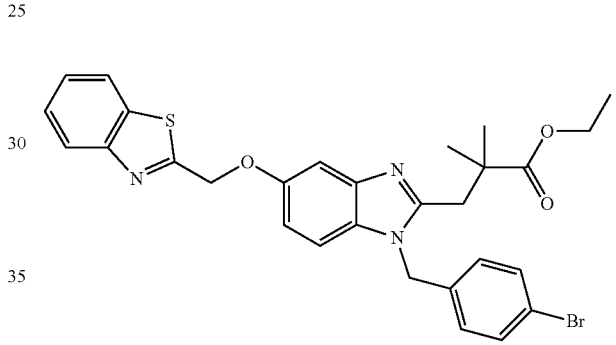

The title compound was prepared using analogous conditions to those described for ethyl 3-(1-(4-bromobenzyl)-5-(quinolin-2-ylmethoxy)-1H-benzo[d]imidazol-2-yl)-2,2-dimethylpropanoate using ethyl 3-(1-(4-bromobenzyl)-5-hydroxy-1H-benzo[d]imidazol-2-yl)-2,2-dimethylpropanoate and 2-(chloromethyl)benzo[d]thiazole. MS (ESI): mass calcd. for $C_{29}H_{28}BrN_3O_3S$, 577.10; m/z found, 578.1 [M+H]$^+$.

Intermediate I

Ethyl 2,2-dimethyl-3-(5-(quinolin-2-ylmethoxy)-1H-benzo[d]imidazol-2-yl)propanoate

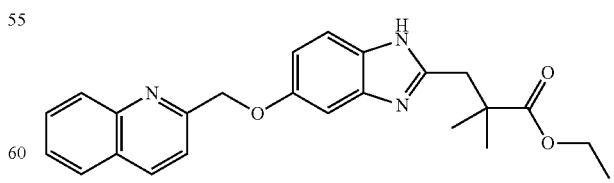

Step A: 2-Nitro-5-(quinolin-2-ylmethoxy)aniline

To a solution of 3-amino-4-nitrophenol (5.0 g, 32 mmol) in acetonitrile (162 mL) was added 4N NaOH (16.2 mL, 4

N) followed by 2-(chloromethyl)quinoline hydrochloride (7.6 g, 34 mmol) and the resulting mixture was stirred at RT for 2 h. The reaction was then heated to 80° C. for 4 h. The reaction mixture was cooled to RT and concentrated to dryness. Water was added to the residue to give a dark orange solid that was isolated by filtration. Trituration using EtOAc then afforded the title compound. MS (ESI): mass calcd. for $C_{16}H_{13}N_3O_3$, 295.10; m/z found, 296.1 [M+H]$^+$. $^1$H NMR (400 MHz, DMSO-$d_6$) 8.42 (d, J=8.5, 1H), 8.02 (dd, J=10.0, 9.2, 2H), 7.83-7.75 (m, 1H), 7.68 (d, J=8.5, 1H), 7.66-7.60 (m, 1H), 7.55 (d, J=3.0, 1H), 7.32 (dd, J=9.2, 3.0, 1H), 7.28 (s, 2H), 7.03 (d, J=9.3, 1H), 5.34 (s, 2H).

Step B: Ethyl 2,2-dimethyl-3-(5-(quinolin-2-ylmethoxy)-1H-benzo[d]imidazol-2-yl)propanoate To 2-nitro-5-(quinolin-2-ylmethoxy)aniline (886 mg, 3 mmol) and 2,2-dimethylsuccinic acid (438 mg, 3 mmol) was added $SnCl_2 \cdot 2H_2O$ (2.79 g, 12 mmol) and HCl (6 mL, 4N in dioxane). The mixture was heated to 160° C. overnight. The mixture was cooled to RT and concentrated to dryness. The resulting residue was dissolved in EtOH followed by the addition of HCl (0.5 mL, 12 N) and then it was heated to 90° C. for 4 h. The reaction was then cooled to RT and then concentrated to dryness. The crude reaction mixture was purified using FCC to afford the title compound. MS (ESI): mass calcd. for $C_{24}H_{25}N_3O_3$, 403.19; m/z found, 404.1 [M+H]$^+$.

Intermediate J

Ethyl 1-((1-(4-bromobenzyl)-5-(quinolin-2-ylmethoxy)-1H-benzo[d]imidazol-2-yl)methyl)cyclopentanecarboxylate

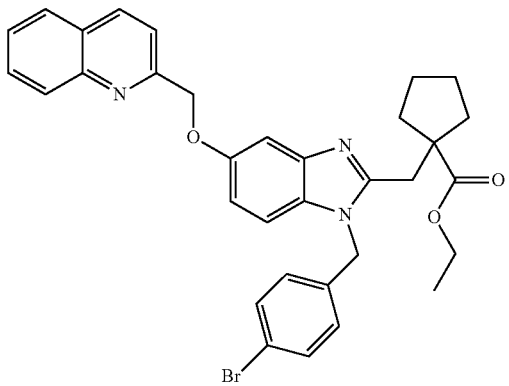 [SMILES: CCOC(=O)C1(Cc2nc3cc(OCc4ccc5ccccc5n4)ccc3n2Cc2ccc(Br)cc2)CCCC1]

To a 25 mL round-bottomed flask was added N-1-(4-bromobenzyl)-4-(quinolin-2-ylmethoxy)benzene-1,2-diamine (80 mg, 0.2 mmol), 2-oxaspiro[4.4]nonane-1,3-dione (28 mg, 0.2 mmol) and acetonitrile (2 mL). The resulting solution was heated to 90° C. After 3 h, the solution was cooled to RT and concentrated to dryness. To the resulting residue were added ethanol (4 mL) and HCl (0.1 mL, 12 N). The solution was heated to 90° C. After 12 h, the mixture was cooled, concentrated to dryness, and purified by reverse phase HPLC to afford the title compound. MS (ESI): mass calcd. for $C_{33}H_{32}BrN_3O_3$, 597.16; m/z found, 598.1 [M+H]$^+$.

Intermediate K racemic Ethyl 3-(1-(4-bromobenzyl)-5-(quinolin-2-ylmethoxy)-1H-benzo[d]imidazol-2-yl)-2-methyl-2-phenylpropanoate

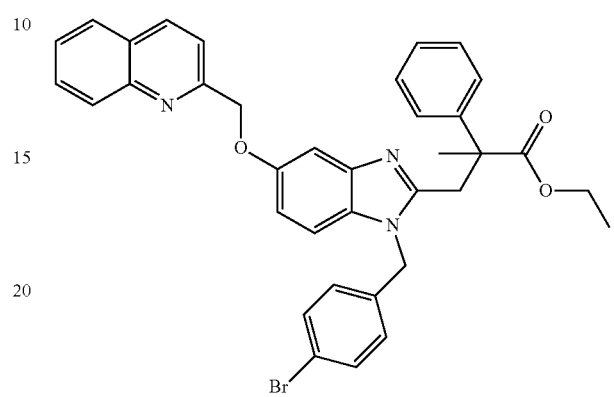

The title compound was prepared using analogous conditions to those described for ethyl 1-((1-(4-bromobenzyl)-5-(quinolin-2-ylmethoxy)-1H-benzo[d]imidazol-2-yl)methyl)cyclopentanecarboxylate using racemic 3-methyl-3-phenyldihydrofuran-2,5-dione. MS (ESI): mass calcd. for $C_{36}H_{32}BrN_3O_3$, 633.16; m/z found, 634.1 [M+H]$^+$.

Intermediate L racemic cis-Ethyl 3-(1-(4-bromobenzyl)-5-(quinolin-2-ylmethoxy)-1H-benzo[d]imidazol-2-yl)-2,2-dimethylcyclopropanecarboxylate

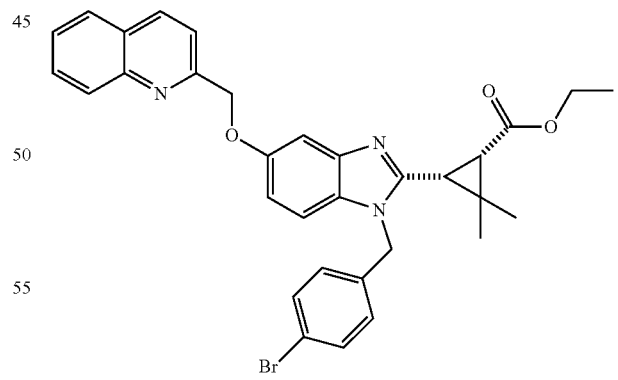

The title compound was prepared using analogous conditions to those described for ethyl 1-((1-(4-bromobenzyl)-5-(quinolin-2-ylmethoxy)-1H-benzo[d]imidazol-2-yl)methyl)cyclopentanecarboxylate using racemic cis-6,6-dimethyl-3-oxabicyclo[3.1.0]hexane-2,4-dione. MS (ESI): mass calcd. for $C_{32}H_{30}BrN_3O_3$, 583.15; m/z found, 584.1 [M+H]$^+$.

Intermediate M

Methyl 1-{[1-(3-bromobenzyl)-5-(quinolin-2-yl-methoxy)-1H-benzimidazol-2-yl]methyl}cyclopentanecarboxylate

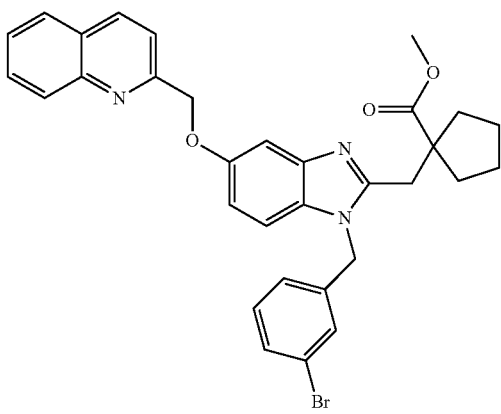 [SMILES: COC(=O)C1(Cc2nc3cc(OCc4ccc5ccccc5n4)ccc3n2Cc2cccc(Br)c2)CCCC1]

Step A: N-(3-bromobenzyl)-2-nitro-4-(quinolin-2-ylmethoxy)aniline

To a mixture of 2-((4-fluoro-3-nitrophenoxy)methyl)quinoline (3.6 g, 12 mmol) and 3-bromobenzyl amine (2 mL, 15 mmol) in DMA (50 mL) was added DIPEA (6 mL, 35 mmol) and heated to 130° C. for 16 h. The mixture was cooled to RT and poured into water (400 mL). The resulting orange/red suspension was extracted with EtOAc and the combined organics were washed with water and brine. The organic layer was concentrated to dryness to afford 5.9 g of a solid that was used without further purification. MS (ESI): mass calcd. for $C_{23}H_{18}BrN_3O_3$, 464.32; m/z found 465.0 [M+H]$^+$. $^1$H NMR (400 MHz; CDCl$_3$) δ 8.32-8.27 (m, 1H), 8.20 (d, J=8.3, 1H), 8.09 (d, J=8.3, 1H), 7.86 (d, J=3.0, 1H), 7.85-7.81 (m, 1H), 7.77-7.71 (m, 1H), 7.63 (d, J=8.3, 1H), 7.58-7.53 (m, 1H), 7.48 (s, 1H), 7.44-7.40 (m, 1H), 7.28-7.20 (m, 3H), 6.71 (d, J=9.3, 1H), 5.33 (s, 2H), 4.51 (d, J=5.8, 2H).

Step B: N1-(3-bromobenzyl)-4-(quinolin-2-yl-methoxy)benzene-1,2-diamine

To a solution of N-(3-bromobenzyl)-2-nitro-4-(quinolin-2-ylmethoxy)aniline (5.9 g, 13 mmol) in THF (200 mL) was added DIPEA (1.1 mL, 6.4 mmol) followed by 5% platinum on carbon (0.4 g, 1.9 mmol). The reaction vessel was evacuated and placed under 1 atmosphere of H$_2$ atmosphere for 23 h. The mixture was then flushed with N$_2$ and filtered through a pad of Celite. The Celite was then rinsed with additional THF and the filtrate was concentrated to dryness. The resulting residue was purified using FCC to provide 3.3 g of the title compound as a tan solid. MS (ESI): mass calcd. for $C_{23}H_{20}BrN_3O$, 434.33; m/z found 435.0 [M+H]$^+$.

Step C: Methyl 1-{[1-(3-bromobenzyl)-5-(quinolin-2-ylmethoxy)-1H-benzimidazol-2-yl]methyl}cyclopentanecarboxylate To a solution of N1-(3-bromobenzyl)-4-(quinolin-2-yl-methoxy)benzene-1,2-diamine (1.0 g, 2.4 mmol) in acetonitrile (20 mL) was added 2-oxaspiro[4.4]nonane-1,3-dione (420 mg, 2.7 mmol) and the solution heated to 80° C. for 8 h. The solution was cooled to RT and concentrated to dryness. To this residue was added acetic acid (15 mL) and the resulting solution was heated to 80° C. for 3 h. The solution was cooled, concentrated to dryness and the resulting residue was taken up in toluene/MeOH (15 mL; 3:1). The solution was treated with TMSCHN$_2$ (1.5 mL, 3 mmol, 2 M in hexanes) dropwise (bubbling observed). The mixture was stirred at RT for 30 min and then concentrated to dryness. The residue was purified using FCC to provide 1.12 g of the title compound. MS (ESI): mass calcd. for $C_{32}H_{30}BrN_3O_3$, 583.15; m/z found, 584.0 [M+H]$^+$. $^1$H NMR (400 MHz, CDCl$_3$) δ 8.18 (d, J=8.5, 1H), 8.09 (d, J=8.7, 1H), 7.82 (d, J=8.2, 1H), 7.75-7.69 (m, 2H), 7.56-7.52 (m, 1H), 7.40 (d, J=7.9, 1H), 7.35 (d, J=2.2, 1H), 7.20 (s, 1H), 7.18-7.14 (m, 1H), 7.05-7.02 (m, 1H), 6.99-6.96 (m, 1H), 6.89-6.86 (m, 1H), 5.42 (s, 2H), 5.33 (s, 2H), 3.62 (s, 3H), 3.08 (s, 2H), 2.26-2.20 (m, 2H), 1.87-1.80 (m, 2H), 1.77-1.64 (m, 4H); 584.0 (M+H) m/z

Intermediate N racemic trans-Ethyl 3-(1-(4-bromobenzyl)-5-(quinolin-2-ylmethoxy)-1H-benzo[d]imidazol-2-yl)-2,2-dimethylcyclopropanecarboxylate

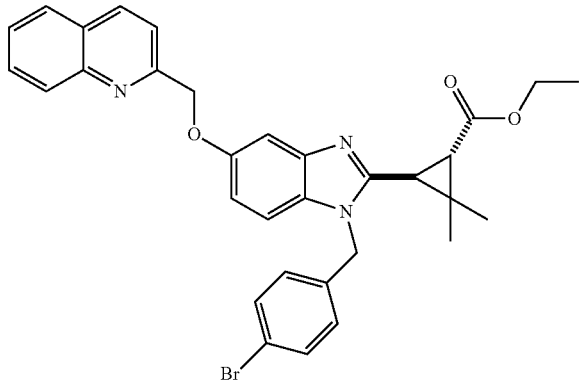

A solution of trimethyl aluminum (0.2 mL, 2 M in toluene) was added to 25 mL round-bottomed flask containing N1-(4-bromobenzyl)-4-(quinolin-2-ylmethoxy)benzene-1,2-diamine (100 mg, 0.23 mmol), trans-diethyl 3,3-dimethylcyclopropane-1,2-dicarboxylate (49 mg, 0.23 mmol), and DCM (4 mL). After 12 h, the solution was partitioned between sat. NaHCO$_3$ (30 mL) and EtOAc (30 mL). The organic layer was separated and the aqueous layer was extracted with EtOAc (2×30 mL). The combine organic layers were dried with sodium sulfate, filtered, and concentrated to dryness. To the residue was added ethanol (2 mL) and concentrated HCl (0.1 mL, 12 N). The solution heated to 90° C. After 5 h, the mixture was cooled, concentrated to dryness, and purified by reverse phase HPLC to afford the title compound. MS (ESI): mass calcd. for $C_{32}H_{30}BrN_3O_3$, 583.15; m/z found, 584.1 [M+H]$^+$.

Intermediate O

Ethyl 1-((1-(4-bromobenzyl)-5-(quinolin-2-yl-methoxy)-1H-benzo[d]imidazol-2-yl)methyl)cyclopentanecarboxylate

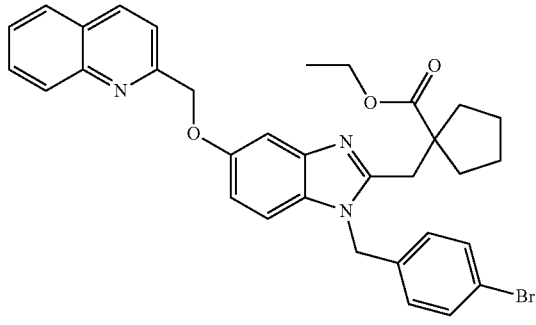 [SMILES: CCOC(=O)C1(Cc2nc3cc(OCc4ccc5ccccc5n4)ccc3n2Cc2ccc(Br)cc2)CCCC1]

To a solution of N' 1-(4-bromobenzyl)-4-(quinolin-2-ylmethoxy)benzene-1,2-diamine (2.0 g, 4.6 mmol) in acetonitrile (40 mL) was added 2-oxaspiro[4.4]nonane-1,3-dione (0.71 g, 4.6 mmol) and the solution heated to 80° C. for 19 h. The solution was cooled and concentrated to dryness. To the resulting residue were added ethanol (40 mL) and then HCl (1.3 mL, 12 N) was added and the resulting mixture heated to 90° C. for 2 days. The reaction was cooled to RT and concentrated to dryness. The residue was dissolved in DCM (50 mL) and washed with sat. NaHCO$_3$ (50 mL). The organics were dried (Na$_2$SO$_4$), filtered and concentrated to dryness. The resulting residue was purified by FCC to afford the title compound. MS (ESI): mass calcd. for C$_{33}$H$_{32}$BrN$_3$O$_3$, 597.16; m/z found, 598.1 [M+H]$^+$. $^1$H NMR (400 MHz, CDCl$_3$) δ 8.19-8.15 (m, 1H), 8.11-8.07 (m, 1H), 7.83-7.80 (m, 1H), 7.76-7.72 (m, 1H), 7.72-7.68 (m, 1H), 7.56-7.51 (m, 1H), 7.43-7.39 (m, 2H), 7.35-7.34 (m, 1H), 7.03-7.00 (m, 1H), 6.98-6.94 (m, 1H), 6.88-6.84 (m, 2H), 5.41 (s, 2H), 5.30 (s, 2H), 4.08-4.02 (m, 2H), 3.07 (s, 2H), 2.28-2.19 (m, 2H), 1.87-1.78 (m, 2H), 1.76-1.64 (m, 4H), 1.14-1.09 (m, 3H).

Intermediate P racemic Ethyl 3-(1-(3-bromobenzyl)-5-(quinolin-2-ylmethoxy)-1H-benzo[d]imidazol-2-yl)-2,2-dimethylcyclopropanecarboxylate

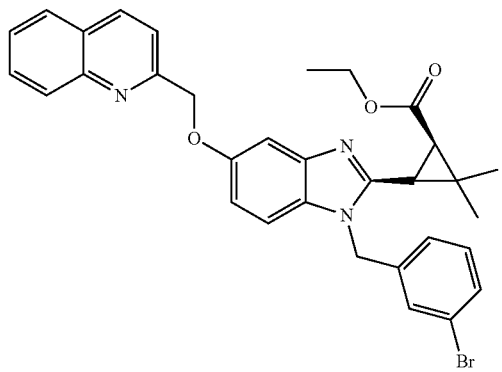

The title compound was prepared using similar methods to those for ethyl 1-((1-(4-bromobenzyl)-5-(quinolin-2-yl-methoxy)-1H-benzo[d]imidazol-2-yl)methyl)cyclopentanecarboxylate using N$^1$-(3-bromobenzyl)-4-(quinolin-2-yl-methoxy)benzene-1,2-diamine and cis-6,6-dimethyl-3-oxabicyclo[3.1.0]hexane-2,4-dione. MS (ESI): mass calcd. for C$_{32}$H$_{30}$BrN$_3$O$_3$, 583.15; m/z found, 584.1 [M+H]$^+$.

Intermediate Q

Ethyl 3-(1-(3-bromobenzyl)-5-(quinolin-2-ylmethoxy)-1H-benzo[d]imidazol-2-yl)-2,2-dimethyl-propanoate

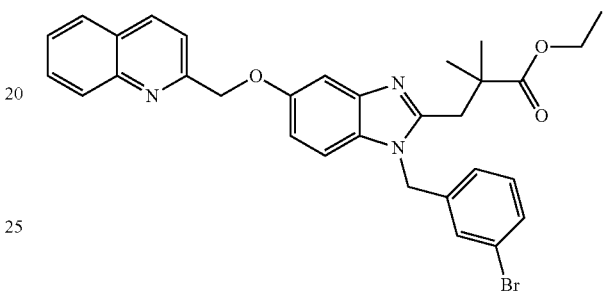

The title compound was prepared using similar methods to those in Example 33 Steps A-E, using 1-bromo-3-(bromomethyl)benzene in Step A. $^1$H NMR (300 MHz, CDCl$_3$) δ 8.17 (d, J=8.3, 1H), 8.09 (d, J=8.6, 1H), 7.81 (d, J=7.3, 1H), 7.72 (ddd, J=8.4, 6.7, 3.2, 2H), 7.57-7.50 (m, 1H), 7.43-7.35 (m, 2H), 7.19 (s, 1H), 7.14 (t, J=7.9, 1H), 7.01 (dt, J=8.8, 5.5, 2H), 6.85 (d, J=7.7, 1H), 5.42 (s, 2H), 5.36 (s, 2H), 4.07 (q, J=7.1, 2H), 3.06 (s, 2H), 1.39 (s, 6H), 1.16 (t, J=7.1, 3H).

Intermediate R 2,2-Dimethyl-3-(5-(quinolin-2-ylmethoxy)-1-(4-(4,4,5,5-tetramethyl-1,3,2-dioxaborolan-2-yl)benzyl)-1H-benzo[d]imidazol-2-yl)propanoic acid

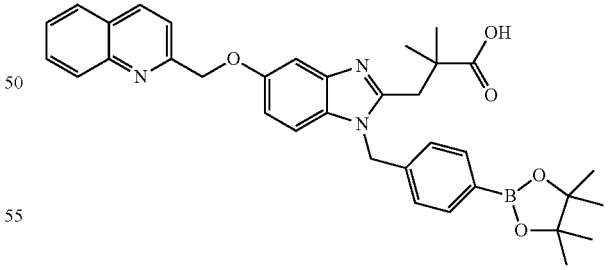

To a 100 mL round bottomed flask were added a stirbar, 3-(1-(4-bromobenzyl)-5-(quinolin-2-ylmethoxy)-1H-benzo[d]imidazol-2-yl)-2,2-dimethylpropanoic acid (2.2 g, 4 mmol), bis(pinacolato)diboron (1.1 g, 4.4 mmol), Pd(dppf)Cl$_2$.CH$_2$Cl$_2$ (450 mg, 0.6 mmol), and KOAc (1.2 g, 12 mmol). The vial was capped and flushed with N$_2$ before adding 20 mL of N$_2$ sparged 1,4-dioxane. The resulting mixture was heated at 90° C. for 10 hs. The vial was cooled to RT, concentrated to dryness, and subjected to FCC purification to afford the title compound (1.5 g, 56%). ¹H NMR (300 MHz, CDCl₃) δ 8.18 (d, J=8.6, 1H), 8.09 (d, J=8.5, 1H), 7.82 (d, J=8.1, 1H), 7.77-7.65 (m, 4H), 7.54 (t, J=7.3, 1H), 7.35 (s, 1H), 7.12 (d, J=8.9, 1H), 7.04-6.99 (m, 3H), 5.42 (s, 2H), 5.34 (s, 2H), 3.02 (s, 2H), 1.33 (s, 12H), 1.24 (s, 6H).

Intermediate S 7,7-dimethyl-2-oxaspiro[4.4]nonane-1,3-dione

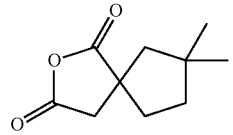

Step A: (E)-Ethyl 2-cyano-2-(3,3-dimethylcyclopentylidene)acetate

To a round bottomed flask equipped with a stir bar, reflux condenser, and Dean Stark trap were added 3,3-dimethylcyclopentanone (3.4 g, 30 mmol), toluene (50 mL), and ethyl 2-cyanoacetate (3.4 g, 30 mmol), ammonium chloride (231 mg, 3 mmol) and acetic acid (0.36 mL, 6 mmol). The reaction mixture was refluxed for 24 h. The reaction was cooled to RT and concentrated to dryness. The residue was diluted with water (100 mL) and extracted with ethyl acetate (2×100 mL). The combined organic phases were dried with Na₂SO₄, concentrated to dryness subjected to FCC to afford the title compound as colorless oil.

Step B: 1-(Cyanomethyl)-3,3-dimethylcyclopentanecarbonitrile

To a round bottomed flask equipped with a stir bar and a reflux condenser, containing (E)-ethyl 2-cyano-2-(3,3-dimethylcyclopentylidene)acetate (9.5 g, 46 mmol) in EtOH (50 mL), was added sodium cyanide (2.3 g, 46 mmol). The reaction mixture was refluxed for 24 h, cooled to RT and concentrated to dryness. The residue was diluted with water (50 mL) and extracted with ethyl acetate (2×50 mL). The combined organics was dried with Na₂SO₄, concentrated to dryness and subjected to FCC to afford the title compound. ¹H NMR (300 MHz, CDCl₃) δ 2.75 (s, 2H), 2.41-2.33 (m, 1H), 2.19 (d, J=15 Hz, 1H), 2.03-1.93 (m, 1H), 1.85-1.63 (m, 3H), 1.20 (s, 3H), 1.11 (s, 3H).

Step C: 1-(Carboxymethyl)-3,3-dimethylcyclopentanecarboxylic acid

To a round bottomed flask equipped with a stir bar and reflux condenser were added 1-(cyanomethyl)-3,3-dimethylcyclopentanecarbonitrile (2.4 g, 15 mmol), acetic acid (50 mL) and HCl (50 mL, 12 N). The reaction mixture was heated to reflux for 48 and cooled to RT. The solids were filtered and washed with cold water (50 mL) to afford the title compound as a colorless solid. ¹H NMR (300 MHz, DMSO-d₆) δ 12.01 (s, 2H), 2.65-2.51 (m, 2H), 2.17-2.08 (m, 1H), 2.02-1.97 (m, 1H), 1.71-1.58 (m, 1H), 1.52-1.39 (m, 2H), 1.38-1.33 (m, 1H), 1.00 (s, 3H), 0.99 (s, 3H).

Step D: 7,7-Dimethyl-2-oxaspiro[4.4]nonane-1,3-dione

To a round bottomed flask equipped with a stir bar and reflux condenser, were added 1-(carboxymethyl)-3,3-dimethylcyclopentanecarboxylic acid (1.1 g, 5.5 mmol) and acetic anhydride (20 mL). The reaction mixture was refluxed for 3 h, cooled to RT, and concentrated to dryness to afford the title compound as a colorless solid. ¹H NMR (300 MHz, DMSO-d₆) δ 2.89 (s, 2H), 2.43-2.24 (m, 1H), 2.20-2.15 (m, 2H), 1.87-1.49 (m, 6H).

Intermediate T 6,6-dimethyl-2-oxaspiro[4.4]nonane-1,3-dione

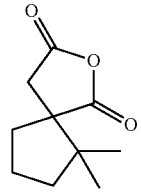

The title compound was prepared using methods analogous to 7,7-dimethyl-2-oxaspiro[4.4]nonane-1,3-dione using 2,2-dimethylcyclopentanone in Step A. ¹H NMR (500 MHz, DMSO-d₆) δ 3.18-2.94 (m, 2H), 2.34-2.18 (m, 1H), 1.98-1.64 (m, 4H), 1.62-1.48 (m, 1H), 0.95 (s, 3H), 0.93 (s, 3H).

Example 1 racemic cis-2-[1-(4-Bromobenzyl)-5-(quinolin-2-ylmethoxy)-1H-benzimidazol-2-yl]cyclohexanecarboxylic acid

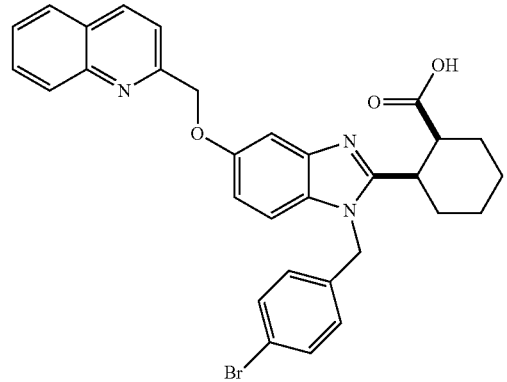

Step A: N-(4-bromobenzyl)-2-nitro-4-(quinolin-2-ylmethoxy)aniline

To a 250 mL round-bottomed flask were added a stir bar, 2-((4-fluoro-3-nitrophenoxy)methyl)quinoline (15.0 g, 40 mmol) and 4-bromobenzyl amine hydrochloride (11 g, 50 mmol), DMA (130 mL), and DIPEA (22 mL, 125 mmol). The resulting mixture was heated to 100° C. After 24 h, the mixture was cooled and concentrated to dryness. The residue was triturated with IPA (200 mL) and the orange solid was collected by vacuum filtration. The collected solid was washed with IPA (2×50 mL) and hexanes (2×50 mL) to afford the title compound (21 g, 84%). MS (ESI): mass calcd. for $C_{23}H_{18}BrN_3O_3$, 463.05; m/z found 464.1 [M+H]$^+$. $^1$H NMR (600 MHz, CDCl$_3$) δ 8.34-8.27 (m, 1H), 8.21 (d, J=8.4, 1H), 8.12-8.06 (m, 1H), 7.87-7.81 (m, 2H), 7.75 (ddd, J=8.4, 6.9, 1.4, 1H), 7.63 (d, J=8.5, 1H), 7.58-7.53 (m, 1H), 7.49-7.46 (m, 2H), 7.25-7.18 (m, 3H), 6.71 (d, J=9.4, 1H), 5.34 (s, 2H), 4.49 (d, J=5.8, 2H).

Step B: N1-(4-bromobenzyl)-4-(quinolin-2-yl-methoxy)benzene-1,2-diamine

Method A: To a 250 mL round-bottomed flask were added a stir bar, N-(4-bromobenzyl)-2-nitro-4-(quinolin-2-yl-methoxy)aniline (11.4 g, 24.5 mmol), THF (75 mL), were added DIPEA (2.1 mL, 12 mmol) followed by 5% platinum on carbon (0.6 g, 2.9 mmol). The reaction vessel was evacuated and then placed under an atmosphere of H$_2$ for 6 h. The mixture was then flushed with N$_2$ and filtered through a pad of Celite. The Celite was then rinsed with additional THF (50 mL). The resulting solution was concentrated to afford the title compound (5.5 g, 51%), which was used without further purification. MS (ESI): mass calcd. for $C_{23}H_{20}BrN_3O$, 433.07; m/z found, 434.1 [M+H]$^+$.

Method B: To a 1 L round-bottomed flask were added a stir bar, N-(4-bromobenzyl)-2-nitro-4-(quinolin-2-yl-methoxy)aniline (6.1 g, 13 mmol), tin (II) chloride dihydrate (12.5 g, 55.4 mmol) and ethanol (250 mL). The resulting mixture was heated to 80° C. After 24 h, the mixture was cooled and partitioned between water (100 mL) and EtOAc (300 mL). The mixture was stirred vigorously while the pH was adjusted to 8 using 2 M sodium carbonate. The organic layer was separated and washed with brine (100 mL), dried with magnesium sulfate, filtered, and concentrated to dryness to afford the title compound (3.1 mg, 54%). The residue was kept under vacuum until use.

Step C: racemic cis-2-[1-(4-Bromobenzyl)-5-(quinolin-2-ylmethoxy)-1H-benzimidazol-2-yl]cyclohexanecarboxylic acid To a 100 mL round-bottomed flask was added N1-(4-bromobenzyl)-4-(quinolin-2-ylmethoxy)benzene-1,2-diamine (1.3 g, 2.9 mmol), cis-hexahydroisobenzofuran-1,3-dione (0.5 g, 2.9 mmol) and acetonitrile (27 mL). The resulting solution was heated to 90° C. After 3 h, the reaction was cooled to RT and HCl (15 mL, 6 N) was added and the mixture was heated to 90° C. for 15 h. The resulting mixture was cooled to RT and concentrated to dryness. The residue was partitioned between water (100 mL) and DCM (100 mL) and the mixture was stirred vigorously while the pH was adjusted to 4-5 using sat. NaHCO$_3$. The organic layer was separated and the aqueous layer was further extracted with DCM (2×100 mL). The combine organic layers were dried with magnesium sulfate, filtered, and concentrated to dryness. The residue was subjected to FCC to give the title compound (750 mg, 44%). MS (ESI): mass calcd. for $C_{31}H_{28}BrN_3O_3$, 569.13; m/z found, 570.1 [M+H]$^+$. $^1$H NMR (500 MHz, CD$_3$OD) δ 8.36 (d, J=8.5, 1H), 8.05 (d, J=8.5, 1H), 7.93 (d, J=8.2, 1H), 7.78 (ddd, J=8.4, 6.9, 1.4, 1H), 7.74 (d, J=8.5, 1H), 7.60 (ddd, J=8.1, 7.0, 1.1, 1H), 7.47-7.41 (m, 2H), 7.29 (d, J=2.3, 1H), 7.19 (d, J=8.8, 1H), 7.05 (d, J=8.5, 2H), 7.01 (dd, J=8.8, 2.4, 1H), 5.53-5.41 (m, 2H), 5.39 (s, 2H), 3.60-3.51 (m, 1H), 2.88-2.76 (m, 1H), 2.43-2.29 (m, 1H), 2.00-1.93 (m, 1H), 1.92-1.69 (m, 4H), 1.52-1.36 (m, 2H).

Example 2

(1R*,2S*)-2-[1-(4-Bromobenzyl)-5-(quinolin-2-ylmethoxy)-1H-benzimidazol-2-yl]cyclohexanecarboxylic acid

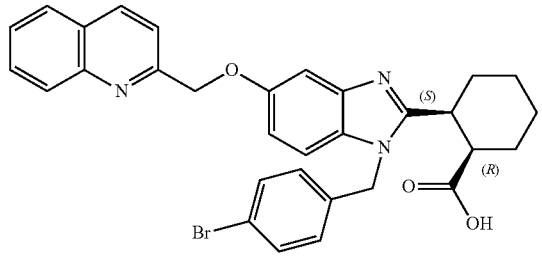

Racemic cis-2-[1-(4-bromobenzyl)-5-(quinolin-2-ylmethoxy)-1H-benzimidazol-2-yl]cyclohexanecarboxylic acid (prepared as described in Example 1) was purified by chiral SFC on (CHIRALCEL OD-H 5 μm 250×20 mm). Mobile phase (55% CO$_2$, 45% MeOH) to yield the tile compound as the first eluting isomer. MS (ESI): mass calcd. for $C_{31}H_{28}BrN_3O_3$, 569.13; m/z found, 570.1 [M+H]$^+$.

Example 3

(1S*,2R*)-2-[1-(4-Bromobenzyl)-5-(quinolin-2-ylmethoxy)-1H-benzimidazol-2-yl]cyclohexanecarboxylic acid

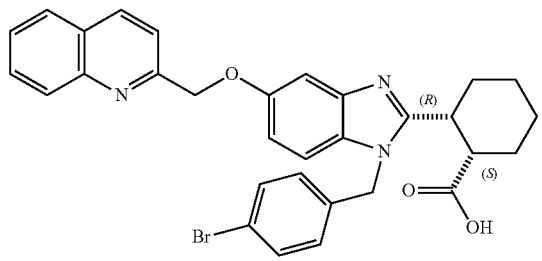

Racemic cis-2-[1-(4-bromobenzyl)-5-(quinolin-2-ylmethoxy)-1H-benzimidazol-2-yl]cyclohexanecarboxylic acid (prepared as described in Example 1) was purified by chiral SFC on (CHIRALCEL OD-H 5 μm 250×20 mm). Mobile phase (55% CO$_2$, 45% MeOH) to yield the tile compound as the second eluting isomer. MS (ESI): mass calcd. for $C_{31}H_{28}BrN_3O_3$, 569.13; m/z found, 570.1 [M+H]$^+$. $^1$H NMR (500 MHz, CD$_3$OD) δ 8.36 (d, J=8.5, 1H), 8.05 (d, J=8.5, 1H), 7.93 (d, J=8.2, 1H), 7.78 (ddd, J=8.4, 6.9, 1.4, 1H), 7.74 (d, J=8.5, 1H), 7.60 (ddd, J=8.1, 7.0, 1.1, 1H), 7.47-7.41 (m, 2H), 7.29 (d, J=2.3, 1H), 7.19 (d, J=8.8, 1H), 7.05 (d, J=8.5, 2H), 7.01 (dd, J=8.8, 2.4, 1H), 5.53-5.41 (m, 2H), 5.39 (s, 2H), 3.60-3.51 (m, 1H), 2.88-2.76 (m, 1H), 2.43-2.29 (m, 1H), 2.00-1.93 (m, 1H), 1.92-1.69 (m, 4H), 1.52-1.36 (m, 2H).

Example 4 racemic cis-2-[1-(3-Bromobenzyl)-5-(quinolin-2-ylmethoxy)-1H-benzimidazol-2-yl]cyclohexanecarboxylic acid as the TFA salt

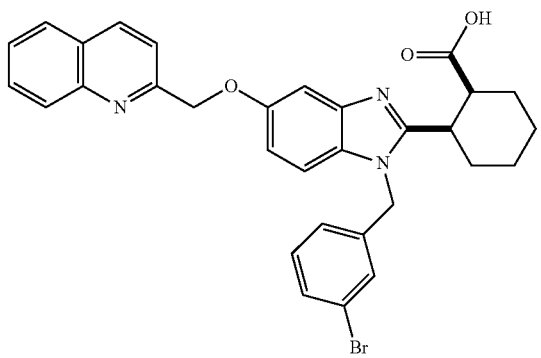

The title compound was prepared using analogous conditions to those described in Example 1 using (3-bromophenyl)methanamine. MS (ESI): mass calcd. for $C_{31}H_{28}BrN_3O_3$, 569.13; m/z found, 570.1 [M+H]$^+$. $^1$H NMR (400 MHz, CD$_3$OD) δ 8.36 (d, J=8.5, 1H), 8.05 (d, J=8.5, 1H), 7.93 (d, J=8.1, 1H), 7.82-7.71 (m, 2H), 7.64-7.56 (m, 1H), 7.42 (d, J=8.0, 1H), 7.35 (s, 1H), 7.29 (d, J=2.3, 1H), 7.23-7.17 (m, 2H), 7.10-6.98 (m, 2H), 5.54 (d, J=17.2, 1H), 5.46 (d, J=17.2, 1H), 5.39 (s, 2H), 3.62-3.51 (m, 1H), 2.86-2.75 (m, 1H), 2.40-2.25 (m, 1H), 2.06-1.96 (m, 1H), 1.91-1.67 (m, 4H), 1.56-1.35 (m, 2H).

Example 5

2,2-Dimethyl-3-{5-(quinolin-2-ylmethoxy)-1-[3-(trifluoromethoxy)benzyl]-1H-benzimidazol-2-yl}propanoic acid

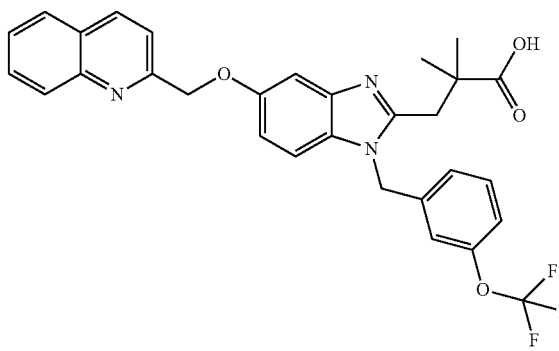

The title compound was prepared using methods similar to those in Example 1 using (3-(trifluoromethoxy)phenyl)methanamine and 2-((4-fluoro-3-nitrophenoxy)methyl)quinolone in Step A and 3,3-dimethyldihydrofuran-2,5-dione in Step C. MS (ESI): mass calcd. for $C_{30}H_{26}F_3N_3O_4$, 549.19; m/z found, 550.2 [M+H]$^+$. $^1$H NMR (500 MHz, CD$_3$OD) δ 8.35 (d, J=8.4, 1H), 8.05 (d, J=8.5, 1H), 7.93 (d, J=8.2, 1H), 7.82-7.67 (m, 2H), 7.60 (t, J=7.5, 1H), 7.36 (t, J=7.7, 1H), 7.30-7.09 (m, 3H), 7.03-6.90 (m, 3H), 5.66 (s, 2H), 5.40 (s, 2H), 3.15-2.97 (broad s, 2H), 1.24 (s, 6H).

Example 6

2,2-Dimethyl-3-{5-(quinolin-2-ylmethoxy)-1-[2-(trifluoromethoxy)benzyl]-1H-benzimidazol-2-yl}propanoic acid

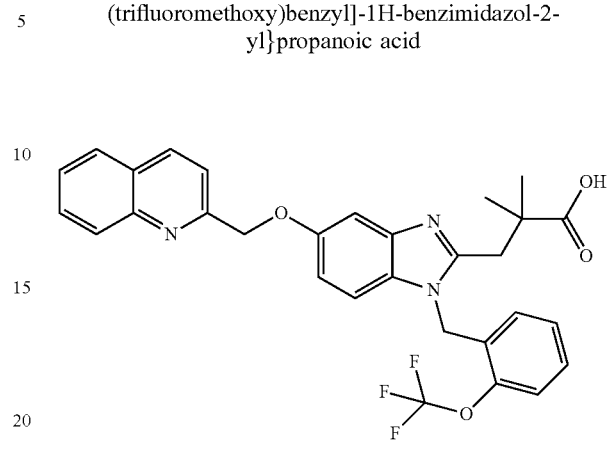

The title compound was prepared using methods similar to those in Example 1 using (2-(trifluoromethoxy)phenyl) in Step A and 3,3-dimethyldihydrofuran-2,5-dione in Step C. MS (ESI): mass calcd. for $C_{30}H_{26}F_3N_3O_4$, 549.19; m/z found, 550.2 [M+H]$^+$. $^1$H NMR (500 MHz, CD$_3$OD) δ 8.35 (d, J=8.5, 1H), 8.05 (d, J=8.5, 1H), 7.93 (d, J=8.2, 1H), 7.81-7.70 (m, 2H), 7.64-7.57 (m, 1H), 7.39-7.32 (m, 2H), 7.24 (d, J=2.3, 1H), 7.22-7.16 (m, 1H), 7.06 (d, J=8.8, 1H), 6.95 (dd, J=8.8, 2.4, 1H), 6.70 (d, J=7.0, 1H), 5.67 (s, 2H), 5.39 (s, 2H), 3.10 (s, 2H), 1.25 (s, 6H).

Example 7

2,2-Dimethyl-3-{5-(quinolin-2-ylmethoxy)-1-[4-(trifluoromethoxy)benzyl]-1H-benzimidazol-2-yl}propanoic acid

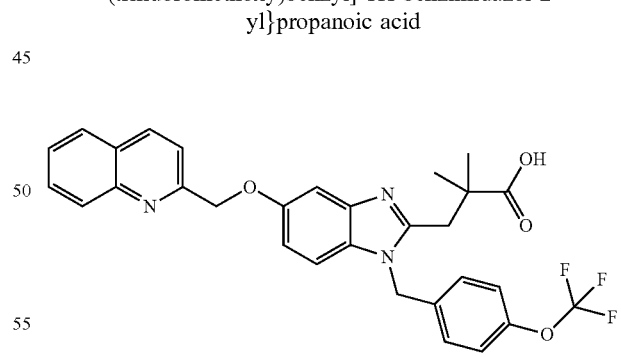

The title compound was prepared using methods similar to those in Example 1 using (4-(trifluoromethoxy)phenyl)methanamine in Step A and 3,3-dimethyldihydrofuran-2,5-dione in Step C. MS (ESI): mass calcd. for $C_{30}H_{26}F_3N_3O_4$, 549.19; m/z found, 550.2 [M+H]$^+$. $^1$H NMR (500 MHz, CD$_3$OD) δ 8.35 (d, J=8.5, 1H), 8.05 (d, J=8.4, 1H), 7.93 (d, J=7.5, 1H), 7.81-7.72 (m, 2H), 7.62-7.58 (m, 1H), 7.21-7.10 (m, 5H), 7.01-6.96 (m, 2H), 5.62 (s, 2H), 5.39 (d, J=9.9, 2H), 3.08 (s, 2H), 1.24 (s, 6H).

Example 8 racemic 1-{[1-(4-Bromobenzyl)-5-(quinolin-2-yl-methoxy)-1H-benzimidazol-2-yl]methyl}-2,2-dimethylcyclopentanecarboxylic acid

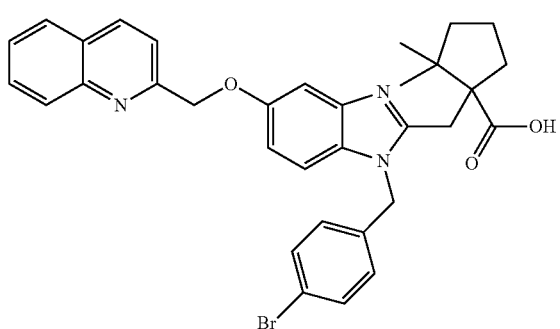 [SMILES: CC1(C)CCCC1(Cc1nc2cc(OCc3ccc4ccccc4n3)ccc2n1Cc1ccc(Br)cc1)C(=O)O]

The title compound was prepared using analogous conditions described in Example 1 using 6,6-dimethyl-2-oxaspiro[4.4]nonane-1,3-dione in Step C. MS (ESI): mass calcd. for $C_{33}H_{32}BrN_3O_3$, 597.16; m/z found, 595.0; 597.0 [M+H]$^+$. $^1$H NMR (400 MHz, CD$_3$OD) δ 8.37 (d, J=8.5, 1H), 8.05 (d, J=8.4, 1H), 7.94 (d, J=8.3, 1H), 7.82-7.76 (m, 1H), 7.74 (d, J=8.5, 1H), 7.65-7.57 (m, 1H), 7.49-7.42 (m, 2H), 7.27-7.22 (m, 2H), 7.04-6.97 (m, 3H), 5.53 (d, J=17.0, 1H), 5.42 (d, J=9.7, 1H), 5.39 (s, 2H), 3.36 (d, J=15.4, 1H), 2.71 (d, J=15.2, 1H), 2.59-2.49 (m, 1H), 2.00-1.88 (m, 1H), 1.82-1.70 (m, 1H), 1.69-1.59 (m, 3H), 1.10 (s, 3H), 0.98 (s, 3H).

Example 9

3-[1-(4-Bromo-2-fluorobenzyl)-5-(quinolin-2-yl-methoxy)-1H-benzimidazol-2-yl]-2,2-dimethylpropanoic acid

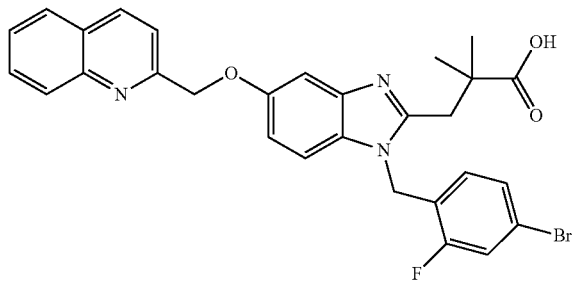 [SMILES: CC(C)(Cc1nc2cc(OCc3ccc4ccccc4n3)ccc2n1Cc1ccc(Br)cc1F)C(=O)O]

The title compound was prepared in a manner analogous to that in Example 1 using 4-bromo-2-fluorobenzylamine in Step A and 2,2-dimethylsuccinic anhydride in Step C. MS (ESI): mass calcd. for $C_{29}H_{25}BrFN_3O_3$, 561.11; m/z found, 562.1 [M+H]$^+$. $^1$H NMR (500 MHz, CD$_3$OD) δ 8.56 (d, J=8.5, 1H), 8.13 (d, J=8.5, 1H), 8.03 (d, J=7.8, 1H), 7.88 (ddd, J=8.4, 7.0, 1.3, 1H), 7.83 (d, J=8.5, 1H), 7.73-7.66 (m, 1H), 7.58 (d, J=9.2, 1H), 7.44 (td, J=4.8, 1.9, 2H), 7.37 (dd, J=8.3, 1.7, 1H), 7.34 (dd, J=9.2, 2.4, 1H), 7.22 (t, J=8.2, 1H), 5.85 (s, 2H), 5.56 (s, 2H), 3.53 (s, 2H), 1.41 (s, 6H).

Example 10

3-[1-(2,4-Difluorobenzyl)-5-(quinolin-2-ylmethoxy)-1H-benzimidazol-2-yl]-2,2-dimethylpropanoic acid

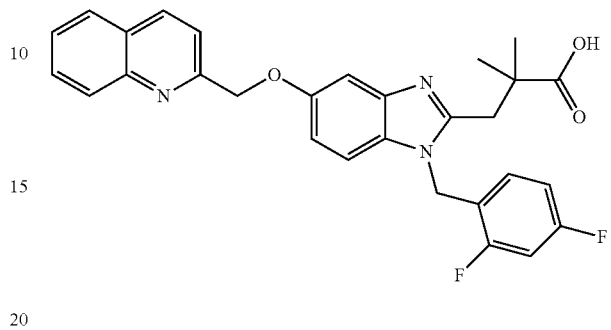

The title compound was prepared in a manner analogous to that Example 1 using 2,4-difluorobenzylamine Step A and 2,2-dimethylsuccinic anhydride in Step C. MS (ESI): mass calcd. for $C_{29}H_{25}F_2N_3O_3$, 501.19; m/z found, 502.2 [M+H]$^+$. $^1$H NMR (500 MHz, CDCl$_3$) δ 8.18 (d, J=8.4, 1H), 8.09 (d, J=8.1, 1H), 7.81 (d, J=8.0, 1H), 7.72 (app t, J=7.3, 1H), 7.66 (d, J=8.4, 1H), 7.54 (app t, J=7.3, 1H), 7.41 (s, 1H), 7.16 (d, J=8.3, 1H), 7.05 (d, J=8.3, 1H), 6.87 (t, J=9.5, 1H), 6.83-6.74 (m, 2H), 5.40 (s, 2H), 5.37 (s, 2H), 3.15 (s, 2H), 1.28 (s, 6H).

Example 11 racemic cis-3-[1-(2,4-Difluorobenzyl)-5-(quinolin-2-ylmethoxy)-1H-benzimidazol-2-yl]-2,2-dimethylcyclopropanecarboxylic acid

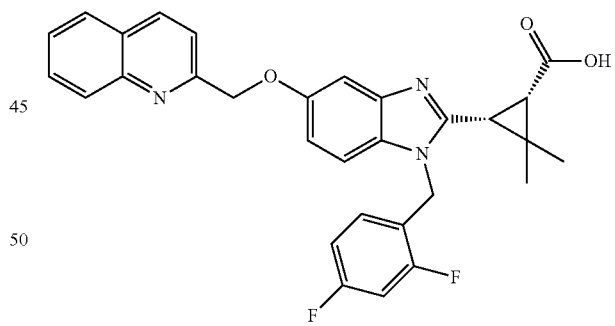

The title compound was prepared in a manner analogous to that in Example 1 using 2,4-difluorobenzylamine in Step A and cis-6,6-dimethyl-3-oxabicyclo[3.1.0]hexane-2,4-dione in Step C. MS (ESI): mass calcd. for $C_{30}H_{25}F_2N_3O_3$, 513.19; m/z found, 514.2 [M+H]$^+$. $^1$H NMR (500 MHz, CD$_3$OD) δ 8.50 (d, J=8.5, 1H), 8.10 (d, J=8.5, 1H), 8.01 (d, J=7.6, 1H), 7.86 (ddd, J=8.4, 6.9, 1.4, 1H), 7.80 (d, J=8.5, 1H), 7.71-7.66 (m, 1H), 7.65 (d, J=9.4, 1H), 7.46-7.42 (m, 1H), 7.41 (d, J=2.2, 1H), 7.36 (dd, J=9.2, 2.4, 1H), 7.07 (ddd, J=11.0, 8.9, 2.5, 1H), 7.01 (td, J=8.1, 1.7, 1H), 5.72 (d, J=16.1, 1H), 5.62 (d, J=16.1, 1H), 5.53 (s, 2H), 2.70 (d, J=8.2, 1H), 2.49 (d, J=8.2, 1H), 1.46 (s, 3H), 1.42 (s, 3H).

Example 12

3-[1-(2,4-Dichlorobenzyl)-5-(quinolin-2-yl-methoxy)-1H-benzimidazol-2-yl]-2,2-dimethylpropanoic acid

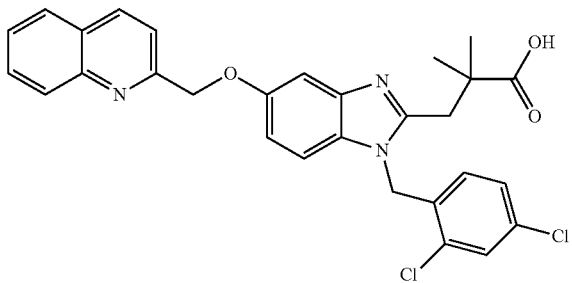 [SMILES: CC(C)(Cc1nc2cc(OCc3ccc4ccccc4n3)ccc2n1Cc1ccc(Cl)cc1Cl)C(=O)O]

The title compound was prepared in a manner analogous to that in Example 1 using 2,4-dichlorobenzylamine in Step A and 2,2-dimethylsuccinic anhydride in Step C. MS (ESI): mass calcd. for $C_{29}H_{25}O_2N_3O_3$, 533.13; m/z found, 534.1 [M+H]$^+$. $^1$H NMR (500 MHz, CD$_3$OD) δ 8.48 (d, J=8.5, 1H), 8.10 (d, J=8.6, 1H), 8.00 (d, J=7.6, 1H), 7.85 (ddd, J=8.5, 7.0, 1.4, 1H), 7.79 (d, J=8.5, 1H), 7.70-7.64 (m, 1H), 7.62 (d, J=2.1, 1H), 7.44 (d, J=9.2, 1H), 7.41 (d, J=2.2, 1H), 7.34-7.25 (m, 2H), 6.96 (d, J=8.4, 1H), 5.88 (s, 2H), 5.53 (s, 2H), 3.47 (s, 2H), 1.40 (s, 6H).

Example 13 racemic cis-3-[1-(2,4-Dichlorobenzyl)-5-(quinolin-2-ylmethoxy)-1H-benzimidazol-2-yl]-2,2-dimethyl-cyclopropanecarboxylic acid

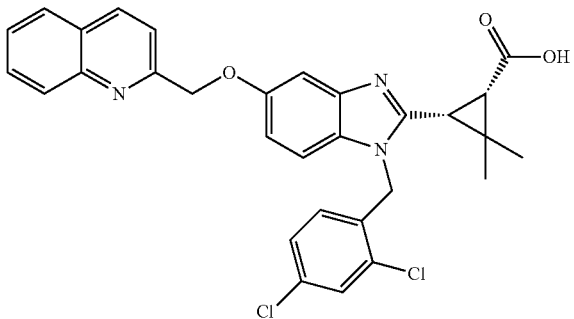 [SMILES: CC1(C)[C@H](c2nc3cc(OCc4ccc5ccccc5n4)ccc3n2Cc2ccc(Cl)cc2Cl)[C@@H]1C(=O)O]

The title compound was prepared in a manner analogous to that in Example 1 using 2,4-dichlorobenzylamine in Step A and cis-6,6-dimethyl-3-oxabicyclo[3.1.0]hexane-2,4-dione in Step C. MS (ESI): mass calcd. for $C_{30}H_{25}O_2N_3O_3$, 545.13; m/z found, 546.1 [M+H]$^+$. $^1$H NMR (500 MHz, CD$_3$OD) δ 8.53 (d, J=8.5, 1H), 8.11 (d, J=8.4, 1H), 8.02 (d, J=7.5, 1H), 7.87 (ddd, J=8.4, 7.0, 1.3, 1H), 7.82 (d, J=8.5, 1H), 7.73-7.66 (m, 1H), 7.63 (d, J=2.1, 1H), 7.51 (d, J=9.2, 1H), 7.44 (d, J=2.3, 1H), 7.36 (dd, J=9.2, 2.3, 1H), 7.33 (dd, J=8.4, 2.1, 1H), 7.06 (d, J=8.4, 1H), 5.76 (d, J=16.7, 1H), 5.71 (d, J=16.8, 1H), 5.55 (s, 2H), 2.65 (d, J=8.2, 1H), 2.45 (d, J=8.2, 1H), 1.42 (s, 3H), 1.41 (s, 3H).

Example 14 racemic cis-3-[1-(4-Bromo-2-fluorobenzyl)-5-(quinolin-2-ylmethoxy)-1H-benzimidazol-2-yl]-2,2-dimethylcyclopropanecarboxylic acid

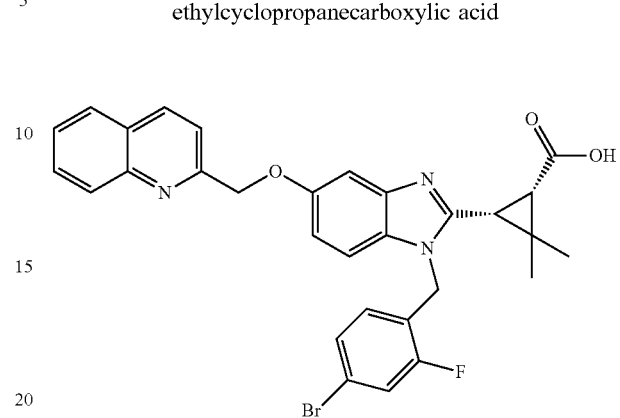

The title compound was prepared in a manner analogous to that in Example 1 using 4-bromo-2-fluorobenzylamine in Step A and cis-6,6-dimethyl-3-oxabicyclo[3.1.0]hexane-2,4-dione in Step C. MS (ESI): mass calcd. for $C_{30}H_{25}BrFN_3O_3$, 573.11; m/z found, 574.0 [M+H]$^+$. $^1$H NMR (500 MHz, CD$_3$OD) δ 8.51 (d, J=8.5, 1H), 8.11 (d, J=8.2, 1H), 8.01 (d, J=7.5, 1H), 7.86 (ddd, J=8.5, 7.0, 1.4, 1H), 7.81 (d, J=8.5, 1H), 7.68 (ddd, J=8.1, 7.0, 1.0, 1H), 7.64 (d, J=9.2, 1H), 7.46 (dd, J=10.0, 1.9, 1H), 7.41-7.38 (m, 2H), 7.37 (dd, J=9.2, 2.4, 1H), 7.27 (t, J=8.2, 1H), 5.72 (d, J=16.3, 1H), 5.63 (d, J=16.3, 1H), 5.54 (s, 2H), 2.69 (d, J=8.2, 1H), 2.49 (d, J=8.2, 1H), 1.45 (s, 3H), 1.42 (s, 3H).

Example 15 racemic cis-2-[1-(4-Bromo-2-fluorobenzyl)-5-(quinolin-2-ylmethoxy)-1H-benzimidazol-2-yl]cyclohexanecarboxylic acid

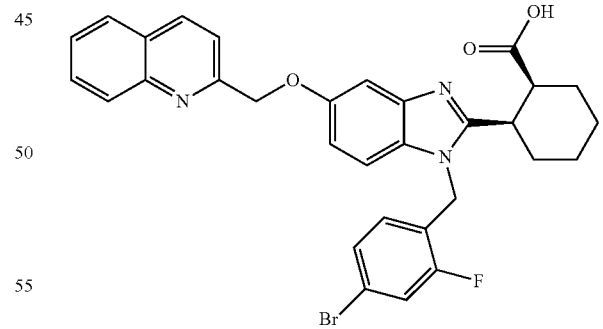

The title compound was prepared in a manner analogous to that in Example 1 using 4-bromo-2-fluorobenzylamine in Step A. MS (ESI): mass calcd. for $C_{31}H_{27}BrFN_3O_3$, 587.12; m/z found, 588.1 [M+H]$^+$. $^1$H NMR (500 MHz, CD$_3$OD) δ 8.36 (d, J=8.5, 1H), 8.05 (d, J=8.5, 1H), 7.93 (d, J=7.2, 1H), 7.78 (ddd, J=8.4, 6.9, 1.4, 1H), 7.74 (d, J=8.5, 1H), 7.61 (ddd, J=8.1, 6.9, 1.1, 1H), 7.42 (d, J=9.8, 1.9, 1H), 7.29 (d, J=1.9, 1H), 7.27-7.21 (m, 2H), 7.05 (dd, J=8.9, 2.4, 1H), 6.78 (t, J=8.2, 1H), 5.56 (d, J=17.4, 1H), 5.50 (d, J=17.4, 1H), 5.40 (s, 2H), 3.62-3.54 (m, 1H), 2.87-2.79 (m, 1H), 2.41-2.31 (m, 1H), 2.06-2.02 (m, 1H), 1.90-1.70 (m, 4H), 1.53-1.42 (m, 2H).

Example 16 racemic trans-2-[1-(4-Bromo-2-fluorobenzyl)-5-(quinolin-2-ylmethoxy)-1H-benzimidazol-2-yl]cyclohexanecarboxylic acid

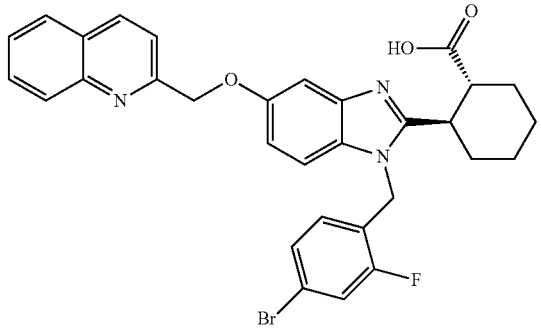 [SMILES: O=C(O)[C@@H]1CCCC[C@H]1c1nc2cc(OCc3ccc4ccccc4n3)ccc2n1Cc1ccc(Br)cc1F]

The title compound was prepared using methods similar to those in Example 1 using 4-bromo-2-fluorobenzylamine in Step A and trans-cyclohexanedicarboxylic anhydride in Step C. MS (ESI): mass calcd. for $C_{31}H_{27}BrFN_3O_3$, 587.12; m/z found, 588.1 [M+H]$^+$. $^1$H NMR (500 MHz, CD$_3$OD) δ 8.62 (d, J=7.1, 1H), 8.16 (d, J=8.5, 1H), 8.07 (d, J=8.2, 1H), 7.92 (app t, J=7.7, 1H), 7.88 (d, J=8.5, 1H), 7.73 (app t, J=9.7, 2H), 7.48 (dd, J=10.0, 1.8, 1H), 7.41-7.36 (m, 3H), 7.32 (app t, J=8.2, 1H), 5.91 (d, J=16.6, 1H), 5.78 (d, J=16.6, 1H), 5.59 (s, 2H), 3.59 (td, J=12.1, 3.4, 1H), 2.99 (td, J=11.4, 3.1, 1H), 2.41-2.34 (m, 1H), 1.98-1.90 (m, 1H), 1.89-1.77 (m, 2H), 1.66-1.34 (m, 4H).

Example 17 racemic 1-{[1-(4-Bromobenzyl)-5-(quinolin-2-ylmethoxy)-1H-benzimidazol-2-yl]methyl}-3,3-dimethylcyclopentanecarboxylic acid as the TFA salt

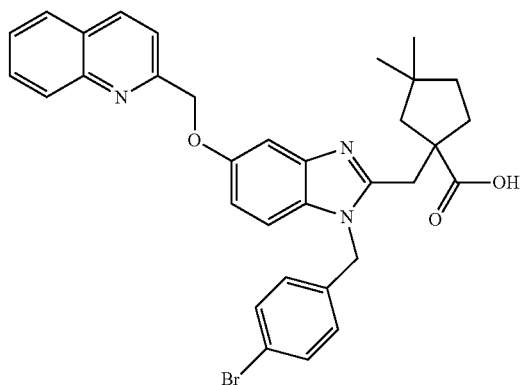 [SMILES: CC1(C)CCC(Cc2nc3cc(OCc4ccc5ccccc5n4)ccc3n2Cc2ccc(Br)cc2)(C(=O)O)C1]

The title compound was prepared using analogous conditions to those described in Example 1 using racemic 7,7-dimethyl-2-oxaspiro[4.4]nonane-1,3-dione in Step C. MS (ESI): mass calcd. for $C_{33}H_{32}BrN_3O_3$, 597.16; m/z found, 598.1 [M+H]$^+$. $^1$H NMR (600 MHz, CD$_3$OD) δ 8.47 (d, J=8.5, 1H), 8.09 (d, J=8.5, 1H), 8.00 (d, J=7.4, 1H), 7.85 (ddd, J=8.4, 6.9, 1.4, 1H), 7.78 (d, J=8.5, 1H), 7.67 (ddd, J=8.1, 6.9, 1.1, 1H), 7.57-7.51 (m, 3H), 7.37 (d, J=2.3, 1H), 7.33 (dd, J=9.1, 2.4, 1H), 7.15 (d, J=8.6, 2H), 5.76-5.66 (m, 2H), 5.49 (d, J=36.7, 2H), 3.57-3.48 (m, 2H), 2.40 (dt, J=12.8, 6.3, 1H), 2.28 (d, J=13.7, 1H), 2.00-1.86 (m, 1H), 1.73-1.52 (m, 3H), 1.08 (d, J=9.8, 6H).

Example 18 racemic cis-2-(1-(4-(5-Methyl-1,2,4-oxadiazol-3-yl)benzyl)-5-(quinolin-2-ylmethoxy)-1H-benzo[d]imidazol-2-yl)cyclohexanecarboxylic acid as the TFA salt

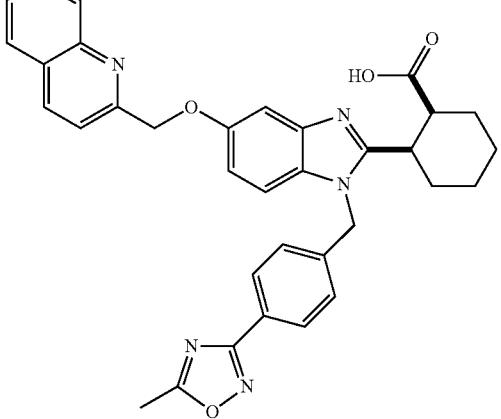

The title compound was prepared using analogous conditions to those described in Example 1 using (4-(5-methyl-1,2,4-oxadiazol-3-yl)phenyl)methanamine in Step A and cis-hexahydroisobenzofuran-1,3-dione Step C. MS (ESI): mass calcd. for $C_{34}H_{31}N_5O_4$, 573.24; m/z found, 574.2 [M+H]$^+$. $^1$H NMR (600 MHz, CD$_3$OD) δ 8.49 (d, J=8.5, 1H), 8.10 (d, J=8.6, 1H), 8.03 (d, J=8.4, 2H), 8.01 (d, J=7.7, 1H), 7.86 (ddd, J=8.4, 6.9, 1.4, 1H), 7.80 (d, J=8.5, 1H), 7.70-7.66 (m, 1H), 7.54 (d, J=9.1, 1H), 7.39 (d, J=2.3, 1H), 7.34 (dd, J=9.1, 2.4, 1H), 7.29 (d, J=8.5, 2H), 5.87 (dd, J=43.2, 17.3, 2H), 5.54 (s, 2H), 3.65 (dt, J=12.1, 3.8, 1H), 2.95 (d, J=4.0, 1H), 2.64 (s, 3H), 2.37-2.25 (m, 1H), 2.23-2.14 (m, 1H), 2.11-2.05 (m, 1H), 2.01-1.92 (m, 1H), 1.84-1.71 (m, 1H), 1.69 (d, J=12.3, 1H), 1.58-1.45 (m, 2H).

Example 19

2-Ethyl-2-({1-[4-(5-methyl-1,2,4-oxadiazol-3-yl)benzyl]-5-(quinolin-2-ylmethoxy)-1H-benzimidazol-2-yl}methyl)butanoic acid as the TFA salt

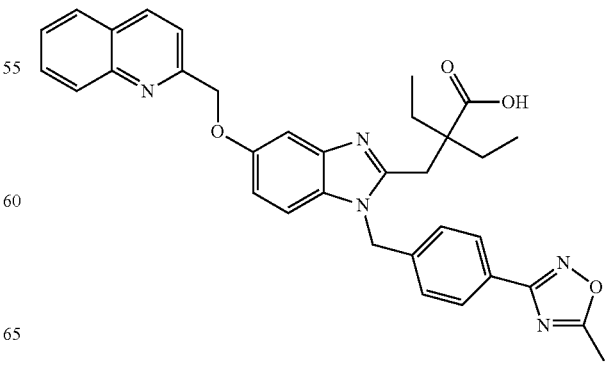

The title compound was prepared using analogous conditions to those described in Example 1 using (4-(5-methyl-1,2,4-oxadiazol-3-yl)phenyl)methanamine in Step A and 3,3-diethyldihydrofuran-2,5-dione in Step C. MS (ESI): mass calcd. for $C_{34}H_{33}N_5O_4$, 575.25; m/z found, 576.1 [M+H]$^+$. $^1$H NMR (600 MHz, CD$_3$OD) δ 8.62 (d, J=8.5, 1H), 8.15 (d, J=8.5, 1H), 8.07 (d, J=8.1, 1H), 8.06-8.03 (m, 2H), 7.92 (ddd, J=8.5, 6.9, 1.4, 1H), 7.87 (d, J=8.5, 1H), 7.74 (ddd, J=8.1, 7.0, 1.0, 1H), 7.62 (d, J=9.2, 1H), 7.47 (d, J=2.3, 1H), 7.39 (d, J=8.5, 2H), 7.36 (dd, J=9.2, 2.4, 1H), 5.87 (s, 2H), 5.59 (s, 2H), 3.45 (s, 2H), 2.64 (s, 3H), 1.87-1.74 (m, 4H), 0.91-0.86 (m, 6H).

Example 20

1-({1-[4-(5-Methyl-1,2,4-oxadiazol-3-yl)benzyl]-5-(quinolin-2-ylmethoxy)-1H-benzimidazol-2-yl}methyl)cyclopentanecarboxylic acid as the TFA salt

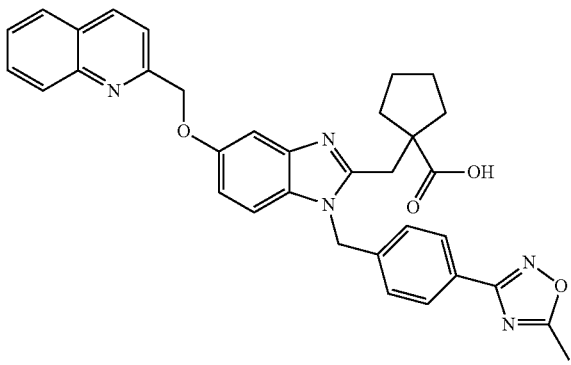 [SMILES: Cc1nc(-c2ccc(Cn3c(CC4(C(=O)O)CCCC4)nc4cc(OCc5ccc6ccccc6n5)ccc43)cc2)no1]

The title compound was prepared using analogous conditions to those described in Example 1 using (4-(5-methyl-1,2,4-oxadiazol-3-yl)phenyl)methanamine in Step A. MS (ESI): mass calcd. for $C_{34}H_{31}N_5O_4$, 573.24; m/z found, 574.2 [M+H]$^+$. $^1$H NMR (600 MHz, CD$_3$OD) δ 8.61 (d, J=8.5, 1H), 8.15 (d, J=8.2, 1H), 8.08-8.00 (m, 3H), 7.90 (ddd, J=18.2, 12.0, 10.1, 1H), 7.85 (app t, J=7.6, 1H), 7.76-7.69 (m, 1H), 7.60 (dd, J=9.0, 4.7, 1H), 7.43 (d, J=2.3, 1H), 7.38 (d, J=8.4, 2H), 7.35 (dd, J=9.2, 2.4, 1H), 5.85 (s, 2H), 5.58 (s, 2H), 3.55 (d, J=13.3, 2H), 2.64 (s, 3H), 2.34-2.23 (m, 2H), 1.85-1.72 (m, 6H).

Example 21 racemic trans-2-[1-(4-Bromobenzyl)-5-(quinolin-2-ylmethoxy)-1H-benzimidazol-2-yl]cyclohexanecarboxylic acid as the TFA salt

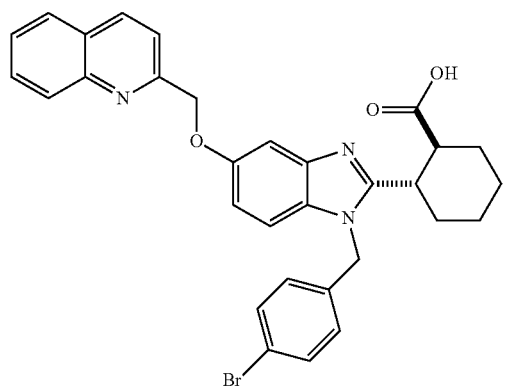

The title compound was prepared using analogous conditions to those described in Example 1 using trans-hexahydroisobenzofuran-1,3-dione in Step C. MS (ESI): mass calcd. for $C_{31}H_{28}BrN_3O_3$, 569.13; m/z found, 570.1 [M+H]$^+$. $^1$H NMR (600 MHz, CD$_3$OD) δ 8.48 (d, J=8.5 Hz, 1H), 8.09 (d, J=8.4 Hz, 1H), 8.02-7.98 (m, 1H), 7.88-7.82 (m, 1H), 7.78 (d, J=8.5 Hz, 1H), 7.70-7.62 (m, 2H), 7.56-7.54 (m, 2H), 7.36-7.33 (m, 2H), 7.29-7.25 (m, 2H), 5.83 (d, J=16.5 Hz, 1H), 5.72 (d, J=16.6 Hz, 1H), 5.53 (s, 2H), 3.55 (td, J=11.9, 3.5 Hz, 1H), 2.98 (td, J=11.7, 3.7 Hz, 1H), 2.37 (dd, J=13.0, 3.6 Hz, 1H), 1.98-1.87 (m, 1H), 1.87-1.72 (m, 2H), 1.65-1.27 (m, 4H).

Example 22 racemic 1-{[1-(4-Bromobenzyl)-5-(quinolin-2-ylmethoxy)-1H-benzimidazol-2-yl]methyl}-2,3-dihydro-1H-indene-1-carboxylic acid as the TFA salt

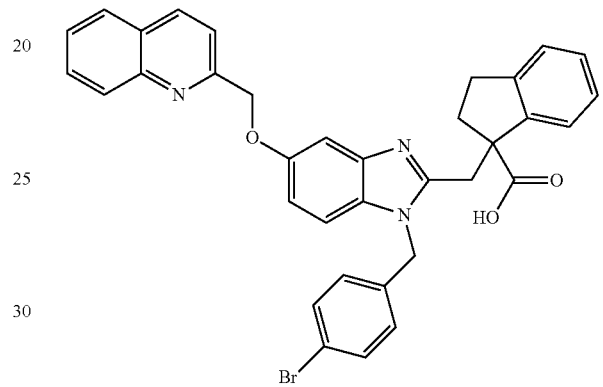

The title compound was prepared using analogous conditions to those described in Example 1 using racemic 2',3'-dihydro-2H-spiro[furan-3,1'-indene]-2,5(4H)-dione in Step C. MS (ESI): mass calcd. for $C_{35}H_{28}BrN_3O_3$, 617.13; m/z found, 618.1 [M+H]$^+$. $^1$H NMR (600 MHz, CD$_3$OD) δ 8.53 (d, J=8.5, 1H), 8.12 (d, J=8.5, 1H), 8.03 (d, J=8.0, 1H), 7.88 (ddd, J=8.4, 6.9, 1.4, 1H), 7.81 (d, J=8.5, 1H), 7.73-7.68 (m, 1H), 7.51-7.45 (m, 3H), 7.42 (d, J=2.3, 1H), 7.35-7.25 (m, 3H), 7.13 (dd, J=11.1, 5.0, 1H), 6.97 (d, J=8.4, 3H), 5.54 (s, 2H), 5.30 (d, J=16.6, 1H), 5.11 (d, J=16.7, 1H), 3.78 (d, J=15.4, 1H), 3.73 (d, J=15.4, 1H), 3.12 (ddd, J=16.1, 8.7, 4.0, 1H), 2.96 (dt, J=16.1, 7.9, 1H), 2.80 (dt, J=13.0, 8.7, 1H), 2.38-2.25 (m, 1H).

Example 23

2-{[1-(4-Bromobenzyl)-5-(quinolin-2-ylmethoxy)-1H-benzimidazol-2-yl]methyl}-2-ethylbutanoic acid as the TFA salt

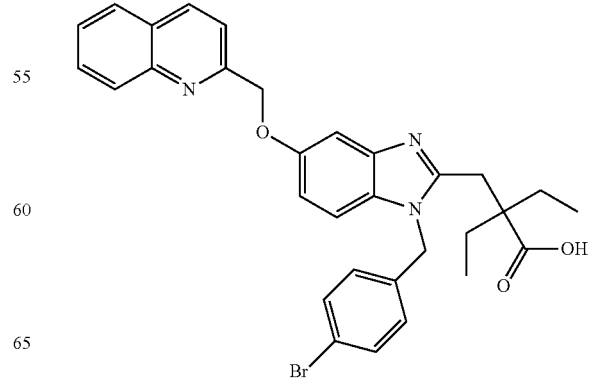

The title compound was prepared using analogous conditions to those described in Example 1 using 3,3-diethyl-dihydrofuran-2,5-dione in Step C. MS (ESI): mass calcd. for $C_{31}H_{30}BrN_3O_3$, 571.15; m/z found, 572.1 [M+H]+. 1H NMR (600 MHz, $CD_3OD$) δ 8.53 (d, J=8.5, 1H), 8.12 (d, J=8.5, 1H), 8.03 (d, J=7.6, 1H), 7.88 (ddd, J=8.5, 6.9, 1.4, 1H), 7.82 (d, J=8.5, 1H), 7.69 (ddd, J=8.1, 7.0, 1.1, 1H), 7.57 (t, J=8.8, 1H), 7.55-7.51 (m, 2H), 7.43 (d, J=2.3, 1H), 7.35 (dd, J=9.2, 2.4, 1H), 7.17 (d, J=8.6, 2H), 5.75 (s, 2H), 5.54 (s, 2H), 3.41 (s, 2H), 1.85-1.71 (m, 4H), 0.88 (t, J=7.5, 6H).

Example 24

2-{[1-(4-Bromobenzyl)-5-(quinolin-2-ylmethoxy)-1H-benzimidazol-2-yl]methyl}-2,3-dihydro-1H-indene-2-carboxylic acid as the TFA salt

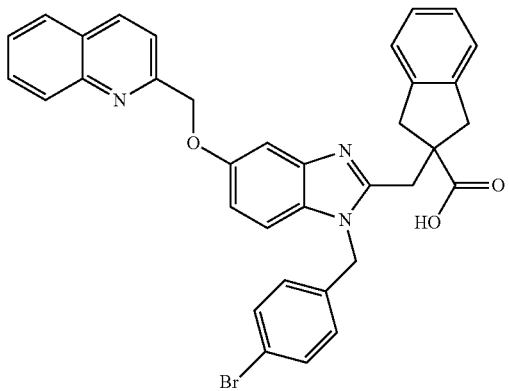 [SMILES: O=C(O)C1(Cc2nc3cc(OCc4ccc5ccccc5n4)ccc3n2Cc2ccc(Br)cc2)Cc2ccccc2C1]

The title compound was prepared using analogous conditions to those described in Example 1 using 1,3'-dihydro-2H-spiro[furan-3,2'-indene]-2,5(4H)-dione in Step C. MS (ESI): mass calcd. for $C_{35}H_{28}BrN_3O_3$, 617.13; m/z found, 618.0 [M+H]+. 1H NMR (500 MHz, DMSO-$d_6$) δ 8.43 (d, J=8.5 Hz, 1H), 8.05 (d, J=8.5 Hz, 1H), 8.02-7.97 (m, 1H), 7.84-7.79 (m, 1H), 7.70 (d, J=8.5 Hz, 1H), 7.64 (t, J=7.4 Hz, 1H), 7.51-7.45 (m, 2H), 7.41 (d, J=8.9 Hz, 1H), 7.25 (d, J=2.4 Hz, 1H), 7.17 (dd, J=5.3, 3.3 Hz, 2H), 7.11-7.03 (m, 5H), 5.50 (s, 2H), 5.44 (s, 2H), (4H under water peak), 3.16 (d, J=16.3 Hz, 2H).

Example 25 racemic cis-3-{1-[(1-Ethyl-1H-indazol-3-yl)methyl]-5-(quinolin-2-ylmethoxy)-1H-benzimidazol-2-yl}-2,2-dimethylcyclopropanecarboxylic acid

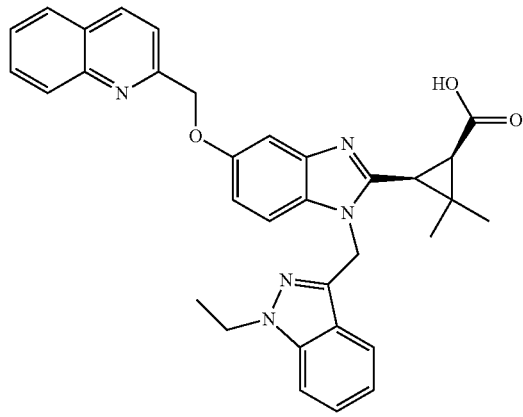 [SMILES: CCn1nc(Cn2c([C@H]3[C@@H](C(=O)O)C3(C)C)nc3cc(OCc4ccc5ccccc5n4)ccc32)c2ccccc21]

Step A: N-((1-ethyl-1H-indazol-3-yl)methyl)-2-nitro-4-(quinolin-2-ylmethoxy)aniline To a 10 mL round-bottomed flask were added 2-((4-fluoro-3-nitrophenoxy)methyl)quinoline (50 mg, 0.17 mmol) and acetonitrile (0.84 mL). To the resulting mixture were added 1-(1-ethyl-1H-indazol-3-yl)methanamine HCl salt (37.4 mg, 0.17 mmol) and $K_2CO_3$ (81 mg, 0.59 mmol). The resulting mixture was heated to 80° C. for 3 days. The mixture was cooled to RT and concentrated to dryness. The residue was purified by FCC to give the title compound. MS (ESI): mass calcd. for $C_{26}H_{23}N_5O_3$, 453.18; m/z found, 454.2 [M+H]+.

Step B: N-1-((1-ethyl-1H-indazol-3-yl)methyl)-4-(quinolin-2-ylmethoxy)benzene-1,2-diamine To a 25 mL round-bottomed flask was added N-((1-ethyl-1H-indazol-3-yl)methyl)-2-nitro-4-(quinolin-2-ylmethoxy)aniline (144 mg, 0.32 mmol) and THF (2.7 mL). To this solution was added DIPEA (34 µL, 0.19 mmol) followed by 5% platinum on carbon (8.4 mg, 0.043 mmol). The reaction vessel was evacuated and placed under one atmosphere of $H_2$ for 6.5 h. The mixture was then flushed with $N_2$ and filtered through a pad of Celite, rinsed with EtOAc and the filtrate was concentrated to dryness. Purification using FCC provided the title compound. MS (ESI): mass calcd. for $C_{26}H_{25}N_5O$, 423.21; m/z found, 424.2 [M+H]+.

Step C: racemic cis-3-{1-[(1-Ethyl-1H-indazol-3-yl)methyl]-5-(quinolin-2-ylmethoxy)-1H-benzimidazol-2-yl}-2,2-dimethylcyclopropanecarboxylic acid To a 25 mL round-bottomed flask was added $N^1$-((1-ethyl-1H-indazol-3-yl)methyl)-4-(quinolin-2-ylmethoxy)benzene-1,2-diamine (37 mg, 0.09 mmol), cis-6,6-dimethyl-3-oxa-bicyclo[3.1.0]hexane-2,4-dione (12 mg, 0.09 mmol) and acetonitrile (0.8 mL). The solution was heated to 80° C. for 4 h. To this solution was added HCl (0.4 mL, 6 N) and the mixture heated to 90° C. for 15 h. The mixture was cooled to RT over 30 minutes. The resulting solids were filtered off and the liquid purified by reverse phase HPLC to afford the title compound. MS (ESI): mass calcd. for $C_{33}H_{31}N_5O_3$, 545.24; m/z found, 546.2 [M+H]+. 1H NMR (500 MHz, $CDCl_3$) δ 8.57 (d, J=8.5, 1H), 8.37 (d, J=8.7, 1H), 7.99 (d, J=8.2, 1H), 7.95-7.89 (m, 2H), 7.76-7.72 (m, 1H), 7.55 (d, J=9.1, 1H), 7.42-7.37 (m, 4H), 7.25-7.22 (m, 1H), 7.16-7.11 (m, 1H), 5.72 (s, 2H), 5.66 (s, 2H), 4.36 (q, J=7.3, 2H), 2.50 (s, 2H), 1.45 (t, J=7.3, 3H), 1.29 (s, 3H), 1.10 (s, 3H).

Example 26

3-[1-(4-Bromobenzyl)-5-(quinolin-2-ylmethoxy)-1H-benzimidazol-2-yl]-2,2-dimethylpropanoic acid

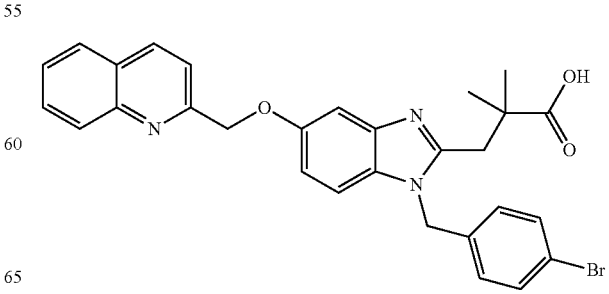

A solution of LiOH (39 mg, 0.9 mmol) in water (2 mL) was added to a 20 mL round-bottomed flask containing ethyl 3-(1-(4-bromobenzyl)-5-(quinolin-2-ylmethoxy)-1H-benzo[d]imidazol-2-yl)-2,2-dimethylpropanoate (106 mg, 0.19 mmol), THF (3 mL), MeOH (3 mL), and water (3 mL). The resulting solution was heated to 80° C. After 2 h, the solution was concentrated to dryness and the residue was treated with sat. ammonium chloride (20 mL) and EtOAc (20 mL). The organic layer was separated and the aqueous layer was further extracted with EtOAc (2×20 mL). The combined organic layers were dried with sodium sulfate, filtered, and concentrated to dryness. The residue was subjected to FCC to give the title compound (84 mg, 83%). MS (ESI): mass calcd. for $C_{29}H_{26}BrN_3O_3$, 543.12; m/z found, 544.2 [M+H]+. $^1$H NMR (500 MHz, $CD_3OD$) δ 9.00 (d, J=8.7, 1H), 8.32 (d, J=8.5, 1H), 8.26 (d, J=8.4, 1H), 8.15-8.08 (m, 2H), 7.94-7.88 (m, 1H), 7.59 (d, J=8.8, 1H), 7.57-7.51 (m, 3H), 7.41 (dd, J=9.1, 2.4, 1H), 7.19 (d, J=8.6, 2H), 5.82 (s, 2H), 5.76 (s, 2H), 3.53 (s, 2H), 1.42 (s, 6H).

Example 27

3-{1-(4-Bromobenzyl)-5-[(6-fluoroquinolin-2-yl)methoxy]-1H-benzimidazol-2-yl}-2,2-dimethylpropanoic acid

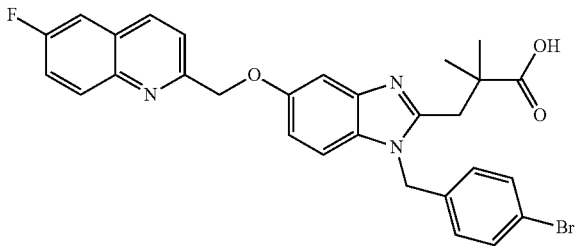 [SMILES: CC(C)(Cc1nc2cc(OCc3ccc4cc(F)ccc4n3)ccc2n1Cc1ccc(Br)cc1)C(=O)O]

The title compound was prepared with similar methods to those for ethyl 3-(1-(4-bromobenzyl)-5-(quinolin-2-ylmethoxy)-1H-benzo[d]imidazol-2-yl)-2,2-dimethylpropanoate using 2-(chloromethyl)-6-fluoroquinoline and similar methods described in Example 26. MS (ESI): mass calcd. for $C_{29}H_{25}BrFN_3O_3$, 561.11; m/z found, 562.0 [M+H]+. (500 MHz, $CD_3OD$) δ 8.35 (d, J=8.6, 1H), 8.13-8.04 (m, 1H), 7.74 (d, J=8.6, 1H), 7.67-7.57 (m, 2H), 7.55-7.43 (m, 3H), 7.35 (d, J=2.2, 1H), 7.26 (dd, J=9.1, 2.4, 1H), 7.12 (d, J=8.5, 2H), 5.73 (s, 2H), 5.45 (s, 2H), 3.42 (s, 2H), 1.38 (s, 6H).

Example 28

3-[5-(1,3-Benzothiazol-2-ylmethoxy)-1-(4-bromobenzyl)-1H-benzimidazol-2-yl]-2,2-dimethylpropanoic acid

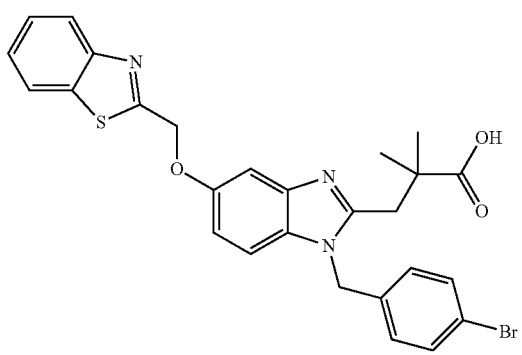 [SMILES: CC(C)(Cc1nc2cc(OCc3nc4ccccc4s3)ccc2n1Cc1ccc(Br)cc1)C(=O)O]

The title compound was prepared using analogous conditions to those described in Example 26 using ethyl 3-(5-(benzo[d]thiazol-2-ylmethoxy)-1-(4-bromobenzyl)-1H-benzo[d]imidazol-2-yl)-2,2-dimethylpropanoate. MS (ESI): mass calcd. for $C_{27}H_{24}BrN_3O_3S$, 549.07; m/z found, 550.1 [M+H]+. $^1$H NMR (500 MHz, $CD_3OD$) δ 8.02-7.95 (m, 2H), 7.57-7.49 (m, 3H), 7.48-7.39 (m, 3H), 7.24 (dd, J=9.1, 2.4, 1H), 7.11 (d, J=8.5, 2H), 5.70 (s, 2H), 5.63 (s, 2H), 3.39 (s, 2H), 1.37 (s, 6H).

Example 29

1-{[1-(4-Bromobenzyl)-5-(quinolin-2-ylmethoxy)-1H-benzimidazol-2-yl]methyl}cyclopentanecarboxylic acid as the TFA salt

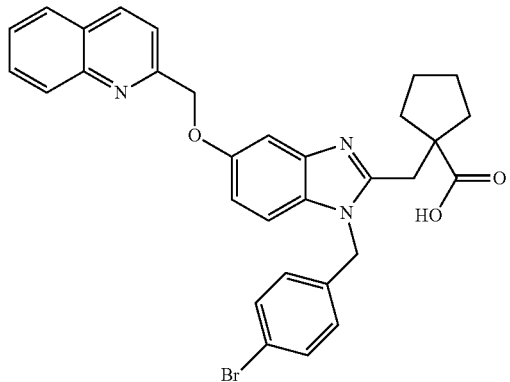 [SMILES: O=C(O)C1(Cc2nc3cc(OCc4ccc5ccccc5n4)ccc3n2Cc2ccc(Br)cc2)CCCC1]

The title compound was prepared using analogous conditions to those described in Example 26 using ethyl 1-((1-(4-bromobenzyl)-5-(quinolin-2-ylmethoxy)-1H-benzo[d]imidazol-2-yl)methyl)cyclopentanecarboxylate. MS (ESI): mass calcd. for $C_{31}H_{28}BrN_3O_3$, 569.13; m/z found, 570.1 [M+H]+. $^1$H NMR (500 MHz, $CD_3OD$) δ 8.53 (d, J=8.5, 1H), 8.12 (d, J=8.5, 1H), 8.03 (d, J=8.1, 1H), 7.88 (ddd, J=8.4, 7.0, 1.3, 1H), 7.82 (s, 1H), 7.70 (t, J=7.6, 1H), 7.57 (d, J=9.2, 1H), 7.55-7.48 (m, 2H), 7.40 (d, J=2.3, 1H), 7.35 (dd, J=9.2, 2.4, 1H), 7.16 (d, J=8.5, 2H), 5.74 (s, 2H), 5.55 (s, 2H), 3.52 (s, 2H), 2.30 (dd, J=9.3, 3.5, 2H), 1.87-1.71 (m, 6H).

Example 30 racemic 3-[1-(4-Bromobenzyl)-5-(quinolin-2-ylmethoxy)-1H-benzimidazol-2-yl]-2-methyl-2-phenylpropanoic acid as the TFA salt

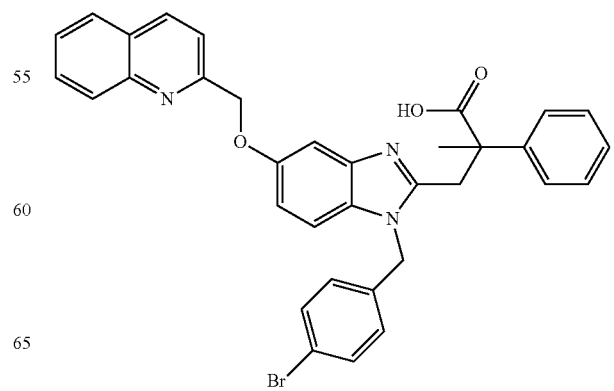

The title compound was prepared using analogous conditions to those described in Example 26 using racemic ethyl 3-(1-(4-bromobenzyl)-5-(quinolin-2-ylmethoxy)-1H-benzo[d]imidazol-2-yl)-2-methyl-2-phenylpropanoate. MS (ESI): mass calcd. for $C_{34}H_{28}BrN_3O_3$, 605.13; m/z found, 606.1 [M+H]⁺. ¹H NMR (500 MHz, CD₃OD) δ 8.59 (dd, J=8.5, 0.7 Hz, 1H), 8.14 (dd, J=8.5, 1.0 Hz, 1H), 8.08-8.03 (m, 1H), 7.95-7.88 (m, 1H), 7.85 (d, J=8.5 Hz, 1H), 7.76-7.70 (m, 1H), 7.49-7.44 (m, 2H), 7.44-7.39 (m, 2H), 7.34-7.28 (m, 4H), 7.27-7.21 (m, 2H), 6.97-6.91 (m, 2H), 5.56 (s, 2H), 5.09 (d, J=16.6 Hz, 1H), 4.98 (d, J=16.6 Hz, 1H), 3.84 (d, J=15.1 Hz, 1H), 3.72 (d, J=15.1 Hz, 1H), 1.84 (s, 3H).

Example 31 racemic cis-3-[1-(4-Bromobenzyl)-5-(quinolin-2-ylmethoxy)-1H-benzimidazol-2-yl]-2,2-dimethylcyclopropanecarboxylic acid as the TFA salt

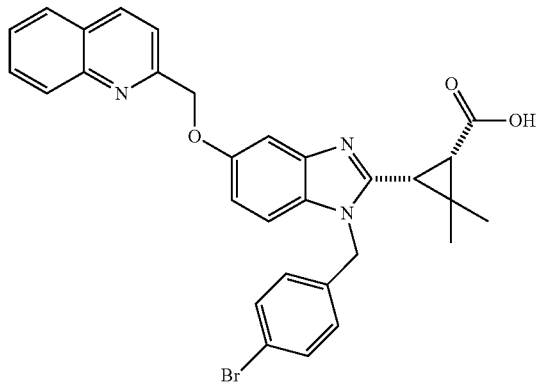

The title compound was prepared using analogous conditions to those described in Example 26 using racemic cis-ethyl 3-(1-(4-bromobenzyl)-5-(quinolin-2-ylmethoxy)-1H-benzo[d]imidazol-2-yl)-2,2-dimethylcyclopropanecarboxylate. MS (ESI): mass calcd. for $C_{30}H_{26}BrN_3O_3$, 555.12; m/z found, 556.1 [M+H]⁺. ¹H NMR (500 MHz, CD₃OD) δ 8.51 (d, J=8.5 Hz, 1H), 8.13-8.09 (m, 1H), 8.04-7.99 (m, 1H), 7.86 (ddd, J=8.5, 6.9, 1.5 Hz, 1H), 7.80 (d, J=8.5 Hz, 1H), 7.68 (ddd, J=8.1, 6.9, 1.2 Hz, 1H), 7.58-7.51 (m, 3H), 7.42 (d, J=2.3 Hz, 1H), 7.35 (dd, J=9.2, 2.4 Hz, 1H), 7.25-7.19 (m, 2H), 5.62 (s, 2H), 5.54 (s, 2H), 2.69 (d, J=8.2 Hz, 1H), 2.48 (d, J=8.2 Hz, 1H), 1.41 (d, J=3.5 Hz, 6H).

Example 32 racemic trans-3-[1-(4-Bromobenzyl)-5-(quinolin-2-ylmethoxy)-1H-benzimidazol-2-yl]-2,2-dimethylcyclopropanecarboxylic acid as the TFA salt

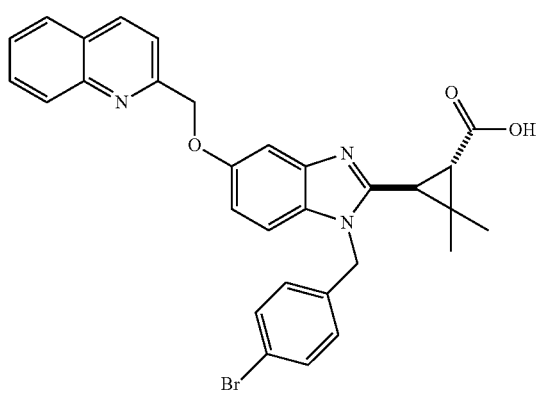

The title compound was prepared using analogous conditions to those described in Example 26 using racemic trans-ethyl 3-(1-(4-bromobenzyl)-5-(quinolin-2-ylmethoxy)-1H-benzo[d]imidazol-2-yl)-2,2-dimethylcyclopropanecarboxylate. MS (ESI): mass calcd. for $C_{30}H_{26}BrN_3O_3$, 555.12; m/z found, 556.0 [M+H]⁺. ¹H NMR (600 MHz, CD₃OD) δ 8.49 (d, J=8.5, 1H), 8.10 (d, J=8.5, 1H), 8.01 (d, J=8.4, 1H), 7.89-7.83 (m, 1H), 7.80 (d, J=8.5, 1H), 7.73 (d, J=9.1, 1H), 7.68 (t, J=7.5, 1H), 7.57 (d, J=8.5, 2H), 7.40 (dd, J=9.1, 2.3, 1H), 7.37 (d, J=2.3, 1H), 7.19 (d, J=8.4, 2H), 5.71 (app q, J=16.6, 2H), 5.54 (s, 2H), 2.85 (d, J=5.9, 1H), 2.62 (d, J=5.9, 1H), 1.26 (s, 3H), 0.92 (s, 3H).

Example 33

3-[1-(2-Bromobenzyl)-5-(quinolin-2-ylmethoxy)-1H-benzimidazol-2-yl]-2,2-dimethylpropanoic acid

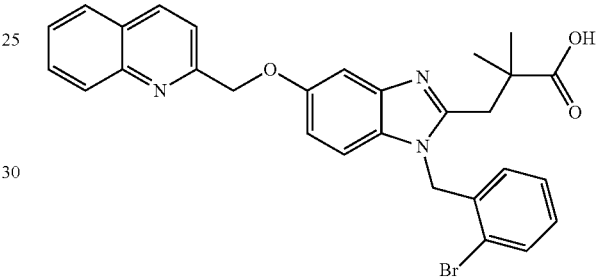

Step A:
N-(2-Bromobenzyl)-4-methoxy-2-nitrobenzenamine

To a solution of 4-methoxy-2-nitrobenzenamine (16.8 g, 0.1 mol) and 1-bromo-2-(bromomethyl)benzene (30 g, 0.12 mol) in CH₃CN (700 mL) was added K₂CO₃ (27.6 g, 0.2 mol). The mixture was heated to reflux for 60 h then cooled to RT filtered and concentrated to dryness. The resulting residue was purified by FCC to provide the title compound.

Step B:
N-1-(2-Bromobenzyl)-4-methoxybenzene-1,2-diamine

To a suspension of N-(2-bromobenzyl)-4-methoxy-2-nitrobenzenamine (20.3 g, 60.2 mmol) in EtOH (200 mL) was added SnCl₂·2H₂O (67.76 g, 301 mmol). The mixture was stirred at 90° C. for 16 h. The resulting mixture was cooled to RT and concentrated to dryness. The aqueous residue was neutralized with saturated NaHCO₃ aqueous solution to ~pH=7, and diluted with CH₂Cl₂ (200 mL). The precipitated solid was removed by filtration and the filtrate was allowed to stand. The organic layer was separated, washed with brine, dried over Na₂SO₄, filtered and concentrated to dryness. The resulting residue was purified by FCC to provide the title compound. ¹H NMR (300 MHz, CDCl₃) δ 7.57 (d, J=7.9, 1H), 7.36 (d, J=7.5, 1H), 7.24 (d, J=7.3, 1H), 7.13 (t, J=7.6, 1H), 6.54 (d, J=8.2, 1H), 6.34-6.28 (m, 2H), 4.30 (s, 2H), 3.72 (s, 3H).

Step C: Ethyl 3-(1-(2-bromobenzyl)-5-methoxy-1H-benzo[d]imidazol-2-yl)-2,2-dimethyl propanoate A solution of N-1-(2-bromobenzyl)-4-methoxybenzene-1,2-diamine (12.2 g, 39.7 mmol) and 3,3-dimethyl-dihydrofuran-2,5-dione (4.59 g, 39.7 mmol) in acetonitrile (100 mL) was stirred at 80° C. for 4 h. The reaction mixture was concentrated to dryness. The resulting residue was dissolved in EtOH (200 mL) followed by HCl (30 mL, 12 N) and then stirred at 90° C. for 16 h. The reaction was cooled to RT, the solvent was removed by evaporation and the aqueous residue was neutralized with sat. NaHCO$_3$ solution to pH=7, then extracted with CH$_2$Cl$_2$ (2×200 mL). The combined organics were washed with brine, dried over Na$_2$SO$_4$, filtered, concentrated and purified using FCC to provide the title compound. $^1$H NMR (300 MHz, DMSO-d$_6$) δ 7.73-7.66 (m, 1H), 7.27-7.16 (m, 3H), 7.13 (d, J=2.4, 1H), 6.76 (dd, J=8.7, 2.4, 1H), 6.34-6.27 (m, 1H), 5.47 (s, 2H), 4.02 (q, J=7.1, 2H), 3.76 (s, 3H), 2.99 (s, 2H), 1.28 (s, 6H), 1.09 (t, J=7.1, 3H).

Step D: Ethyl 3-(1-(2-bromobenzyl)-5-hydroxy-1H-benzo[d]imidazol-2-yl)-2,2-dimethyl propanoate A solution of BBr$_3$ (7.36 mL, 80.1 mmol) in 50 mL CH$_2$Cl$_2$ was added drop-wise to a solution of ethyl 3-(1-(2-bromobenzyl)-5-methoxy-1H-benzo[d]imidazol-2-yl)-2,2-dimethyl propanoate (11.53 g, 25.9 mmol) in CH$_2$Cl$_2$ (200 mL) at −78° C. The mixture was warmed to 5° C. and stirred for 1.5 h. The reaction mixture was added slowly to sat. NaHCO$_3$ solution with rapid stirring and stirred for an additional 1 h. The organic layer was separated and the aqueous was extracted with CH$_2$Cl$_2$ (2×200 mL). The combined organic layers were dried over Na$_2$SO$_4$, filtered, concentrated and purified by FCC to provide the title compound. $^1$H NMR (300 MHz, CDCl$_3$) δ 7.65-7.59 (m, 1H), 7.33 (s, 1H), 7.14 (dd, J=6.9, 4.1, 2H), 6.97 (d, J=8.7, 1H), 6.79 (dd, J=8.5, 2.2, 1H), 6.33 (d, J=9.1, 1H), 5.41 (s, 2H), 4.09 (d, J=7.1, 2H), 3.07 (s, 2H), 1.40 (s, 6H), 1.20 (t, J=7.1, 3H).

Step E: Ethyl 3-(1-(2-bromobenzyl)-5-(quinolin-2-ylmethoxy)-1H-benzo[d]imidazol-2-yl)-2,2-dimethylpropanoate To a mixture of ethyl 3-(1-(2-bromobenzyl)-5-hydroxy-1H-benzo[d]imidazol-2-yl)-2,2-dimethyl propanoate (4.4 g, 10.2 mmol) and 2-(chloromethyl)quinoline hydrochloride (2.9 g, 13.3 mol) were added Cs$_2$CO$_3$ (6.7 g, 20 mmol) and DMF (100 mL). The mixture was stirred at RT for 0.5 h and then heated to 100° C. for 16 h. The reaction mixture was cooled to RT then concentrated to dryness. The resulting residue was diluted with brine (100 mL) and extracted with EtOAc (3×100 mL). The combined organic layers were dried over Na$_2$SO$_4$, filtered, concentrated and purified by FCC to give the title compound. $^1$H NMR (300 MHz, DMSO-d$_6$) δ 8.38 (d, J=8.6, 1H), 7.99 (dd, J=14.4, 8.3, 2H), 7.76 (dd, J=11.8, 4.9, 1H), 7.67 (dd, J=8.1, 4.1, 2H), 7.63-7.55 (m, 1H), 7.26-7.16 (m, 4H), 6.90 (dd, J=8.8, 2.4, 1H), 6.30 (dd, J=5.6, 3.7, 1H), 5.45 (s, 2H), 5.36 (s, 2H), 3.98 (q, J=7.1, 2H), 2.96 (s, 2H), 1.25 (s, 6H), 1.03 (t, J=7.1, 3H).

Step F: 3-[1-(2-Bromobenzyl)-5-(quinolin-2-ylmethoxy)-1H-benzimidazol-2-yl]-2,2-dimethylpropanoic acid To a solution of ethyl 3-(1-(2-bromobenzyl)-5-hydroxy-1H-benzo[d]imidazol-2-yl)-2,2-dimethylpropanoate (100 mg, 0.17 mmol) in MeOH (2 mL) was added NaOH (28 mg, 0.68 mmol) and water (2 mL). The mixture was stirred at 80° C. overnight. The mixture was cooled and acidified to pH=4-5 with 6 N HCl, then extracted with EtOAc (3×20 mL). The combined organic layers were dried over Na$_2$SO$_4$, filtered, concentrated to dryness and purified by reverse phase HPLC to give the title compound. MS (ESI): mass calcd. for C$_{29}$H$_{26}$BrN$_3$O$_3$, 543.12; m/z found, 544.0 [M+H]$^+$. $^1$H NMR (300 MHz, DMSO-d$_6$) δ 8.54 (d, J=8.5, 1H), 8.11 (d, J=8.1, 1H), 8.05 (d, J=8.0, 1H), 7.85 (t, J=7.7, 1H), 7.78-7.65 (m, 3H), 7.42-7.37 (m, 2H), 7.31-7.24 (m, 3H), 6.89-6.86 (m, 1H), 5.81 (s, 2H), 5.54 (s, 2H), 3.44 (s, 2H), 1.30 (s, 6H).

Example 34

3-[1-(3-Bromobenzyl)-5-(quinolin-2-ylmethoxy)-1H-benzimidazol-2-yl]-2,2-dimethylpropanoic acid

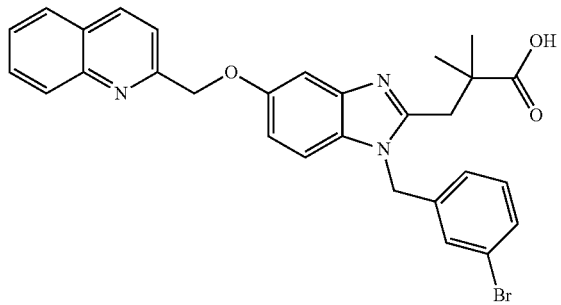

The title compound was prepared using similar methods to those in Example 33 using 1-bromo-3-(bromomethyl)benzene in Step A. MS (ESI): mass calcd. for C$_{29}$H$_{26}$BrN$_3$O$_3$, 543.12; m/z found, 544.1 [M+H]$^+$. $^1$H NMR (300 MHz, DMSO-d$_6$) δ 12.19 (s, 1H), 8.40 (d, J=8.6, 1H), 8.03 (d, J=8.5, 1H), 7.98 (d, J=7.6, 1H), 7.78 (app t, J=7.0, 1H), 7.69 (d, J=8.5, 1H), 7.61 (app t, J=8.0, 1H), 7.46 (d, J=7.7, 1H), 7.34 (d, J=8.8, 1H), 7.30-7.22 (m, 2H), 7.19 (d, J=2.3, 1H), 6.99-6.92 (m, 2H), 5.48 (s, 2H), 5.38 (s, 2H), 3.01 (s, 2H), 1.24 (s, 6H).

Example 35 racemic cis-2-[1-(4-Cyanobenzyl)-5-(quinolin-2-ylmethoxy)-1H-benzimidazol-2-yl]cyclohexanecarboxylic acid as a hydrochloride salt

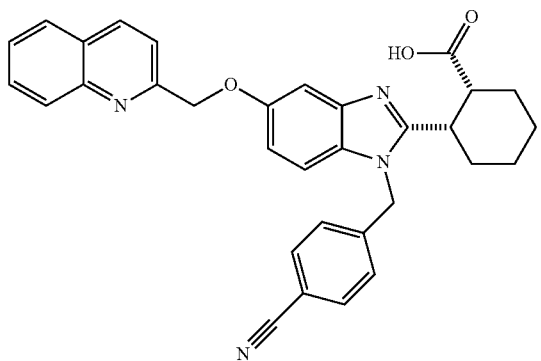

Step A: 2-((4-fluoro-3-nitrophenoxy)methyl)quinoline

To a solution of 4-fluoro-3-nitrophenol (8.1 g, 38 mmol) and 2-(chloromethyl)quinoline (6.0 g, 38 mmol) in DMF (100 mL) were added $K_2CO_3$ (21 g, 153 mmol) followed by KI (317 mg, 1.9 mmol). The mixture was stirred at 50° C. for 5 h. The mixture was cooled to RT, water (100 mL) was added, and the mixture was extracted with EtOAc (3×150 mL). The organics were combined, washed with brine (50 mL), dried ($Na_2SO_4$), filtered and concentrated to dryness. The residue was purified by FCC to afford the title compound. $^1$H NMR (300 MHz, $CDCl_3$) δ 8.27 (d, J=9, 1H), 8.15 (d, J=9, 1H), 7.87 (d, J=9, 1H), 7.80-7.72 (m, 2H), 7.65-7.56 (m, 2H), 7.32-7.26 (m, 1H), 7.23-7.16 (m, 1H), 5.44 (s, 2H).

Step B: 4-((2-Amino-4-(quinolin-2-ylmethoxy)phenylamino)methyl)benzonitrile

To a solution of 2-((4-fluoro-3-nitrophenoxy)methyl)quinoline (298 mg, 1 mmol) and 4-(aminomethyl)benzonitrile (132 mg, 1 mmol) in acetonitrile (1 mL) was added DIPEA (2 mL, 12 mmol). The mixture was stirred at 80° C. overnight. The mixture was cooled to RT, water (20 mL) was added, and the mixture was extracted with DCM (3×20 mL). The organics were combined, washed with brine (20 mL), dried ($Na_2SO_4$), filtered and concentrated to dryness. The residue was recrystallized from ethanol to give 4-((2-nitro-4-(quinolin-2-ylmethoxy)phenylamino)methyl)benzonitrile. The recrystallized 4-((2-nitro-4-(quinolin-2-ylmethoxy)phenylamino)methyl)benzonitrile (307 mg, 0.75 mmol) was then dissolved in ethanol (20 mL) and $SnCl_2.2H_2O$ (1 g, 4.5 mmol) was added. The resulting mixture was stirred at 90° C. overnight. The mixture was cooled to RT and the pH adjusted to ~pH 8-9 by the addition of sat. aq. $NaHCO_3$. The aqueous mixture was stirred at RT for 30 min. and then extracted with DCM (3×20 mL). The organics were combined, washed with brine (20 mL), dried ($Na_2SO_4$), filtered and concentrated to dryness to afford the title compound, which was used without further purification. MS (ESI): mass calcd. for $C_{24}H_{20}N_4O$, 380.16; m/z found, 381.0 $[M+H]^+$.

Step C: racemic cis-2-[1-(4-Cyanobenzyl)-5-(quinolin-2-ylmethoxy)-1H-benzimidazol-2-yl]cyclohexanecarboxylic acid as a hydrochloride salt 4-((2-amino-4-(quinolin-2-ylmethoxy)phenylamino) methyl)benzonitrile (280 mg, 0.54 mmol) and cis-hexahydroisobenzofuran-1,3-dione (83.2 mg, 0.54 mmol) were dissolved in acetonitrile (10 mL) and the mixture heated to 60° C. After 2 h, HCl (3 mL, 6 N) was added and the resulting mixture stirred at 60° C. overnight. The mixture was then cooled to RT and the pH was adjusted to pH 8-9 with sat $NaHCO_3$. The aqueous layer was then extracted with EtOAc (3×20 mL). The organics were combined, washed with brine (20 mL), dried ($Na_2SO_4$), filtered and concentrated to dryness. The residue was purified by HPLC to afford the title compound. MS (ESI): mass calcd. for $C_{32}H_{28}N_4O_3$, 516.22; m/z found, 517.0 $[M+H]^+$. $^1$H NMR (500 MHz, DMSO-$d_6$) δ 14.72 (s, 1H), 8.60 (d, J=8.5, 1H), 8.16 (d, J=8.6, 1H), 8.09 (d, J=8.1, 1H), 7.95-7.77 (m, 4H), 7.71 (app t, J=7.5, 1H), 7.51 (d, J=9.1, 1H), 7.41 (d, J=2.2, 1H), 7.35 (d, J=8.3, 2H), 7.31 (dd, J=9.1, 2.2, 1H), 6.03-5.88 (m, 2H), 5.59 (s, 2H), 3.77-3.62 (m, 1H), 2.89-2.88 (m, 1H), 2.23-2.09 (m, 1H), 2.02 (t, J=14.3, 2H), 1.91-1.71 (m, 2H), 1.63-1.52 (m, 1H), 1.48-1.33 (m, 2H).

Example 36 racemic cis-2-[1-Benzyl-5-(quinolin-2-ylmethoxy)-1H-benzimidazol-2-yl]cyclohexanecarboxylic acid as the hydrochloride salt

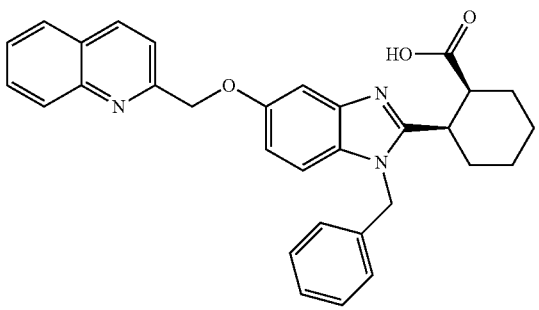 [SMILES: O=C(O)[C@H]1CCCC[C@H]1c1nc2cc(OCc3ccc4ccccc4n3)ccc2n1Cc1ccccc1]

The title compound was prepared using similar methods to those in Example 35 using phenylmethanamine in Step B. MS (ESI): mass calcd. for $C_{31}H_{29}N_3O_3$, 491.22; m/z found, 492.0 $[M+H]^+$. $^1$H NMR (400 MHz, DMSO-$d_6$) δ 8.46 (d, J=8.6, 1H), 8.06 (d, J=8.7, 1H), 8.02 (d, J=7.7, 1H), 7.82 (app t, J=7.7, 1H), 7.71 (d, J=8.4, 1H), 7.65 (app t, J=7.4, 1H), 7.54 (d, J=9.0, 1H), 7.41-7.26 (m, 5H), 7.22-7.13 (m, 2H), 5.89-5.71 (m, 2H), 5.52 (s, 2H), 3.70-3.67 (m, 1H), 2.92-2.83 (m, 1H), 2.24-2.10 (m, 1H), 2.04-1.95 (m, 2H), 1.84-1.77 (m, 2H), 1.64-1.54 (m, 1H), 1.47-1.33 (m, 2H).

Example 37 racemic cis-2-{5-(Quinolin-2-ylmethoxy)-1-[2-(trifluoromethoxy)benzyl]-1H-benzimidazol-2-yl}cyclohexanecarboxylic acid as the hydrochloride salt

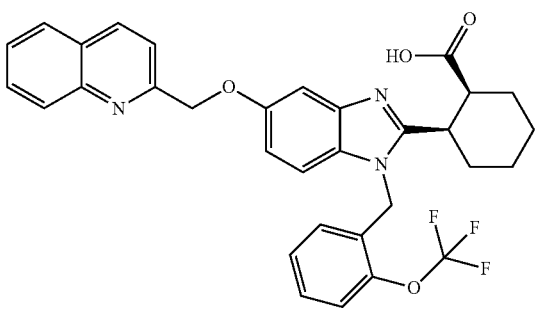 [SMILES: O=C(O)[C@H]1CCCC[C@H]1c1nc2cc(OCc3ccc4ccccc4n3)ccc2n1Cc1ccccc1OC(F)(F)F]

The title compound was prepared using similar methods to those in Example 35 using (2-(trifluoromethoxy)phenyl)methanamine in Step B. MS (ESI): mass calcd. for $C_{32}H_{28}F_3N_3O_4$, 575.20; m/z found, 576.0 $[M+H]^+$. $^1$H NMR (400 MHz, DMSO-$d_6$) δ 8.49 (d, J=8.5, 1H), 8.08 (d, J=8.3, 1H), 8.04 (d, J=8.2, 1H), 7.84 (app t, J=7.6, 1H), 7.74 (d, J=8.4, 1H), 7.67 (app t, J=7.5, 1H), 7.57-7.45 (m, 3H), 7.41-7.24 (m, 3H), 7.02 (d, J=7.6, 1H), 5.85 (s, 2H), 5.53 (s, 2H), 3.68-3.66 (m, 1H), 2.78-2.77 (m, 1H), 2.23-2.12 (m, 1H), 2.10-2.01 (m, 1H), 1.96-1.88 (m, 1H), 1.88-1.80 (m, 1H), 1.78-1.68 (m, 1H), 1.62-1.53 (m, 1H), 1.45-1.32 (m, 2H).

Example 38 racemic cis-2-[1-(2-Methylbenzyl)-5-(quinolin-2-ylmethoxy)-1H-benzimidazol-2-yl]cyclohexanecarboxylic acid as the hydrochloride salt

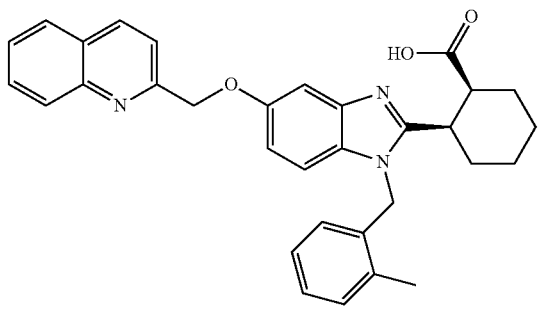 [SMILES: Cc1ccccc1Cn1c([C@@H]2CCCC[C@@H]2C(=O)O)nc2cc(OCc3ccc4ccccc4n3)ccc21]

The title compound was prepared using similar methods to those in Example 35 using o-tolylmethanamine in Step B. MS (ESI): mass calcd. for $C_{32}H_{31}N_3O_3$, 505.24; m/z found, 506.0 [M+H]$^+$. $^1$H NMR (500 MHz, DMSO-d$_6$) δ 9.23 (d, J=8.6, 1H), 8.46 (d, J=8.6, 1H), 8.40 (d, J=8.2, 1H), 8.31-8.21 (m, 2H), 8.03 (app t, J=7.3, 1H), 7.66 (d, J=2.2, 1H), 7.57 (d, J=9.1, 1H), 7.47 (dd, J=9.1, 2.3, 1H), 7.36 (d, J=7.5, 1H), 7.28 (t, J=7.4, 1H), 7.07 (app t, J=7.5, 1H), 6.50 (d, J=7.7, 1H), 5.91 (s, 2H), 5.89-5.74 (m, 2H), 3.73-3.68 (m, 1H), 2.85-2.84 (m, 1H), 2.51 (s, 3H), 2.45-2.31 (m, 1H), 2.21-2.12 (m, 2H), 2.03-2.00 (m, 1H), 1.84-1.66 (m, 2H), 1.63-1.44 (m, 2H).

Example 39 racemic cis-2-{5-(Quinolin-2-ylmethoxy)-1-[2-(trifluoromethyl)benzyl]-1H-benzimidazol-2-yl}cyclohexanecarboxylic acid as the hydrochloride salt

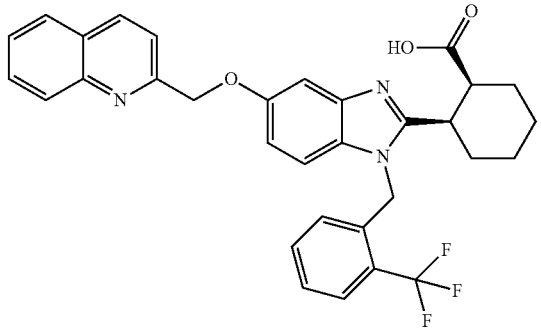 [SMILES: O=C(O)[C@H]1CCCC[C@H]1c1nc2cc(OCc3ccc4ccccc4n3)ccc2n1Cc1ccccc1C(F)(F)F]

The title compound was prepared using similar methods to those in Example 35 using (2-(trifluoromethyl)phenyl) methanamine in Step B. MS (ESI): mass calcd. for $C_{32}H_{28}F_3N_3O_3$, 559.21; m/z found, 560.0 [M+H]$^+$. $^1$H NMR (400 MHz, DMSO-d$_6$) δ 8.51 (d, J=8.5, 1H), 8.09 (d, J=8.5, 1H), 8.05 (d, J=8.0, 1H), 7.91 (d, J=7.3, 1H), 7.85 (t, J=7.6, 1H), 7.75 (d, J=8.5, 1H), 7.67 (t, J=7.5, 1H), 7.62-7.50 (m, 2H), 7.42-7.34 (m, 2H), 7.29 (d, J=9.1, 1H), 6.81 (d, J=7.5, 1H), 5.99-5.80 (m, 2H), 5.54 (s, 2H), 3.69-3.66 (m, 1H), 2.82-2.76 (m, 1H), 2.24-2.13 (m, 1H), 2.10-2.02 (m, 1H), 2.00-1.92 (m, 1H), 1.88-1.79 (m, 1H), 1.77-1.67 (m, 1H), 1.61-1.52 (m, 1H), 1.46-1.33 (m, 2H).

Example 40 racemic cis-2-{1-[3-Fluoro-4-(trifluoromethoxy)benzyl]-5-(quinolin-2-ylmethoxy)-1H-benzimidazol-2-yl}cyclohexanecarboxylic acid as the hydrochloride salt

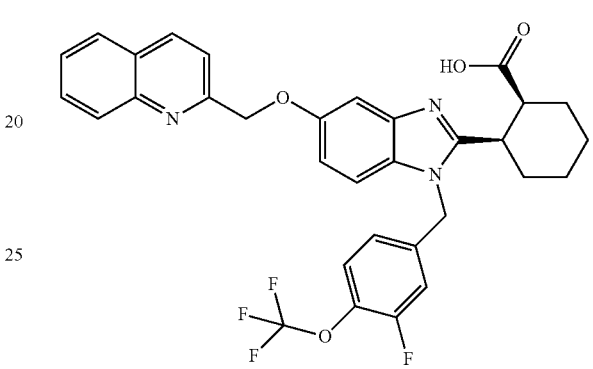

The title compound was prepared using similar methods to those in Example 35 using (3-fluoro-4-(trifluoromethoxy)phenyl)methanamine in Step B. MS (ESI): mass calcd. for $C_{32}H_{27}F_4N_3O_4$, 593.19; m/z found, 594.0 [M+H]$^+$. $^1$H NMR (400 MHz, CD$_3$OD) δ 8.83 (d, J=8.6, 1H), 8.27 (d, J=8.7, 1H), 8.19 (d, J=8.1, 1H), 8.08-7.99 (m, 2H), 7.85 (t, J=7.6, 1H), 7.58 (d, J=9.1, 1H), 7.51 (d, J=2.2, 1H), 7.50-7.40 (m, 2H), 7.20 (dd, J=10.8, 2.0, 1H), 7.08 (d, J=8.8, 1H), 5.95-5.82 (m, 2H), 5.71 (s, 2H), 3.72-3.67 (m, 1H), 2.98-2.97 (m, 1H), 2.40-2.28 (m, 1H), 2.26-2.22 (m, 1H), 2.14-2.11 (m, 1H), 2.00 (s, 1H), 1.90-1.79 (m, 1H), 1.74-1.72 (m, 1H), 1.65-1.48 (m, 2H).

Example 41 racemic cis-2-{1-[2-Fluoro-4-(trifluoromethoxy)benzyl]-5-(quinolin-2-ylmethoxy)-1H-benzimidazol-2-yl}cyclohexanecarboxylic acid as the hydrochloride salt

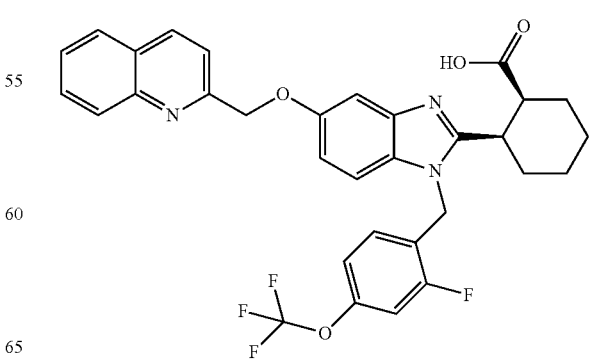

The title compound was prepared using similar methods to those in Example 35 using (2-fluoro-4-(trifluoromethoxy)phenyl)methanamine in Step B. MS (ESI): mass calcd. for $C_{32}H_{27}F_4N_3O_4$, 593.19; m/z found, 593.9 [M+H]$^+$. $^1$H NMR (400 MHz, CD$_3$OD) δ 8.80-8.70 (m, 1H), 8.24 (d, J=8.5, 1H), 8.16 (d, J=8.3, 1H), 8.04-7.93 (m, 2H), 7.82 (app t, J=7.0, 1H), 7.64 (d, J=9.1, 1H), 7.52-7.46 (m, 1H), 7.42 (dd, J=9.1, 1.8, 1H), 7.31 (d, J=10.2, 1H), 7.23 (app t, J=8.2, 1H), 7.16 (d, J=9.2, 1H), 5.91 (s, 2H), 5.68-5.67 (m, 2H), 3.77-3.73 (m, 1H), 3.03-3.02 (m, 1H), 2.47-2.33 (m, 1H), 2.29-2.25 (m, 1H), 2.15-1.97 (m, 2H), 1.97-1.80 (m, 1H), 1.79-1.70 (m, 1H), 1.67-1.51 (m, 2H).

Example 42

(1R*,2S*)-2-{1-[2-Fluoro-4-(trifluoromethoxy)benzyl]-5-(quinolin-2-ylmethoxy)-1H-benzimidazol-2-yl}cyclohexanecarboxylic acid

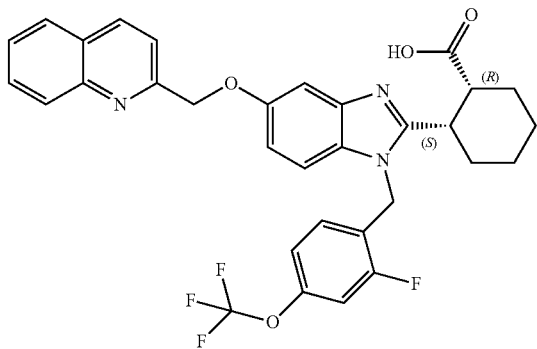

Racemic cis-2-{1-[2-fluoro-4-(trifluoromethoxy)benzyl]-5-(quinolin-2-ylmethoxy)-1H-benzimidazol-2-yl}cyclohexanecarboxylic acid (prepared as described in Example 41) was purified by chiral SFC on (CHIRALCEL OD-H 5 μm 250×20 mm). Mobile phase (60% CO$_2$, 40% MeOH) to yield the title compound as the first eluting isomer. MS (ESI): mass calcd. for $C_{32}H_{27}F_4N_3O_4$, 593.19; m/z found, 594.2 [M+H]$^+$.

Example 43

(1S*,2R*)-2-{1-[2-Fluoro-4-(trifluoromethoxy)benzyl]-5-(quinolin-2-ylmethoxy)-1H-benzimidazol-2-yl}cyclohexanecarboxylic acid

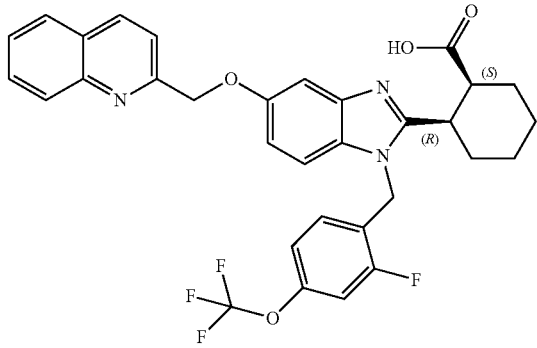

Racemic cis-2-{1-[2-fluoro-4-(trifluoromethoxy)benzyl]-5-(quinolin-2-ylmethoxy)-1H-benzimidazol-2-yl}cyclohexanecarboxylic acid (prepared as described in Example 41) was purified by chiral SFC on (CHIRALCEL OD-H 5 μm 250×20 mm). Mobile phase (60% CO$_2$, 40% MeOH) to yield the title compound as the second eluting isomer. MS (ESI): mass calcd. for $C_{32}H_{27}F_4N_3O_4$, 593.19; m/z found, 594.2 [M+H]$^+$. $^1$H NMR (400 MHz, CD$_3$OD) δ 8.35 (d, J=8.5, 1H), 8.05 (d, J=8.4, 1H), 7.93 (d, J=6.9, 1H), 7.81-7.75 (m, 1H), 7.73 (d, J=8.5, 1H), 7.64-7.56 (m, 1H), 7.29 (s, 1H), 7.25-7.16 (m, 2H), 7.08-6.96 (m, 2H), 6.94 (t, J=8.4, 1H), 5.60 (d, J=17.5, 1H), 5.52 (d, J=17.4, 1H), 5.39 (s, 2H), 3.65-3.54 (m, 1H), 2.88-2.74 (m, 1H), 2.45-2.28 (m, 1H), 2.05-1.94 (m, 1H), 1.94-1.71 (m, 4H), 1.53-1.39 (m, 2H).

Example 44 racemic cis-2-[1-(4-Methylbenzyl)-5-(quinolin-2-ylmethoxy)-1H-benzimidazol-2-yl]cyclohexanecarboxylic acid as the hydrochloride salt

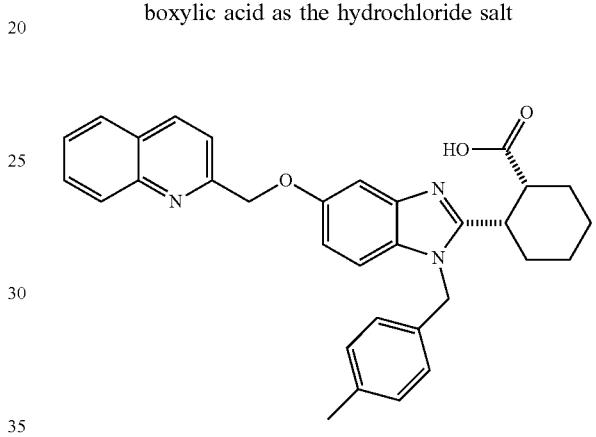

The title compound was prepared using similar methods to those in Example 35 using p-tolylmethanamine in Step B. MS (ESI): mass calcd. for $C_{32}H_{31}N_3O_3$, 505.24; m/z found, 506.2 [M+H]$^+$. $^1$H NMR (400 MHz, DMSO-d$_6$) δ 14.46 (s, 1H), 8.55-8.48 (m, 1H), 8.13-8.07 (m, 1H), 8.05 (d, J=7.8, 1H), 7.88-7.82 (m, 1H), 7.78-7.72 (m, 1H), 7.68 (app t, J=7.5, 1H), 7.53 (d, J=9.0, 1H), 7.37-7.33 (m, 1H), 7.32-7.28 (m, 1H), 7.17 (d, J=7.8, 2H), 7.11-7.05 (m, 2H), 5.83-5.69 (m, 2H), 5.55 (s, 2H), 3.74-3.66 (m, 1H), 2.95-2.89 (m, 1H), 2.28 (s, 3H), 2.21-2.12 (m, 1H), 2.08-1.95 (m, 2H), 1.90-1.74 (m, 2H), 1.64-1.55 (m, 1H), 1.46-1.34 (m, 2H).

Example 45 racemic cis-2-{5-(Quinolin-2-ylmethoxy)-1-[4-(trifluoromethoxy)benzyl]-1H-benzimidazol-2-yl}cyclohexanecarboxylic acid as the hydrochloride salt

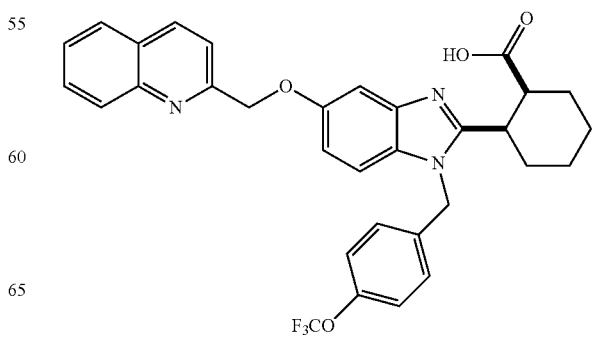

The title compound was prepared using similar methods to those in Example 35 using (4-(trifluoromethoxy)phenyl)methanamine in Step B. MS (ESI): mass calcd. for $C_{32}H_{28}F_3N_3O_4$, 575.20; m/z found, 576.0 [M+H]$^+$. $^1$H NMR (500 MHz, DMSO-$d_6$) δ 14.52 (s, 1H), 8.48 (d, J=8.6, 1H), 8.07 (d, J=8.6, 1H), 8.03 (d, J=7.9, 1H), 7.83 (app t, J=7.7, 1H), 7.72 (d, J=8.5, 1H), 7.66 (app t, J=7.5, 1H), 7.55 (d, J=9.3, 1H), 7.43-7.26 (m, 6H), 5.90-5.78 (m, 2H), 5.53 (s, 2H), 3.70-3.67 (m, 1H), 2.92-2.86 (m, 1H), 2.21-1.93 (m, 3H), 1.87-1.74 (m, 2H), 1.63-1.53 (m, 1H), 1.46-1.35 (m, 2H).

Example 46 racemic cis-2-{5-(Quinolin-2-ylmethoxy)-1-[4-(trifluoromethyl)benzyl]-1H-benzimidazol-2-yl}cyclohexanecarboxylic acid as the hydrochloride salt

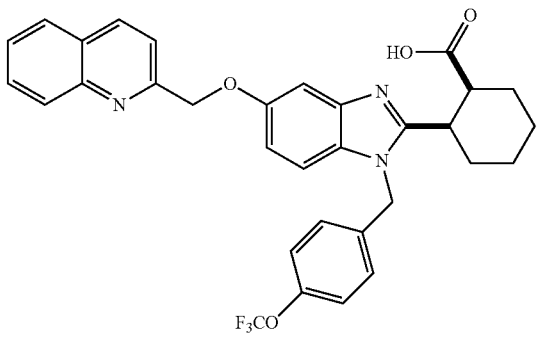

The title compound was prepared using similar methods to those in Example 35 using (4-(trifluoromethyl)phenyl)methanamine in Step B. MS (ESI): mass calcd. for $C_{32}H_{28}F_3N_3O_3$, 559.21; m/z found, 559.9 [M+H]$^+$. $^1$H NMR (400 MHz, DMSO-$d_6$) δ 8.48 (d, J=8.5, 1H), 8.07 (d, J=8.5, 1H), 8.03 (d, J=8.0, 1H), 7.86-7.80 (m, 1H), 7.77-7.69 (m, 3H), 7.66 (app t, J=7.9, 1H), 7.54-7.48 (m, 1H), 7.41-7.32 (m, 3H), 7.31-7.25 (m, 1H), 5.99-5.85 (m, 2H), 5.52 (s, 2H), 3.72-3.64 (m, 1H), 2.92-2.85 (m, 1H), 2.19-2.03 (m, 2H), 2.01-1.94 (m, 1H), 1.86-1.74 (m, 2H), 1.61-1.53 (m, 1H), 1.46-1.33 (m, 2H).

Example 47 racemic cis-2-[1-(3-Cyanobenzyl)-5-(quinolin-2-ylmethoxy)-1H-benzimidazol-2-yl]cyclohexanecarboxylic acid as the hydrochloride salt

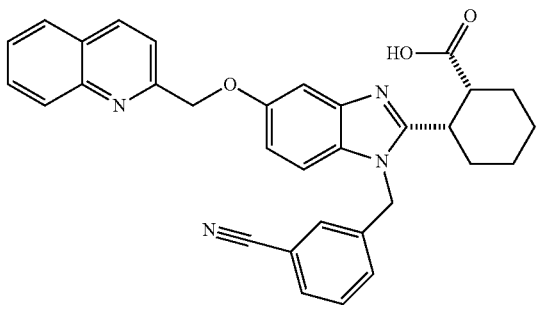

The title compound was prepared using similar methods to those in Example 35 using 3-(aminomethyl)benzonitrile in Step B. MS (ESI): mass calcd. for $C_{32}H_{28}N_4O_3$, 516.22; m/z found, 517.0 [M+H]$^+$. $^1$H NMR (500 MHz, DMSO-$d_6$) δ 8.56 (d, J=8.5, 1H), 8.13 (d, J=8.5, 1H), 8.07 (d, J=8.1, 1H), 7.92-7.85 (m, 1H), 7.83 (d, J=7.6, 1H), 7.78 (d, J=8.5, 1H), 7.75-7.66 (m, 2H), 7.59 (app t, J=7.7, 1H), 7.54 (d, J=8.0, 1H), 7.50 (d, J=9.1, 1H), 7.39 (d, J=2.2, 1H), 7.29 (dd, J=9.1, 2.1, 1H), 5.94-5.83 (m, 2H), 5.57 (s, 2H), 3.73-3.70 (m, 1H), 2.92-2.91 (m, 1H), 2.18-2.12 (m, 1H), 2.07-2.00 (m, 2H), 1.91-1.73 (m, 2H), 1.63-1.52 (m, 1H), 1.51-1.34 (m, 2H).

Example 48 racemic cis-2-(5-(quinolin-2-ylmethoxy)-1-(3-(trifluoromethoxy)benzyl)-1H-benzo[d]imidazol-2-yl)cyclohexanecarboxylic acid as the hydrochloride salt

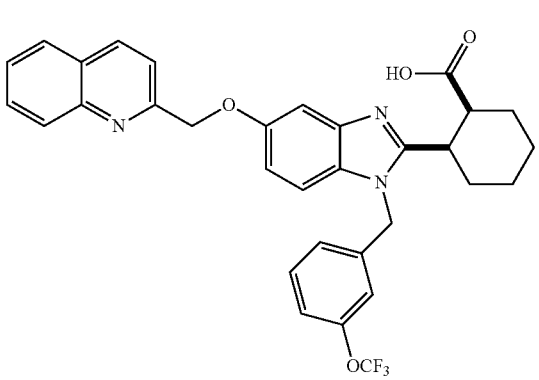

The title compound was prepared using similar methods to those in Example 35 using (3-(trifluoromethoxy)phenyl)methanamine in Step B. MS (ESI): mass calcd. for $C_{32}H_{28}F_3N_3O_4$, 575.20; m/z found, 576.0 [M+H]$^+$. $^1$H NMR (500 MHz, DMSO-$d_6$) δ 8.51 (d, J=8.5, 1H), 8.09 (d, J=8.4, 1H), 8.05 (d, J=7.8, 1H), 7.85 (app t, J=7.6, 1H), 7.74 (d, J=8.5, 1H), 7.67 (app t, J=7.2, 1H), 7.54-7.48 (m, 2H), 7.38-7.25 (m, 4H), 7.18 (d, J=7.6, 1H), 5.95-5.81 (m, 2H), 5.54 (s, 2H), 3.71-3.68 (m, 1H), 2.88-2.87 (m, 1H), 2.21-1.93 (m, 3H), 1.91-1.71 (m, 2H), 1.64-1.53 (m, 1H), 1.50-1.31 (m, 2H).

Example 49 racemic cis-2-[1-(3-Methylbenzyl)-5-(quinolin-2-ylmethoxy)-1H-benzimidazol-2-yl]cyclohexanecarboxylic acid as the hydrochloride salt

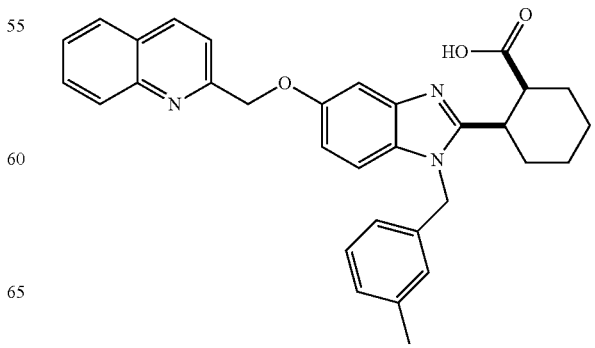

The title compound was prepared using similar methods to those in Example 35 using m-tolylmethanamine in Step B. MS (ESI): mass calcd. for $C_{32}H_{31}N_3O_3$, 505.24; m/z found, 506.0 [M+H]+. 1H NMR (500 MHz, DMSO-$d_6$) δ 14.54 (s, 1H), 8.56 (d, J=8.4, 1H), 8.13 (d, J=8.5, 1H), 8.07 (d, J=8.0, 1H), 7.87 (app t, J=7.7, 1H), 7.78 (d, J=8.5, 1H), 7.69 (app t, J=7.5, 1H), 7.54 (d, J=9.1, 1H), 7.38 (d, J=2.1, 1H), 7.31 (dd, J=9.1, 2.3, 1H), 7.25 (app t, J=7.6, 1H), 7.14 (d, J=7.6, 1H), 6.98 (s, 1H), 6.96 (d, J=7.8, 1H), 5.84-5.70 (m, 2H), 5.57 (s, 2H), 3.71-3.68 (m, 1H), 2.88-2.87 (m, 1H), 2.24 (s, 3H), 2.21-2.12 (m, 1H), 2.04-1.98 (m, 2H), 1.85-1.77 (m, 2H), 1.64-1.53 (m, 1H), 1.42-1.38 (m, 2H).

Example 50 racemic cis-2-(5-(quinolin-2-ylmethoxy)-1-(3-(trifluoromethyl)benzyl)-1H-benzo[d]imidazol-2-yl)cyclohexanecarboxylic acid as the hydrochloride salt

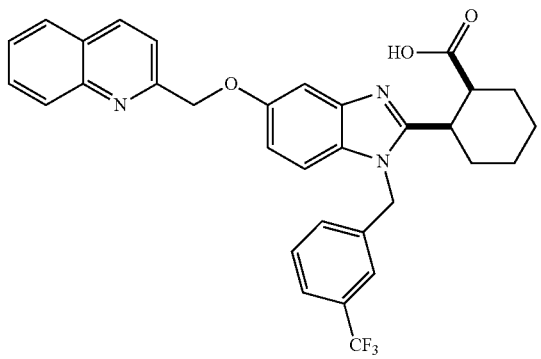

The title compound was prepared using similar methods to those in Example 35 using (3-(trifluoromethyl)phenyl)methanamine in Step B. MS (ESI): mass calcd. for $C_{32}H_{28}F_3N_3O_3$, 559.21; m/z found, 559.9 [M+H]+. 1H NMR (500 MHz, DMSO-$d_6$) δ 14.67 (s, 1H), 8.56 (d, J=8.5, 1H), 8.13 (d, J=8.5, 1H), 8.07 (d, J=8.2, 1H), 7.87 (app t, J=7.6, 1H), 7.78 (d, J=8.5, 1H), 7.73-7.67 (m, 3H), 7.60 (app t, J=7.8, 1H), 7.53 (d, J=9.1, 1H), 7.42-7.39 (m, 2H), 7.31 (dd, J=9.1, 2.0, 1H), 6.01-5.86 (m, 2H), 5.57 (s, 2H), 3.74-3.71 (m, 1H), 2.86-2.85 (m, 1H), 2.24-2.09 (m, 1H), 2.01 (s, 2H), 1.92-1.71 (m, 2H), 1.63-1.53 (m, 1H), 1.48-1.33 (m, 2H).

Example 51 racemic cis-2-[1-(2-Cyanobenzyl)-5-(quinolin-2-ylmethoxy)-1H-benzimidazol-2-yl]cyclohexanecarboxylic acid as the hydrochloride salt

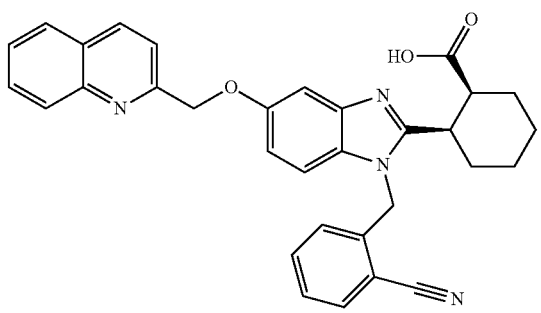 [SMILES: N#Cc1ccccc1Cn1c([C@@H]2CCCC[C@@H]2C(=O)O)nc2cc(OCc3ccc4ccccc4n3)ccc21]

Step A: racemic cis-2-(1-(2-Bromobenzyl)-5-(quinolin-2-ylmethoxy)-1H-benzo[d]imidazol-2-yl)cyclohexanecarboxylic acid The title compound was prepared using similar methods to those in Step B of Example 35 using (2-bromophenyl)methanamine.

Step B: racemic cis-2-[1-(2-Cyanobenzyl)-5-(quinolin-2-ylmethoxy)-1H-benzimidazol-2-yl]cyclohexanecarboxylic acid as the hydrochloride salt To a reaction vessel was added a solution of racemic cis-2-(1-(2-bromobenzyl)-5-(quinolin-2-ylmethoxy)-1H-benzo[d]imidazol-2-yl)cyclohexanecarboxylic acid (192 mg, 0.34 mmol) in DMF (5 mL). Then zinc (II) cyanide (80 mg, 0.7 mmol) and Pd(PPh$_3$)$_4$ (79 mg, 0.07 mmol) were added and the vessel was flushed with N$_2$ and capped. The mixture was irradiated for 2 h at 150° C. in the microwave. The mixture was cooled to RT and concentrated to dryness. The residue was partitioned between water (20 mL) and EtOAc (20 mL). The layers were separated and the aqueous was further extracted with EtOAc (2×20 mL). The organics were combined, washed with brine, dried (Na$_2$SO$_4$), filtered and concentrated to dryness. The residue was purified by HPLC to afford the title compound. MS (ESI): mass calcd. for $C_{32}H_{28}N_4O_3$, 516.22; m/z found, 517.2 [M+H]+. 1H NMR (400 MHz, DMSO-$d_6$) δ 8.41 (d, J=8.5, 1H), 8.04 (d, J=8.5, 1H), 8.00 (d, J=7.7, 1H), 7.94 (d, J=7.7, 1H), 7.80 (app t, J=7.6, 1H), 7.70 (d, J=8.5, 1H), 7.62 (app t, J=7.6, 1H), 7.56 (app t, J=7.5, 1H), 7.49 (app t, J=7.5, 1H), 7.26 (d, J=8.1, 1H), 7.22 (s, 1H), 6.93 (dd, J=8.8, 2.2, 1H), 6.84 (d, J=7.9, 1H), 5.73 (s, 2H), 5.38 (s, 2H), 3.62-3.59 (m, 1H), 3.07-2.96 (m, 1H), 2.14-2.06 (m, 1H) 1.80-1.72 (m, 2H), 1.67-1.25 (m, 5H).

Example 52 racemic cis-2-{1-(4-Bromobenzyl)-5-[(6-fluoroquinolin-2-yl)methoxy]-1H-benzimidazol-2-yl}cyclohexanecarboxylic acid as the formic acid salt

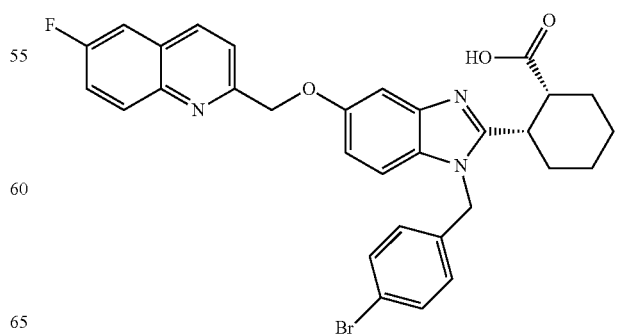

Step A: 4-((4-Bromobenzyl)amino)-3-nitrophenol

To a solution of 4-fluoro-3-nitrophenol (20 g, 127 mmol) in acetonitrile (50 mL) were added 4-(bromophenyl)methanamine (23.7 g, 127 mmol) followed by DIPEA (44 mL, 255 mmol). The mixture was heated to 90° C. for 64 h. The mixture was cooled to RT and concentrated to dryness. The residue was dissolved in DCM (500 mL) and washed with water (2×100 mL). The organics were dried with $Na_2SO_4$, filtered and concentrated to dryness. The residue was purified by FCC to afford the title compound. $^1$H NMR (300 MHz, DMSO-$d_6$) δ 9.37 (s, 1H), 8.41-8.37 (m, 1H), 7.51 (d, J=8.4, 2H), 7.42 (d, J=2.9, 1H), 7.29 (d, J=8.4, 2H), 7.03 (dd, J=9.2, 2.9, 1H), 6.76 (d, J=9.3, 1H), 4.54 (d, J=6.2, 2H).

Step B: 3-Amino-4-((4-bromobenzyl)amino)phenol

To a solution of 4-((4-bromobenzyl)amino)-3-nitrophenol (20 g, 63 mmol) in ethanol (200 mL) was added $SnCl_2 \cdot 2H_2O$ (71 g, 314 mmol) and the resulting mixture stirred at 90° C. for 1 h. The mixture was cooled to RT and concentrated to dryness. The aqueous residue was then treated with sat. aq. $NaHCO_3$ to ~pH 7 and extracted with DCM (5×1 L). The organics were combined, dried ($Na_2SO_4$), filtered and concentrated to dryness. The residue was purified by FCC to afford the title compound. $^1$H NMR (300 MHz, DMSO-$d_6$) 8.17 (s, 1H), 7.48 (d, J=8.4, 2H), 7.30 (d, J=8.3, 2H), 6.11 (dd, J=17.2, 5.5, 2H), 5.90-5.74 (m, 1H), 4.54 (s, 2H), 4.48 (t, J=5.7, 1H), 4.13 (d, J=5.5, 2H).

Step C: racemic cis-2-(1-(4-Bromobenzyl)-5-hydroxy-1H-benzo[d]imidazol-2-yl)cyclohexanecarboxylic acid 3-Amino-4-((4-bromobenzyl)amino)phenol (7.8 g, 27 mmol) and cis-hexahydroisobenzofuran-1,3-dione (4.1 g, 27 mmol) were dissolved in acetonitrile (200 mL) and the mixture heated to 80° C. After 18 h, HCl (50 mL, 6 N) was added and the resulting mixture stirred at 60° C. for 16 h. The mixture was then cooled to RT and the pH was adjusted to ~pH 7 with sat.$NaHCO_3$. The aqueous was then extracted with EtOAc (3×200 mL). The combined organics were washed with water (200 mL), dried with $Na_2SO_4$, filtered and concentrated to dryness. The residue was purified by FCC to afford the title compound. $^1$H NMR (300 MHz, DMSO-$d_6$) δ 12.13 (s, 1H), 8.93 (s, 1H), 7.47 (d, J=8.4, 2H), 7.06 (dd, J=8.6, 2.7, 3H), 6.89 (d, J=2.1, 1H), 6.60 (dd, J=8.6, 2.2, 1H), 5.52-5.26 (m, 2H), 3.63 (d, J=4.4, 1H), 2.70 (d, J=10.7, 1H), 2.55 (d, J=8.9, 1H), 1.81 (d, J=8.9, 2H), 1.61 (dd, J=32.5, 21.3, 3H), 1.34 (s, 2H).

Step D: racemic cis-2-{1-(4-Bromobenzyl)-5-[(6-fluoroquinolin-2-yl)methoxy]-1H-benzimidazol-2-yl}cyclohexanecarboxylic acid as the formic acid salt To a solution of racemic cis-2-(1-(4-bromobenzyl)-5-hydroxy-1H-benzo[d]imidazol-2-yl)cyclohexanecarboxylic acid (300 mg, 0.7 mmol) in DMF (2 mL) were added $Cs_2CO_3$ (683 mg, 2.1 mmol) and 2-(bromomethyl)-6-fluoroquinoline (336 mg, 1.4 mmol). The mixture was heated to 50° C. for 1 h. The mixture was cooled to RT, diluted with brine (20 mL) and extracted with EtOAc (2×20 mL). The organics were combined, washed with brine (2×20 mL), dried with $Na_2SO_4$, filtered and concentrated to dryness. The residue was then dissolved in THF (6 mL) and LiOH (6 mL, 1 N aq.) was added. The resulting mixture was stirred at RT for 18 h. The pH of the mixture was then adjusted to pH 7 by treatment with 1 N aq. HCl. A solid precipitated out of solution and was collected by filtration. The solid was then purified by reverse phase HPLC to afford the title compound. MS (ESI): mass calcd. for $C_{31}H_{27}BrFN_3O_3$, 587.12; m/z found, 588.1 [M+H]$^+$. $^1$H NMR (400 MHz, DMSO-$d_6$) δ 8.41 (d, J=8.6, 1H), 8.11 (dd, J=9.2, 5.5, 1H), 7.81 (dd, J=9.4, 2.8, 1H), 7.77-7.67 (m, 2H), 7.49 (d, J=8.4, 2H), 7.22 (d, J=8.7, 2H), 7.11 (d, J=7.8, 2H), 6.91 (dd, J=8.7, 2.0, 1H), 5.45 (s, 2H), 5.37 (s, 2H), 3.71-3.65 (m, 1H), 2.73-2.52 (m, 2H), 1.88-1.77 (m, 2H), 1.72-1.52 (m, 3H), 1.38-1.27 (m, 2H).

Example 53 racemic trans-2-{1-(4-Bromobenzyl)-5-[(8-fluoroquinolin-2-yl)methoxy]-1H-benzimidazol-2-yl}cyclohexanecarboxylic acid

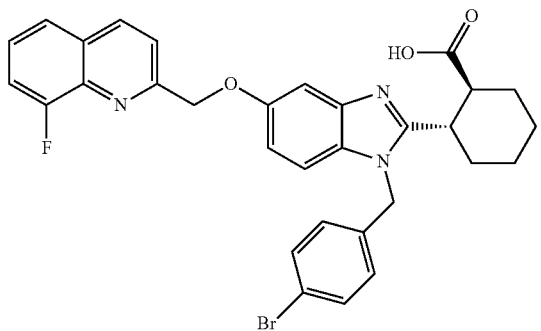 [SMILES: O=C(O)[C@H]1CCCC[C@@H]1c1nc2cc(OCc3ccc4cccc(F)c4n3)ccc2n1Cc1ccc(Br)cc1]

The title compound was prepared using similar methods to those in Example 52 using trans-hexahydroisobenzofuran-1,3-dione in Step C and 2-(bromomethyl)-8-fluoroquinoline in Step D. MS (ESI): mass calcd. for $C_{31}H_{27}BrFN_3O_3$, 587.12; m/z found, 587.8 [M+H]$^+$. $^1$H NMR (400 MHz, DMSO-$d_6$) δ 8.48 (d, J=8.4, 1H), 7.83 (d, J=6.9, 1H), 7.78 (d, J=8.6, 1H), 7.67-7.56 (m, 2H), 7.50 (d, J=8.3, 2H), 7.24-7.16 (m, 4H), 6.91 (dd, J=8.7, 2.2, 1H), 5.47 (s, 2H), 5.39 (s, 2H), 3.15-3.04 (m, 1H), 2.94-2.80 (m, 1H), 2.15-2.03 (m, 1H), 1.81-1.72 (m, 1H), 1.69-1.53 (m, 2H), 1.43-1.26 (m, 4H).

Example 54 racemic cis-2-{1-(4-Bromobenzyl)-5-[(8-fluoroquinolin-2-yl)methoxy]-1H-benzimidazol-2-yl}cyclohexanecarboxylic acid as the formic acid salt

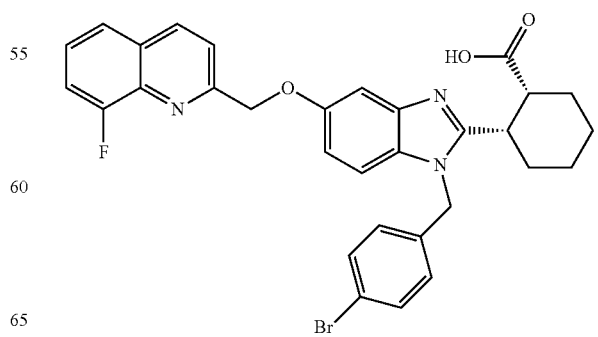

The title compound was prepared using similar methods to those in Example 52, using 2-(bromomethyl)-8-fluoroquinoline in Step D. MS (ESI): mass calcd. for $C_{31}H_{27}BrFN_3O_3$, 587.12; m/z found, 588.1 [M+H]$^+$. $^1$H NMR (400 MHz, DMSO-d$_6$) δ 12.06 (s, 1H), 8.49 (d, J=8.5 Hz, 1H), 7.89-7.77 (m, 2H), 7.61 (t, J=7.4 Hz, 2H), 7.49 (d, J=8.0 Hz, 2H), 7.23 (d, J=11.3 Hz, 2H), 7.10 (d, J=7.8 Hz, 2H), 6.93 (d, J=8.8 Hz, 1H), 5.53-5.35 (m, 4H), 3.71-3.63 (m, 1H), 2.71-2.60 (m, 1H), 1.90-1.47 (m, 5H), 1.40-1.20 (m, 3H).

Example 55 racemic cis-2-{1-(4-Bromobenzyl)-5-[(7-chloroquinolin-2-yl)methoxy]-1H-benzimidazol-2-yl}cyclohexanecarboxylic acid as the formic acid salt

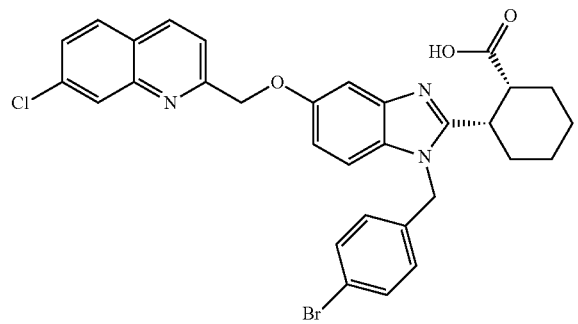 [SMILES: O=C(O)[C@@H]1CCCC[C@@H]1c1nc2cc(OCc3ccc4ccc(Cl)cc4n3)ccc2n1Cc1ccc(Br)cc1]

The title compound was prepared using similar methods to those in Example 52 using 2-(bromomethyl)-7-chloroquinoline in Step D. MS (ESI): mass calcd. for $C_{31}H_{27}BrClN_3O_3$, 603.09; m/z found, 604.0 [M+H]$^+$. $^1$H NMR (500 MHz, DMSO-d$_6$) δ 12.21 (s, 1H), 8.47 (d, J=8.6, 1H), 8.10 (d, J=2.0, 1H), 8.06 (d, J=8.7, 1H), 7.74 (d, J=8.5, 1H), 7.66 (dd, J=8.7, 2.1, 1H), 7.50 (d, J=8.3, 2H), 7.27 (s, 1H), 7.25 (d, J=2.1, 1H), 7.09 (d, J=8.4, 2H), 6.98 (s, 1H), 5.63-5.44 (m, 2H), 5.41 (s, 2H), 3.72-3.62 (m, 1H), 2.74 (s, 1H), 2.46 (s, 1H), 1.92-1.47 (m, 5H), 1.35 (s, 2H).

Example 56 racemic cis-2-{1-(4-Bromobenzyl)-5-[(6-chloroquinolin-2-yl)methoxy]-1H-benzimidazol-2-yl}cyclohexanecarboxylic acid

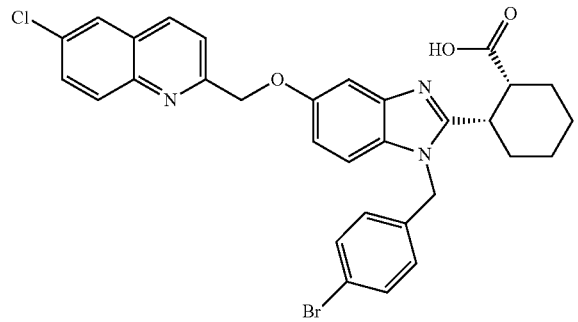 [SMILES: O=C(O)[C@@H]1CCCC[C@@H]1c1nc2cc(OCc3ccc4cc(Cl)ccc4n3)ccc2n1Cc1ccc(Br)cc1]

The title compound was prepared using similar methods to those in Example 52 using 2-(bromomethyl)-6-chloroquinoline in Step D. MS (ESI): mass calcd. for $C_{31}H_{27}BrClN_3O_3$, 603.09; m/z found, 604.1 [M+H]$^+$. $^1$H NMR (500 MHz, DMSO-d$_6$) δ 8.41 (d, J=8.6, 1H), 8.15 (d, J=2.3, 1H), 8.06 (d, J=9.0, 1H), 7.81 (dd, J=9.0, 2.4, 1H), 7.75 (d, J=8.6, 1H), 7.52 (d, J=8.2, 2H), 7.36 (s, 1H), 7.27 (d, J=2.1, 1H), 7.11-7.09 (m, 3H), 5.61 (s, 2H), 5.43 (s, 2H), 3.71-3.64 (m, 1H), 2.79 (m, 1H), 2.35-1.30 (m, 8H).

Example 57

1-({5-(Quinolin-2-ylmethoxy)-1-[4-(trifluoromethyl)benzyl]-1H-benzimidazol-2-yl}methyl)cyclopentanecarboxylic acid

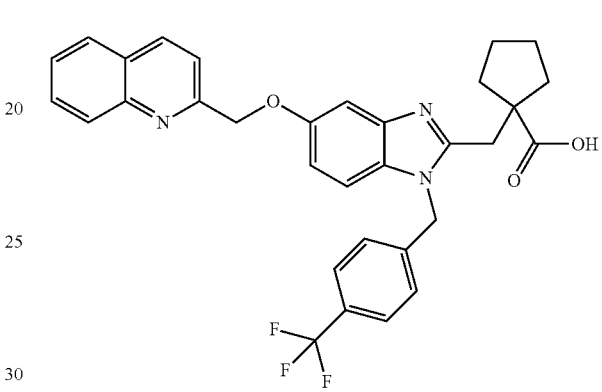

Step A: 2-Nitro-4-(quinolin-2-ylmethoxy)-N-(4-(trifluoromethyl)benzyl)aniline

To a 25 mL round bottom flask under a nitrogen atmosphere were added 2-((4-fluoro-3-nitrophenoxy)methyl)quinoline (195 mg, 0.65 mmol), 4-(trifluoromethyl)-benzylamine (112 mg, 0.65 mmol), acetonitrile (1 mL) and DIPEA (0.34 mL, 1.96 mmol). The mixture was heated to 80° C. for 24 h at which point the reaction was cooled to RT and concentrated to dryness. The resulting residue was washed with water (2×20 mL) and then dissolved in EtOAc, dried over Na$_2$SO$_4$, filtered and then concentrated. The material was used without further purification. MS (ESI): mass calcd. for $C_{24}H_{18}F_3N_3O_3$, 453.13; m/z found, 454.1[M+H]$^+$.

Step B: 4-(Quinolin-2-ylmethoxy)-N1-(4-(trifluoromethyl)benzyl)benzene-1,2-diamine To a 50 mL round-bottomed flask were added a stir bar, 2-nitro-4-(quinolin-2-ylmethoxy)-N-(4-(trifluoromethyl)benzyl)aniline (310 mg, 0.69 mmol), THF (6.9 mL), and DIPEA (60 μL, 0.3 mmol) followed by 5% platinum on carbon (15 mg, 0.08 mmol). The reaction vessel was evacuated and then placed under one atmosphere of hydrogen for 16 h. The mixture was then flushed with N$_2$ and filtered through a pad of Celite. The Celite was then rinsed with additional THF (25 mL). The resulting solution was concentrated to dryness to afford the title compound which was used without further purification. MS (ESI): mass calcd. for $C_{24}H_{20}F_3N_3O$, 423.16; m/z found, 424.1 [M+H]$^+$.

Step C: 1-({5-(Quinolin-2-ylmethoxy)-1-[4-(trifluoromethyl)benzyl]-1H-benzimidazol-2-yl}methyl)cyclopentanecarboxylic acid To a 10 mL round bottomed flask, equipped with a reflux condenser, were added 4-(quinolin-2-ylmethoxy)-N1-(4-

(trifluoromethyl)benzyl)benzene-1,2-diamine (53 mg, 0.12 mmol), 2-oxaspiro[4.4]nonane-1,3-dione (19 mg, 0.12 mmol) and acetonitrile (1.3 mL). The flask was heated to 80° C. for 72 hours. The mixture was concentrated and the residue was dissolved in ethanol (2 mL) followed by the slow addition of HCl (0.6 mL, 12 N). The mixture was then heated to 80° C. until the starting material had been consumed. The reaction mixture was cooled to RT, concentrated to dryness and the resulting residue was dissolved in THF (3.4 mL) and methanol (3.4 mL). To this solution was added LiOH (3.6 mL, 1 M aq.) and the reaction was monitored by LCMS until the ester was consumed. The reaction mixture was then partitioned between 1 mL of aqueous $NH_4Cl$ and EtOAc. The aqueous layer was further extracted with EtOAc (3×20 mL). The combined organics were dried over sodium sulfate, filtered and concentrated to dryness. The crude residue was purified using reverse phase HPLC to provide the title compound. MS (ESI): mass calcd. for $C_{32}H_{28}F_3N_3O_3$, 559.21; m/z found, 5602 [M+H]$^+$. $^1$H NMR (500 MHz, CDCl$_3$) δ 8.13 (d, J=8.4 Hz, 1H), 8.07 (d, J=8.5 Hz, 1H), 7.79 (d, J=8.2 Hz, 1H), 7.71 (t, J=7.7 Hz, 1H), 7.62 (d, J=8.5 Hz, 1H), 7.58-7.44 (m, 3H), 7.35 (s, 1H), 7.14-6.85 (m, 4H), 5.32 (s, 4H), 3.04 (s, 2H), 2.43-2.14 (m, 2H), 1.75-1.31 (m, 7H).

Example 58

1-{[1-(4-Fluorobenzyl)-5-(quinolin-2-ylmethoxy)-1H-benzimidazol-2-yl]methyl}cyclopentanecarboxylic acid as the TFA salt

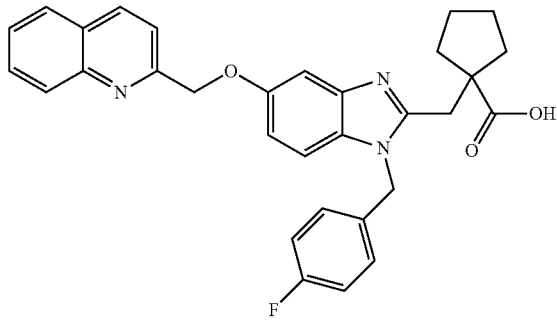 [SMILES: O=C(O)C1(Cc2nc3cc(OCc4ccc5ccccc5n4)ccc3n2Cc2ccc(F)cc2)CCCC1]

The title compound was prepared using analogous conditions described in Example 57 using 1-(bromomethyl)-4-fluorobenzene in Step A. MS (ESI): mass calcd. for $C_{31}H_{28}FN_3O_3$, 509.21; m/z found, 510.2 [M+H]$^+$. $^1$H NMR (500 MHz, CDCl$_3$) δ 8.20 (d, J=8.5 Hz, 1H), 8.11 (d, J=8.5 Hz, 1H), 7.86-7.80 (m, 1H), 7.78-7.66 (m, 2H), 7.56 (ddd, J=8.2, 6.9, 1.2 Hz, 1H), 7.34 (d, J=2.4 Hz, 1H), 7.18 (d, J=8.9 Hz, 1H), 7.11-6.98 (m, 5H), 5.43 (s, 2H), 5.28 (s, 2H), 3.04 (s, 2H), 2.40-2.36 (m, 2H), 1.73-1.69 (m, 2H), 1.48-1.41 (m, 4H).

Example 59

1-({5-(Quinolin-2-ylmethoxy)-1-[4-methoxybenzyl]-1H-benzimidazol-2-yl}methyl)cyclopentanecarboxylic acid as the TFA salt

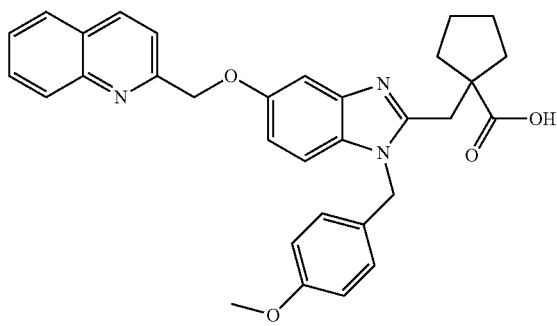 [SMILES: COc1ccc(Cn2c(CC3(C(=O)O)CCCC3)nc3cc(OCc4ccc5ccccc5n4)ccc32)cc1]

The title compound was prepared using analogous conditions described in Example 57 using 1-(bromomethyl)-4-methoxybenzene in Step A. MS (ESI): mass calcd. for $C_{32}H_{31}N_3O_4$, 521.62; m/z found, 522.2 [M+H]$^+$. $^1$H NMR (500 MHz, CDCl$_3$) δ 8.45 (d, J=8.5 Hz, 1H), 8.26 (dd, J=8.4, 1.2 Hz, 1H), 8.10 (s, 3H), 7.96-7.90 (m, 1H), 7.84 (ddd, J=8.5, 6.9, 1.4 Hz, 1H), 7.80 (d, J=8.5 Hz, 1H), 7.67 (ddd, J=8.1, 6.9, 1.1 Hz, 1H), 7.50 (d, J=2.4 Hz, 1H), 7.26-7.22 (m, 1H), 7.13 (dd, J=9.1, 2.3 Hz, 1H), 7.01-6.92 (m, 2H), 6.86-6.77 (m, 2H), 5.50 (d, J=12.6 Hz, 4H), 3.75 (s, 3H), 3.38 (s, 2H), 2.23-2.09 (m, 2H), 1.70-1.47 (m, 6H).

Example 60

1-({5-(Quinolin-2-ylmethoxy)-1-[4-(trifluoromethoxy)benzyl]-1H-benzimidazol-2-yl}methyl)cyclopentanecarboxylic acid as the TFA salt

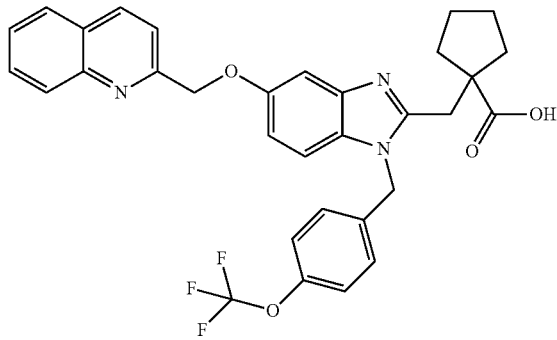 [SMILES: O=C(O)C1(Cc2nc3cc(OCc4ccc5ccccc5n4)ccc3n2Cc2ccc(OC(F)(F)F)cc2)CCCC1]

The title compound was prepared using analogous conditions described in Example 57 using 1-(bromomethyl)-4-(trifluoromethoxy)benzene in Step A. MS (ESI): mass calcd. for $C_{32}H_{28}F_3N_3O_4$, 575.20; m/z found, 576.2 [M+H]$^+$. $^1$H NMR (500 MHz, CDCl$_3$) δ 8.19 (d, J=8.8 Hz, 1H), 8.10 (d, J=8.5 Hz, 1H), 7.83 (d, 1H), 7.74 (t, J=7.7 Hz, 1H), 7.68 (d, J=8.5 Hz, 1H), 7.55 (t, J=7.5 Hz, 1H), 7.35 (d, J=2.3 Hz, 1H), 7.16 (t, J=8.2 Hz, 3H), 7.06 (t, J=10.3 Hz, 3H), 5.42 (s, 2H), 5.31 (s, 2H), 3.03 (s, 2H), 2.43-2.29 (m, 2H), 1.77-1.64 (m, 2H), 1.49-1.36 (m, 4H).

Example 61

1-{[1-(Pyridin-2-ylmethyl)-5-(quinolin-2-ylmethoxy)-1H-benzimidazol-2-yl]methyl}cyclopentanecarboxylic acid

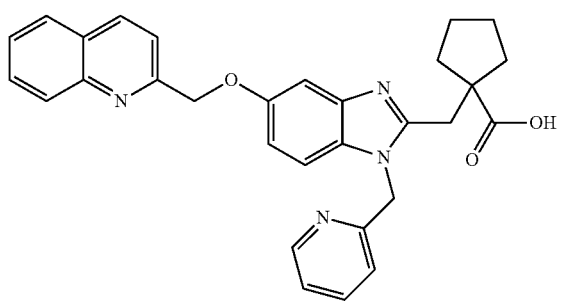 [SMILES: O=C(O)C1(Cc2nc3cc(OCc4ccc5ccccc5n4)ccc3n2Cc2ccccn2)CCCC1]

The title compound was prepared using analogous conditions described in Example 57 using 2-(bromomethyl)pyridine in Step A. MS (ESI): mass calcd. for C₃₀H₂₈N₄O₃, 492.22; m/z found, 493.2 [M+H]⁺. ¹H NMR (500 MHz, CDCl₃) δ 8.55 (d, J=4.8 Hz, 1H), 8.16 (d, J=8.5 Hz, 1H), 8.09 (d, J=8.4 Hz, 1H), 7.81 (d, J=8.2 Hz, 1H), 7.77-7.52 (m, 4H), 7.33 (d, J=2.3 Hz, 1H), 7.24-7.14 (m, 2H), 7.06-6.99 (m, 1H), 6.84 (d, J=7.8 Hz, 1H), 5.38 (s, 4H), 3.17 (s, 2H), 2.37-2.32 (m, 1H), 1.85-1.55 (m, 3H), 1.54-1.46 (m, 4H).

Example 62

1-{[1-(Pyridin-3-ylmethyl)-5-(quinolin-2-ylmethoxy)-1H-benzimidazol-2-yl]methyl}cyclopentanecarboxylic acid

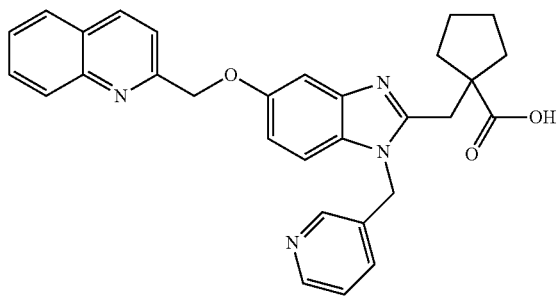 [SMILES: O=C(O)C1(Cc2nc3cc(OCc4ccc5ccccc5n4)ccc3n2Cc2cccnc2)CCCC1]

The title compound was prepared using analogous conditions described in Example 57 using 3-(bromomethyl)pyridine in Step A. MS (ESI): mass calcd. for C₃₀H₂₈N₄O₃, 492.22; m/z found, 493.3 [M+H]⁺. ¹H NMR (500 MHz, CDCl₃) δ 8.55 (t, J=3.2 Hz, 1H), 8.48 (d, J=1.9 Hz, 1H), 8.19 (d, J=8.5 Hz, 1H), 8.15-8.07 (m, 1H), 7.83 (dd, J=7.9, 1.4 Hz, 1H), 7.74 (ddd, J=8.5, 6.9, 1.5 Hz, 1H), 7.68 (d, J=8.5 Hz, 1H), 7.55 (ddd, J=8.1, 7.0, 1.2 Hz, 1H), 7.35 (d, J=2.3 Hz, 1H), 7.27-7.20 (m, 5H), 7.13 (d, J=8.8 Hz, 1H), 7.05 (dd, J=8.8, 2.3 Hz, 1H), 5.42 (s, 2H), 5.35 (s, 2H), 3.08 (s, 2H), 2.46-2.28 (m, 2H), 1.82-1.61 (m, 2H), 1.61-1.39 (m, 4H).

Example 63

1-{[1-(4-Chlorobenzyl)-5-(quinolin-2-ylmethoxy)-1H-benzimidazol-2-yl]methyl}cyclopentanecarboxylic acid

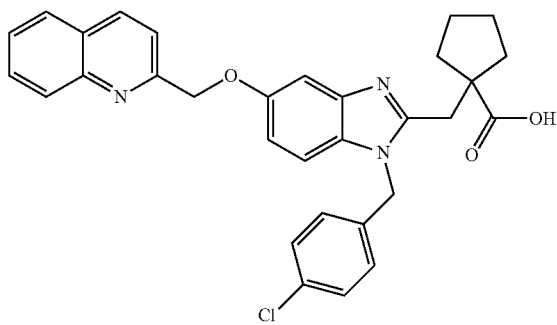 [SMILES: O=C(O)C1(Cc2nc3cc(OCc4ccc5ccccc5n4)ccc3n2Cc2ccc(Cl)cc2)CCCC1]

The title compound was prepared using analogous conditions described in Example 57 using 1-(bromomethyl)-4-chlorobenzene in Step A. MS (ESI): mass calcd. for C₃₁H₂₈ClN₃O₃, 525.18; m/z found, 526.2 [M+H]⁺. ¹H NMR (500 MHz, CDCl₃) δ 8.19 (d, J=8.5 Hz, 1H), 8.10 (d, J=8.5 Hz, 1H), 7.83 (d, J=7.6 Hz, 1H), 7.77-7.70 (m, 1H), 7.68 (d, J=8.5 Hz, 1H), 7.59-7.51 (m, 1H), 7.34 (d, J=2.2 Hz, 1H), 7.29 (d, J=8.4 Hz, 2H), 7.13 (d, J=8.9 Hz, 1H), 7.05 (dd, J=8.9, 2.2 Hz, 1H), 6.95 (d, J=8.4 Hz, 2H), 5.42 (s, 2H), 5.28 (s, 2H), 3.04 (s, 2H), 2.43-2.31 (m, 2H), 1.76-1.65 (m, 2H), 1.54-1.39 (m, 4H).

Example 64

3-{1-[1-(4-Bromophenyl)propyl]-5-(quinolin-2-ylmethoxy)-1H-benzimidazol-2-yl}-2,2-dimethylpropanoic acid

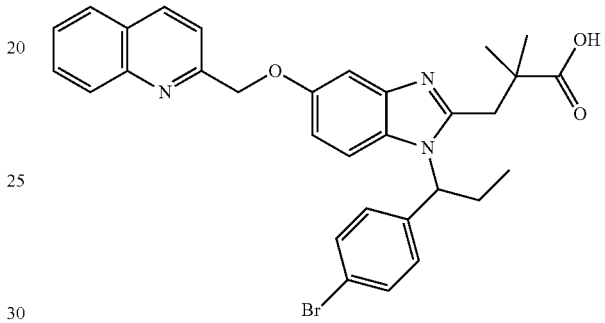

Step A: Ethyl 3-(1-(1-(4-bromophenyl)propyl)-5-(quinolin-2-ylmethoxy)-1H-benzo[d]imidazol-2-yl)-2,2-dimethylpropanoate A suspension of ethyl 2,2-dimethyl-3-(5-(quinolin-2-ylmethoxy)-1H-benzo[d]imidazol-2-yl)propanoate) (300 mg, 0.74 mmol), 1-bromo-4-(1-bromopropyl)benzene (413 mg, 1.49 mmol) and cesium carbonate (727 mg, 2.23 mmol) in DMF (3.7 mL) was heated to 100° C. for 3 days. The mixture was cooled and partitioned between water and EtOAc. The organic layer was dried and concentrated to a residue. Purification using FCC afforded the title compound. MS (ESI): mass calcd. for C₃₃H₃₄BrN₃O₃, 599.18; m/z found, 600.1 [M+H]⁺. ¹H NMR (400 MHz, CDCl₃) δ 8.14 (d, J=8.5, 1H), 8.05 (d, J=8.5 Hz, 1H), 7.83 (d, J=8.2, 1H), 7.74 (ddd, J=8.4, 6.9, 1.4, 1H), 7.62-7.53 (m, 3H), 7.28-7.25 (m, 2H), 6.97-6.92 (m, 3H), 6.62 (d, J=2.3, 1H), 5.38 (dd, J=10.0, 5.9, 1H), 5.34-5.22 (m, 2H), 4.05 (qd, J=7.1, 0.8, 2H), 3.08 (q, J=15.6, 2H), 2.42-2.23 (m, 2H), 1.37 (s, 3H), 1.35 (s, 3H), 1.15 (t, J=7.1, 3H), 0.72 (t, J=7.3, 3H).

Step B: 3-{1-[1-(4-Bromophenyl)propyl]-6-(quinolin-2-ylmethoxy)-1H-benzimidazol-2-yl}-2,2-dimethylpropanoic acid To a solution of ethyl 3-(1-(1-(4-bromophenyl)propyl)-5-(quinolin-2-ylmethoxy)-1H-benzo[d]imidazol-2-yl)-2,2-dimethylpropanoate (36 mg, 0.060 mmol) in THF (0.3 mL) and MeOH (0.3 mL) was added LiOH (0.3 mL, 1 N) and the resulting solution was allowed to stir over night. The resulting reaction mixture was partitioned between sat. NH₄Cl and EtOAc, and the organic layer was separated, dried and concentrated to afford the title compound. MS (ESI): mass calcd. for C₃₁H₃₀BrN₃O₃, 571.15; m/z found, 572.1 [M+H]⁺. ¹H NMR (500 MHz, CDCl₃) δ 8.19 (d, J=8.5, 1H), 8.10 (d, J=8.4, 1H), 7.82 (d, J=8.0, 1H), 7.74 (ddd, J=8.4, 7.0, 1.3, 1H), 7.67 (d, J=8.5, 1H), 7.55 (dd, J=11.0, 4.0, 1H), 7.47 (d, J=8.5, 2H), 7.33 (d, J=2.0, 1H), 7.07-7.01 (m, 3H), 6.96 (dd, J=9.0, 2.2, 1H), 5.44-5.39 (m, 3H), 3.02 (s, 2H), 2.56-2.45 (m, 1H), 2.45-2.35 (m, 1H), 1.29 (s, 3H), 1.28 (s, 3H), 0.85 (t, J=7.3, 3H).

Example 65

2,2-Dimethyl-3-[1-(4-methylbenzyl)-5-(quinolin-2-ylmethoxy)-1H-benzimidazol-2-yl]propanoic acid

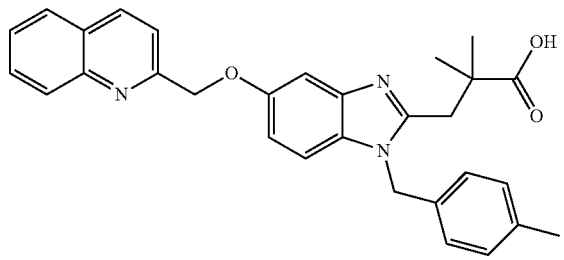 [SMILES: Cc1ccc(Cn2c(CC(C)(C)C(=O)O)nc3cc(OCc4ccc5ccccc5n4)ccc32)cc1]

The title compound was prepared using analogous conditions described in Example 64 using 1-(bromomethyl)-4-methylbenzene in Step A. MS (ESI): mass calcd. for $C_{30}H_{29}N_3O_3$, 479.22; m/z found, 480.2 [M+H]$^+$. $^1$H NMR (500 MHz, CDCl$_3$) δ 8.19 (d, J=8.5 Hz, 1H), 8.10 (d, J=8.5 Hz, 1H), 7.83 (d, J=8.0 Hz, 1H), 7.74 (ddd, J=8.4, 6.9, 1.5 Hz, 1H), 7.69 (d, J=8.4 Hz, 1H), 7.55 (ddd, J=8.1, 7.0, 1.2 Hz, 1H), 7.34 (d, J=2.4 Hz, 1H), 7.21 (d, J=8.9 Hz, 1H), 7.12 (d, J=7.8 Hz, 2H), 7.07 (d, J=8.0 Hz, 1H), 6.92 (d, J=7.8 Hz, 2H), 5.43 (s, 2H), 5.28 (s, 2H), 2.99 (s, 2H), 2.32 (s, 3H), 1.24 (s, 6H).

Example 66

3-[1-(4-Fluorobenzyl)-5-(quinolin-2-ylmethoxy)-1H-benzimidazol-2-yl]-2,2-dimethylbrobanoic acid

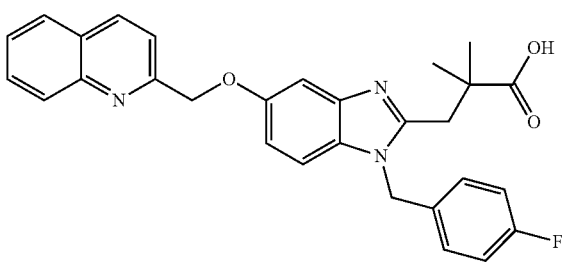 [SMILES: CC(C)(Cc1nc2cc(OCc3ccc4ccccc4n3)ccc2n1Cc1ccc(F)cc1)C(=O)O]

The title compound was prepared using analogous conditions described in Example 64 using 1-(bromomethyl)-4-fluorobenzene in Step A. MS (ESI): mass calcd. for $C_{29}H_{26}FN_3O_3$, 483.20; m/z found, 484.1 [M+H]$^+$. $^1$H NMR (500 MHz, CDCl$_3$) δ 8.18 (d, J=8.5 Hz, 1H), 8.10 (d, J=8.5 Hz, 1H), 7.87-7.79 (m, 1H), 7.73 (ddd, J=8.4, 6.8, 1.4 Hz, 1H), 7.68 (d, J=8.5 Hz, 1H), 7.54 (ddd, J=8.0, 6.8, 1.1 Hz, 1H), 7.35 (d, J=2.4 Hz, 1H), 7.14 (d, J=8.8 Hz, 1H), 7.05 (dd, J=9.0, 2.4 Hz, 1H), 7.00 (d, J=6.8 Hz, 4H), 5.41 (s, 2H), 5.29 (d, J=1.7 Hz, 2H), 3.00 (s, 2H), 1.26 (s, 6H).

Example 67

3-[1-(3-Chlorobenzyl)-5-(quinolin-2-ylmethoxy)-1H-benzimidazol-2-yl]-2,2-dimethylpropanoic acid as the TFA acid salt

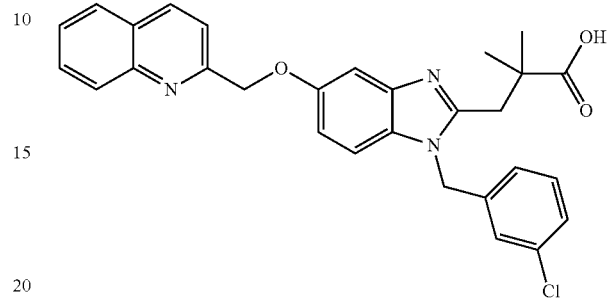

The title compound was prepared using analogous conditions described in Example 64 using 1-(bromomethyl)-3-chlorobenzene in Step A. MS (ESI): mass calcd. for $C_{29}H_{26}ClN_3O_3$, 499.17; m/z found, 500.1 [M+H]$^+$. $^1$H NMR (500 MHz, CDCl$_3$) δ 13.65 (s, 2H), 8.59 (d, J=8.5 Hz, 1H), 8.35 (d, J=8.7 Hz, 1H), 8.04-7.97 (m, 1H), 7.92 (t, J=8.8 Hz, 2H), 7.74 (t, J=7.5 Hz, 1H), 7.54 (d, J=2.2 Hz, 1H), 7.30 (t, J=8.6 Hz, 2H), 7.24-7.18 (m, 1H), 7.03 (s, 1H), 6.88 (d, J=7.6 Hz, 1H), 5.66 (s, 2H), 5.57 (s, 2H), 3.32 (s, 2H), 1.27 (s, 6H).

Example 68

2,2-Dimethyl-3-[1-(3-methylbenzyl)-5-(quinolin-2-ylmethoxy)-1H-benzimidazol-2-yl]propanoic acid

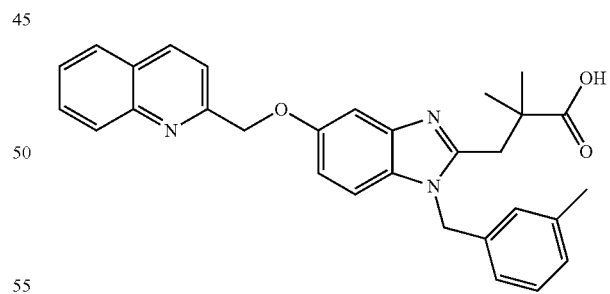

The title compound was prepared using analogous conditions described in Example 64 using 1-(bromomethyl)-3-methylbenzene in Step A. MS (ESI): mass calcd. for $C_{30}H_{29}N_3O_3$, 479.22; m/z found, 480.2 [M+H]$^+$. $^1$H NMR (500 MHz, CDCl$_3$) δ 8.17 (d, J=8.5 Hz, 1H), 8.09 (d, J=8.5 Hz, 1H), 7.81 (d, J=8.1 Hz, 1H), 7.75-7.62 (m, 2H), 7.53 (t, J=7.5 Hz, 1H), 7.36 (s, 1H), 7.23-7.13 (m, 2H), 7.09 (d, J=7.6 Hz, 1H), 7.02 (dd, J=8.8, 2.4 Hz, 1H), 6.88-6.77 (m, 2H), 5.41 (s, 2H), 5.29 (s, 2H), 3.07 (s, 2H), 2.27 (s, 3H), 1.24 (s, 6H).

Example 69

3-[1-(2-Chlorobenzyl)-5-(quinolin-2-ylmethoxy)-1H-benzimidazol-2-yl]-2,2-dimethylpropanoic acid as the TFA salt

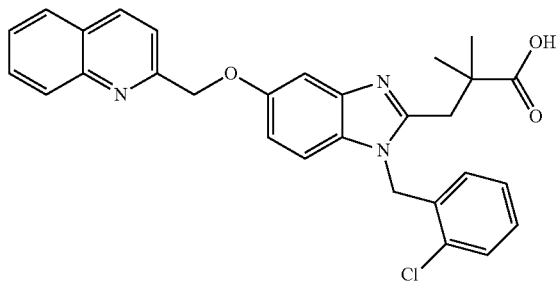 [SMILES: CC(C)(Cc1nc2cc(OCc3ccc4ccccc4n3)ccc2n1Cc1ccccc1Cl)C(=O)O]

The title compound was prepared using analogous conditions described in Example 64 using 1-(bromomethyl)-2-chlorobenzene in Step A. MS (ESI): mass calcd. for $C_{29}H_{26}ClN_3O_3$, 499.17; m/z found, 500.1 [M+H]$^+$. $^1$H NMR (500 MHz, CDCl$_3$) δ 8.55 (d, J=8.3 Hz, 1H), 8.33 (d, J=8.6 Hz, 1H), 7.98 (d, J=8.2 Hz, 1H), 7.94-7.86 (m, 2H), 7.73 (t, J=7.6 Hz, 1H), 7.57 (s, 1H), 7.35-7.27 (m, 2H), 7.25-7.20 (m, 2H), 7.04 (s, 1H), 6.88 (d, J=7.2 Hz, 1H), 5.65 (s, 2H), 5.55 (s, 2H), 3.33 (s, 2H), 1.29 (s, 6H).

Example 70

3-[1-(4-Methoxybenzyl)-5-(quinolin-2-ylmethoxy)-1H-benzimidazol-2-yl]-2,2-dimethylpropanoic acid as the TFA salt

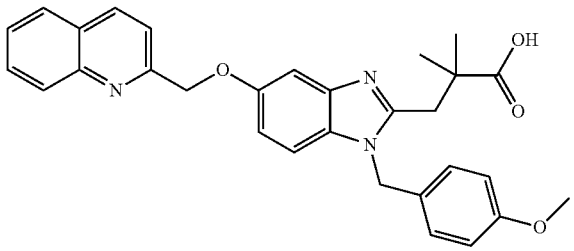 [SMILES: COc1ccc(Cn2c(CC(C)(C)C(=O)O)nc3cc(OCc4ccc5ccccc5n4)ccc32)cc1]

The title compound was prepared using analogous conditions described in Example 64 using 1-(bromomethyl)-4-methoxybenzene in Step A. MS (ESI): mass calcd. for $C_{30}H_{29}N_3O_4$, 495.22; m/z found, 496.1 [M+H]$^+$. $^1$H NMR (500 MHz, CDCl$_3$) δ 8.52 (d, J=8.5 Hz, 1H), 8.33 (d, J=8.7 Hz, 1H), 7.97 (d, J=8.2 Hz, 1H), 7.94-7.83 (m, 2H), 7.75-7.68 (m, 1H), 7.58 (s, 1H), 7.35-7.27 (m, 2H), 6.98 (d, J=8.3 Hz, 2H), 6.90-6.84 (m, 2H), 5.64 (s, 2H), 5.47 (s, 2H), 3.79 (s, 3H), 3.38 (s, 2H), 1.29 (s, 6H).

Example 71

2,2-Dimethyl-3-{5-(quinolin-2-ylmethoxy)-1-[4-(trifluoromethyl)benzyl]-1H-benzimidazol-2-yl}propanoic acid as the TFA salt

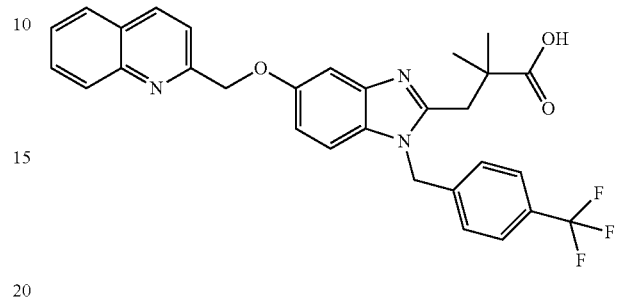

The title compound was prepared using analogous conditions described in Example 64 using 1-(bromomethyl)-4-(trifluoromethyl)benzene in Step A. MS (ESI): mass calcd. for $C_{30}H_{26}F_3N_3O_3$, 533.19; m/z found, 534.2 [M+H]$^+$. $^1$H NMR (500 MHz, CDCl$_3$) δ 8.44 (d, J=8.6 Hz, 1H), 8.26 (d, J=8.6 Hz, 1H), 7.94 (d, J=8.1 Hz, 1H), 7.85 (t, J=7.6 Hz, 1H), 7.81 (d, J=8.5 Hz, 1H), 7.68 (t, J=7.6 Hz, 1H), 7.61 (d, J=8.2 Hz, 2H), 7.56 (s, 1H), 7.19 (s, 2H), 7.14 (d, J=8.1 Hz, 2H), 5.65 (s, 2H), 5.57 (s, 2H), 3.30 (s, 2H), 1.28 (s, 6H).

Example 72

3-{1-[1-(4-Bromophenyl)ethyl]-5-(quinolin-2-ylmethoxy)-1H-benzimidazol-2-yl}-2,2-dimethylpropanoic acid

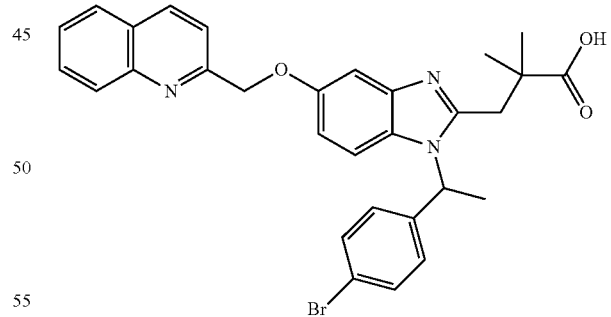

The title compound was prepared in a manner analogous to that in Example 64 using 1-bromo-4-(1-bromoethyl)benzene in Step A. MS (ESI): mass calcd. for $C_{30}H_{28}BrN_3O_3$, 557.13; m/z found, 558.1 [M+H]$^+$. $^1$H NMR (500 MHz, DMSO-d$_6$) δ 8.38 (d, J=8.4 Hz, 1H), 8.02 (d, J=8.5 Hz, 1H), 7.97 (d, J=8.0 Hz, 1H), 7.78 (t, J=7.2 Hz, 1H), 7.66 (d, J=8.5 Hz, 1H), 7.61 (t, J=7.1 Hz, 1H), 7.54-7.47 (m, 2H), 7.20-7.11 (m, 3H), 6.91 (d, J=8.8 Hz, 1H), 6.78 (dd, J=8.9, 2.3, 1H), 6.00 (d, J=6.9 Hz, 1H), 5.34 (s, 2H), 3.09 (s, 2H), 1.85 (d, J=6.9 Hz, 3H), 1.24 (s, 6H).

Example 73

3-[1-(3,4-Dichlorobenzyl)-5-(quinolin-2-yl-methoxy)-1H-benzimidazol-2-yl]-2,2-dimethylpropanoic acid

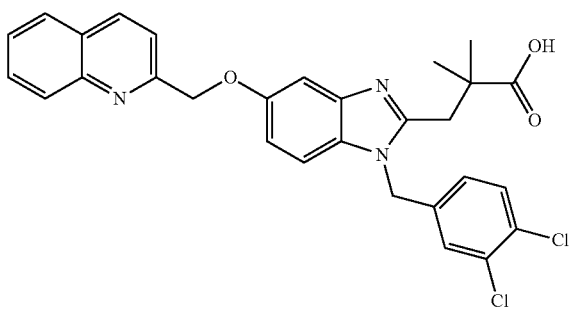 [SMILES: CC(C)(Cc1nc2cc(OCc3ccc4ccccc4n3)ccc2n1Cc1ccc(Cl)c(Cl)c1)C(=O)O]

The title compound was prepared in a manner analogous to that in Example 64 using 4-(bromomethyl)-1,2-dichlorobenzene in Step A. MS (ESI): mass calcd. for $C_{29}H_{25}Cl_2N_3O_3$, 533.13; m/z found, 534.1 [M+H]$^+$. $^1$H NMR (500 MHz, CDCl$_3$) δ 8.19 (d, J=8.0, 1H), 8.10 (d, J=8.2, 1H), 7.82 (d, J=7.7, 1H), 7.76-7.70 (m, 1H), 7.68 (d, J=8.3, 1H), 7.55 (t, J=7.2, 1H), 7.37 (s, 2H), 7.14 (s, 1H), 7.06 (dd, J=21.9, 8.3, 2H), 6.79 (d, J=7.5, 1H), 5.41 (s, 2H), 5.30 (s, 2H), 3.02 (s, 2H), 1.30 (s, 6H).

Example 74

3-{1-[4-Fluoro-3-(trifluoromethyl)benzyl]-5-(quinolin-2-ylmethoxy)-1H-benzimidazol-2-yl}-2,2-dimethylpropanoic acid

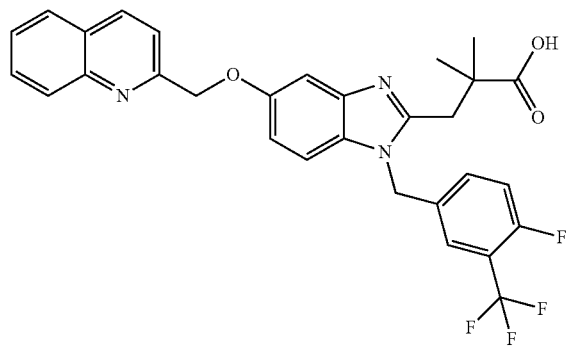 [SMILES: CC(C)(Cc1nc2cc(OCc3ccc4ccccc4n3)ccc2n1Cc1ccc(F)c(C(F)(F)F)c1)C(=O)O]

The title compound was prepared in a manner analogous to that in Example 64 using 4-(bromomethyl)-1-fluoro-2-(trifluoromethyl)benzene in Step A. MS (ESI): mass calcd. for $C_{30}H_{25}F_4N_3O_3$, 551.18; m/z found, 552.1 [M+H]$^+$. $^1$H NMR (500 MHz, CD$_3$OD) δ 8.35 (d, J=8.5, 1H), 8.05 (d, J=8.4, 1H), 7.93 (d, J=7.4, 1H), 7.80-7.76 (m, 1H), 7.74 (d, J=8.5, 1H), 7.60 (ddd, J=8.1, 7.0, 1.1, 1H), 7.45 (d, J=6.9, 1H), 7.25 (dt, J=13.4, 5.4, 4H), 7.04 (dd, J=8.9, 2.3, 1H), 5.58 (s, 2H), 5.40 (s, 2H), 3.12 (s, 2H), 1.31 (s, 6H).

Example 75

3-[1-(3-Chloro-4-fluorobenzyl)-5-(quinolin-2-yl-methoxy)-1H-benzimidazol-2-yl]-2,2-dimethylpropanoic acid

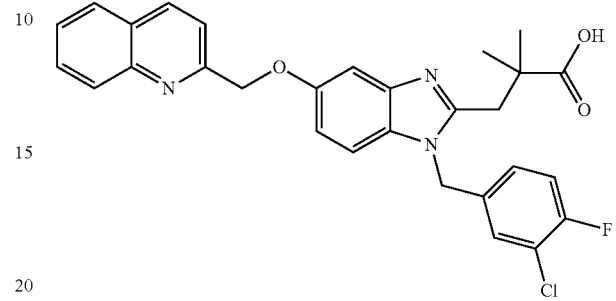

The title compound was prepared in a manner analogous to that in Example 64 using 4-(bromomethyl)-2-chloro-1-fluorobenzene in Step A. MS (ESI): mass calcd. for $C_{29}H_{25}ClFN_3O_3$, 517.16; m/z found, 518.1 [M+H]$^+$. $^1$H NMR (500 MHz, CDCl$_3$) δ 8.19 (d, J=8.5, 1H), 8.10 (d, J=8.4, 1H), 7.82 (d, J=8.1, 1H), 7.76-7.71 (m, 1H), 7.68 (d, J=8.5, 1H), 7.55 (t, J=7.5, 1H), 7.37 (d, J=2.0, 1H), 7.13-7.02 (m, 4H), 6.87-6.81 (m, 1H), 5.41 (s, 2H), 5.29 (s, 2H), 3.03 (s, 2H), 1.29 (s, 6H).

Example 76

3-[1-Benzyl-5-(quinolin-2-ylmethoxy)-1H-benzimidazol-2-yl]-2,2-dimethylpropanoic acid

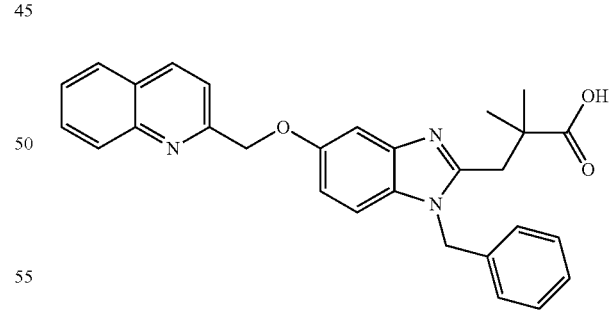

The title compound was prepared using analogous conditions described in Example 64 using ethyl 3-(1-benzyl-6-(quinolin-2-ylmethoxy)-1H-benzo[d]imidazol-2-yl)-2,2-dimethylpropanoate and (bromomethyl)benzene in Step A. MS (ESI): mass calcd. for $C_{29}H_{27}N_3O_3$, 465.21; m/z found, 466.0 [M+H]$^+$. $^1$H NMR (400 MHz, CDCl$_3$) δ 8.13-7.94 (m, 2H), 7.80-7.65 (m, 2H), 7.63-7.47 (m, 2H), 7.34-7.04 (m, 4H), 6.99-6.73 (m, 4H), 5.21 (s, 4H), 3.03 (s, 2H), 1.14 (s, 6H).

Example 77

3-[1-(4-Chlorobenzyl)-5-(quinolin-2-ylmethoxy)-1H-benzimidazol-2-yl]-2,2-dimethylpropanoic acid

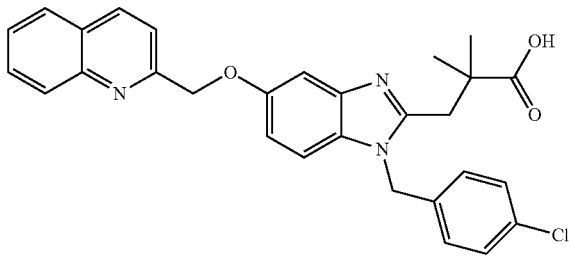 [SMILES: CC(C)(Cc1nc2cc(OCc3ccc4ccccc4n3)ccc2n1Cc1ccc(Cl)cc1)C(=O)O]

The title compound was prepared using analogous conditions described in Example 64 using 1-(bromomethyl)-4-chlorobenzene in Step A. MS (ESI): mass calcd. for $C_{29}H_{26}ClN_3O_3$, 499.17; m/z found, 500.1 [M+H]$^+$. $^1$H NMR (500 MHz, CDCl$_3$) δ 8.19 (d, J=8.4 Hz, 1H), 8.11 (d, J=8.4 Hz, 1H), 7.83 (d, J=8.3 Hz, 1H), 7.80-7.70 (m, 1H), 7.69 (d, J=8.5 Hz, 1H), 7.59-7.51 (m, 1H), 7.36 (d, J=2.3 Hz, 1H), 7.30 (d, J=8.5 Hz, 2H), 7.15 (d, J=8.9 Hz, 1H), 7.07 (dd, J=8.9, 2.3 Hz, 1H), 6.96 (d, J=8.5 Hz, 2H), 5.43 (s, 2H), 5.30 (s, 2H), 2.99 (s, 2H), 1.27 (s, 6H).

Example 78

3-[1-{4-[(3,3-Difluoropiperidin-1-yl)methyl]benzyl}-5-(quinolin-2-ylmethoxy)-1H-benzimidazol-2-yl]-2,2-dimethylpropanoic acid as the hydrochloric acid salt

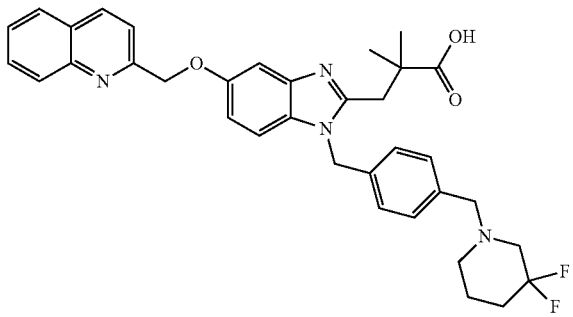 [SMILES: CC(C)(Cc1nc2cc(OCc3ccc4ccccc4n3)ccc2n1Cc1ccc(CN2CCCC(F)(F)C2)cc1)C(=O)O]

Step A: 3-(1-(4-formylbenzyl)-5-(quinolin-2-ylmethoxy)-1H-benzo[d]imidazol-2-yl)-2,2-dimethylpropanoic acid The title compound was prepared using analogous conditions described in Step A of Example 64 using 4-(bromomethyl)benzaldehyde.

Step B: Ethyl 3-(1-(4-formylbenzyl)-5-(quinolin-2-ylmethoxy)-1H-benzo[d]imidazol-2-yl)-2,2-dimethylpropanoate To a 10 mL flask were added 3-(1-(4-formylbenzyl)-5-(quinolin-2-ylmethoxy)-1H-benzo[d]imidazol-2-yl)-2,2-dimethylpropanoic acid (160 mg, 0.31 mmol), 3,3-difluoropiperidine (58 mg, 0.37 mmol), sodium triacetoxyborohydride (130 mg, 0.61 mmol) and DCE (3.0 mL) and was stirred at RT overnight. The mixture was diluted with DCM (5 mL) and poured into water (10 mL) then extracted with DCM (3×10 mL), dried over Na$_2$SO$_4$, and concentrated to dryness. The residue was purified using FCC to provide the title compound. MS (ESI): mass calcd. for $C_{37}H_{40}F_2N_4O_3$, 626.75; m/z found, 627.2 [M+H]$^+$. $^1$H NMR (600 MHz, CDCl$_3$) δ 8.17 (d, J=8.5, 1H), 8.09 (d, J=8.5, 1H), 7.80 (t, J=11.1, 1H), 7.72 (ddd, J=13.3, 7.6, 3.9, 2H), 7.55-7.50 (m, 1H), 7.35 (d, J=2.3, 1H), 7.22 (t, J=10.3, 2H), 7.07 (t, J=10.5, 1H), 6.99-6.93 (m, 3H), 5.42 (s, 2H), 5.34 (s, 2H), 4.09 (q, J=7.1, 2H), 3.53 (s, 2H), 3.05 (s, 2H), 2.61-2.53 (m, 2H), 2.40 (dd, J=16.1, 11.1, 2H), 1.90-1.80 (m, 2H), 1.78-1.70 (m, 2H), 1.36 (s, 6H), 1.16 (t, J=7.1, 3H).

Step C: 3-[1-{4-[(3,3-Difluoropiperidin-1-yl)methyl]benzyl}-5-(quinolin-2-ylmethoxy)-1H-benzimidazol-2-yl]-2,2-dimethylpropanoic acid as the hydrochloric acid salt To a solution of ethyl 3-(1-(4-formylbenzyl)-5-(quinolin-2-ylmethoxy)-1H-benzo[d]imidazol-2-yl)-2,2-dimethylpropanoate (50 mg, 0.080 mmol) in THF (0.3 mL), MeOH (0.3 mL) and H$_2$O (0.3 mL) was added LiOH (33 mg, 0.80 mmol) and the resulting solution was heated to 50° C. and stirred for 2 h. The crude reaction mixture was cooled to RT and the pH was adjusted to 3 with 1M HCl. The resulting solid was filtered to afford the title compound. MS (ESI): mass calcd. for $C_{35}H_{36}F_2N_4O_3$, 598.28; m/z found, 599.1 [M+H]$^+$. $^1$H NMR (500 MHz, CD$_3$OD) δ 8.36 (d, J=8.2, 1H), 8.05 (d, J=8.5, 1H), 7.94 (d, J=8.1, 1H), 7.78 (t, J=7.7, 1H), 7.74 (d, J=8.4, 1H), 7.61 (t, J=7.4, 1H), 7.31-7.23 (m, 4H), 7.04 (d, J=8.2, 3H), 5.51 (s, 2H), 5.40 (s, 2H), 3.55 (s, 2H), 3.13 (s, 2H), 2.56 (t, J=11.4, 2H), 2.48-2.36 (m, 2H), 1.92-1.78 (m, 2H), 1.76-1.68 (m, 2H), 1.28 (s, 6H).

Example 79

2,2-Dimethyl-3-[1-(naphthalen-2-ylmethyl)-5-(quinolin-2-ylmethoxy)-1H-benzimidazol-2-yl]propanoic acid

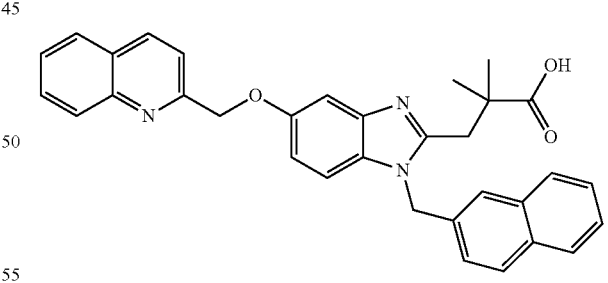

To a 100 mL round-bottomed flask were added a stirbar, ethyl 2,2-dimethyl-3-(5-(quinolin-2-ylmethoxy)-1H-benzo[d]imidazol-2-yl)propanoate (300 mg, 0.75 mmol), 2-(chloromethyl)naphthalene (168 mg, 0.75 mmol), potassium carbonate (310 mg, 2.25 mmol), and DMF (20 mL). The mixture was heated to 70° C. After 18 h, the flask was cooled to RT and concentrated to dryness. The resulting residue was dissolved in MeOH (9 mL) and THF (9 mL). To the solution was added 5% aqueous NaOH (2 mL) and the mixture was stirred at 40° C. overnight. The mixture was cooled and acidified to pH=4-5 with 6 N HCl, then extracted with EtOAc (3×20 mL). The combined organic layers were dried over Na$_2$SO$_4$, filtered, concentrated to dryness and purified by reverse phase HPLC to give the title compound. MS (ESI): mass calcd. for C$_{33}$H$_{29}$N$_3$O$_3$, 515.22; m/z found, 516.2 [M+H]$^+$. $^1$H NMR (500 MHz, CD$_3$OD) δ 8.34 (d, J=8.5, 1H), 8.04 (d, J=8.4, 1H), 7.92 (d, J=8.2, 1H), 7.84-7.66 (m, 5H), 7.59 (t, J=7.5, 1H), 7.48-7.40 (m, 3H), 7.31-7.21 (m, 2H), 7.19 (dd, J=8.5, 1.7, 1H), 7.01 (dd, J=8.8, 2.4, 1H), 5.67 (s, 2H), 5.40 (s, 2H), 3.17 (s, 2H), 1.30 (s, 6H).

Example 80

2,2-Dimethyl-3-[5-(quinolin-2-ylmethoxy)-1-(quinolin-6-ylmethyl)-1H-benzimidazol-2-yl]propanoic acid

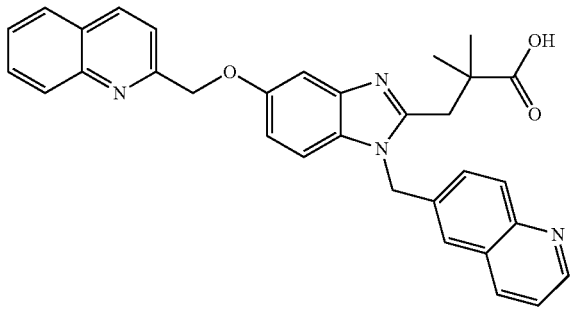 [SMILES: CC(C)(Cc1nc2cc(OCc3ccc4ccccc4n3)ccc2n1Cc1ccc2ncccc2c1)C(=O)O]

The title compound was prepared with similar methods to those in Example 79 using 6-(chloromethyl)quinolone. MS (ESI): mass calcd. for C$_{32}$H$_{28}$N$_4$O$_3$, 516.22; m/z found, 517.2 [M+H]$^+$. $^1$H NMR (500 MHz, CD$_3$OD) δ 8.54 (d, J=8.4, 1H), 8.37 (d, J=8.4, 1H), 8.11 (d, J=8.5, 1H), 8.02 (d, J=8.1, 1H), 7.95-7.84 (m, 2H), 7.82 (d, J=8.5, 1H), 7.76-7.66 (m, 3H), 7.66-7.53 (m, 3H), 7.44 (d, J=2.3, 1H), 7.30 (dd, J=9.1, 2.3, 1H), 6.12 (s, 2H), 5.54 (s, 2H), 3.57 (s, 2H), 1.41 (s, 6H).

Example 81

3-[1-(1,3-Benzothiazol-6-ylmethyl)-5-(quinolin-2-ylmethoxy)-1H-benzimidazol-2-yl]-2,2-dimethylpropanoic acid

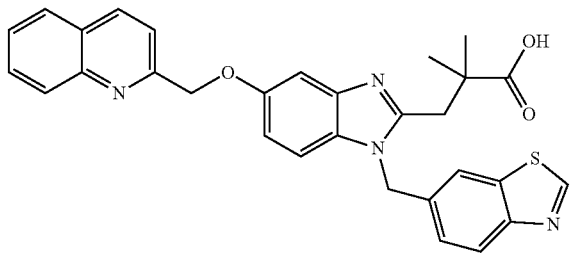 [SMILES: CC(C)(Cc1nc2cc(OCc3ccc4ccccc4n3)ccc2n1Cc1ccc2ncsc2c1)C(=O)O]

The title compound was prepared with similar methods to those in Example 79 using 6-(chloromethyl)benzo[d]thiazole. MS (ESI): mass calcd. for C$_{30}$H$_{26}$N$_4$O$_3$S, 522.17; m/z found, 523.2 [M+H]$^+$. $^1$H NMR (500 MHz, CD$_3$OD) δ 9.34 (s, 1H), 9.22 (d, J=8.5, 1H), 8.45-8.35 (m, 2H), 8.25-8.19 (m, 2H), 8.09 (d, J=8.5, 1H), 8.06-7.97 (m, 2H), 7.68-7.60 (m, 2H), 7.51 (d, J=8.0, 1H), 7.42 (dd, J=9.2, 2.2, 1H), 6.04 (s, 2H), 5.87 (s, 2H), 3.61 (s, 2H), 1.45 (s, 6H).

Example 82

2,2-Dimethyl-3-{1-[(1-methyl-1,2,3,4-tetrahydroquinolin-6-yl)methyl]-5-(quinolin-2-ylmethoxy)-1H-benzimidazol-2-yl}propanoic acid

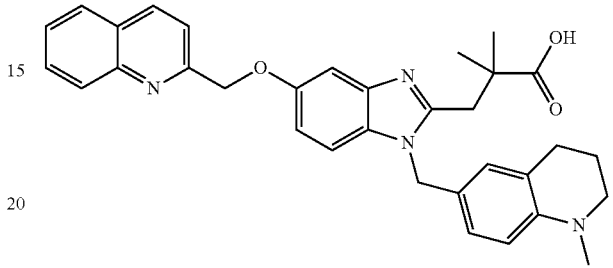

The title compound was prepared with similar methods to those in Example 79 using 6-(chloromethyl)-1-methyl-1,2,3,4-tetrahydroquinoline. MS (ESI): mass calcd. for C$_{33}$H$_{34}$N$_4$O$_3$, 534.26; m/z found, 535.2 [M+H]$^+$. $^1$H NMR (500 MHz, CD$_3$OD) δ 8.35 (d, J=8.5, 1H), 8.04 (d, J=8.4, 1H), 7.93 (d, J=7.5, 1H), 7.82-7.70 (m, 2H), 7.60 (t, J=7.6, 1H), 7.35 (d, J=8.9, 1H), 7.24 (d, J=2.3, 1H), 7.06 (dd, J=8.9, 2.4, 1H), 6.76 (d, J=8.5, 1H), 6.67 (s, 1H), 6.50 (d, J=8.4, 1H), 5.40 (s, 2H), 5.34 (s, 2H), 3.19-3.14 (m, 4H), 2.81 (s, 3H), 2.63 (t, J=6.4, 2H), 1.96-1.84 (m, 2H), 1.29 (s, 6H).

Example 83

2,2-Dimethyl-3-{1-[3-(methylsulfonyl)benzyl]-5-(quinolin-2-ylmethoxy)-1H-benzimidazol-2-yl}propanoic acid

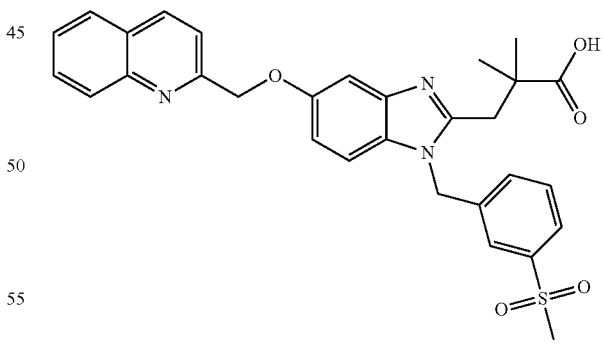

The title compound was prepared with similar methods to those in Example 79 using 1-(chloromethyl)-3-(methylsulfonyl)benzene. $^1$H NMR MS (ESI): mass calcd. for C$_{30}$H$_{29}$N$_3$O$_5$S, 543.18; m/z found, 544.2 [M+H]$^+$. (500 MHz, CD$_3$OD) δ 8.50 (d, J=8.4, 1H), 8.10 (d, J=8.2, 1H), 8.01 (d, J=8.2, 1H), 7.95 (d, J=8.1, 1H), 7.90-7.74 (m, 3H), 7.71-7.61 (m, 2H), 7.57-7.47 (m, 2H), 7.42 (d, J=2.2, 1H), 7.32 (dd, J=9.1, 2.4, 1H), 5.94 (s, 2H), 5.54 (s, 2H), 3.51 (s, 2H), 3.10 (s, 3H), 1.41 (s, 6H).

Example 84

3-[1-(2,1,3-Benzoxadiazol-5-ylmethyl)-5-(quinolin-2-ylmethoxy)-1H-benzimidazol-2-yl]-2,2-dimethylpropanoic acid

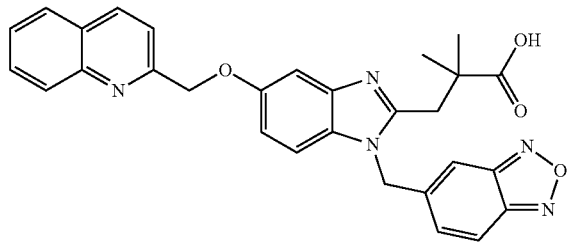 [SMILES: CC(C)(Cc1nc2cc(OCc3ccc4ccccc4n3)ccc2n1Cc1ccc2nonc2c1)C(=O)O]

A suspension of 2,2-dimethyl-3-(5-(quinolin-2-ylmethoxy)-1H-benzo[d]imidazol-2-yl)propanoic acid (300 mg, 0.75 mmol), 5-(bromomethyl)benzo[c][1,2,5]oxadiazole (168 mg, 0.75 mmol) and potassium carbonate (310 mg, 2.25 mmol) in DMF (20 mL) was heated to 70° C. for 18 h. The mixture was cooled to RT and concentrated to dryness. The residue was dissolved in THF/MeOH (18 mL, 1:1) and treated with 5% aq. NaOH (2 mL). The mixture was stirred at 40° C. for 16 h. The reaction was allowed to cool to RT and then concentrated to dryness. The residue was diluted with water (30 mL), washed with EtOAc (20 mL), and then treated with 6N aq. HCl to ~pH 6. The aqueous was then extracted with DCM (2×30 mL). The organics were combined, dried with Na$_2$SO$_4$, filtered and concentrated to dryness. The residue was purified by reverse phase HPLC to afford the title compound. MS (ESI): mass calcd. for C$_{29}$H$_{26}$N$_5$O$_4$, 507.19; m/z found, 507.9 [M+H]$^+$. $^1$H NMR (300 MHz, DMSO-d$_6$) δ 8.44 (d, J=8.6, 1H), 8.11-7.98 (m, 3H), 7.85-7.77 (m, 1H), 7.71 (d, J=8.5, 1H), 7.68-7.61 (m, 2H), 7.58-7.52 (m, 1H), 3.35-3.33 (m, 2H), 7.50-7.43 (m, 1H), 7.38-7.33 (m, 1H), 7.21-7.12 (m, 1H), 5.84 (s, 2H), 5.47 (s, 2H), 1.30 (s, 6H).

Example 85

3-[1-(Isoquinolin-6-ylmethyl)-5-(quinolin-2-ylmethoxy)-1H-benzimidazol-2-yl]-2,2-dimethylpropanoic acid—Hydrochloric acid salt

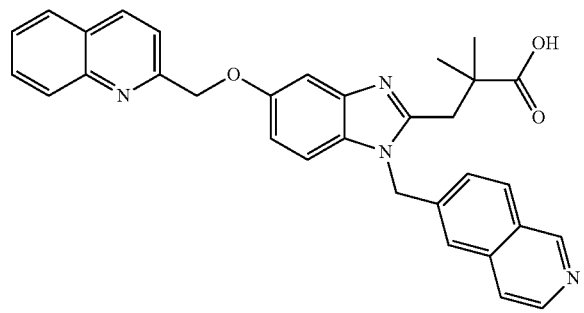 [SMILES: CC(C)(Cc1nc2cc(OCc3ccc4ccccc4n3)ccc2n1Cc1ccc2cnccc2c1)C(=O)O]

The title compound was prepared using similar methods to those in Example 84 using 6-(bromomethyl)isoquinoline. MS (ESI): mass calcd. for C$_{32}$H$_{28}$N$_4$O$_3$, 516.22; m/z found, 517.2 [M+H]$^+$. $^1$H NMR (300 MHz, DMSO-d$_6$) δ 9.77 (s, 1H), 8.61 (d, J=6.4, 1H), 8.48 (d, J=8.6, 2H), 8.29 (d, J=6.5, 1H), 8.07-8.00 (m, 2H), 7.97-7.94 (m, 1H), 7.86-7.79 (m, 2H), 7.74-7.61 (m, 3H), 7.51-7.47 (m, 1H), 7.44-7.41 (m, 1H), 7.23-7.18 (m, 1H), 6.10 (s, 2H), 5.49 (s, 2H), 3.46 (s, 2H), 1.30 (s, 6H).

Example 86

2,2-Dimethyl-3-{1-[(1-methyl-1H-indazol-5-yl)methyl]-5-(quinolin-2-ylmethoxy)-1H-benzimidazol-2-yl}propanoic acid as the hydrochloric acid salt

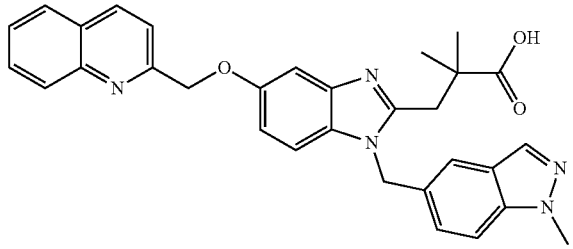 [SMILES: Cn1ncc2cc(Cn3c(CC(C)(C)C(=O)O)nc4cc(OCc5ccc6ccccc6n5)ccc43)ccc21]

The title compound was prepared using similar methods to those in Example 84 using 5-(bromomethyl)-1-methyl-1H-indazole. MS (ESI): mass calcd. for C$_{31}$H$_{29}$N$_5$O$_3$, 519.23; m/z found, 520.2 [M+H]$^+$. $^1$H NMR (300 MHz, DMSO-d$_6$) δ 8.51 (d, J=8.5, 1H), 8.09 (d, J=8.4, 1H), 8.04 (d, J=8.0, 1H), 8.01-7.98 (m, 1H), 7.87-7.80 (m, 1H), 7.73 (d, J=8.5, 1H), 7.70-7.67 (m, 1H), 7.67-7.62 (m, 1H), 7.60 (d, J=5.9, 1H), 7.57-7.54 (m, 1H), 7.39-7.36 (m, 1H), 7.35-7.30 (m, 1H), 7.27-7.22 (m, 1H), 5.86 (s, 2H), 5.52 (s, 2H), 4.01 (s, 3H), 1.31 (s, 6H), 3.57-3.50 (m, 2H).

Example 87 racemic 3-[1-(4-Cyanobenzyl)-5-(quinolin-2-ylmethoxy)-1H-benzimidazol-2-yl]-2,2-dimethylcyclopropanecarboxylic acid

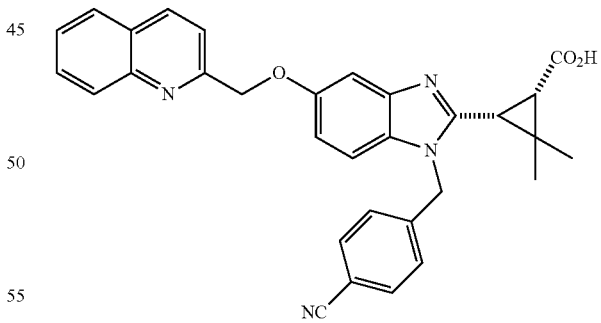

Step A. 4-(((2-Nitro-4-(quinolin-2-ylmethoxy)phenyl)amino)methyl)benzonitrile To a mixture of 2-((4-fluoro-3-nitrophenoxy)methyl)quinoline (2.0 g, 6.7 mmol) and 4-(aminomethyl)benzonitrile (1.1 g, 8.3 mmol) in DMA (20 mL) was added DIPEA (3.5 mL, 20 mmol) and heated to 100° C. for 16 h. The mixture was cooled and poured into water (400 mL). The resulting solids were collected by filtration to provide 2.76 g of the title compound. The material was used without further purification. MS (ESI): mass calcd. for $C_{24}H_{18}N_4O_3$, 410.43; m/z found 411.1 [M+H]$^+$.

Step B. 4-(((2-Amino-4-(quinolin-2-ylmethoxy) phenyl)amino)methyl)benzonitrile

To a solution of 4-(((2-nitro-4-(quinolin-2-ylmethoxy) phenyl)amino)methyl)benzonitrile (2.8 g, 6.7 mmol) in EtOAc (100 mL) was added $SnCl_2 \cdot 2H_2O$ (9.4 g, 42 mmol) and the mixture heated to 70° C. for 3 h. The mixture was then cooled to RT and basified to pH=8 by addition of 2 M $Na_2CO_3$ and stirred at RT. After 12 hours, the mixture was extracted with EtOAc and concentrated to dryness. The residue was then purified by FCC to afford 0.69 g of the title compound. MS (ESI): mass calcd. for $C_{24}H_{20}N_4O$, 380.45; m/z found 381.2 [M+H]$^+$.

Step C racemic 3-[1-(4-Cyanobenzyl)-5-(quinolin-2-ylmethoxy)-1H-benzimidazol-2-yl]-2,2-dimethyl-cyclopropanecarboxylic acid To a solution of 4-(((2-amino-4-(quinolin-2-ylmethoxy) phenyl)amino)methyl)benzonitrile (124 mg, 0.33 mmol) in acetonitrile (3 mL) was added cis-6,6-dimethyl-3-oxabicyclo[3.1.0]hexane-2,4-dione (49 mg, 0.33 mmol) and the solution heated to 80° C. for 4 h. AcOH (1 mL) was then added and the heating continued at 80° C. for an additional 16 h. The resulting mixture was cooled to RT and the mixture was concentrated to dryness. The residue purified using FCC to provide 81.4 mg of the title compound. MS (ESI): mass calcd. for $C_{31}H_{26}N_4O_3$, 502.20; m/z found, 503.2 [M+H]$^+$. $^1$H NMR (400 MHz, CDCl$_3$) δ 8.21 (d, J=8.6 Hz, 1H), 8.11 (d, J=8.3 Hz, 1H), 7.84 (d, J=8.1 Hz, 1H), 7.78-7.73 (m, 1H), 7.70-7.65 (m, 3H), 7.59-7.54 (m, 1H), 7.33 (d, J=2.3 Hz, 1H), 7.19-7.09 (m, 4H), 5.49-5.39 (m, 4H), 2.32 (d, J=8.3 Hz, 1H), 1.99 (d, J=8.3 Hz, 1H), 1.20 (s, 3H), 1.01 (s, 3H).

Example 88

1-{[1-(4-Cyanobenzyl)-5-(quinolin-2-ylmethoxy)-1H-benzimidazol-2-yl]methyl}cyclopentanecarboxylic acid

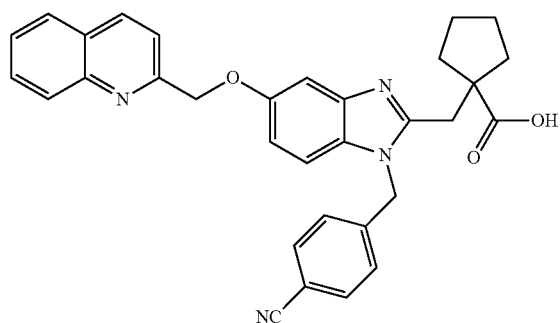 [SMILES: N#Cc1ccc(Cn2c(CC3(C(=O)O)CCCC3)nc3cc(OCc4ccc5ccccc5n4)ccc32)cc1]

The title compound was prepared using similar methods to those in Example 87 using 2-oxaspiro[4.4]nonane-1,3-dione in Step C. MS (ESI): mass calcd. for $C_{32}H_{28}N_4O_3$, 516.22; m/z found, 517.3 [M+H]$^+$. $^1$H NMR (500 MHz, CDCl$_3$) δ 8.22 (d, J=8.3 Hz, 1H), 8.12 (d, J=8.5 Hz, 1H), 7.83 (d, J=8.1 Hz, 1H), 7.77-7.70 (m, 2H), 7.62-7.54 (m, 3H), 7.41-7.39 (m, 1H), 7.12-7.08 (m, 2H), 7.06-7.01 (m, 2H), 5.48 (s, 2H), 5.39 (s, 2H), 3.05 (s, 2H), 2.39-2.25 (m, 2H), 1.73-1.38 (m, 6H).

Example 89

1-{[1-(3-Bromobenzyl)-5-(quinolin-2-ylmethoxy)-1H-benzimidazol-2-yl]methyl}cyclopentanecarboxylic acid

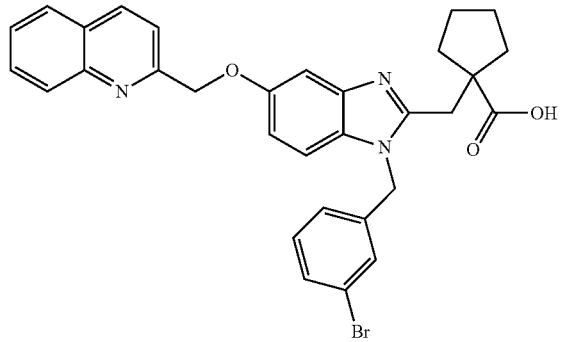 [SMILES: O=C(O)C1(Cc2nc3cc(OCc4ccc5ccccc5n4)ccc3n2Cc2cccc(Br)c2)CCCC1]

To a 20 mL vial were added ethyl 1-{[1-(3-bromobenzyl)-5-(quinolin-2-ylmethoxy)-1H-benzimidazol-2-yl]methyl}cyclopentanecarboxylate (57 mg, 0.09 mmol), THF (1 mL) and MeOH (1 mL) followed by LiOH (1 mL, 1 M). The reaction mixture was capped and heated to 80° C. for 3 h. The mixture was then cooled to RT, water (5 mL) was added to the mixture and the pH was adjusted to ~4 using 1 M HCl. To this mixture was added DCM (5 mL) and stirred for 1 h at RT. The organic layer was separated and the aqueouse layer was further extracted with DCM. The combined organics were dried, filtered and concentrated to dryness. The residue was then purified by FCC to provide the title compound. MS (ESI): mass calcd. for $C_{31}H_{28}BrN_3O_3$, 569.13; m/z found, 570.1 [M+H]$^+$. $^1$H NMR (400 MHz, CDCl$_3$) δ 8.20 (d, J=8.6, 1H), 8.11 (d, J=8.3, 1H), 7.83 (d, J=8.3, 1H), 7.77-7.72 (m, 1H), 7.69 (d, J=8.6, 1H) 7.58-7.53 (m, 1H), 7.45 (d, J=7.8, 1H), 7.36-7.34 (m, 1H), 7.23 (s, 1H), 7.21-7.15 (m, 2H), 7.11-7.06 (m, 1H), 6.90 (d, J=7.6, 1H), 5.44 (s, 2H), 5.28 (s, 2H), 3.04 (s, 2H), 2.44-2.34 (m, 2H), 1.77-1.66 (m, 2H), 1.50-1.41 (m, 4H)

Example 90

1-{[1-(3-Cyanobenzyl)-5-(quinolin-2-ylmethoxy)-1H-benzimidazol-2-yl]methyl}cyclopentanecarboxylic acid

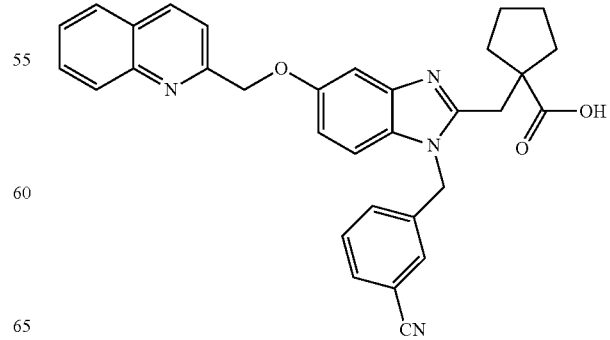

Step A. Methyl 1-((1-(3-cyanobenzyl)-5-(quinolin-2-ylmethoxy)-1H-benzo[d]imidazol-2-yl)methyl)cyclopentanecarboxylate To a 5 mL microwave vial were added methyl 1-{[1-(3-bromobenzyl)-5-(quinolin-2-ylmethoxy)-1H-benzimidazol-2-yl]methyl}cyclopentanecarboxylate (94 mg, 0.16 mmol), CuCN (31 mg, 0.34 mmol), pyridine (0.5 mL) and DMA (1.5 mL). The vial was flushed with $N_2$, then capped and irradiated in the microwave at 200° C. for 4 h. The resulting mixture was cooled to RT, poured into water (10 mL) and extracted with EtOAc. The organics were concentrated to dryness and the resulting residue was purified by FCC to provide 40 mg of the title compound. MS (ESI): mass calcd. for $C_{33}H_{30}N_4O_3$, 530.63; m/z found, 531.2 $[M+H]^+$.

Step B. 1-{[1-(3-Cyanobenzyl)-5-(quinolin-2-ylmethoxy)-1H-benzimidazol-2-yl]methyl}cyclopentanecarboxylic acid The title compound was prepared using similar methods to those in Step B of Example 97. MS (ESI): mass calcd. for $C_{32}H_{28}N_4O_3$, 516.22; m/z found, 517.3 $[M+H]^+$. $^1$H NMR (500 MHz, CDCl$_3$) δ 8.19 (d, J=8.5, 1H), 8.10 (d, J=8.5, 1H), 7.82 (d, J=8.5, 1H), 7.75-7.71 (m, 1H), 7.68 (d, J=8.5, 1H), 7.60-7.53 (m, 2H), 7.44-7.40 (m, 1H), 7.36-7.33 (m, 2H), 7.19-7.16 (m, 1H), 7.08-7.02 (m, 2H), 5.40 (s, 2H), 5.35 (s, 2H), 3.05 (s, 2H), 2.40-2.32 (m, 2H), 1.77-1.68 (m, 2H); 1.58-1.45 (m, 4H).

Example 91

1-{[1-(Biphenyl-3-ylmethyl)-5-(quinolin-2-ylmethoxy)-1H-benzimidazol-2-yl]methyl}cyclopentanecarboxylic acid

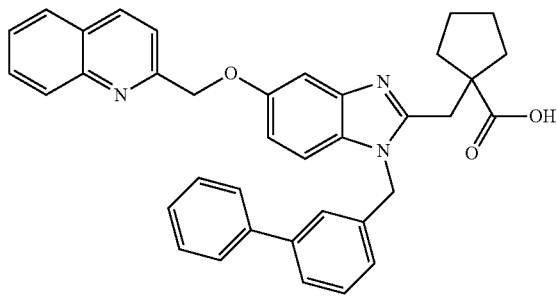 [SMILES: O=C(O)C1(Cc2nc3cc(OCc4ccc5ccccc5n4)ccc3n2Cc2cccc(-c3ccccc3)c2)CCCC1]

Step A. methyl 1-((1-([1,1'-biphenyl]-3-ylmethyl)-5-(quinolin-2-ylmethoxy)-1H-benzo[d]imidazol-2-yl)methyl)cyclopentanecarboxylate To a 5 mL microwave vial were added methyl 1-{[1-(3-bromobenzyl)-5-(quinolin-2-ylmethoxy)-1H-benzimidazol-2-yl]methyl}cyclopentanecarboxylate (62 mg, 0.1 mmol), Pd(dppf)Cl$_2$ (8.3 mg, 0.01 mmol), phenylboronic acid (45 mg, 0.35 mmol), K$_3$PO$_4$ (78 mg, 0.37 mmol) and 1,4-dioxane (1.5 mL). The vial was flushed with N$_2$ then capped and placed in a heating block at 100° C. After 6 h the mixture was cooled to RT, transferred to a round-bottomed flask, and concentrated to dryness. The residue was purified using FCC to provide the title compound. MS (ESI): mass calcd. for $C_{38}H_{35}N_3O_3$, 581.71; m/z found 582.1 $[M+H]^+$.

Step B. 1-{[1-(Biphenyl-3-ylmethyl)-5-(quinolin-2-ylmethoxy)-1H-benzimidazol-2-yl]methyl}cyclopentanecarboxylic acid To a 20 mL vial were added methyl 1-((1-([1,1-biphenyl]-3-ylmethyl)-5-(quinolin-2-ylmethoxy)-1H-benzo[d]imidazol-2-yl)methyl)cyclopentane-carboxylate (51.4 mg, 0.08 mmol), THF (1 mL) and MeOH (1 mL) followed by with LiOH (1 mL, 1 M). The reaction mixture was capped and heated to 80° C. for 3 h. The mixture was cooled to RT, water (5 mL) was added and the pH was adjusted to ~4 using 1 M HCl. To the mixture was added DCM (5 mL) and the mixture was stirred for 1 h at RT. The organic layer was separated then concentrated to dryness. The resulting residue was purified using FCC to provide the title compound. MS (ESI): mass calcd. for $C_{37}H_{33}N_3O_3$, 567.25; m/z found, 568.1 $[M+H]^+$. $^1$H NMR (500 MHz, CDCl$_3$) δ 8.19 (d, J=8.6, 1H), 8.11 (d, J=8.1, 1H), 7.83 (d, J=8.3, 1H), 7.77-7.71 (m, 1H), 7.69 (d, J=8.6, 1H) 7.58-7.51 (m, 2H), 7.49-7.33 (m, 7H), 7.29 (s, 1H), 7.25-7.22 (m, 1H), 7.11-7.06 (m, 1H), 6.96 (d, J=7.6, 1H), 5.44 (s, 2H), 5.37 (s, 2H), 3.09 (s, 2H), 2.41-2.33 (m, 2H), 1.71-1.63 (m, 2H), 1.47-1.36 (m, 4H).

Example 92

1-({1-[(4'-Fluorobiphenyl-3-yl)methyl]-5-(quinolin-2-ylmethoxy)-1H-benzimidazol-2-yl}methyl)cyclopentanecarboxylic acid

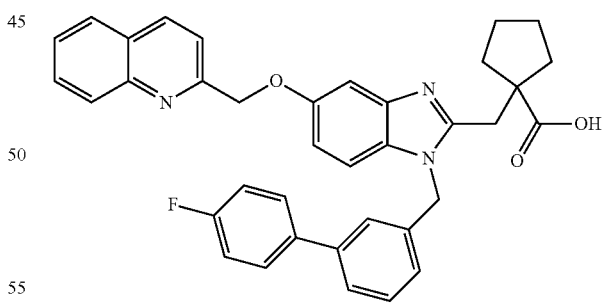

The title compound was prepared using similar methods to those in Example 91 using 4-fluoroboronic acid in Step A. MS (ESI): mass calcd. for $C_{37}H_{32}FN_3O_3$, 585.24; m/z found, 586.1 $[M+H]^+$. $^1$H NMR (400 MHz, CDCl$_3$) δ 8.19 (d, J=8.4 Hz, 1H), 8.10 (d, J=8.4 Hz, 1H), 7.85-7.80 (m, 1H), 7.77-7.71 (m, 1H), 7.69 (d, J=8.5 Hz, 1H), 7.58-7.53 (m, 1H), 7.49-7.45 (m, 1H), 7.44-7.37 (m, 3H), 7.35-7.34 (m, 1H), 7.24-7.20 (m, 2H), 7.12-7.06 (m, 3H), 6.96-6.92 (m, 1H), 5.44-5.34 (m, 4H), 3.08 (s, 2H), 2.41-2.34 (m, 2H), 1.71-1.64 (m, 2H), 1.47-1.37 (m, 4H).

Example 93

1-{[1-{[4'-(Methylsulfonyl)biphenyl-3-yl]methyl}-5-(quinolin-2-ylmethoxy)-1H-benzimidazol-2-yl]methyl}cyclopentanecarboxylic acid

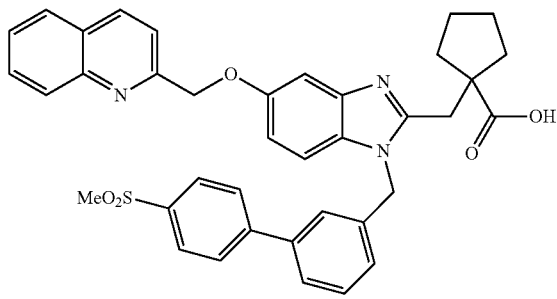 [SMILES: CS(=O)(=O)c1ccc(-c2cccc(Cn3c(CC4(C(=O)O)CCCC4)nc4cc(OCc5ccc6ccccc6n5)ccc43)c2)cc1]

The title compound was prepared using similar methods to those in Example 91 using (4-(methylsulfonyl)phenyl)boronic acid in Step A. MS (ESI): mass calcd. for $C_{38}H_{35}N_3O_5S$, 645.23; m/z found, 646.1 [M+H]$^+$. $^1$H NMR (500 MHz, CDCl$_3$) δ 8.19 (d, J=8.5, 1H), 8.10 (d, J=8.5, 1H), 7.99-7.95 (m, 2H), 7.83 (d, J=8.2, 1H), 7.76-7.71 (m, 1H), 7.68 (d, J=8.5, 1H), 7.65-7.61 (m, 2H), 7.58-7.52 (m, 2H), 7.46-7.42 (m, 1H), 7.36-7.34 (m, 1H), 7.25 (s, 1H), 7.20 (d, J=8.8, 1H), 7.09-7.03 (m, 2H), 5.42 (s, 2H), 5.40 (s, 2H), 3.09 (s, 2H), 3.07 (s, 3H), 2.41-2.33 (m, 2H), 1.73-1.65 (m, 2H), 1.58-1.39 (m, 4H).

Example 94

1-({1-[3-(2-Methoxypyrimidin-5-yl)benzyl]-5-(quinolin-2-ylmethoxy)-1H-benzimidazol-2-yl}methyl)cyclopentanecarboxylic acid

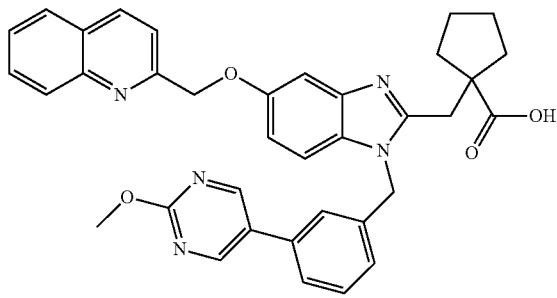 [SMILES: COc1ncc(-c2cccc(Cn3c(CC4(C(=O)O)CCCC4)nc4cc(OCc5ccc6ccccc6n5)ccc43)c2)cn1]

The title compound was prepared using similar methods to those in Example 91 using (2-methoxypyrimidin-5-yl)boronic acid in Step A. MS (ESI): mass calcd. for $C_{36}H_{33}N_5O_4$, 599.25; m/z found, 600.1 [M+H]$^+$. $^1$H NMR (400 MHz, CDCl$_3$) δ 8.61 (s, 2H), 8.20 (d, J=8.3, 1H), 8.11 (d, J=8.3, 1H), 7.83 (d, J=8.0, 1H), 7.77-7.72 (m, 1H), 7.69 (d, J=8.6, 1H), 7.58-7.53 (m, 1H), 7.47-7.41 (m, 2H), 7.36-7.34 (m, 1H), 7.22-7.18 (m, 2H), 7.10-7.07 (m, 1H), 7.02-6.99 (m, 1H), 5.44 (s, 2H), 5.38 (s, 2H), 4.05 (s, 3H), 3.07 (s, 2H), 2.43-2.35 (m, 2H), 1.74-1.66 (m, 2H), 1.50-1.38 (m, 4H).

Example 95

1-({1-[3-(6-Methoxypyridin-3-yl)benzyl]-5-(quinolin-2-ylmethoxy)-1H-benzimidazol-2-yl}methyl)cyclopentanecarboxylic acid

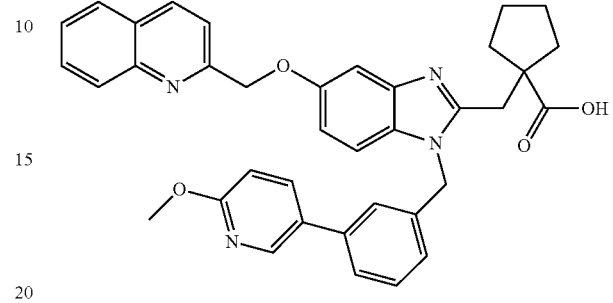

The title compound was prepared using similar methods to those in Example 91 using (6-methoxypyridin-3-yl)boronic acid in Step A. MS (ESI): mass calcd. for $C_{37}H_{34}N_4O_4$, 598.26; m/z found, 599.1 [M+H]$^+$. $^1$H NMR (400 MHz, CDCl$_3$) δ 8.27-8.25 (m, 1H), 8.20 (d, J=8.6, 1H), 8.11 (d, J=8.6, 1H), 7.83 (d, J=8.3, 1H), 7.77-7.72 (m, 1H), 7.70 (d, J=8.6, 1H), 7.68-7.64 (m, 1H), 7.58-7.53 (m, 1H), 7.48-7.44 (m, 1H), 7.42-7.73 (m, 1H), 7.36-7.34 (m, 1H), 7.25-7.22 (m, 1H), 7.21-7.19 (m, 1H), 7.11-7.07 (m, 1H), 6.98-6.95 (m, 1H), 6.81-6.78 (m, 1H), 5.44 (s, 2H), 5.37 (s, 2H), 3.97 (s, 3H), 3.07 (s, 2H), 2.42-2.32 (m, 2H), 1.72-1.63 (m, 2H), 1.48-1.35 (m, 4H); 599.1.

Example 96

1-({1-[(3',4'-Difluorobiphenyl-3-yl)methyl]-5-(quinolin-2-ylmethoxy)-1H-benzimidazol-2-yl}methyl)cyclopentanecarboxylic acid

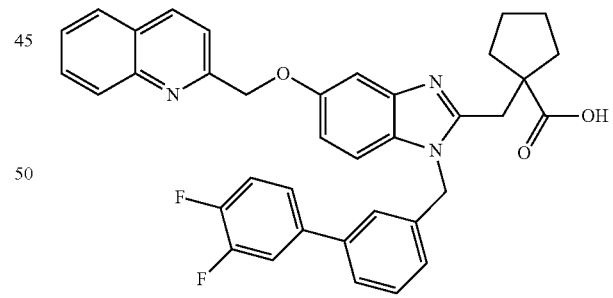

The title compound was prepared using similar methods to those in Example 91 using 3,4-difluoroboronic acid in Step A. MS (ESI): mass calcd. for $C_{37}H_{31}F_2N_3O_3$, 603.23; m/z found, 604.1 [M+H]$^+$. $^1$H NMR (400 MHz, CDCl$_3$) δ 8.20 (d, J=8.5 Hz, 1H), 8.11 (d, J=8.6 Hz, 1H), 7.85-7.81 (m, 1H), 7.77-7.72 (m, 1H), 7.69 (d, J=8.5 Hz, 1H), 7.58-7.53 (m, 1H), 7.47-7.44 (m, 1H), 7.41-7.37 (m, 1H), 7.35 (d, J=2.3 Hz, 1H), 7.30-7.27 (m, 1H), 7.24-7.16 (m, 4H), 7.11-7.07 (m, 1H), 6.98-6.94 (m, 1H), 5.45-5.35 (m, 4H), 3.07 (s, 2H), 2.43-2.36 (m, 2H), 1.73-1.66 (m, 2H), 1.48-1.39 (m, 4H).

Example 97

1-{[1-({4'-[(Methylsulfonyl)amino]biphenyl-3-yl}methyl)-5-(quinolin-2-ylmethoxy)-1H-benzimidazol-2-yl]methyl}cyclopentanecarboxylic acid

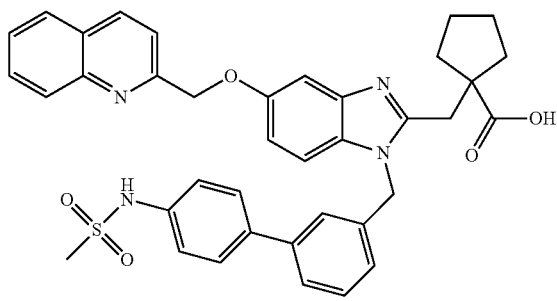 [SMILES: CS(=O)(=O)Nc1ccc(-c2cccc(Cn3c(CC4(C(=O)O)CCCC4)nc4cc(OCc5ccc6ccccc6n5)ccc43)c2)cc1]

Step A. Methyl 1-((1-((4'-(methylsulfonamido)-[1,1'-biphenyl]-3-yl)methyl)-5-(quinolin-2-ylmethoxy)-1H-benzo[d]imidazol-2-yl)methyl)cyclopentanecarboxylate To a 5 mL microwave vial were added methyl 1-{[1-(3-bromobenzyl)-5-(quinolin-2-ylmethoxy)-1H-benzimidazol-2-yl]methyl}cyclopentanecarboxylate (126 mg, 0.21 mmol), Pd(dppf)Cl$_2$.DCM (18 mg, 0.02 mmol), N-(4-(4,4,5,5-tetramethyl-1,3,2-dioxaborolan-2-yl)phenyl)methanesulfonamide (192 mg, 0.65 mmol), Na$_2$CO$_3$ (0.3 mL, 2 M) and 1,4-dioxane (2.5 mL). The vial was flushed with N$_2$ then capped and placed in a heating block at 80° C. After 16 h mixture was cooled to RT, transferred to a round-bottomed flask and was concentrated to dryness. The residue was purified using FCC to provide the title compound. MS (ESI): mass calcd. for C$_{39}$H$_{38}$N$_4$O$_5$S, 674.82; m/z found, 675.2 [M+H]$^+$.

Step B. 1-{[1-({4'-[(Methylsulfonyl)amino]biphenyl-3-yl}methyl)-5-(quinolin-2-ylmethoxy)-1H-benzimidazol-2-yl]methyl}cyclopentanecarboxylic acid To a 20 mL vial were added ethyl 1-((1-((4'-(methylsulfonamido)-[1,1'-biphenyl]-3-yl)methyl)-5-(quinolin-2-ylmethoxy)-1H-benzo[d]imidazol-2-yl)methyl)cyclopentanecarboxylate (117 mg, 0.17 mmol), THF (2 mL) and MeOH (2 mL) followed by LiOH (1 mL, 1 M). The reaction vial was capped and the mixture was stirred at RT for 16 h. The mixture was cooled to RT, water (5 mL) was added and the pH was adjusted to ~4 using 1 M HCl. To the mixture was added DCM (5 mL) and the mixture was stirred for 1 h at RT. The organic layer was separated then concentrated to dryness. The resulting residue was purified using FCC to provide the title compound. MS (ESI): mass calcd. for C$_{38}$H$_{36}$N$_4$O$_5$S, 660.24; m/z found, 661.3 [M+H]$^+$. (500 MHz; DMSO-d$_6$) δ 8.39 (d, J=8.5, 1H), 8.03 (d, J=8.2, 1H), 7.98 (d, J=8.2, 1H), 7.81-7.76 (m, 1H), 7.69 (d, J=8.5, 1H), 7.63-7.59 (m, 1H), 7.56-7.50 (m, 3H), 7.40-7.34 (m, 3H), 7.29-7.25 (m, 2H), 7.20-7.18 (m, 1H), 7.02-6.99 (m, 1H), 6.95-6.91 (m, 1H), 5.50 (s, 2H), 5.37 (s, 2H), 3.16 (s, 2H), 3.01 (s, 3H), 2.16-2.09 (m, 2H), 1.72-1.52 (m, 6H).

Example 98

1-({5-(Quinolin-2-ylmethoxy)-1-[3-(1,3-thiazol-4-yl)benzyl]-1H-benzimidazol-2-yl}methyl)cyclopentanecarboxylic acid

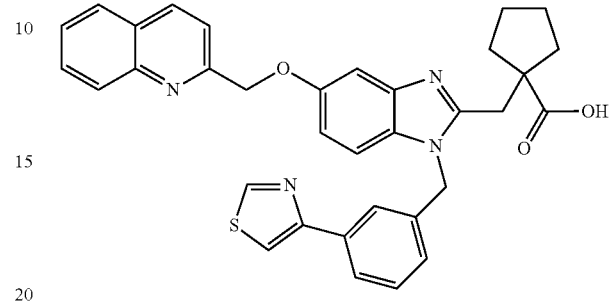

The title compound was prepared using similar methods to those in Example 97 using 4-(4,4,5,5-tetramethyl-1,3,2-dioxaborolan-2-yl)thiazole in Step A. MS (ESI): mass calcd. for C$_{34}$H$_{30}$N$_4$O$_3$S, 574.20; m/z found, 575.2 [M+H]$^+$. $^1$H NMR (500 MHz, CDCl$_3$) δ 8.88-8.84 (m, 1H), 8.18 (d, J=8.5 Hz, 1H), 8.10 (d, J=8.5 Hz, 1H), 7.83-7.79 (m, 2H), 7.78-7.71 (m, 2H), 7.68 (d, J=8.5 Hz, 1H), 7.57-7.53 (m, 1H), 7.51-7.48 (m, 1H), 7.39-7.34 (m, 2H), 7.21 (d, J=8.8 Hz, 1H), 7.09-7.04 (m, 1H), 6.94-6.90 (m, 1H), 5.43 (s, 2H), 5.36 (s, 2H), 3.10 (s, 2H), 2.42-2.34 (m, 2H), 1.72-1.65 (m, 2H), 1.51-1.42 (m, 4H).

Example 99

1-({1-[3-(1-Methyl-1H-pyrazol-4-yl)benzyl]-5-(quinolin-2-ylmethoxy)-1H-benzimidazol-2-yl}methyl)cyclopentanecarboxylic acid

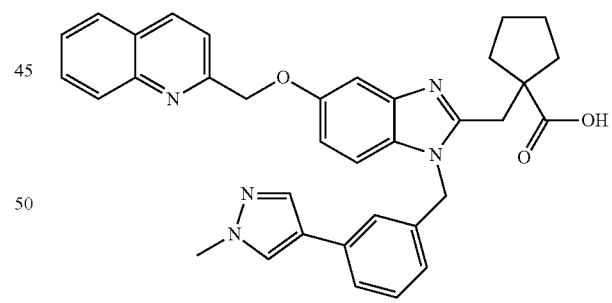

The title compound was prepared using similar methods to those in Example 97 using 1-methyl-4-(4,4,5,5-tetramethyl-1,3,2-dioxaborolan-2-yl)-1H-pyrazole in Step A. MS (ESI): mass calcd. for C$_{35}$H$_{33}$N$_5$O$_3$, 571.26; m/z found, 572.3 [M+H]$^+$. $^1$H NMR (500 MHz, CDCl$_3$) δ 8.19 (d, J=8.4 Hz, 1H), 8.13-8.08 (m, 1H), 7.84-7.80 (m, 1H), 7.76-7.71 (m, 1H), 7.69 (d, J=8.5 Hz, 1H), 7.67-7.65 (m, 1H), 7.57-7.53 (m, 1H), 7.51-7.49 (m, 1H), 7.41-7.37 (m, 1H), 7.35 (d, J=2.3 Hz, 1H), 7.32-7.27 (m, 1H), 7.20 (d, J=8.8 Hz, 1H), 7.14-7.11 (m, 1H), 7.07 (dd, J=8.9, 2.4 Hz, 1H), 6.84-6.80 (m, 1H), 5.43 (s, 2H), 5.31 (s, 2H), 3.90 (s, 3H), 3.08 (s, 2H), 2.41-2.33 (m, 2H), 1.72-1.65 (m, 2H), 1.49-1.41 (m, 4H).

Example 100

1-{[1-(3-Furan-3-ylbenzyl)-5-(quinolin-2-yl-methoxy)-1H-benzimidazol-2-yl]methyl}cyclopentanecarboxylic acid

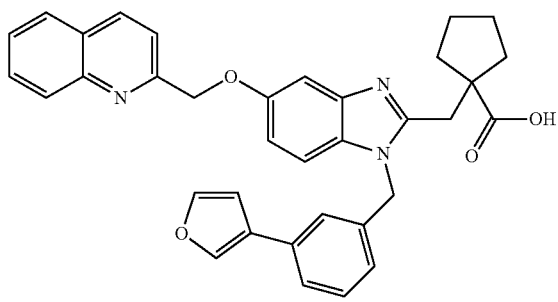 [SMILES: O=C(O)C1(Cc2nc3cc(OCc4ccc5ccccc5n4)ccc3n2Cc2cccc(-c3ccoc3)c2)CCCC1]

The title compound was prepared using similar methods to those in Example 97 using furan-3-ylboronic acid in Step A. MS (ESI): mass calcd. for $C_{35}H_{31}N_3O_4$, 557.23; m/z found, 558.3 [M+H]$^+$. $^1$H NMR (500 MHz, CDCl$_3$) δ 8.19 (d, J=8.5, 1H), 8.11 (d, J=8.5, 1H), 7.83 (d, J=8.2, 1H), 7.76-7.72 (m, 1H), 7.69 (d, J=8.5, 1H), 7.66-7.64 (m, 1H), 7.57-7.53 (m, 1H), 7.46-7.45 (m, 1H), 7.43-7.41 (m, 1H), 7.35 (d, J=2.2, 1H), 7.33-7.29 (m, 1H), 7.22 (d, J=8.8, 1H), 7.17 (s, 1H), 7.10-7.07 (m, 1H), 6.87-6.84 (m, 1H), 6.59-6.58 (m, 1H), 5.44 (s, 2H), 5.32 (s, 2H), 3.07 (s, 2H), 2.41-2.34 (m, 2H), 1.72-1.65 (m, 2H), 1.47-1.37 (m, 4H).

Example 101

1-({1-[3-(3,5-Dimethylisoxazol-4-yl)benzyl]-5-(quinolin-2-ylmethoxy)-1H-benzimidazol-2-yl}methyl)cyclopentanecarboxylic acid

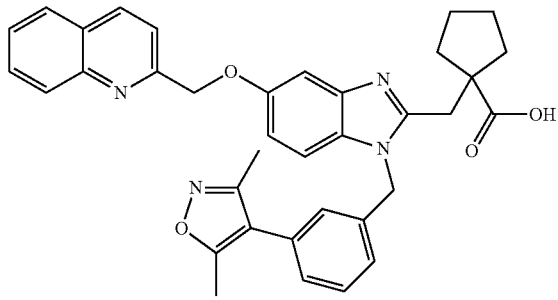 [SMILES: Cc1noc(C)c1-c1cccc(Cn2c(CC3(C(=O)O)CCCC3)nc3cc(OCc4ccc5ccccc5n4)ccc32)c1]

The title compound was prepared using similar methods to those in Example 97 using (3,5-dimethylisoxazol-4-yl)boronic acid in Step A. MS (ESI): mass calcd. for $C_{36}H_{34}N_4O_4$, 586.26; m/z found, 587.2 [M+H]$^+$. $^1$H NMR (500 MHz, CDCl$_3$) δ 8.20 (d, J=8.5, 1H), 8.11 (d, J=8.2, 1H), 7.83 (d, J=8.2, 1H), 7.76-7.72 (m, 1H), 7.68 (d, J=8.5, 1H), 7.58-7.54 (m, 1H), 7.42-7.39 (m, 1H), 7.35 (d, J=2.2, 1H), 7.22-7.18 (m, 2H), 7.11-7.07 (m, 1H), 7.04-7.01 (m, 1H), 6.85-6.83 (m, 1H), 5.44 (s, 2H), 5.35 (s, 2H), 3.05 (s, 2H), 2.41-2.34 (m, 2H), 2.25 (s, 3H), 2.12 (s, 3H), 1.73-1.66 (m, 2H), 1.47-1.38 (m, 4H).

Example 102 racemic cis-3-{1-[2-Fluoro-4-(6-methoxypyridin-3-yl)benzyl]-5-(quinolin-2-ylmethoxy)-1H-benzimidazol-2-yl}-2,2-dimethylcyclopropanecarboxylic acid

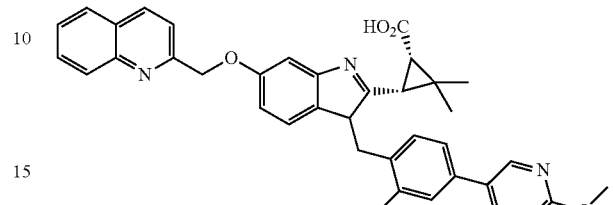

The title compound was prepared using similar methods to those in Example 97 using racemic methyl cis-3-[1-(4-bromo-2-fluorobenzyl)-5-(quinolin-2-ylmethoxy)-1H-benzimidazol-2-yl]-2,2-dimethylcyclopropanecarboxylate and (6-methoxypyridin-3-yl)boronic acid in Step A. MS (ESI): mass calcd. for $C_{36}H_{31}FN_4O_4$, 602.23; m/z found, 603.1 [M+H]$^+$. $^1$H NMR (500 MHz, CDCl$_3$) δ 8.34 (d, J=2.5, 1H), 8.20 (d, J=8.5, 1H), 8.11 (d, J=8.5, 1H), 7.83 (d, J=8.2, 1H), 7.76-7.70 (m, 2H), 7.68 (d, J=8.5, 1H), 7.57-7.53 (m, 1H), 7.33-7.23 (m, 4H), 7.14-7.11 (m, 1H), 6.93-6.89 (m, 1H), 6.82 (d, J=8.5, 1H), 5.46 (d, J=17, 1H), 5.43 (s, 2H), 5.41 (d, J=17, 1H), 3.97 (s, 3H), 2.34 (d, J=8.2, 1H), 2.14 (d, J=8.2, 1H), 1.32 (s, 3H), 1.05 (s, 3H).

Example 103 racemic cis-3-{1-[(3,4'-Difluorobiphenyl-4-yl)methyl]-5-(quinolin-2-ylmethoxy)-1H-benzimidazol-2-yl}-2,2-dimethylcyclopropanecarboxylic acid

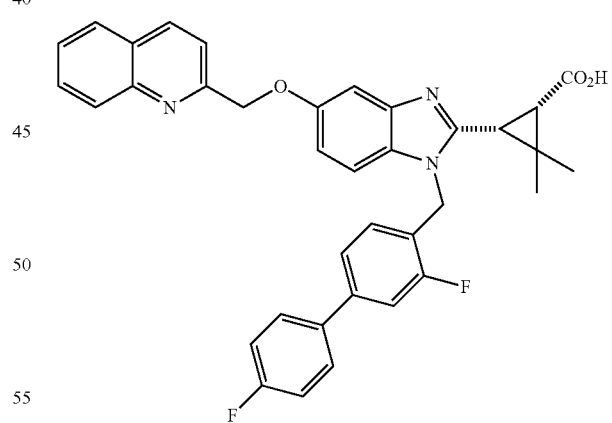

The title compound was prepared using similar methods to those in Example 97 using racemic methyl cis-3-[1-(4-bromo-2-fluorobenzyl)-5-(quinolin-2-ylmethoxy)-1H-benzimidazol-2-yl]-2,2-dimethylcyclopropanecarboxylate and (4-fluorophenyl)boronic acid in Step A. MS (ESI): mass calcd. for $C_{36}H_{29}F_2N_3O_3$, 589.22; m/z found, 590.1 [M+H]$^+$. $^1$H NMR (500 MHz, CDCl$_3$) δ 8.20 (d, J=8.5 Hz, 1H), 8.12-8.09 (m, 1H), 7.84-7.81 (m, 1H), 7.76-7.72 (m, 1H), 7.68 (d, J=8.5 Hz, 1H), 7.58-7.53 (m, 1H), 7.51-7.46 (m, 2H), 7.34-7.30 (m, 2H), 7.28 (d, J=8.9 Hz, 1H), 7.25-

7.23 (m, 1H), 7.16-7.10 (m, 3H), 6.92-6.88 (m, 1H), 5.49-5.38 (m, 4H), 2.34 (d, J=8.2 Hz, 1H), 2.14 (d, J=8.2 Hz, 1H), 1.31 (s, 3H), 1.04 (s, 3H).

Example 104 racemic cis-2,2-Dimethyl-3-{5-(quinolin-2-yl-methoxy)-1-[(3,3',4'-trifluorobiphenyl-4-yl)methyl]-1H-benzimidazol-2-yl}cyclopropanecarboxylic acid

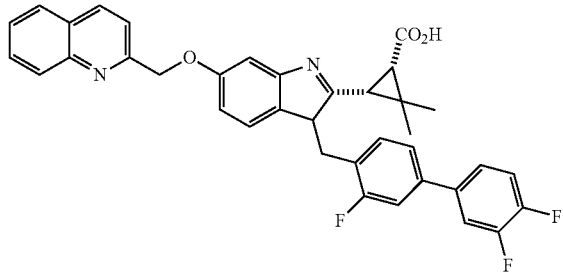

The title compound was prepared using similar methods to those in Example 97 using racemic methyl cis-3-[1-(4-bromo-2-fluorobenzyl)-5-(quinolin-2-ylmethoxy)-1H-benzimidazol-2-yl]-2,2-dimethylcyclopropanecarboxylate and (3,4-difluorophenyl)boronic acid in Step A. MS (ESI): mass calcd. for $C_{36}H_{28}F_3N_3O_3$, 607.21; m/z found, 608.1 [M+H]$^+$. $^1$H NMR (500 MHz, CDCl$_3$) δ 8.20 (d, J=8.5, 1H), 8.11 (d, J=8.5, 1H), 7.83 (d, J=8.2, 1H), 7.76-7.72 (m, 1H), 7.68 (d, J=8.5, 1H), 7.58-7.54 (m, 1H), 7.35-7.20 (m, 7H), 7.14-7.11 (m, 1H), 6.93-6.88 (m, 1H), 5.46 (d, J=17, 1H), 5.43 (s, 2H), 5.41 (d, J=17, 1H), 2.34 (d, J=8.2, 1H), 2.13 (d, J=8.2, 1H), 1.31 (s, 3H), 1.05 (s, 3H).

Example 105

1-({5-(Quinolin-2-ylmethoxy)-1-[4-(1,3-thiazol-4-yl)benzyl]-1H-benzimidazol-2-yl}methyl)cyclopentanecarboxylic acid

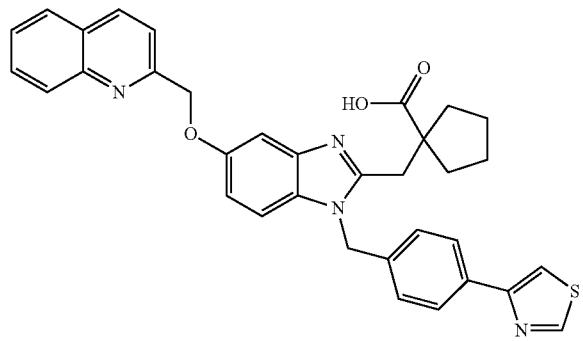 [SMILES: O=C(O)C1(Cc2nc3cc(OCc4ccc5ccccc5n4)ccc3n2Cc2ccc(-c3cscn3)cc2)CCCC1]

The title compound was prepared using similar methods to those in Example 97 using ethyl 1-((1-(4-bromobenzyl)-5-(quinolin-2-ylmethoxy)-1H-benzo[d]imidazol-2-yl)methyl)cyclopentanecarboxylate and thiazole-4-boronic acid pinacol ester in Step A. MS (ESI): mass calcd. for $C_{34}H_{30}N_4O_3S$, 574.20; m/z found, 575.1 [M+H]$^+$. $^1$H NMR (400 MHz, CDCl$_3$) δ 8.90-8.86 (m, 1H), 8.21 (d, J=8.5 Hz, 1H), 8.11 (d, J=8.4 Hz, 1H), 7.88 (d, J=8.3 Hz, 2H), 7.86-7.82 (m, 1H), 7.78-7.72 (m, 1H), 7.70 (d, J=8.5 Hz, 1H), 7.59-7.54 (m, 1H), 7.54-7.51 (m, 1H), 7.40-7.35 (m, 1H), 7.22-7.17 (m, 1H), 7.13-7.05 (m, 3H), 5.43 (s, 2H), 5.38 (s, 2H), 3.14 (s, 2H), 2.38-2.28 (m, 2H), 1.76-1.67 (m, 2H), 1.58-1.49 (m, 4H).

Example 106 racemic cis-2,2-Dimethyl-3-{5-(quinolin-2-yl-methoxy)-1-[3-(1,3-thiazol-4-yl)benzyl]-1H-benzimidazol-2-yl}cyclopropanecarboxylic acid

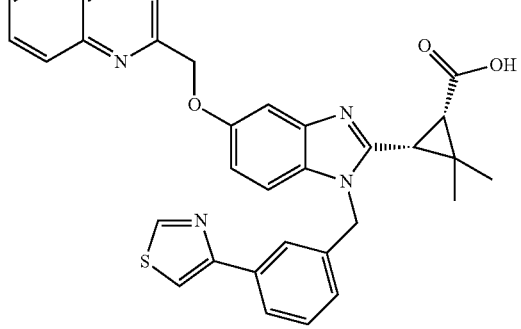

The title compound was prepared using similar methods to those in Example 97 using racemic cis-ethyl 3-(1-(3-bromobenzyl)-5-(quinolin-2-ylmethoxy)-1H-benzo[d]imidazol-2-yl)-2,2-dimethylcyclopropanecarboxylate and thiazole-4-boronic acid pinacol ester in Step A. MS (ESI): mass calcd. for $C_{33}H_{28}N_4O_3S$, 560.19; m/z found, 561.2 [M+H]$^+$. $^1$H NMR (500 MHz, CDCl$_3$) δ 8.89-8.87 (m, 1H), 8.23 (d, J=8.5, 1H), 8.11 (d, J=8.5, 1H), 7.87-7.83 (m, 2H), 7.81-7.78 (m, 1H), 7.77-7.73 (m, 1H), 7.70 (d, J=8.5, 1H), 7.59-7.55 (m, 1H), 7.54-7.52 (m, 1H), 7.43-7.39 (m, 1H), 7.34-7.31 (m, 2H), 7.15-7.11 (m, 1H), 6.99-6.96 (m, 1H), 5.51-5.38 (m, 4H), 2.29 (d, J=8.2, 1H), 2.16 (d, J=8.2, 1H), 1.18 (s, 3H), 1.01 (s, 3H).

Example 107

1-({1-[4-(3,5-Dimethylisoxazol-4-yl)benzyl]-5-(quinolin-2-ylmethoxy)-1H-benzimidazol-2-yl}methyl)cyclopentanecarboxylic acid

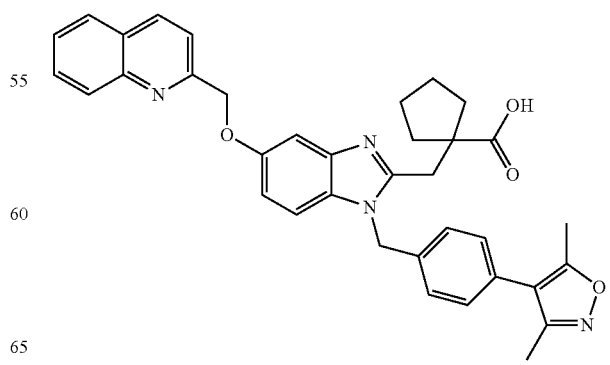

The title compound was prepared using similar methods to those in Example 97 using ethyl 1-((1-(4-bromobenzyl)-5-(quinolin-2-ylmethoxy)-1H-benzo[d]imidazol-2-yl)methyl)cyclopentanecarboxylate and 3,5-dimethylisoxazole-4-boronic acid in Step A. MS (ESI): mass calcd. for $C_{36}H_{34}N_4O_4$, 586.26; m/z found, 587.3 [M+H]$^+$. $^1$H NMR (400 MHz, CDCl$_3$) δ 8.22 (d, J=8.5, 1H), 8.11 (d, J=8.5, 1H), 7.84 (d, J=8.1, 1H), 7.78-7.75 (m, 1H), 7.74-7.70 (m, 1H), 7.59-7.54 (m, 1H), 7.37-7.35 (m, 1H), 7.23-7.19 (m, 3H), 7.12-7.10 (m, 1H), 7.10-7.05 (m, 2H), 5.43 (s, 2H), 5.38 (s, 2H), 3.11 (s, 2H), 2.36 (s, 3H), 2.35-2.27 (m, 2H), 2.23 (s, 3H), 1.74-1.67 (m, 2H), 1.60-1.47 (m, 4H).

Example 108 racemic cis-2,2-Dimethyl-3-{5-(quinolin-2-ylmethoxy)-1-[4-(1,3-thiazol-4-yl)benzyl]-1H-benzimidazol-2-yl}cyclopropanecarboxylic acid

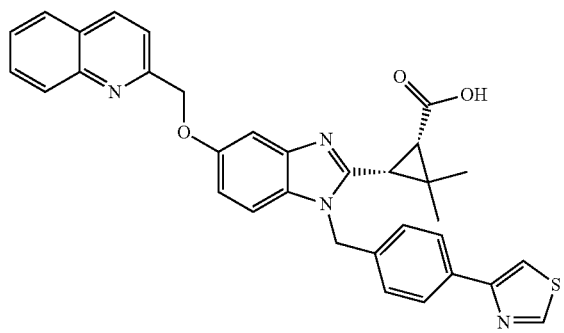 [SMILES: CC1(C)[C@H](c2nc3cc(OCc4ccc5ccccc5n4)ccc3n2Cc2ccc(-c3cscn3)cc2)[C@@H]1C(=O)O]

The title compound was prepared using similar methods to those in Example 97 using racemic cis-ethyl 3-(1-(4-bromobenzyl)-5-(quinolin-2-ylmethoxy)-1H-benzo[d]imidazol-2-yl)-2,2-dimethylcyclopropanecarboxylate and thiazole-4-boronic acid pinacol ester in Step A. MS (ESI): mass calcd. for $C_{33}H_{28}N_4O_3S$, 560.19; m/z found, 561.2 [M+H]$^+$. $^1$H NMR (500 MHz, CDCl$_3$) δ 8.89-8.85 (m, 1H), 8.20 (d, J=8.5, 1H), 8.11 (d, J=8.5, 1H), 7.92 (d, J=8.3, 2H), 7.85-7.81 (m, 1H), 7.77-7.71 (m, 1H), 7.68 (d, J=8.5, 1H), 7.57-7.53 (m, 2H), 7.34-7.31 (m, 1H), 7.25-7.23 (m, 1H), 7.16-7.08 (m, 3H), 5.47-5.33 (m, 4H), 2.30 (d, J=8.2, 1H), 2.08 (d, J=8.2, 1H), 1.21 (s, 3H), 1.01 (s, 3H).

Example 109 racemic cis-2-(5-((6-fluoroquinolin-2-yl)methoxy)-1-((4'-(trifluoromethyl)-[1,1'-biphenyl]-4-yl)methyl)-1H-benzo[d]imidazol-2-yl)cyclohexanecarboxylic acid

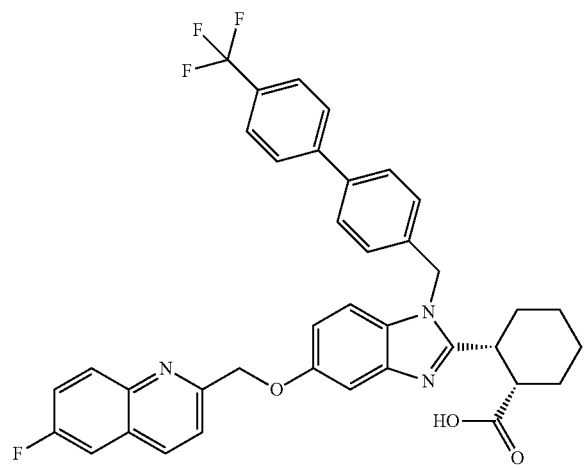 [SMILES: O=C(O)[C@H]1CCCC[C@H]1c1nc2cc(OCc3ccc4cc(F)ccc4n3)ccc2n1Cc1ccc(-c2ccc(C(F)(F)F)cc2)cc1]

The title compound was prepared using similar methods to those in Example 97 using (4-(trifluoromethyl)phenyl)boronic acid and racemic (1R,2S)-2-(1-(4-bromobenzyl)-5-((6-fluoroquinolin-2-yl)methoxy)-1H-benzo[d]imidazol-2-yl)cyclohexanecarboxylic acid-4-(4,4,5,5-tetramethyl-1,3,2-dioxaborolan-2-yl)thiazole in Step A. MS (ESI): mass calcd. for $C_{38}H_{31}F_4N_3O_3$, 653.23; m/z found, 654.2 [M+H]$^+$. $^1$H NMR (500 MHz, CD$_3$OD) δ 8.33 (d, J=8.4, 1H), 8.11-8.05 (m, 1H), 7.81-7.74 (m, 3H), 7.70 (d, J=8.3, 2H), 7.66-7.56 (m, 4H), 7.30 (d, J=2.4, 1H), 7.27-7.22 (m, 3H), 7.02 (dd, J=8.8, 2.4, 1H), 5.60 (d, J=17.1, 1H), 5.54 (d, J=17.2, 1H), 5.39 (s, 2H), 3.65-3.55 (m, 1H), 2.90-2.80 (m, 1H), 2.42-2.31 (m, 1H), 2.08-1.98 (m, 1H), 1.92-1.73 (m, 4H), 1.54-1.38 (m, 2H).

Example 110

1-{[1-(4-Furan-3-ylbenzyl)-5-(quinolin-2-ylmethoxy)-1H-benzimidazol-2-yl]methyl}cyclopentanecarboxylic acid

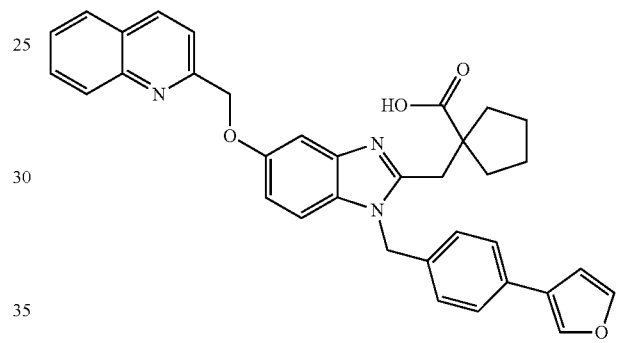

Step A. Ethyl 1-((1-(4-(furan-3-yl)benzyl)-5-(quinolin-2-ylmethoxy)-1H-benzo[d]imidazol-2-yl)methyl)cyclopentanecarboxylate To a 5 mL microwave vial were added ethyl 1-((1-(4-bromobenzyl)-5-(quinolin-2-ylmethoxy)-1H-benzo[d]imidazol-2-yl)methyl)cyclopentanecarboxylate (62 mg, 0.1 mmol), Pd(PPh$_3$)$_4$ (12 mg, 0.01 mmol), furan-3-boronic acid (18 mg, 0.16 mmol), K$_3$PO$_4$ (99 mg, 0.47 mmol), DME (1.1 mL) and water (0.56 mL). The vial was capped and irradiated in the microwave reactor at 120° C. for 30 minutes. The mixture was then partitioned between water (20 mL) and EtOAc (20 mL). The layers were separated and the aqueous further extracted with EtOAc (2×20 mL). The organics were combined, dried (Na$_2$SO$_4$), filtered and concentrated to dryness. The residue was purified using reverse phase HPLC to afford the title compound. MS (ESI): mass calcd. for $C_{37}H_{35}N_3O_4$, 585.26; m/z found, 586.2 [M+H]$^+$.

Step B. 1-{[1-(4-Furan-3-ylbenzyl)-5-(quinolin-2-ylmethoxy)-1H-benzimidazol-2-yl]methyl}cyclopentanecarboxylic acid To a 20 mL vial were added ethyl 1-((1-(4-(furan-3-yl)benzyl)-5-(quinolin-2-ylmethoxy)-1H-benzo[d]imidazol-2-yl)methyl)cyclopentanecarboxylate (60 mg, 0.1 mmol), THF (1.3 mL) and MeOH (1.3 mL) followed by LiOH (1.4 mL, 1 M). The reaction mixture was heated at 80° C. for 1.5 h. The mixture was cooled to RT and concentrated to dryness. Water (5 mL) was added and the pH was adjusted to ~5-6 using 1 M HCl. To the mixture was added DCM (5 mL) and the mixture was stirred for 1 h at RT. The organic layer was separated then concentrated to dryness. The resulting residue was purified using FCC or reverse phase HPLC to provide the title compound. MS (ESI): mass calcd. for $C_{35}H_{31}N_3O_4$, 557.23; m/z found, 558.2 [M+H]$^+$. $^1$H NMR (500 MHz, CDCl$_3$) δ 8.22 (d, J=8.5, 1H), 8.10 (d, J=8.5, 1H), 7.84 (d, J=8.1, 1H), 7.77-7.69 (m, 3H), 7.58-7.54 (m, 1H), 7.48-7.46 (m, 1H), 7.42 (d, J=8.1, 2H), 7.35-7.34 (m, 1H), 7.16 (d, J=8.8, 1H), 7.04-7.01 (m, 3H), 6.65 (s, 1H), 5.42 (s, 2H), 5.35 (s, 2H), 3.12 (s, 2H), 2.32-2.26 (m, 2H), 1.73-1.68 (m, 2H), 1.65-1.52 (m, 4H).

Example 111

1-({1-[4-(6-Methoxypyridin-3-yl)benzyl]-5-(quinolin-2-ylmethoxy)-1H-benzimidazol-2-yl}methyl)cyclopentanecarboxylic acid as the TFA salt

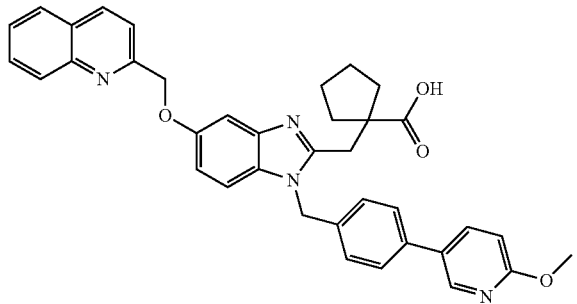 [SMILES: COc1ccc(-c2ccc(Cn3c(CC4(C(=O)O)CCCC4)nc4cc(OCc5ccc6ccccc6n5)ccc43)cc2)cn1]

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 2-methoxy-5-pyridineboronic acid in Step A. MS (ESI): mass calcd. for $C_{37}H_{34}N_4O_4$, 598.26; m/z found, 599.1 [M+H]$^+$. $^1$H NMR (400 MHz, CDCl$_3$) δ 8.48 (d, J=8.5, 1H), 8.33-8.30 (m, 1H), 8.27 (d, J=8.6, 1H), 7.97-7.92 (m, 1H), 7.89-7.81 (m, 2H), 7.73 (dd, J=8.6, 2.6, 1H), 7.71-7.65 (m, 1H), 7.60-7.57 (m, 1H), 7.50-7.46 (m, 2H), 7.31-7.28 (m, 1H), 7.23-7.19 (m, 1H), 7.14-7.09 (m, 2H), 6.81 (d, J=8.6, 1H), 5.62-5.57 (m, 4H), 3.96 (s, 3H), 3.44 (s, 2H), 2.27-2.18 (m, 2H), 1.75-1.64 (m, 6H).

Example 112

1-{[5-(Quinolin-2-ylmethoxy)-1-{4-[6-(trifluoromethyl)pyridin-3-yl]benzyl}-1H-benzimidazol-2-yl]methyl}cyclopentanecarboxylic acid as the TFA salt

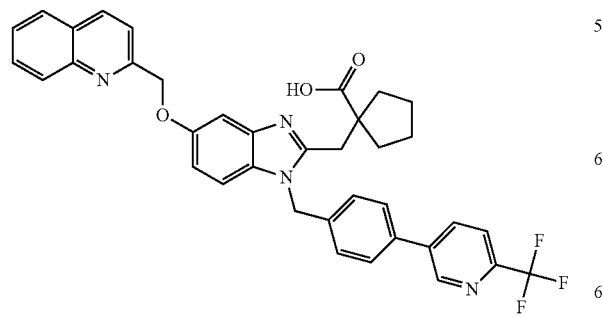

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 2-trifluoromethylpyridine-5-boronic acid in Step A. MS (ESI): mass calcd. for $C_{37}H_{31}F_3N_4O_3$, 636.23; m/z found, 637.0 [M+H]$^+$. $^1$H NMR (400 MHz, CDCl$_3$) δ 8.90-8.86 (m, 1H), 8.49 (d, J=8.5, 1H), 8.31-8.25 (m, 1H), 8.02-7.99 (m, 1H), 7.98-7.93 (m, 1H), 7.91-7.83 (m, 2H), 7.76 (d, J=8.0, 1H), 7.72-7.67 (m, 1H), 7.61-7.56 (m, 3H), 7.32-7.29 (m, 1H), 7.25-7.19 (m, 3H), 5.68 (s, 2H), 5.59 (s, 2H), 3.46 (s, 2H), 2.97 (s, 1H), 2.90-2.88 (m, 1H), 2.64 (s, 1H), 2.30-2.20 (m, 2H), 1.74-1.72 (m, 3H).

Example 113

1-({1-[(4'-Fluorobiphenyl-4-yl)methyl]-5-(quinolin-2-ylmethoxy)-1H-benzimidazol-2-yl}methyl)cyclopentanecarboxylic acid as the TFA salt

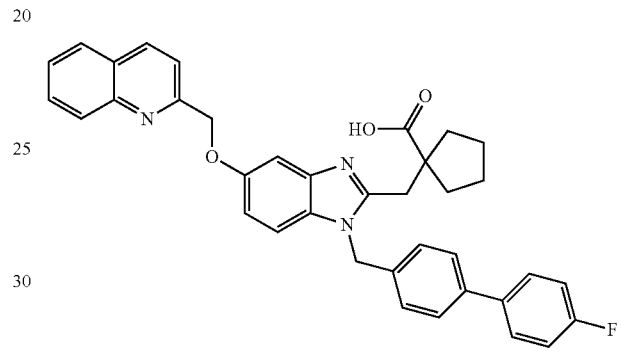

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 4-fluorophenyl boronic acid in Step A. MS (ESI): mass calcd. for $C_{37}H_{32}FN_3O_3$, 585.24; m/z found, 586.0 [M+H]$^+$. $^1$H NMR (400 MHz, CDCl$_3$) δ 8.50 (d, J=8.5, 1H), 8.35-8.31 (m, 1H), 8.00-7.94 (m, 1H), 7.91-7.85 (m, 2H), 7.72-7.67 (m, 2H), 7.54-7.51 (m, 2H), 7.51-7.47 (m, 2H), 7.37-7.33 (m, 1H), 7.28-7.25 (m, 1H), 7.16-7.09 (m, 4H), 5.64 (s, 2H), 5.61 (s, 2H), 3.48 (s, 2H), 3.42-3.40 (m, 1H), 2.97 (s, 1H), 2.89-2.88 (m, 1H), 2.33-2.26 (m, 2H), 1.78-1.75 (m, 3H).

Example 114

1-({1-[4-(6-Ethoxypyridin-3-yl)benzyl]-5-(quinolin-2-ylmethoxy)-1H-benzimidazol-2-yl}methyl)cyclopentanecarboxylic acid as the TFA salt

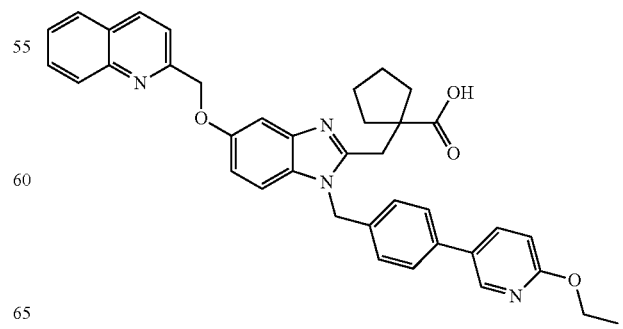

123

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 2-ethoxypyridine-5-boronic acid in Step A. MS (ESI): mass calcd. for $C_{38}H_{36}N_4O_4$, 612.27; m/z found, 613.1 [M+H]$^+$. $^1$H NMR (400 MHz, CDCl$_3$) δ 8.65 (d, J=8.6, 1H), 8.39 (d, J=8.6, 1H), 8.35-8.33 (m, 1H), 8.04-8.02 (m, 1H), 7.97-7.94 (m, 2H), 7.80-7.75 (m, 2H), 7.52-7.50 (m, 1H), 7.48 (d, J=8.3, 2H), 7.32-7.28 (m, 1H), 7.21-7.17 (m, 1H), 7.10 (d, J=8.3, 2H), 6.82 (d, J=8.5, 1H), 5.68 (s, 2H), 5.63 (s, 2H), 4.38 (q, J=7.1, 2H), 3.42 (s, 2H), 2.25-2.18 (m, 2H), 1.71-1.59 (m, 6H), 1.42 (t, J=7.1, 3H).

Example 115

1-{[1-{4-[6-(Dimethylamino)pyridin-3-yl]benzyl}-5-(quinolin-2-ylmethoxy)-1H-benzimidazol-2-yl]methyl}cyclopentanecarboxylic acid as the TFA salt

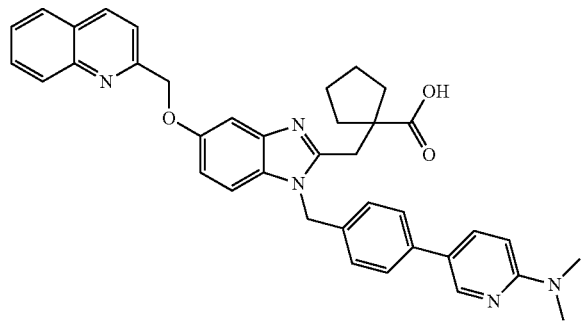 [SMILES: CN(C)c1ccc(-c2ccc(Cn3c(CC4(C(=O)O)CCCC4)nc4cc(OCc5ccc6ccccc6n5)ccc43)cc2)cn1]

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 6-(dimethylamino)pyridine-3-boronic acid in Step A. MS (ESI): mass calcd. for $C_{38}H_{37}N_5O_3$, 611.29; m/z found, 612.2 [M+H]$^+$. $^1$H NMR (400 MHz, CDCl$_3$) δ 8.48-8.45 (m, 1H), 8.33 (d, J=8.4, 1H), 8.15 (d, J=8.5, 1H), 8.05-8.01 (m, 1H), 7.91-7.87 (m, 1H), 7.82-7.77 (m, 1H), 7.74 (d, J=8.5, 1H), 7.64-7.59 (m, 1H), 7.56-7.54 (m, 1H), 7.53-7.50 (m, 2H), 7.28-7.24 (m, 1H), 7.21-7.16 (m, 3H), 6.97 (d, J=9.4, 1H), 5.62 (s, 2H), 5.48 (s, 2H), 3.48 (s, 2H), 3.41-3.38 (m, 2H), 3.35 (s, 6H), 2.64 (s, 1H), 2.29-2.23 (m, 2H), 1.78-1.76 (m, 3H).

Example 116

1-({1-[(3',4'-Difluorobiphenyl-4-yl)methyl]-5-(quinolin-2-ylmethoxy)-1H-benzimidazol-2-yl}methyl)cyclopentanecarboxylic acid as the TFA salt

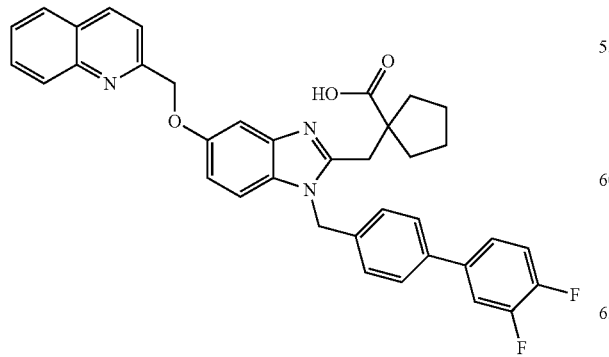

124

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 3,4-difluorophenylboronic acid in Step A. MS (ESI): mass calcd. for $C_{37}H_{31}F_2N_3O_3$, 603.23; m/z found, 604.1 [M+H]$^+$. $^1$H NMR (400 MHz, CDCl$_3$) δ 8.65 (d, J=8.6, 1H), 8.40 (d, J=8.6, 1H), 8.03 (d, J=8.2, 1H), 7.98-7.94 (m, 2H), 7.81-7.75 (m, 1H), 7.53-7.51 (m, 1H), 7.49-7.46 (m, 2H), 7.32-7.28 (m, 2H), 7.23-7.18 (m, 3H), 7.10 (d, J=8.3, 2H), 5.68 (s, 2H), 5.63 (s, 2H), 3.42 (s, 2H), 2.26-2.18 (m, 2H), 1.74-1.57 (m, 6H).

Example 117

1-{[1-{4-[2-(Dimethylamino)pyrimidin-5-yl]benzyl}-5-(quinolin-2-ylmethoxy)-1H-benzimidazol-2-yl]methyl}cyclopentanecarboxylic acid as the TFA salt

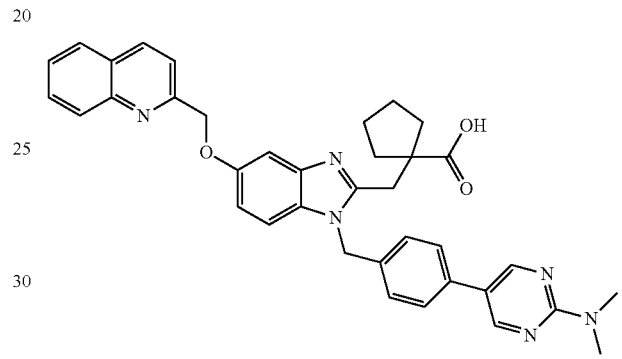

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 2-dimethylamino-pyrimidine-5-boronic acid pinacol ester in Step A. MS (ESI): mass calcd. for $C_{37}H_{36}N_6O_3$, 612.28; m/z found, 613.2 [M+H]$^+$. $^1$H NMR (400 MHz, CDCl$_3$) δ 8.54 (s, 2H), 8.40 (d, J=8.5, 1H), 8.20 (d, J=8.5, 1H), 7.94-7.91 (m, 1H), 7.86-7.81 (m, 1H), 7.79 (d, J=8.5, 1H), 7.67-7.62 (m, 1H), 7.61-7.58 (m, 1H), 7.49-7.45 (m, 2H), 7.34-7.31 (m, 1H), 7.25-7.21 (m, 1H), 7.17-7.14 (m, 2H), 5.61 (s, 2H), 5.55-5.50 (m, 2H), 3.49 (s, 2H), 3.41-3.39 (m, 1H), 3.25 (s, 6H), 2.32-2.23 (m, 2H), 1.78-1.72 (m, 5H).

Example 118

1-{[1-(Biphenyl-4-ylmethyl)-5-(quinolin-2-ylmethoxy)-1H-benzimidazol-2-yl]methyl}cyclopentanecarboxylic acid as the TFA salt

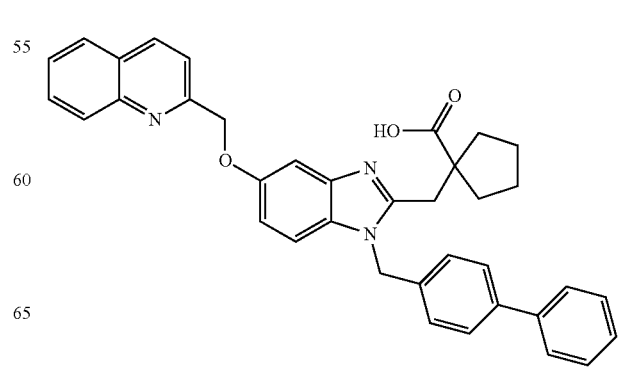

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and phenylboronic acid in Step A. MS (ESI): mass calcd. for $C_{37}H_{33}N_3O_3$, 567.25; m/z found, 568.1 [M+H]+. $^1$H NMR (400 MHz, CDCl$_3$) δ 8.66 (d, J=8.5, 1H), 8.40 (d, J=8.5, 1H), 8.05-8.01 (m, 1H), 7.98-7.93 (m, 2H), 7.80-7.75 (m, 1H), 7.57-7.49 (m, 5H), 7.45-7.40 (m, 2H), 7.37-7.31 (m, 2H), 7.23-7.20 (m, 1H), 7.10 (d, J=8.3, 2H), 5.70 (s, 2H), 5.62 (s, 2H), 3.42 (s, 2H), 2.26-2.17 (m, 2H), 1.72-1.57 (m, 6H).

Example 119

1-{[1-{[4'-(1-Methylethyl)biphenyl-4-yl]methyl}-5-(quinolin-2-ylmethoxy)-1H-benzimidazol-2-yl]methyl}cyclopentanecarboxylic acid as the TFA salt

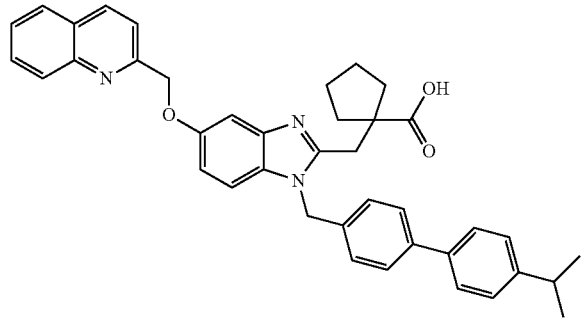 [SMILES: CC(C)c1ccc(-c2ccc(Cn3c(CC4(C(=O)O)CCCC4)nc4cc(OCc5ccc6ccccc6n5)ccc43)cc2)cc1]

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 4-isopropylbenzeneboronic acid in Step A. MS (ESI): mass calcd. for $C_{40}H_{39}N_3O_3$, 609.30; m/z found, 610.2 [M+H]+. $^1$H NMR (500 MHz, CDCl$_3$) δ 8.31 (d, J=8.5, 1H), 8.15 (d, J=8.4, 1H), 7.88 (d, J=8.4, 1H), 7.81-7.76 (m, 1H), 7.73 (d, J=8.4, 1H), 7.62-7.58 (m, 2H), 7.58-7.55 (m, 2H), 7.49-7.45 (m, 2H), 7.32-7.30 (m, 3H), 7.22-7.19 (m, 1H), 7.14-7.10 (m, 2H), 5.57 (s, 2H), 5.48 (s, 2H), 3.47 (s, 2H), 3.42-3.40 (m, 1H), 2.98-2.91 (m, 1H), 2.30-2.24 (m, 2H), 1.77-1.70 (m, 5H), 1.28 (d, J=6.9, 6H).

Example 120

1-{[1-({3'-[(Methylsulfonyl)amino]biphenyl-4-yl}methyl)-5-(quinolin-2-ylmethoxy)-1H-benzimidazol-2-yl]methyl}cyclopentanecarboxylic acid as the TFA

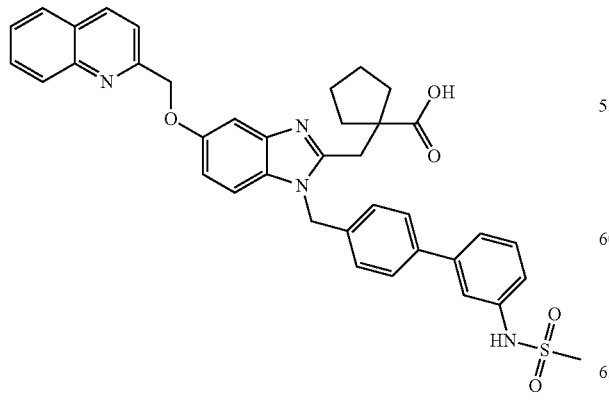

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 3-methylsulfonylaminophenylboronic acid in Step A. MS (ESI): mass calcd. for $C_{38}H_{36}N_4O_5S$, 660.24; m/z found, 661.1 [M+H]+. $^1$H NMR (500 MHz, CDCl$_3$) δ 8.35-8.32 (m, 1H), 8.16 (d, J=8.6, 1H), 7.89 (d, J=8.2, 1H), 7.82-7.77 (m, 1H), 7.75-7.72 (m, 1H), 7.64-7.57 (m, 2H), 7.57-7.53 (m, 3H), 7.51-7.43 (m, 1H), 7.42-7.37 (m, 2H), 7.33-7.30 (m, 1H), 7.27-7.23 (m, 1H), 7.22-7.18 (m, 1H), 7.15-7.11 (m, 2H), 5.64-5.58 (m, 2H), 5.49-5.46 (m, 2H), 3.47 (s, 2H), 3.44-3.40 (m, 1H), 2.99 (s, 3H), 2.30-2.24 (m, 2H), 1.76-1.71 (m, 5H).

Example 121

1-{[1-{4-[6-Methoxy-5-(trifluoromethyl)pyridin-3-yl]benzyl}-5-(quinolin-2-ylmethoxy)-1H-benzimidazol-2-yl]methyl}cyclopentanecarboxylic acid as the TFA salt

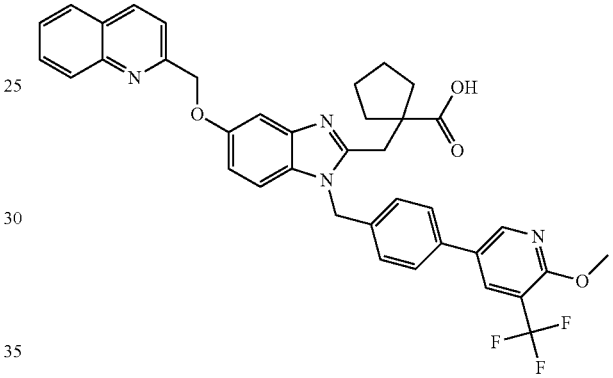

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 2-methoxy-5-(4,4,5,5-tetramethyl-1,3,2-dioxaborolan-2-yl)-3-(trifluoromethyl)pyridine in Step A. MS (ESI): mass calcd. for $C_{38}H_{33}F_3N_4O_4$, 666.25; m/z found, 667.0 [M+H]+. $^1$H NMR (400 MHz, CDCl$_3$) δ 8.70 (d, J=8.5, 1H), 8.48-8.45 (m, 1H), 8.44-8.40 (m, 1H), 8.07-8.04 (m, 1H), 8.02-7.96 (m, 3H), 7.83-7.78 (m, 1H), 7.53-7.48 (m, 3H), 7.33-7.29 (m, 1H), 7.23-7.19 (m, 1H), 7.14 (d, J=8.3, 2H), 5.72 (s, 2H), 5.65 (s, 2H), 4.07 (s, 3H), 3.43 (s, 2H), 2.28-2.20 (m, 2H), 1.74-1.60 (m, 6H).

Example 122

1-{[1-{[4'-(Methylsulfonyl)biphenyl-4-yl]methyl}-5-(quinolin-2-ylmethoxy)-1H-benzimidazol-2-yl]methyl}cyclopentanecarboxylic acid

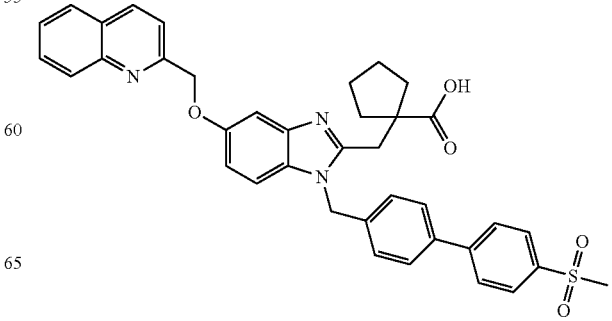

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 4-(methylsulfonyl)phenyl boronic acid in Step A. MS (ESI): mass calcd. for $C_{38}H_{35}N_3O_5S$, 645.23; m/z found, 646.2 [M+H]$^+$. $^1$H NMR (500 MHz, CDCl$_3$) δ 8.22-8.18 (m, 1H), 8.10-8.06 (m, 1H), 8.00-7.96 (m, 2H), 7.85-7.80 (m, 1H), 7.76-7.72 (m, 1H), 7.72-7.67 (m, 3H), 7.57-7.52 (m, 3H), 7.46-7.41 (m, 1H), 7.18-7.14 (m, 1H), 7.14-7.10 (m, 2H), 7.08-7.03 (m, 1H), 5.42 (s, 2H), 5.39 (s, 2H), 4.15-4.04 (m, 1H), 3.09 (s, 3H), 2.27-2.19 (m, 3H), 2.05 (s, 2H), 1.77-1.68 (m, 2H), 1.28-1.24 (m, 1H), 1.00-0.91 (m, 1H).

Example 123

1-({1-[4-(2-Methoxypyrimidin-5-yl)benzyl]-5-(quinolin-2-ylmethoxy)-1H-benzimidazol-2-yl}methyl)cyclopentanecarboxylic acid

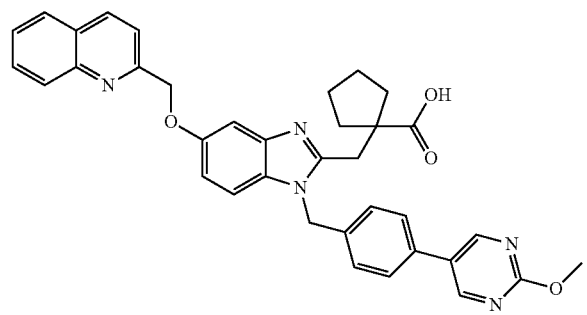 [SMILES: COc1ncc(-c2ccc(Cn3c(CC4(C(=O)O)CCCC4)nc4cc(OCc5ccc6ccccc6n5)ccc43)cc2)cn1]

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 2-methoxypyrimidine-5-boronic acid in Step A. MS (ESI): mass calcd. for $C_{36}H_{33}N_5O_4$, 599.25; m/z found, 600.2 [M+H]$^+$. $^1$H NMR (500 MHz, CDCl$_3$) δ 8.64 (s, 2H), 8.21-8.16 (m, 1H), 8.09-8.04 (m, 1H), 7.83-7.79 (m, 1H), 7.74-7.69 (m, 1H), 7.69-7.64 (m, 1H), 7.56-7.51 (m, 1H), 7.48-7.41 (m, 3H), 7.18-7.13 (m, 1H), 7.13-7.08 (m, 2H), 7.08-7.03 (m, 1H), 5.40 (s, 2H), 5.38 (s, 2H), 4.05 (s, 3H), 3.25-3.18 (m, 1H), 2.31-2.21 (m, 2H), 1.84-1.79 (m, 2H), 1.54-1.42 (m, 5H).

Example 124

1-({1-[4-(1-Methyl-1H-pyrazol-4-yl)benzyl]-5-(quinolin-2-ylmethoxy)-1H-benzimidazol-2-yl}methyl)cyclopentanecarboxylic acid

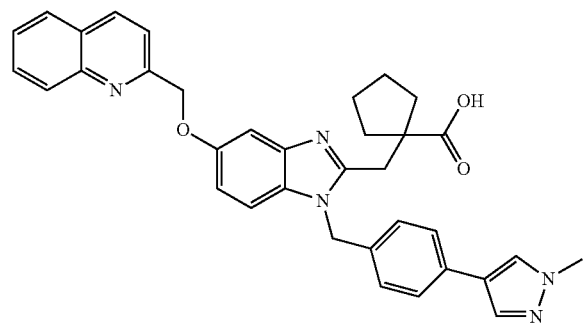 [SMILES: Cn1cc(-c2ccc(Cn3c(CC4(C(=O)O)CCCC4)nc4cc(OCc5ccc6ccccc6n5)ccc43)cc2)cn1]

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 1-methyl-4-(4,4,5,5-tetramethyl-1,3,2-dioxaborolan-2-yl)-1H-pyrazole in Step A. MS (ESI): mass calcd. for $C_{35}H_{33}N_5O_3$, 571.26; m/z found, 572.2 [M+H]$^+$. $^1$H NMR (500 MHz, CDCl$_3$) δ 8.20 (d, J=8.4, 1H), 8.11 (d, J=8.4, 1H), 7.83 (d, J=8.0, 1H), 7.76-7.67 (m, 3H), 7.58-7.53 (m, 2H), 7.42-7.37 (m, 3H), 7.24-7.20 (m, 1H), 7.12-7.08 (m, 1H), 7.03-6.99 (m, 2H), 5.43 (s, 2H), 5.32 (s, 2H), 3.93 (s, 3H), 3.14-3.08 (m, 2H), 2.41-2.30 (m, 4H), 1.73-1.67 (m, 2H), 1.46-1.43 (m, 2H).

Example 125

1-({1-[4-(1H-Pyrazol-4-yl)benzyl]-5-(quinolin-2-ylmethoxy)-1H-benzimidazol-2-yl}methyl)cyclopentanecarboxylic acid

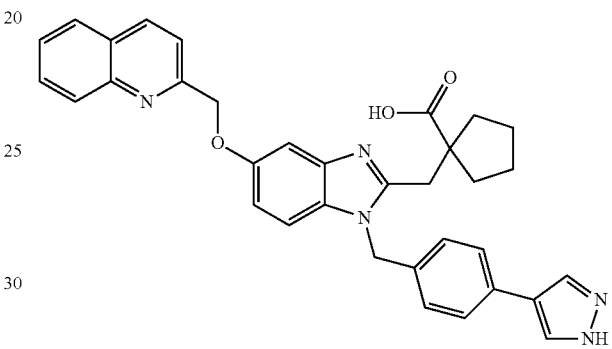

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate, 4.5 equivalents 4-pyrazoleboronic acid pinacol ester and 0.2 equivalents Pd(PPh$_3$)$_4$ in Step A. MS (ESI): mass calcd. for $C_{34}H_{31}N_5O_3$, 557.24; m/z found, 558.2 [M+H]$^+$. $^1$H NMR (500 MHz, CDCl$_3$) δ 8.21 (d, J=8.5, 1H), 8.10 (d, J=8.4, 1H), 7.84 (d, J=7.6, 1H), 7.78 (s, 2H), 7.77-7.73 (m, 1H), 7.71 (d, J=8.5, 1H), 7.59-7.54 (m, 1H), 7.43 (d, J=8.2, 2H), 7.36-7.34 (m, 1H), 7.18 (d, J=8.9, 1H), 7.07-7.04 (m, 1H), 7.02 (d, J=8.1, 2H), 5.42 (s, 2H), 5.34 (s, 2H), 3.43-3.41 (m, 1H), 3.13 (s, 2H), 1.74-1.66 (m, 2H), 1.58-1.50 (m, 4H), 1.30-1.24 (m, 1H).

Example 126

1-{[1-({4'-[(Methylsulfonyl)amino]biphenyl-4-yl}methyl)-5-(quinolin-2-ylmethoxy)-1H-benzimidazol-2-yl]methyl}cyclopentanecarboxylic acid

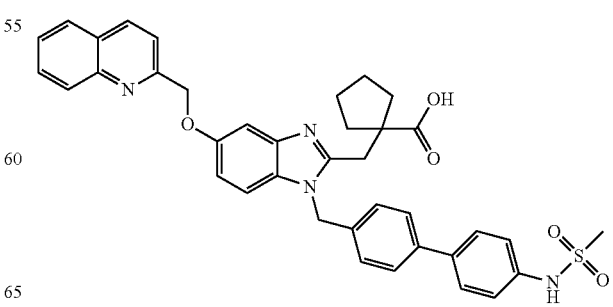

The title compound was prepared using similar methods to those in Example 110 using ethyl 1-((1-(4-bromobenzyl)-5-(quinolin-2-ylmethoxy)-1H-benzo[d]imidazol-2-yl)methyl)cyclopentanecarboxylate and 4-(methanesulfonylamino)phenyl boronic acid in Step A. MS (ESI): mass calcd. for $C_{38}H_{36}N_4O_5S$, 660.24; m/z found, 661.2 [M+H]$^+$. $^1$H NMR (500 MHz, CDCl$_3$) δ 8.19 (d, J=8.5, 1H), 8.10 (d, J=8.4, 1H), 7.84-7.81 (m, 1H), 7.76-7.72 (m, 1H), 7.69 (d, J=8.5, 1H), 7.57-7.53 (m, 1H), 7.51-7.47 (m, 4H), 7.36-7.34 (m, 1H), 7.29-7.27 (m, 2H), 7.23-7.20 (m, 1H), 7.10-7.07 (m, 3H), 5.43 (s, 2H), 5.34 (s, 2H), 3.08 (s, 2H), 3.04 (s, 3H), 2.41-2.34 (m, 2H), 1.73-1.66 (m, 2H), 1.48-1.44 (m, 3H), 1.28-1.23 (m, 1H).

Example 127 racemic cis-3-{1-[4-(2-Methoxypyrimidin-5-yl)benzyl]-5-(quinolin-2-ylmethoxy)-1H-benzimidazol-2-yl}-2,2-dimethylcyclopropanecarboxylic acid

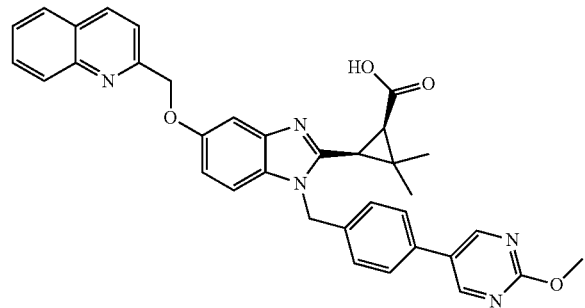 [SMILES: COc1ncc(-c2ccc(Cn3c([C@H]4[C@@H](C(=O)O)C4(C)C)nc4cc(OCc5ccc6ccccc6n5)ccc43)cc2)cn1]

The title compound was prepared using similar methods to those in Example 110 using racemic cis-ethyl 3-(1-(4-bromobenzyl)-5-(quinolin-2-ylmethoxy)-1H-benzo[d]imidazol-2-yl)-2,2-dimethylcyclopropanecarboxylate and 2-methoxypyrimidine-5-boronic acid in Step A. MS (ESI): mass calcd. for $C_{35}H_{31}N_5O_4$, 585.24; m/z found, 586.2 [M+H]$^+$. $^1$H NMR (500 MHz, CDCl$_3$) δ 8.69 (s, 2H), 8.24 (d, J=8.5, 1H), 8.11 (d, J=8.5, 1H), 7.87-7.83 (m, 1H), 7.79-7.74 (m, 1H), 7.71 (d, J=8.5, 1H), 7.60-7.55 (m, 1H), 7.52 (d, J=8.3, 2H), 7.41-7.39 (m, 1H), 7.31-7.29 (m, 1H), 7.21 (d, J=8.3, 2H), 7.17-7.14 (m, 1H), 5.49 (s, 2H), 5.45 (s, 2H), 4.06 (s, 3H), 2.38-2.35 (m, 1H), 2.23-2.21 (m, 1H), 1.24 (s, 3H), 1.04 (s, 3H).

Example 128 racemic cis-3-{1-[3-(2-Methoxypyrimidin-5-yl)benzyl]-5-(quinolin-2-ylmethoxy)-1H-benzimidazol-2-yl}-2,2-dimethylcyclopropanecarboxylic acid

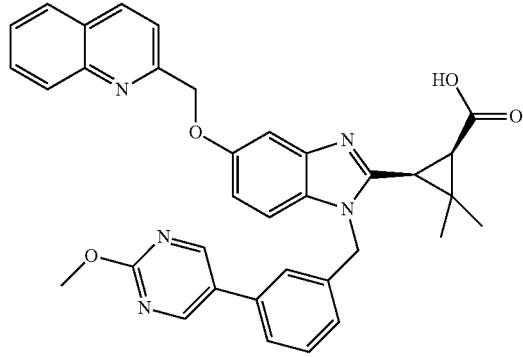 [SMILES: COc1ncc(-c2cccc(Cn3c([C@H]4[C@@H](C(=O)O)C4(C)C)nc4cc(OCc5ccc6ccccc6n5)ccc43)c2)cn1]

The title compound was prepared using similar methods to those in Example 110 using racemic cis-ethyl 3-(1-(3-bromobenzyl)-5-(quinolin-2-ylmethoxy)-1H-benzo[d]imidazol-2-yl)-2,2-dimethylcyclopropanecarboxylate and 2-methoxypyrimidine-5-boronic acid in Step A. MS (ESI): mass calcd. for $C_{35}H_{31}N_5O_4$, 585.24; m/z found, 586.2 [M+H]$^+$. $^1$H NMR (500 MHz, CDCl$_3$) δ 8.63 (s, 2H), 8.23 (d, J=8.3, 1H), 8.11 (d, J=8.8, 1H), 7.85 (d, J=8.3, 1H), 7.78-7.74 (m, 1H), 7.70 (d, J=8.5, 1H), 7.60-7.55 (m, 1H), 7.51-7.45 (m, 2H), 7.35-7.32 (m, 1H), 7.27-7.25 (m, 1H), 7.25-7.23 (m, 1H), 7.15-7.11 (m, 1H), 7.07-7.04 (m, 1H), 5.52-5.46 (m, 1H), 5.44 (s, 2H), 5.43-5.38 (m, 1H), 4.06 (s, 3H), 2.32-2.29 (m, 1H), 2.11-2.08 (m, 1H), 1.20 (s, 3H), 0.99 (s, 3H).

Example 129 racemic cis-3-{1-[(3',4'-Difluorobiphenyl-4-yl)methyl]-5-(quinolin-2-ylmethoxy)-1H-benzimidazol-2-yl}-2,2-dimethylcyclopropanecarboxylic acid

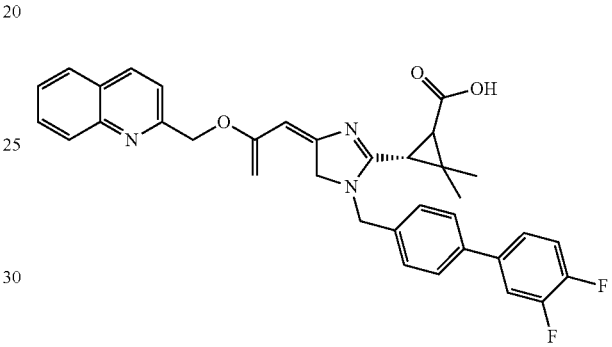

The title compound was prepared using similar methods to those in Example 110 using racemic cis-ethyl 3-(1-(4-bromobenzyl)-5-(quinolin-2-ylmethoxy)-1H-benzo[d]imidazol-2-yl)-2,2-dimethylcyclopropanecarboxylate and 3,4-difluorophenylboronic acid in Step A. MS (ESI): mass calcd. for $C_{36}H_{29}F_2N_3O_3$, 589.22; m/z found, 590.1 [M+H]$^+$. $^1$H NMR (400 MHz, CDCl$_3$) δ 8.24 (d, J=8.5, 1H), 8.11 (d, J=8.6, 1H), 7.85 (d, J=8.2, 1H), 7.79-7.73 (m, 1H), 7.71 (d, J=8.5, 1H), 7.60-7.55 (m, 1H), 7.53-7.49 (m, 2H), 7.39-7.36 (m, 1H), 7.35-7.30 (m, 1H), 7.29-7.28 (m, 1H), 7.27-7.21 (m, 2H), 7.18-7.12 (m, 3H), 5.51-5.38 (m, 4H), 2.35-2.31 (m, 1H), 2.14-2.11 (m, 1H), 1.21 (s, 3H), 1.03 (s, 3H).

Example 130 racemic cis-3-{1-[(3',4'-Difluorobiphenyl-3-yl)methyl]-5-(quinolin-2-ylmethoxy)-1H-benzimidazol-2-yl}-2,2-dimethylcyclopropanecarboxylic acid

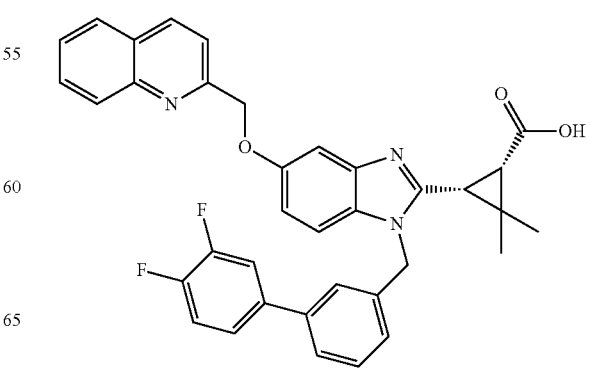

131

The title compound was prepared using similar methods to those in Example 110 using racemic cis-ethyl 3-(1-(3-bromobenzyl)-5-(quinolin-2-ylmethoxy)-1H-benzo[d]imidazol-2-yl)-2,2-dimethylcyclopropanecarboxylate and 3,4-difluorophenylboronic acid in Step A. MS (ESI): mass calcd. for $C_{36}H_{29}F_2N_3O_3$, 589.22; m/z found, 590.1 [M+H]$^+$. $^1$H NMR (400 MHz, CDCl$_3$) δ 8.23 (d, J=8.5, 1H), 8.11 (d, J=8.4, 1H), 7.87-7.83 (m, 1H), 7.79-7.73 (m, 1H), 7.70 (d, J=8.5, 1H), 7.60-7.54 (m, 1H), 7.51-7.47 (m, 1H), 7.45-7.40 (m, 1H), 7.34-7.29 (m, 2H), 7.27-7.25 (m, 2H), 7.24-7.18 (m, 2H), 7.16-7.11 (m, 1H), 7.02-6.97 (m, 1H), 5.52-5.35 (m, 4H), 2.29 (d, J=8.2, 1H), 2.11 (d, J=8.2, 1H), 1.17 (s, 3H), 0.98 (s, 3H).

Example 131 racemic cis-3-{1-[(4'-Fluorobiphenyl-4-yl)methyl]-5-(quinolin-2-ylmethoxy)-1H-benzimidazol-2-yl}-2,2-dimethylcyclopropanecarboxylic acid

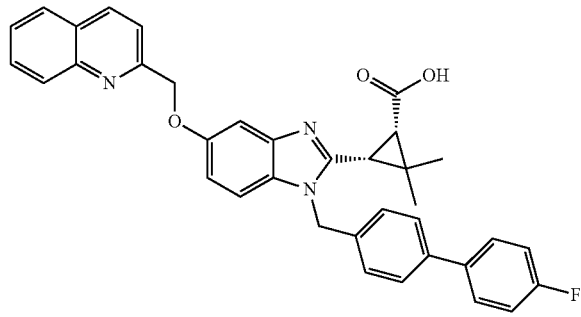 [SMILES: CC1(C)[C@H](c2nc3cc(OCc4ccc5ccccc5n4)ccc3n2Cc2ccc(-c3ccc(F)cc3)cc2)[C@@H]1C(=O)O]

The title compound was prepared using similar methods to those in Example 110 using racemic cis-ethyl 3-(1-(4-bromobenzyl)-5-(quinolin-2-ylmethoxy)-1H-benzo[d]imidazol-2-yl)-2,2-dimethylcyclopropanecarboxylate and 4-fluorophenyl boronic acid in Step A. MS (ESI): mass calcd. for $C_{36}H_{30}FN_3O_3$, 571.23; m/z found, 572.3 [M+H]$^+$. $^1$H NMR (400 MHz, CDCl$_3$) δ 8.23 (d, J=8.5, 1H), 8.11 (d, J=8.6, 1H), 7.85 (d, J=8.0, 1H), 7.79-7.73 (m, 1H), 7.70 (d, J=8.5, 1H), 7.60-7.55 (m, 1H), 7.54-7.47 (m, 4H), 7.34-7.32 (m, 1H), 7.28-7.26 (m, 1H), 7.16-7.09 (m, 5H), 5.49-5.34 (m, 4H), 2.31 (d, J=8.1, 1H), 2.12 (d, J=8.2, 1H), 1.21 (s, 3H), 1.02 (s, 3H).

Example 132 racemic cis-3-{1-[(4'-Fluorobiphenyl-3-yl)methyl]-5-(quinolin-2-ylmethoxy)-1H-benzimidazol-2-yl}-2,2-dimethylcyclopropanecarboxylic acid

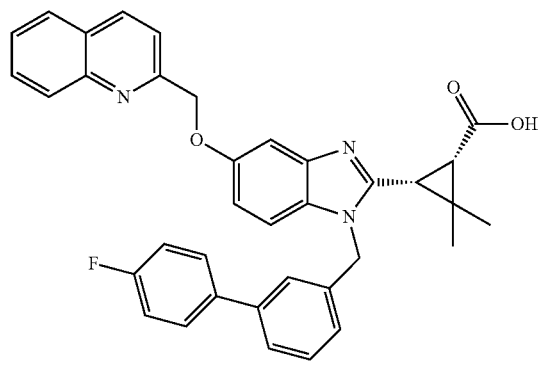 [SMILES: CC1(C)[C@H](c2nc3cc(OCc4ccc5ccccc5n4)ccc3n2Cc2cccc(-c3ccc(F)cc3)c2)[C@@H]1C(=O)O]

132

The title compound was prepared using similar methods to those in Example 110 using racemic cis-ethyl 3-(1-(3-bromobenzyl)-5-(quinolin-2-ylmethoxy)-1H-benzo[d]imidazol-2-yl)-2,2-dimethylcyclopropanecarboxylate and 4-fluorophenylboronic acid in Step A. MS (ESI): mass calcd. for $C_{36}H_{30}FN_3O_3$, 571.23; m/z found, 572.3 [M+H]$^+$. $^1$H NMR (400 MHz, CDCl$_3$) δ 8.25 (d, J=8.5, 1H), 8.12 (d, J=8.5, 1H), 7.86 (d, J=8.2, 1H), 7.80-7.74 (m, 1H), 7.71 (d, J=8.4, 1H), 7.61-7.55 (m, 1H), 7.54-7.50 (m, 1H), 7.46-7.39 (m, 3H), 7.37-7.34 (m, 1H), 7.33-7.30 (m, 1H), 7.29-7.26 (m, 1H), 7.17-7.08 (m, 3H), 7.01-6.97 (m, 1H), 5.54-5.37 (m, 4H), 2.34-2.30 (m, 1H), 2.15 (d, J=8.2, 1H), 1.18 (s, 3H), 1.01 (s, 3H).

Example 133 racemic cis-2-{1-[4-(2-Methoxypyrimidin-5-yl)benzyl]-5-(quinolin-2-ylmethoxy)-1H-benzimidazol-2-yl}cyclohexanecarboxylic acid as the TFA salt

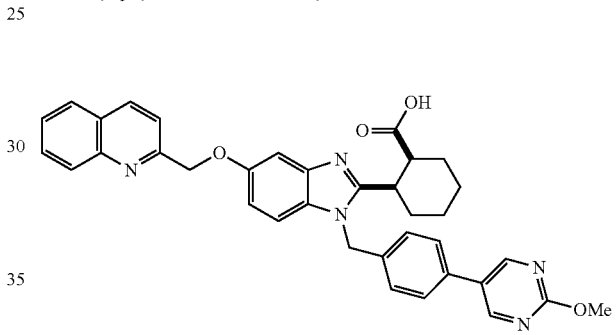

To a 5 mL microwave vial were added a stir-bar, racemic cis-2-[1-(4-bromobenzyl)-5-(quinolin-2-ylmethoxy)-1H-benzimidazol-2-yl]cyclohexanecarboxylic acid (70 mg, 0.12 mmol), (2-methoxypyrimidin-5-yl)boronic acid (57 mg, 0.39 mmol), Pd(dppf)Cl$_2$.CH$_2$Cl$_2$ (9 mg, 0.01 mmol), and sodium carbonate (0.3 mL, 2 M in water). The vial was capped and flushed with nitrogen before adding 2 mL N$_2$ sparged 1,4-dioxane and heating at 80° C. for 4 hours. The vial was cooled to RT and the reaction mixture subjected to reverse phase HPLC purification to give the title compound (38 mg, 43%). MS (ESI): mass calcd. for $C_{36}H_{33}N_5O_4$, 599.25; m/z found, 600.2 [M+H]$^+$. $^1$H NMR (600 MHz, CD$_3$OD) δ 8.80 (s, 2H), 8.53-8.49 (m, J=8.5, 1H), 8.11 (d, J=8.5, 1H), 8.01 (t, J=8.4, 1H), 7.90-7.84 (m, 1H), 7.81 (d, J=8.5, 1H), 7.71-7.64 (m, 3H), 7.56 (d, J=9.2, 1H), 7.39 (d, J=2.3, 1H), 7.35-7.32 (m, 1H), 7.28 (d, J=8.3, 2H), 5.89 (d, J=17.1, 1H), 5.82 (d, J=17.1, 1H), 5.55 (s, 2H), 4.04 (s, 3H), 3.71-3.64 (m, 1H), 2.97 (d, J=3.9, 1H), 2.37-2.28 (m, 1H), 2.23-2.14 (m, 1H), 2.10-2.04 (m, 1H), 2.00-1.94 (m, 1H), 1.85-1.74 (m, 1H), 1.74-1.65 (m, 1H), 1.54 (dt, J=25.6, 13.0, 2H).

Example 134 racemic cis-2-[1-(4-Pyrimidin-5-ylbenzyl)-5-(quinolin-2-ylmethoxy)-1H-benzimidazol-2-yl]cyclohexanecarboxylic acid as the TFA salt

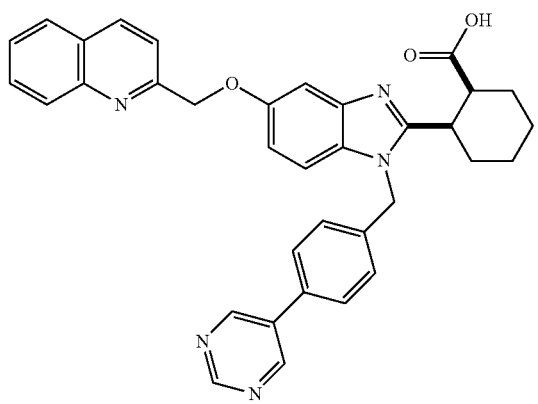

The title compound was prepared using analogous conditions to those described in Example 133 using racemic cis-2-[1-(4-bromobenzyl)-5-(quinolin-2-ylmethoxy)-1H-benzimidazol-2-yl]cyclohexanecarboxylic acid and pyrimidin-5-ylboronic acid. MS (ESI): mass calcd. for $C_{35}H_{31}N_5O_3$, 569.24; m/z found, 570.2 [M+H]$^+$. $^1$H NMR (600 MHz, CD$_3$OD) δ 9.14 (s, 1H), 9.05 (s, 2H), 8.52 (d, J=8.5, 1H), 8.12 (d, J=8.5, 1H), 8.02 (d, J=7.5, 1H), 7.87 (ddd, J=8.4, 6.9, 1.4, 1H), 7.81 (d, J=8.5, 1H), 7.76-7.73 (m, 2H), 7.69 (ddd, J=8.1, 7.0, 1.1, 1H), 7.56 (d, J=9.1, 1H), 7.40 (d, J=2.3, 1H), 7.36-7.31 (m, 3H), 5.92 (d, J=17.2, 1H), 5.84 (d, J=17.2, 1H), 5.55 (s, 2H), 3.70-3.65 (m, 1H), 3.01-2.94 (m, 1H), 2.37-2.29 (m, 1H), 2.22-2.15 (m, 1H), 2.10-2.05 (m, 1H), 2.01-1.96 (m, 1H), 1.84-1.77 (m, 1H), 1.73-1.66 (m, 1H), 1.60-1.50 (m, 2H).

Example 135 racemic cis-2-[5-(Quinolin-2-ylmethoxy)-1-{4-[6-(trifluoromethyl)pyridin-3-yl]benzyl}-1H-benzimidazol-2-yl]cyclohexanecarboxylic acid as the TFA salt

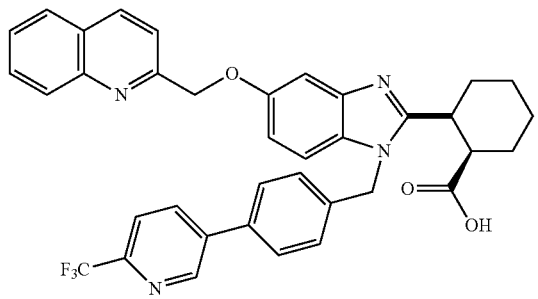

The title compound was prepared using analogous conditions to those described in Example 133 using racemic cis-2-[1-(4-bromobenzyl)-5-(quinolin-2-ylmethoxy)-1H-benzimidazol-2-yl]cyclohexanecarboxylic acid and (6-(trifluoromethyl)pyridin-3-yl)boronic acid. MS (ESI): mass calcd. for $C_{37}H_{31}F_3N_4O_3$, 636.23; m/z found, 637.2 [M+H]$^+$. $^1$H NMR (600 MHz, CD$_3$OD) δ 8.95 (d, J=2.1, 1H), 8.52 (d, J=8.5, 1H), 8.26 (dd, J=8.1, 2.1, 1H), 8.12 (d, J=8.0, 1H), 8.02 (d, J=7.5, 1H), 7.91-7.85 (m, 2H), 7.82 (d, J=8.5, 1H), 7.77-7.74 (m, 2H), 7.72-7.68 (m, 1H), 7.56 (d, J=9.1, 1H), 7.40 (d, J=2.3, 1H), 7.37-7.29 (m, 3H), 5.92 (d, J=17.2, 1H), 5.85 (d, J=17.2, 1H), 5.56 (s, 2H), 3.68 (dt, J=12.1, 3.7, 1H), 3.04-2.92 (m, 1H), 2.38-2.26 (m, 1H), 2.24-2.16 (m, 1H), 2.13-2.05 (m, 1H), 2.02-1.96 (m, 1H), 1.85-1.76 (m, 1H), 1.74-1.66 (m, 1H), 1.61-1.46 (m, 2H).

Example 136 racemic cis-2-[1-({4'-[(Methylsulfonyl)amino]biphenyl-4-yl}methyl)-5-(quinolin-2-ylmethoxy)-1H-benzimidazol-2-yl]cyclohexanecarboxylic acid as the TFA salt

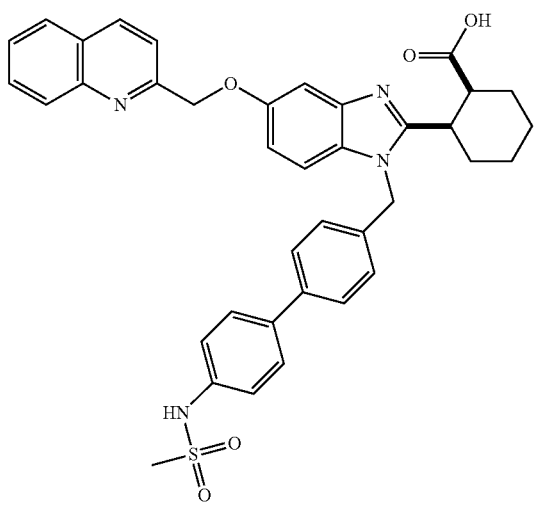

The title compound was prepared using analogous conditions to those described in Example 133 using racemic cis-2-[1-(4-bromobenzyl)-5-(quinolin-2-ylmethoxy)-1H-benzimidazol-2-yl]cyclohexanecarboxylic acid and N-(4-(4,4,5,5-tetramethyl-1,3,2-dioxaborolan-2-yl)phenyl)methanesulfonamide. MS (ESI): mass calcd. for $C_{38}H_{36}N_4O_5S$, 660.24; m/z found, 661.2 [M+H]$^+$. $^1$H NMR (600 MHz, CD$_3$OD) δ 8.49 (d, J=8.5, 1H), 8.10 (d, J=8.5, 1H), 8.01 (d, J=7.8, 1H), 7.86 (ddd, J=8.4, 6.9, 1.4, 1H), 7.80 (d, J=8.5, 1H), 7.68 (ddd, J=8.1, 7.0, 1.1, 1H), 7.63-7.60 (m, 2H), 7.60-7.54 (m, 3H), 7.38 (d, J=2.3, 1H), 7.36-7.29 (m, 3H), 7.21 (d, J=8.4, 2H), 5.85 (d, J=17.0, 1H), 5.79 (d, J=17.0, 1H), 5.54 (s, 2H), 3.66 (dt, J=12.2, 3.7, 1H), 2.97 (s, 4H), 2.38-2.28 (m, 1H), 2.25-2.16 (m, 1H), 2.12-2.04 (m, 1H), 2.00-1.94 (m, 1H), 1.85-1.75 (m, 1H), 1.71-1.64 (m, 1H), 1.59-1.47 (m, 2H).

Example 137 racemic cis-2-[5-(Quinolin-2-ylmethoxy)-1-{3-[6-(trifluoromethyl)pyridin-3-yl]benzyl}-1H-benzimidazol-2-yl]cyclohexanecarboxylic acid as the TFA salt

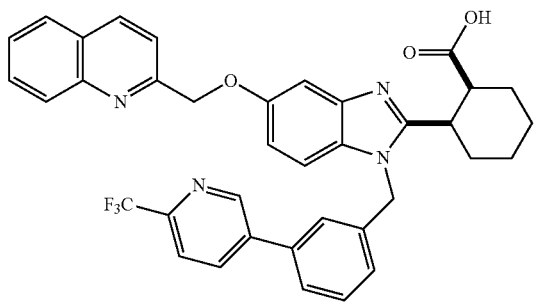

The title compound was prepared using analogous conditions to those described in Example 133 using racemic cis-2-[1-(3-bromobenzyl)-5-(quinolin-2-ylmethoxy)-1H-benzimidazol-2-yl]cyclohexanecarboxylic acid and (6-(trifluoromethyl)pyridin-3-yl)boronic acid. MS (ESI): mass calcd. for $C_{37}H_{31}F_3N_4O_3$, 636.23; m/z found, 637.2 [M+H]+. 1H NMR (400 MHz, CD3OD) δ 8.84 (d, J=2.1, 1H), 8.47 (d, J=8.5, 1H), 8.17 (dd, J=8.2, 1.9, 1H), 8.09 (d, J=8.4, 1H), 7.99 (d, J=7.5, 1H), 7.86-7.80 (m, 2H), 7.78 (d, J=8.5, 1H), 7.71 (d, J=19.0, 1H), 7.67 (ddd, J=8.1, 7.0, 1.1, 1H), 7.60-7.51 (m, 2H), 7.46 (s, 1H), 7.38 (d, J=2.2, 1H), 7.35-7.26 (m, 2H), 5.95 (d, J=17.2, 1H), 5.85 (d, J=17.2, 1H), 5.52 (s, 2H), 3.71 (dt, J=12.0, 3.6, 1H), 2.98-2.91 (m, J=3.8, 1H), 2.36-2.23 (m, 1H), 2.22-2.13 (m, J=13.9, 1H), 2.12-2.05 (m, J=12.1, 1H), 2.01-1.91 (m, J=12.8, 1H), 1.84-1.63 (m, 2H), 1.62-1.46 (m, 2H).

Example 138 racemic cis-2-[1-({4'-[(Methylsulfonyl)amino]biphenyl-3-yl}methyl)-5-(quinolin-2-ylmethoxy)-1H-benzimidazol-2-yl]cyclohexanecarboxylic acid as the TFA salt

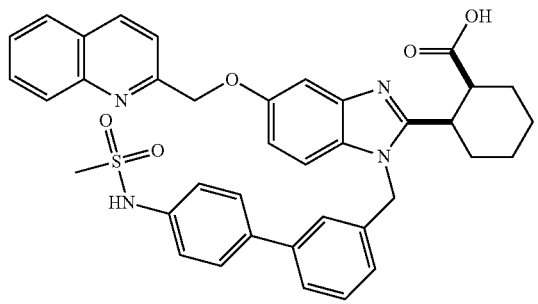

The title compound was prepared using analogous conditions to those described in Example 133 using racemic cis-2-[1-(3-bromobenzyl)-5-(quinolin-2-ylmethoxy)-1H-benzimidazol-2-yl]cyclohexanecarboxylic acid and N-(4-(4,4,5,5-tetramethyl-1,3,2-dioxaborolan-2-yl)phenyl)methanesulfonamide. MS (ESI): mass calcd. for $C_{38}H_{36}N_4O_5S$, 660.24; m/z found, 661.2 [M+H]+. 1H NMR (400 MHz, CD3OD) δ 8.53 (d, J=8.6, 1H), 8.12 (d, J=8.5, 1H), 8.03 (d, J=8.2, 1H), 7.87 (ddt, J=16.3, 10.6, 5.3, 1H), 7.82 (d, J=8.5, 1H), 7.73-7.64 (m, 1H), 7.60 (d, J=7.8, 1H), 7.55 (d, J=9.1, 1H), 7.51-7.41 (m, 3H), 7.39 (d, J=2.2, 1H), 7.36-7.26 (m, 4H), 7.13 (d, J=7.7, 1H), 5.90 (d, J=17.0, 1H), 5.80 (d, J=17.1, 1H), 5.55 (s, 2H), 3.69 (dd, J=8.5, 3.8, 1H), 3.02-2.91 (m, 4H), 2.39-2.24 (m, 1H), 2.23-2.14 (m, 1H), 2.12-2.03 (m, 1H), 2.00-1.92 (m, 1H), 1.84-1.62 (m, 2H), 1.62-1.42 (m, 2H).

Example 139 racemic cis-2-[5-(Quinolin-2-ylmethoxy)-1-{[4'-(trifluoromethyl)biphenyl-4-yl]methyl}-1H-benzimidazol-2-yl]cyclohexanecarboxylic acid as the TFA salt

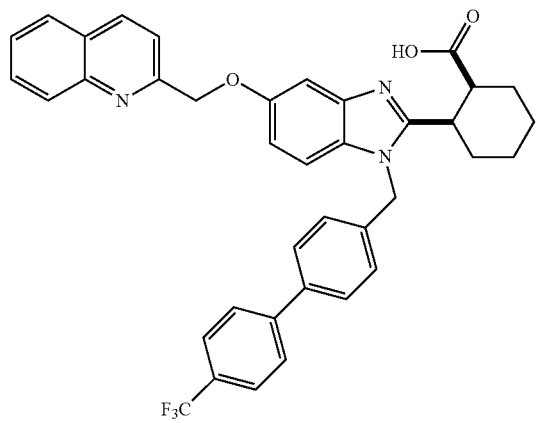

The title compound was prepared using analogous conditions to those described in Example 133 using racemic cis-2-[1-(4-bromobenzyl)-5-(quinolin-2-ylmethoxy)-1H-benzimidazol-2-yl]cyclohexanecarboxylic acid and (4-(trifluoromethyl)phenyl)boronic acid. MS (ESI): mass calcd. for $C_{38}H_{32}F_3N_3O_3$, 635.24; m/z found, 636.1 [M+H]+. 1H NMR (500 MHz, CD3OD) δ 8.54 (d, J=8.5, 1H), 8.13 (d, J=8.6, 1H), 8.03 (d, J=7.9, 1H), 7.88 (t, J=7.3, 1H), 7.83 (d, J=8.5, 1H), 7.79 (d, J=8.3, 2H), 7.73 (d, J=8.4, 2H), 7.72-7.68 (m, 3H), 7.57 (d, J=9.1, 1H), 7.40 (d, J=1.8, 1H), 7.38-7.31 (m, 1H), 7.27 (d, J=8.1, 2H), 5.86 (dd, J=36.8, 17.0, 2H), 5.56 (s, 2H), 3.68 (d, J=12.1, 1H), 2.99 (d, J=3.6, 1H), 2.39-2.28 (m, 1H), 2.21 (d, J=12.7, 1H), 2.08 (d, J=11.3, 1H), 1.98 (d, J=10.1, 1H), 1.80 (d, J=13.6, 1H), 1.70 (d, J=11.7, 1H), 1.53 (dd, J=22.3, 12.6, 2H).

Example 140 racemic cis-2-[1-{[3-Fluoro-4'-(trifluoromethyl)biphenyl-4-yl]methyl}-5-(quinolin-2-ylmethoxy)-1H-benzimidazol-2-yl]cyclohexanecarboxylic acid as the TFA salt

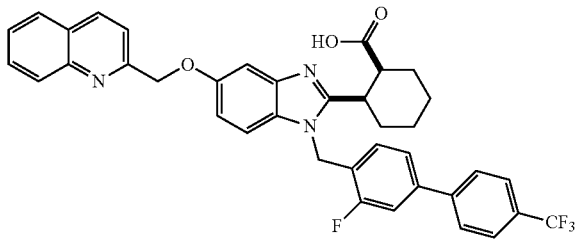

The title compound was prepared using analogous conditions to those described in Example 133 using racemic cis-2-(1-(4-Bromo-2-fluorobenzyl)-5-(quinolin-2-ylmethoxy)-1H-benzo[d]imidazol-2-yl)cyclohexanecarboxylic acid and (4-(trifluoromethyl)phenyl)boronic acid. MS (ESI): mass calcd. for $C_{38}H_{31}F_4N_3O_3$, 653.23; m/z found, 654.1 [M+H]$^+$. $^1$H NMR (500 MHz, CD$_3$OD) δ 8.42 (d, J=8.5, 1H), 8.07 (dd, J=8.5, 1.1, 1H), 7.97 (d, J=8.3, 2H), 7.83-7.79 (m, 3H), 7.75 (d, J=8.4, 3H), 7.64 (ddd, J=8.1, 7.0, 1.1, 1H), 7.62-7.56 (m, 2H), 7.50 (dd, J=7.9, 1.8, 1H), 7.37-7.31 (m, 2H), 7.19 (t, J=8.0, 1H), 5.88 (s, 2H), 5.50 (s, 2H), 3.73 (dt, J=12.3, 3.9, 1H), 3.04 (d, J=4.4, 1H), 2.36 (d, J=12.3, 1H), 2.24 (d, J=14.4, 1H), 2.09-2.02 (m, 1H), 1.98 (d, J=8.9, 1H), 1.85 (s, OH), 1.72 (s, 1H), 1.55 (q, J=11.3, 2H).

Example 141 racemic cis-2-[5-(Quinolin-2-ylmethoxy)-1-{[4'-(trifluoromethyl)biphenyl-3-yl]methyl}-1H-benzimidazol-2-yl]cyclohexanecarboxylic acid as the TFA salt

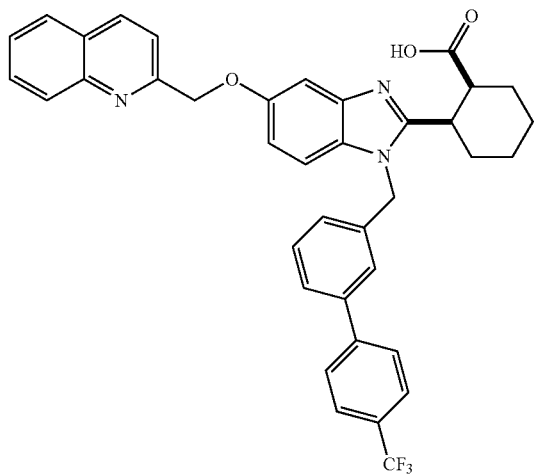

The title compound was prepared using analogous conditions to those described in Example 133 using racemic cis-2-[1-(3-bromobenzyl)-5-(quinolin-2-ylmethoxy)-1H-benzimidazol-2-yl]cyclohexane carboxylic acid and (4-(trifluoromethyl)phenyl)boronic acid. MS (ESI): mass calcd. for $C_{38}H_{32}F_3N_3O_3$, 635.24; m/z found, 636.1 [M+H]$^+$. $^1$H NMR (500 MHz, CD$_3$OD) δ 8.47 (d, J=8.4, 1H), 8.09 (dd, J=8.6, 1.0, 1H), 8.02-7.95 (m, 1H), 7.85 (ddd, J=8.5, 6.9, 1.4, 1H), 7.78 (d, J=8.5, 1H), 7.73-7.64 (m, 6H), 7.54 (s, 1H), 7.51 (t, J=7.8, 1H), 7.43 (d, J=1.9, 1H), 7.39 (d, J=2.3, 1H), 7.33 (dd, J=9.1, 2.4, 1H), 7.24-7.21 (m, 1H), 5.92 (d, J=17.0, 1H), 5.83 (d, J=17.1, 1H), 5.52 (s, 2H), 3.70 (dt, J=12.2, 3.8, 1H), 2.96 (q, J=4.3, 1H), 2.31 (dd, J=12.3, 3.8, 1H), 2.18 (dd, J=13.6, 3.2, 1H), 2.09 (s, 1H), 1.98 (d, J=10.7, 1H), 1.83-1.72 (m, 1H), 1.69 (d, J=9.7, 1H), 1.55 (td, J=12.5, 6.4, 2H).

Example 142

1-({1-[3-(1H-Pyrazol-5-yl)benzyl]-5-(quinolin-2-ylmethoxy)-1H-benzimidazol-2-yl}methyl)cyclopentanecarboxylic acid

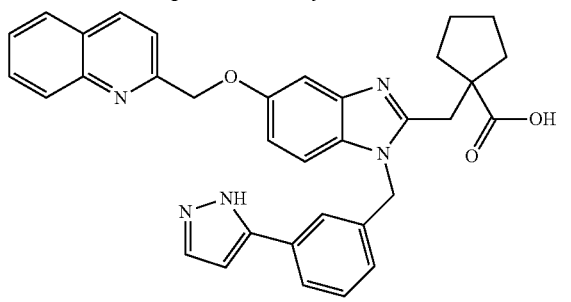

Step A. Methyl 1-((5-(quinolin-2-ylmethoxy)-1-(3-(1-((2-(trimethylsilyl)ethoxy)methyl)-1H-pyrazol-5-yl)benzyl)-1H-benzo[d]imidazol-2-yl)methyl)cyclopentanecarboxylate To a 5 mL microwave vial were added methyl 1-{[1-(3-bromobenzyl)-5-(quinolin-2-ylmethoxy)-1H-benzimidazol-2-yl]methyl}cyclopentane carboxylate (59 mg, 0.1 mmol), Pd(Ph$_3$)$_4$ (10 mg, 0.008 mmol), (1-((2-(trimethylsilyl)ethoxy)methyl)-1H-pyrazol-5-yl)boronic acid (65 mg, 0.26 mmol), Na$_2$CO$_3$ (0.15 mL, 2 M) and 1,4-dioxane (1.5 mL). The vial was flushed with N$_2$ then capped and placed in a heating block at 100° C. After 16 h the mixture was cooled to RT, transferred to a round-bottomed flask and concentrated to dryness. The residue was purified using FCC to provide the title compound. MS (ESI): mass calcd. for $C_{41}H_{47}N_5O_4Si$, 701.94; m/z found 702.0 [M+H]$^+$.

Step B. Methyl 1-((1-(3-(1H-pyrazol-5-yl)benzyl)-5-(quinolin-2-ylmethoxy)-1H-benzo[d]imidazol-2-yl)methyl)cyclopentanecarboxylate To a 20 mL vial was added methyl 1-((5-(quinolin-2-ylmethoxy)-1-(3-(1-((2-(trimethylsilyl)ethoxy)methyl)-1H-pyrazol-5-yl)benzyl)-1H-benzo[d]imidazol-2-yl)methyl)cyclopentanecarboxylate (51 mg, 0.08 mmol) and THF (2 mL) followed by treatment with TBAF (0.4 mL, 1 M). The reaction mixture was heated to 70° C. After 24 hours the mixture was cooled to RT and concentrated to dryness. The residue was purified using FCC to provide the title compound. MS (ESI): mass calcd. for $C_{35}H_{33}N_5O_3$, 571.68; m/z found 572.2 [M+H]$^+$.

Step C. 1-({1-[3-(1H-Pyrazol-5-yl)benzyl]-5-(quinolin-2-ylmethoxy)-1H-benzimidazol-2-yl}methyl)cyclopentanecarboxylic acid The title compound was prepared using similar methods to those in Step B of Example 91. MS (ESI): mass calcd. for $C_{34}H_{31}N_5O_3$, 557.24; m/z found, 558.3 [M+H]$^+$. $^1$H NMR (600 MHz, CDCl$_3$) δ 8.15 (d, J=8.5 Hz, 1H), 8.08 (d, J=8.5 Hz, 1H), 7.81-7.78 (m, 1H), 7.75-7.70 (m, 1H), 7.65 (d, J=8.4 Hz, 1H), 7.59 (d, J=7.8 Hz, 1H), 7.56-7.50 (m, 3H), 7.36-7.30 (m, 2H), 7.14-7.07 (m, 1H), 7.00-6.94 (m, 2H), 6.52-6.48 (m, 1H), 5.36 (d, J=19.1 Hz, 4H), 3.14 (s, 2H), 2.35 (q, J=7.4 Hz, 2H), 1.74-1.48 (m, 6H).

Example 143

1-({1-[3-(Cyanomethyl)benzyl]-5-(quinolin-2-ylmethoxy)-1H-benzimidazol-2-yl}methyl)cyclopentanecarboxylic acid

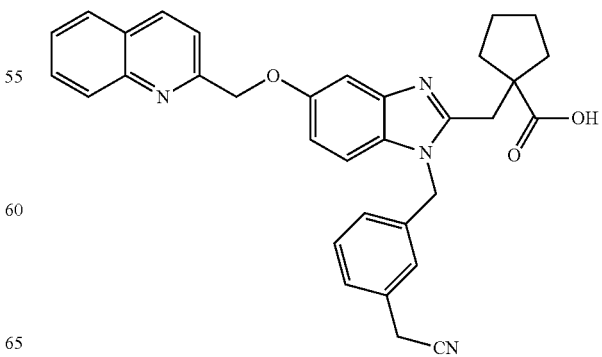

The title compound was prepared using similar methods to those in Steps A and C of Example 142 using 4-(4,4,5,5-tetramethyl-1,3,2-dioxaborolan-2-yl)isoxazole in Step A. MS (ESI): mass calcd. for $C_{33}H_{30}N_4O_3$, 530.23; m/z found, 531.3 [M+H]$^+$. $^1$H NMR (400 MHz, CDCl$_3$) δ 8.19 (d, J=8.5, 1H), 8.10 (d, J=8.5, 1H), 7.83 (d, J=7.7, 1H), 7.76-7.72 (m, 1H), 7.70-7.67 (m, 1H), 7.57-7.53 (m, 1H), 7.36-7.26 (m, 3H), 7.16-7.12 (m, 1H), 7.08-7.02 (m, 2H), 6.95-6.91 (m, 1H), 5.42 (s, 2H), 5.32 (s, 2H), 3.69 (s, 2H), 3.06 (s, 2H), 2.41-2.33 (m, 2H), 1.75-1.67 (m, 2H), 1.52-1.42 (m, 4H).

Example 144

3-{1-[4-(6-Methoxypyridin-3-yl)benzyl]-5-(quinolin-2-ylmethoxy)-1H-benzimidazol-2-yl}-2,2-dimethylpropanoic acid as the TFA salt

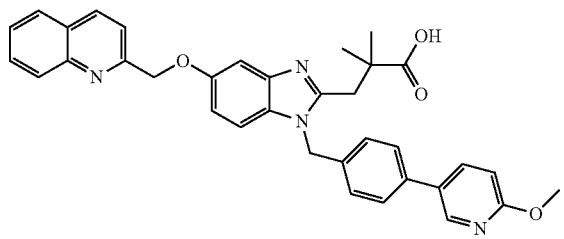 [SMILES: COc1ccc(-c2ccc(Cn3c(CC(C)(C)C(=O)O)nc4cc(OCc5ccc6ccccc6n5)ccc43)cc2)cn1]

To a 5 mL microwave vial were added ethyl 3-(1-(4-bromobenzyl)-5-(quinolin-2-ylmethoxy)-1H-benzo[d]imidazol-2-yl)-2,2-dimethylpropanoate (100 mg, 0.18 mmol), Pd(Ph$_3$)$_4$ (20 mg, 0.02 mmol), (6-methoxypyridin-3-yl)boronic acid (27 mg, 0.18 mmol), potassium phosphate (111 mg, 0.52 mmol), DME (3 mL), and water (1.5 mL). The vial was flushed with N$_2$ then capped and placed in a heating block at 90° C. After 12 h, the mixture was cooled and transferred to a 25 mL round-bottomed flask and concentrated to dryness. To the crude residue was added THF (3 mL), MeOH (3 mL), water (3 mL), and a solution of LiOH (39 mg, 0.9 mmol) in water (2 mL). The resulting solution was heated to 80° C. After 2 h, the solution was concentrated to dryness and the residue was purified by reverse phase HPLC to afford the title compound (75 mg, 62%). MS (ESI): mass calcd. for $C_{35}H_{32}N_4O_4$, 572.24; m/z found, 573.2 [M+H]$^+$. $^1$H NMR (500 MHz, CD$_3$OD) δ 8.53-8.47 (m, 1H), 8.35 (dd, J=2.6, 0.7 Hz, 1H), 8.13-8.07 (m, 1H), 8.04-7.98 (m, 1H), 7.93 (dd, J=8.7, 2.6 Hz, 1H), 7.89-7.83 (m, 1H), 7.80 (d, J=8.5 Hz, 1H), 7.70-7.66 (m, 1H), 7.63-7.58 (m, 3H), 7.41 (d, J=2.3 Hz, 1H), 7.35-7.31 (m, 3H), 6.89 (dd, J=8.7, 0.7 Hz, 1H), 5.85 (s, 2H), 5.54 (s, 2H), 3.94 (s, 3H), 3.52 (s, 2H), 1.40 (s, 6H).

Example 145

2,2-Dimethyl-3-[5-(quinolin-2-ylmethoxy)-1-{4-[6-(trifluoromethyl)pyridin-3-yl]benzyl}-1H-benzimidazol-2-yl]propanoic acid as the TFA salt

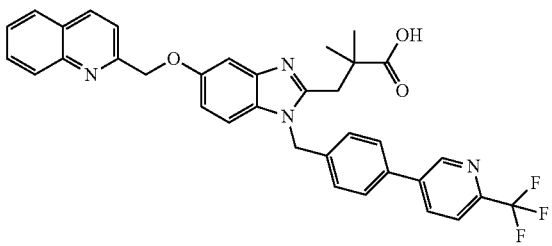 [SMILES: CC(C)(Cc1nc2cc(OCc3ccc4ccccc4n3)ccc2n1Cc1ccc(-c2ccc(C(F)(F)F)nc2)cc1)C(=O)O]

The title compound was prepared using analogous conditions to those described in Example 144 using ethyl 3-(1-(4-bromobenzyl)-5-(quinolin-2-ylmethoxy)-1H-benzo[d]imidazol-2-yl)-2,2-dimethylpropanoate and (6-(trifluoromethyl)pyridin-3-yl)boronic acid. MS (ESI): mass calcd. for $C_{35}H_{29}F_3N_4O_3$, 610.22; m/z found, 611.2 [M+H]$^+$. $^1$H NMR (500 MHz, CD$_3$OD) δ 8.95 (d, J=2.1, 1H), 8.49 (d, J=8.5, 1H), 8.26 (dd, J=8.1, 2.0, 1H), 8.10 (d, J=8.5, 1H), 8.01 (d, J=7.8, 1H), 7.91-7.82 (m, 2H), 7.81-7.71 (m, 3H), 7.68 (ddd, J=8.1, 7.0, 1.1, 1H), 7.58 (d, J=9.2, 1H), 7.42 (d, J=2.3, 1H), 7.40 (d, J=8.4, 2H), 7.33 (dd, J=9.2, 2.4, 1H), 5.90 (s, 2H), 5.54 (s, 2H), 3.53 (s, 2H), 1.41 (s, 6H).

Example 146

3-{1-[4-(2-Methoxypyrimidin-5-yl)benzyl]-5-(quinolin-2-ylmethoxy)-1H-benzimidazol-2-yl}-2,2-dimethylpropanoic acid as the TFA salt

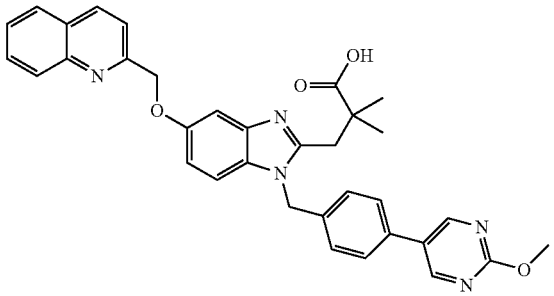 [SMILES: COc1ncc(-c2ccc(Cn3c(CC(C)(C)C(=O)O)nc4cc(OCc5ccc6ccccc6n5)ccc43)cc2)cn1]

The title compound was prepared using analogous conditions to those described in Example 144 using ethyl 3-(1-(4-bromobenzyl)-5-(quinolin-2-ylmethoxy)-1H-benzo[d]imidazol-2-yl)-2,2-dimethylpropanoate and (2-methoxypyrimidin-5-yl)boronic acid. MS (ESI): mass calcd. for $C_{34}H_{31}N_5O_4$, 573.24; m/z found, 574.2 [M+H]$^+$. $^1$H NMR (500 MHz, CD$_3$OD) δ 8.80 (s, 2H), 8.50 (dd, J=8.6, 0.8 Hz, 1H), 8.12-8.08 (m, 1H), 8.01 (dd, J=8.3, 1.3 Hz, 1H), 7.89-7.83 (m, 1H), 7.79 (d, J=8.5 Hz, 1H), 7.70-7.64 (m, 3H), 7.58 (d, J=9.2 Hz, 1H), 7.41 (d, J=2.3 Hz, 1H), 7.39-7.35 (m, 2H), 7.33 (dd, J=9.2, 2.4 Hz, 1H), 5.87 (s, 2H), 5.53 (s, 2H), 4.04 (s, 3H), 3.52 (s, 2H), 1.41 (s, 6H).

Example 147

3-{1-[3-(6-Methoxypyridin-3-yl)benzyl]-5-(quinolin-2-ylmethoxy)-1H-benzimidazol-2-yl}-2,2-dimethylpropanoic acid

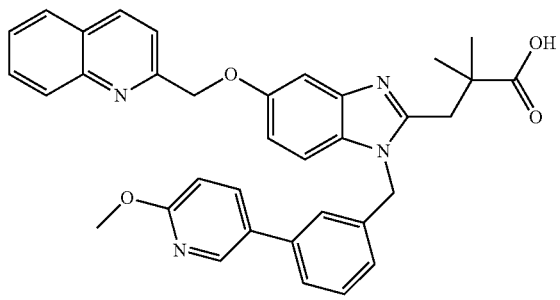 [SMILES: COc1ccc(-c2cccc(Cn3c(CC(C)(C)C(=O)O)nc4cc(OCc5ccc6ccccc6n5)ccc43)c2)cn1]

The title compound was prepared using similar methods to those in Example 33 using 1-bromo-3-(bromomethyl)benzene in Step A and by inserting the following procedure between Step E and F. To a 5 mL microwave vial were added a stirbar, ethyl 3-(1-(3-bromobenzyl)-5-(quinolin-2-ylmethoxy)-1H-benzo[d]imidazol-2-yl)-2,2-dimethylpropanoate (230 mg, 0.4 mmol), 6-methoxypyridin-3-ylboronic acid (92 mg, 0.6 mmol), Pd(dppf)Cl$_2$·CH$_2$Cl$_2$ (29 mg, 0.04 mmol), and K$_2$CO$_3$ (221 mg, 1.6 mmol). The vial was capped and flushed with nitrogen before adding 8 mL of N$_2$ sparged 1,4-dioxane and 2 mL of N$_2$ sparged water. The resulting mixture was heated at 80° C. for 12 hours. The vial was cooled to RT, concentrated to dryness, and subjected to FCC purification to afford ethyl 3-(1-(3-(6-methoxypyridin-3-yl)benzyl)-5-(quinolin-2-ylmethoxy)-1H-benzo[d]imidazol-2-yl)-2,2-dimethylpropanoate. MS (ESI): mass calcd. for C$_{37}$H$_{36}$N$_4$O$_4$, 600.27; m/z found, 601.1 [M+H]$^+$. The title compound was then prepared using similar methods to those in Example 33 Step F to afford the title compound. MS (ESI): mass calcd. for C$_{36}$H$_{32}$N$_4$O$_4$, 572.24; m/z found, 573.3 [M+H]$^+$. $^1$H NMR (300 MHz, DMSO-d$_6$) δ 12.21 (s, 1H), 8.43-8.32 (m, 2H), 8.02 (d, J=8.5, 1H), 7.97 (d, J=8.3, 1H), 7.90 (dd, J=8.7, 2.5, 1H), 7.81-7.73 (m, 1H), 7.67 (d, J=8.5, 1H), 7.60 (t, J=7.4, 1H), 7.53 (d, J=6.9, 1H), 7.45-7.31 (m, 3H), 7.18 (d, J=1.6, 1H), 6.98-6.85 (m, 3H), 5.52 (s, 2H), 5.36 (s, 2H), 3.87 (s, 3H), 3.07 (s, 2H), 1.25 (s, 6H).

Example 148

3-{1-[2-(6-Methoxypyridin-3-yl)benzyl]-5-(quinolin-2-ylmethoxy)-1H-benzimidazol-2-yl}-2,2-dimethylpropanoic acid

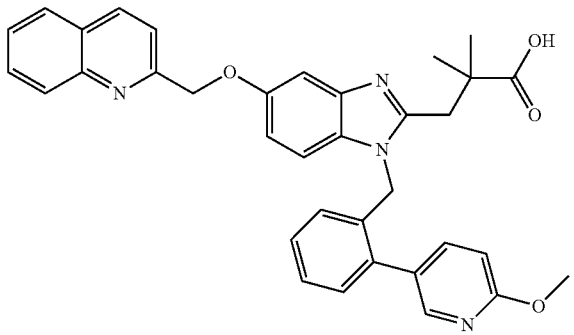 [SMILES: COc1ccc(-c2ccccc2Cn2c(CC(C)(C)C(=O)O)nc3cc(OCc4ccc5ccccc5n4)ccc32)cn1]

The title compound was prepared with similar methods to those in Example 33 and as in Example 147 using (6-methoxypyridin-3-yl)boronic acid. MS (ESI): mass calcd. for C$_{36}$H$_{32}$N$_4$O$_4$, 572.24; m/z found, 573.1 [M+H]$^+$. $^1$H NMR (500 MHz, CD$_3$OD) δ 8.36 (d, J=8.5, 1H), 8.06-8.03 (m, 2H), 7.93 (d, J=8.3, 1H), 7.82-7.70 (m, 2H), 7.63-7.57 (m, 1H), 7.50 (dd, J=8.5, 2.5, 1H), 7.38-7.30 (m, 1H), 7.30-7.18 (m, 2H), 7.18 (d, J=2.2, 1H), 7.04 (d, J=8.8, 1H), 6.96 (dd, J=8.8, 2.3, 1H), 6.87 (d, J=7.7, 1H), 6.77 (d, J=8.5, 1H), 5.44 (s, 2H), 5.39 (s, 2H), 3.93 (s, 3H), 2.81 (s, 2H), 1.20 (s, 6H).

Example 149

2,2-Dimethyl-3-{1-[4-(1H-Pyrrol-2-yl)benzyl]-5-(quinolin-2-ylmethoxy)-1H-benzimidazol-2-yl}propanoic acid

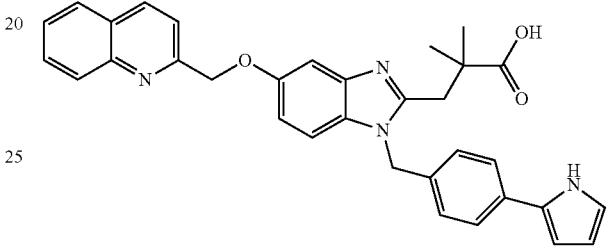

The title compound was prepared with similar methods to those in Example 33 by using 1-bromo-4-(bromomethyl)benzene in Step A and as in Example 147 using (1H-pyrrol-2-yl)boronic acid. MS (ESI): mass calcd. for C$_{33}$H$_{30}$N$_4$O$_3$, 530.23; m/z found, 531.2 [M+H]$^+$. $^1$H NMR (500 MHz, CD$_3$OD) δ 8.44 (d, J=8.0, 1H), 8.07 (d, J=8.4, 1H), 7.98 (d, J=8.5, 1H), 7.83 (t, J=7.7, 1H), 7.76 (d, J=8.5, 1H), 7.69-7.58 (m, 2H), 7.55 (d, J=8.4, 2H), 7.38 (d, J=2.3, 1H), 7.33 (dd, J=9.1, 2.4, 1H), 7.20 (d, J=8.5, 2H), 6.80-6.78 (m, 1H), 6.51-6.45 (m, 1H), 6.15-6.12 (m, 1H), 5.76 (s, 2H), 5.51 (s, 2H), 3.51 (s, 2H), 1.39 (s, 6H).

Example 150

2,2-Dimethyl-3-[1-({4'-[(methylsulfonyl)amino]biphenyl-4-yl}methyl)-5-(quinolin-2-ylmethoxy)-1H-benzimidazol-2-yl]propanoic acid

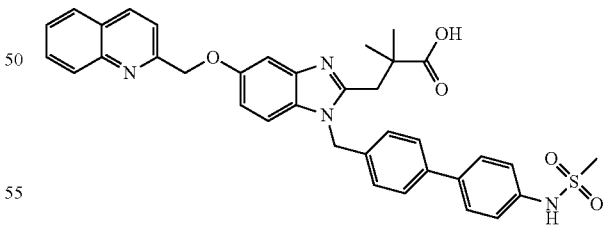

The title compound was prepared with similar methods to those in Example 33 by using 1-bromo-4-(bromomethyl)benzene in Step A and as in Example 147 using (4-(methylsulfonamido)phenyl)boronic acid. MS (ESI): mass calcd. for C$_{36}$H$_{34}$N$_4$O$_5$S, 634.22; m/z found, 635.3 [M+H]$^+$. $^1$H NMR (500 MHz, CD$_3$OD) δ 8.45 (d, J=8.2, 1H), 8.08 (d, J=8.5, 1H), 7.98 (d, J=8.9, 1H), 7.83 (t, J=7.7, 1H), 7.76 (d, J=8.5, 1H), 7.69-7.55 (m, 6H), 7.39 (d, J=2.1, 1H), 7.35-7.27 (m, 5H), 5.84 (s, 2H), 5.51 (s, 2H), 3.52 (s, 2H), 2.98 (s, 3H), 1.41 (s, 6H).

Example 151

2,2-Dimethyl-3-{1-[(3'-methylbiphenyl-4-yl)methyl]-5-(quinolin-2-ylmethoxy)-1H-benzimidazol-2-yl}propanoic acid

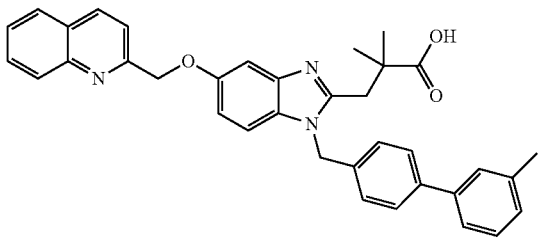 [SMILES: Cc1cccc(-c2ccc(Cn3c(CC(C)(C)C(=O)O)nc4cc(OCc5ccc6ccccc6n5)ccc43)cc2)c1]

The title compound was prepared with similar methods to those in Example 33 by using 1-bromo-4-(bromomethyl)benzene in Step A and as in Example 147 using m-tolylboronic acid. MS (ESI): mass calcd. for $C_{36}H_{33}N_3O_3$, 555.25; m/z found, 556.2 [M+H]+. 1H NMR (500 MHz, CD3OD) δ 8.46 (d, J=8.4, 1H), 8.08 (d, J=8.4, 1H), 7.99 (d, J=7.3, 1H), 7.84 (t, J=7.7, 1H), 7.77 (d, J=8.5, 1H), 7.67 (d, J=6.9, 1H), 7.64-7.59 (m, 3H), 7.43-7.26 (m, 7H), 7.16 (d, J=7.7, 1H), 5.84 (s, 2H), 5.52 (s, 2H), 3.52 (s, 2H), 2.39 (s, 3H), 1.41 (s, 6H).

Example 152

2,2-Dimethyl-3-{1-[(4'-methylbiphenyl-4-yl)methyl]-5-(quinolin-2-ylmethoxy)-1H-benzimidazol-2-yl}propanoic acid

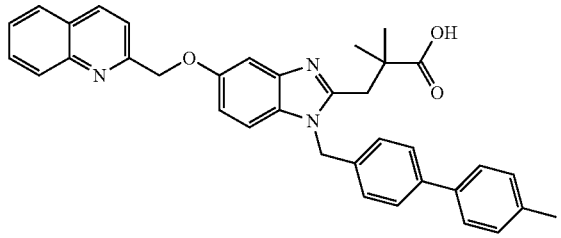 [SMILES: Cc1ccc(-c2ccc(Cn3c(CC(C)(C)C(=O)O)nc4cc(OCc5ccc6ccccc6n5)ccc43)cc2)cc1]

The title compound was prepared with similar methods to those in Example 33 by using 1-bromo-4-(bromomethyl)benzene in Step A and as in Example 147 using p-tolylboronic acid. MS (ESI): mass calcd. for $C_{36}H_{33}N_3O_3$, 555.25; m/z found, 556.2 [M+H]+. 1H NMR (500 MHz, CD3OD) δ 8.46 (d, J=8.5, 1H), 8.08 (d, J=7.9, 1H), 7.99 (d, J=7.2, 1H), 7.87-7.81 (m, 1H), 7.77 (d, J=8.5, 1H), 7.70-7.58 (m, 4H), 7.47 (d, J=8.2, 2H), 7.39 (d, J=2.1, 1H), 7.33 (dd, J=9.1, 2.4, 1H), 7.29 (d, J=8.3, 2H), 7.23 (d, J=7.9, 2H), 5.83 (s, 2H), 5.52 (s, 2H), 3.52 (s, 2H), 2.36 (s, 3H), 1.41 (s, 6H).

Example 153

2,2-Dimethyl-3-{1-[4-(1-methyl-1H-pyrazol-5-yl)benzyl]-5-(quinolin-2-ylmethoxy)-1H-benzimidazol-2-yl}propanoic acid

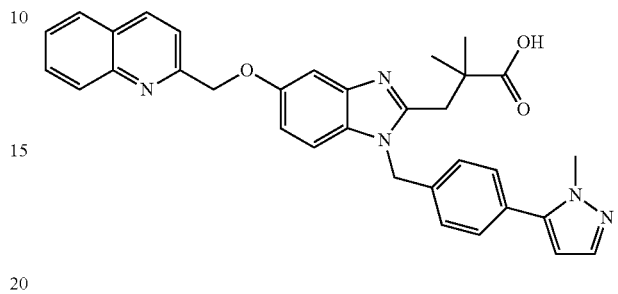

The title compound was prepared with similar methods to those in Example 33 by using 1-bromo-4-(bromomethyl)benzene in Step A and as in Example 147 using (1-methyl-1H-pyrazol-5-yl)boronic acid. MS (ESI): mass calcd. for $C_{33}H_{31}N_5O_3$, 545.24; m/z found, 546.2 [M+H]+. 1H NMR (500 MHz, CD3OD) δ 8.53 (s, 1H), 8.11 (d, J=7.5, 1H), 8.02 (d, J=8.5, 1H), 7.93-7.78 (m, 2H), 7.69 (t, J=7.7, 1H), 7.60 (d, J=9.0, 1H), 7.53-7.46 (m, 3H), 7.42 (s, 1H), 7.39-7.32 (m, 3H), 6.36 (d, J=2.0, 1H), 5.89 (s, 2H), 5.55 (s, 2H), 3.84 (s, 3H), 3.53 (s, 2H), 1.41 (s, 6H).

Example 154

2,2-Dimethyl-3-{5-(quinolin-2-ylmethoxy)-1-[(4'-sulfamoylbiphenyl-4-yl)methyl]-1H-benzimidazol-2-yl}propanoic acid

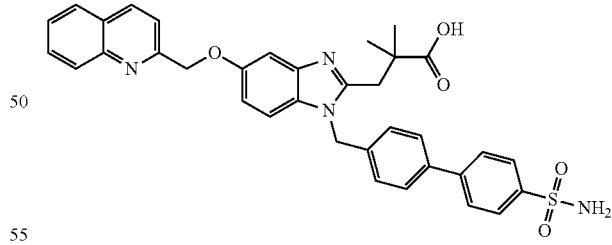

The title compound was prepared with similar methods to those in Example 33 by using 1-bromo-4-(bromomethyl)benzene in Step A and as in Example 147 using (4-sulfamoylphenyl)boronic acid. MS (ESI): mass calcd. for $C_{35}H_{32}N_4O_5S$, 620.20; m/z found, 621.2 [M+H]+. 1H NMR (500 MHz, CD3OD) δ 8.50 (s, 1H), 8.09 (d, J=7.6, 1H), 8.04-7.98 (m, 1H), 7.95 (d, J=8.4, 2H), 7.91-7.73 (m, 4H), 7.73-7.63 (m, 3H), 7.59 (d, J=9.1, 1H), 7.41 (s, 1H), 7.38-7.30 (m, 3H), 5.88 (s, 2H), 5.53 (s, 2H), 3.53 (s, 2H), 1.41 (s, 6H).

Example 155

3-{1-[(2'-Fluorobiphenyl-4-yl)methyl]-5-(quinolin-2-ylmethoxy)-1H-benzimidazol-2-yl}-2,2-dimethyl-propanoic acid

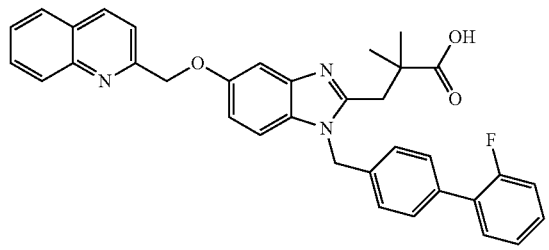 [SMILES: CC(C)(Cc1nc2cc(OCc3ccc4ccccc4n3)ccc2n1Cc1ccc(-c2ccccc2F)cc1)C(=O)O]

The title compound was prepared with similar methods to those in Example 33 by using 1-bromo-4-(bromomethyl)benzene in Step A and as in Example 147 using (2-fluorophenyl)boronic acid. MS (ESI): mass calcd. for $C_{35}H_{30}FN_3O_3$, 559.22; m/z found, 560.2 [M+H]$^+$. $^1$H NMR (500 MHz, CD$_3$OD) δ 8.67 (s, 1H), 8.17 (d, J=8.1, 1H), 8.09 (d, J=8.2, 1H), 7.99-7.85 (m, 2H), 7.75 (t, J=8.2, 1H), 7.63 (d, J=9.1, 1H), 7.56 (dd, J=8.2, 1.5, 2H), 7.49-7.29 (m, 6H), 7.28-7.12 (m, 2H), 5.88 (s, 2H), 5.62 (s, 2H), 3.55 (s, 2H), 1.42 (s, 6H).

Example 156

3-{1-[(3'-Fluorobiphenyl-4-yl)methyl]-5-(quinolin-2-ylmethoxy)-1H-benzimidazol-2-yl}-2,2-dimethyl-propanoic acid

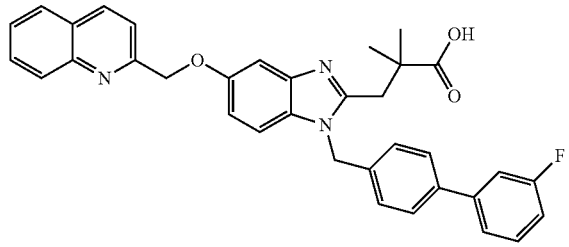 [SMILES: CC(C)(Cc1nc2cc(OCc3ccc4ccccc4n3)ccc2n1Cc1ccc(-c2cccc(F)c2)cc1)C(=O)O]

The title compound was prepared with similar methods to those in Example 33 by using 1-bromo-4-(bromomethyl)benzene in Step A and as in Example 147 using (3-fluorophenyl)boronic acid. MS (ESI): mass calcd. for $C_{35}H_{30}FN_3O_3$, 559.22; m/z found, 560.2 [M+H]$^+$. $^1$H NMR (500 MHz, CD$_3$OD) δ 8.47 (d, J=8.6, 1H), 8.09 (d, J=8.7, 1H), 7.99 (d, J=7.6, 1H), 7.87-7.82 (m, 1H), 7.78 (d, J=8.5, 1H), 7.70-7.62 (m, 3H), 7.59 (d, J=9.2, 1H), 7.49-7.38 (m, 3H), 7.37-7.29 (m, 4H), 7.13-7.04 (m, 1H), 5.86 (s, 2H), 5.53 (s, 2H), 3.52 (s, 2H), 1.41 (s, 6H).

Example 157

3-{1-[(4'-Fluorobiphenyl-4-yl)methyl]-5-(quinolin-2-ylmethoxy)-1H-benzimidazol-2-yl}-2,2-dimethyl-propanoic acid

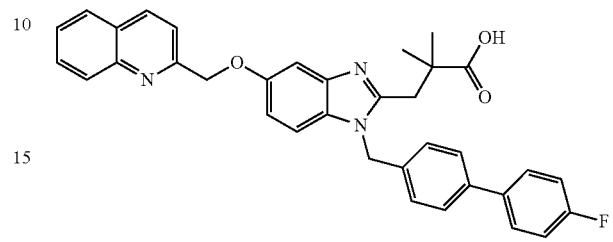

The title compound was prepared with similar methods to those in Example 33 by using 1-bromo-4-(bromomethyl)benzene in Step A and as in Example 147 using (4-fluorophenyl)boronic acid. MS (ESI): mass calcd. for $C_{35}H_{30}FN_3O_3$, 559.22; m/z found, 560.2 [M+H]$^+$. $^1$H NMR (500 MHz, CD$_3$OD) δ 8.61 (d, J=8.6, 1H), 8.14 (d, J=8.5, 1H), 8.06 (d, J=7.9, 1H), 7.96-7.83 (m, 2H), 7.72 (t, J=7.1, 1H), 7.65-7.55 (m, 5H), 7.45 (d, J=2.3, 1H), 7.39-7.27 (m, 3H), 7.20-7.11 (m, 2H), 5.85 (s, 2H), 5.58 (s, 2H), 3.54 (s, 2H), 1.42 (s, 6H).

Example 158

2,2-Dimethyl-3-[5-(quinolin-2-ylmethoxy)-1-{3-[6-(trifluoromethyl)pyridin-3-yl]benzyl}-1H-benzimidazol-2-yl]propanoic acid

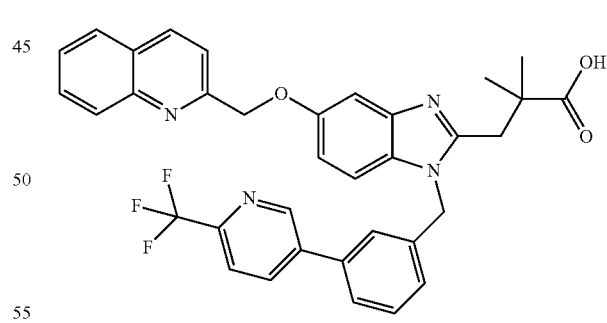

The title compound was prepared with similar methods to those in Example 33 by using 1-bromo-3-(bromomethyl)benzene in Step A and as in Example 147 using (6-(trifluoromethyl)pyridin-3-yl)boronic acid. MS (ESI): mass calcd. for $C_{35}H_{29}F_3N_4O_3$, 610.21; m/z found, 611.2 [M+H]$^+$. $^1$H NMR (500 MHz, DMSO-d$_6$) δ 9.05 (d, J=1.6, 1H), 8.62 (s, 1H), 8.34 (d, J=7.9, 1H), 8.10 (brs, 2H), 8.00 (d, J=8.2, 1H), 7.93-7.68 (m, 5H), 7.63 (d, J=9.0, 1H), 7.53 (t, J=7.7, 1H), 7.43 (s, 1H), 7.36 (d, J=7.4, 1H), 7.30 (d, J=9.2, 1H), 5.88 (s, 2H), 5.59 (s, 2H), 3.57 (s, 2H), 1.33 (s, 6H).

Example 159

2'-{[2-(2-Carboxy-2-methylpropyl)-5-(quinolin-2-ylmethoxy)-1H-benzimidazol-1-yl]methyl}biphenyl-3-carboxylic acid

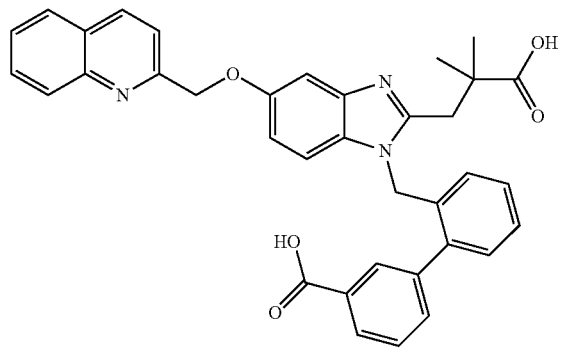 [SMILES: CC(C)(Cc1nc2cc(OCc3ccc4ccccc4n3)ccc2n1Cc1ccccc1-c1cccc(C(=O)O)c1)C(=O)O]

The title compound was prepared with similar methods to those in Example 33 by using 1-bromo-3-(bromomethyl)benzene in Step A and as in Example 147 using 3-boronobenzoic acid. MS (ESI): mass calcd. for $C_{36}H_{31}N_3O_5$, 585.22; m/z found, 586.2 [M+H]$^+$. $^1$H NMR (500 MHz, CD$_3$OD) δ 8.49 (d, J=8.4, 1H), 8.23 (t, J=1.7, 1H), 8.09 (d, J=8.3, 1H), 8.04-8.01 (m, 1H), 8.01-7.98 (m, 1H), 7.89-7.81 (m, 2H), 7.79 (d, J=8.5, 1H), 7.72-7.64 (m, 3H), 7.61 (d, J=9.1, 1H), 7.55 (t, J=7.8, 1H), 7.41 (d, J=2.1, 1H), 7.37-7.31 (m, 3H), 5.87 (s, 2H), 5.53 (s, 2H), 3.53 (s, 2H), 1.42 (s, 6H).

Example 160

3-{1-[(3'-Cyanobiphenyl-4-yl)methyl]-5-(quinolin-2-ylmethoxy)-1H-benzimidazol-2-yl}-2,2-dimethylpropanoic acid

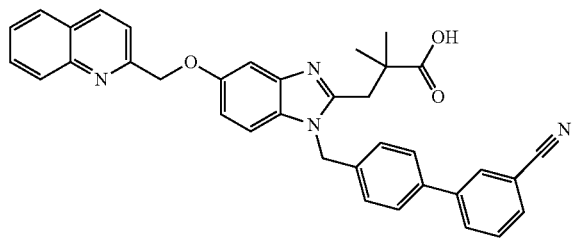 [SMILES: CC(C)(Cc1nc2cc(OCc3ccc4ccccc4n3)ccc2n1Cc1ccc(-c2cccc(C#N)c2)cc1)C(=O)O]

The title compound was prepared with similar methods to those in Example 33 by using 1-bromo-4-(bromomethyl)benzene in Step A and as in Example 147 using (3-cyanophenyl)boronic acid. MS (ESI): mass calcd. for $C_{36}H_{30}N_4O_3$, 566.23; m/z found, 567.1 [M+H]$^+$. $^1$H NMR (500 MHz, CD$_3$OD) δ 8.42 (d, J=8.4, 1H), 8.06 (d, J=8.3, 1H), 8.00-7.88 (m, 3H), 7.85-7.78 (m, 1H), 7.77-7.55 (m, 7H), 7.39-7.29 (m, 4H), 5.86 (s, 2H), 5.50 (s, 2H), 3.51 (s, 2H), 1.41 (s, 6H).

Example 161

3-{1-[(4'-Cyanobiphenyl-4-yl)methyl]-5-(quinolin-2-ylmethoxy)-1H-benzimidazol-2-yl}-2,2-dimethylpropanoic acid

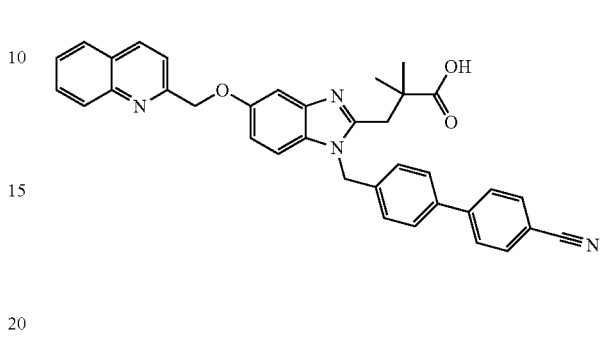

The title compound was prepared with similar methods to those in Example 33 by using 1-bromo-4-(bromomethyl)benzene in Step A and as in Example 147 using (4-cyanophenyl)boronic acid. MS (ESI): mass calcd. for $C_{36}H_{30}N_4O_3$, 566.23; m/z found, 567.1 [M+H]$^+$. $^1$H NMR (500 MHz, CD$_3$OD) δ 8.52 (d, J=8.5, 1H), 8.11 (d, J=8.5, 1H), 8.02 (d, J=8.2, 1H), 7.91-7.77 (m, 6H), 7.72-7.67 (m, 3H), 7.59 (d, J=9.1, 1H), 7.42 (d, J=2.2, 1H), 7.39-7.31 (m, 3H), 5.89 (s, 2H), 5.55 (s, 2H), 3.53 (s, 2H), 1.41 (s, 6H).

Example 162

2,2-Dimethyl-3-[1-{[4'-(methylsulfonyl)biphenyl-4-yl]methyl}-5-(quinolin-2-ylmethoxy)-1H-benzimidazol-2-yl]propanoic acid

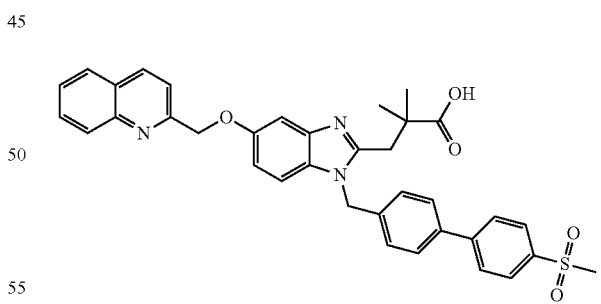

The title compound was prepared with similar methods to those in Example 33 by using 1-bromo-4-(bromomethyl)benzene in Step A and as in Example 147 using (4-(methylsulfonyl)phenyl)boronic acid. MS (ESI): mass calcd. for $C_{36}H_{33}N_3O_5S$, 619.21; m/z found, 620.1 [M+H]$^+$. $^1$H NMR (500 MHz, CD$_3$OD) δ 8.45 (d, J=8.6, 1H), 8.08 (d, J=8.2, 1H), 8.03-7.97 (m, 3H), 7.88-7.80 (m, 3H), 7.78-7.71 (m, 3H), 7.69-7.61 (m, 1H), 7.58 (d, J=9.2, 1H), 7.42-7.29 (m, 4H), 5.88 (s, 2H), 5.52 (s, 2H), 3.52 (s, 2H), 3.15 (s, 3H), 1.41 (s, 6H).

Example 163

2,2-Dimethyl-3-[1-(4-pyridin-3-ylbenzyl)-5-(quinolin-2-ylmethoxy)-1H-benzimidazol-2-yl]propanoic acid

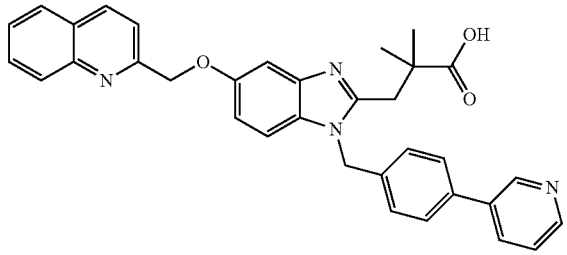 [SMILES: CC(C)(Cc1nc2cc(OCc3ccc4ccccc4n3)ccc2n1Cc1ccc(-c2cccnc2)cc1)C(=O)O]

The title compound was prepared with similar methods to those in Example 33 by using 1-bromo-4-(bromomethyl)benzene in Step A and using as in Example 147 pyridin-3-ylboronic acid. MS (ESI): mass calcd. for $C_{34}H_{30}N_4O_3$, 542.23; m/z found, 543.1 [M+H]$^+$. $^1$H NMR (500 MHz, CD$_3$OD) δ 9.06 (s, 1H), 8.76 (d, J=5.4, 1H), 8.68 (d, J=8.4, 1H), 8.51 (d, J=8.6, 1H), 8.10 (d, J=8.8, 1H), 8.03-7.96 (m, 2H), 7.89-7.84 (m, 1H), 7.82-7.79 (m, 3H), 7.71-7.66 (m, 1H), 7.57 (d, J=9.2, 1H), 7.48-7.39 (m, 3H), 7.32 (dd, J=9.2, 2.3, 1H), 5.92 (s, 2H), 5.54 (s, 2H), 3.53 (s, 2H), 1.42 (s, 6H).

Example 164

2,2-Dimethyl-3-[1-(4-pyridin-2-ylbenzyl)-5-(quinolin-2-ylmethoxy)-1H-benzimidazol-2-yl]propanoic acid

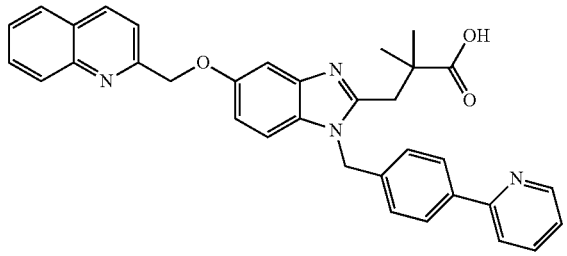 [SMILES: CC(C)(Cc1nc2cc(OCc3ccc4ccccc4n3)ccc2n1Cc1ccc(-c2ccccn2)cc1)C(=O)O]

The title compound was prepared with similar methods to those in Example 33 by using 1-bromo-4-(bromomethyl)benzene in Step A and as in Example 147 using pyridin-2-ylboronic acid. MS (ESI): mass calcd. for $C_{34}H_{30}N_4O_3$, 542.23; m/z found, 543.2 [M+H]$^+$. $^1$H NMR (500 MHz, CD$_3$OD) δ 8.72 (d, J=5.4, 1H), 8.59 (d, J=8.6, 1H), 8.28 (m, 1H), 8.16-8.02 (m, 3H), 8.00-7.82 (m, 4H), 7.72 (t, J=6.8, 2H), 7.57 (d, J=9.2, 1H), 7.49-7.41 (m, 3H), 7.33 (dd, J=9.2, 2.3, 1H), 5.94 (s, 2H), 5.58 (s, 2H), 3.54 (s, 2H), 1.42 (s, 6H).

Example 165

2,2-Dimethyl-3-{5-(quinolin-2-ylmethoxy)-1-[(4'-sulfamoylbiphenyl-3-yl)methyl]-1H-benzimidazol-2-yl}propanoic acid

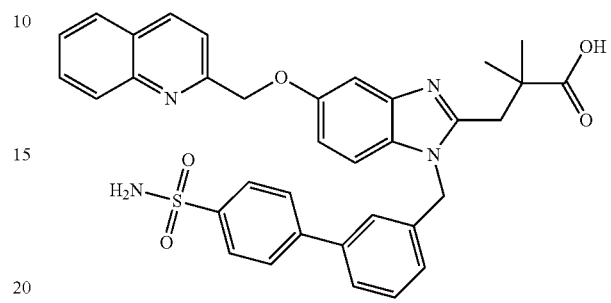

The title compound was prepared with similar methods to those in Example 33 by using 1-bromo-3-(bromomethyl)benzene in Step A and as in Example 147 using (2-sulfamoylphenyl)boronic acid. MS (ESI): mass calcd. for $C_{35}H_{32}N_4O_5S$, 620.20; m/z found, 621.2 [M+H]$^+$. $^1$H NMR (500 MHz, DMSO-d$_6$) δ 8.45 (d, J=8.4, 1H), 8.05 (d, J=8.2, 1H), 8.01 (d, J=8.1, 1H), 7.92-7.76 (m, 5H), 7.75-7.58 (m, 5H), 7.50-7.34 (m, 4H), 7.30-7.19 (m, 2H), 5.84 (s, 2H), 5.50 (s, 2H), 3.51 (s, 2H), 1.31 (s, 6H).

Example 166

2,2-Dimethyl-3-{1-[3-(1H-pyrrol-2-yl)benzyl]-5-(quinolin-2-ylmethoxy)-1H-benzimidazol-2-yl}propanoic acid

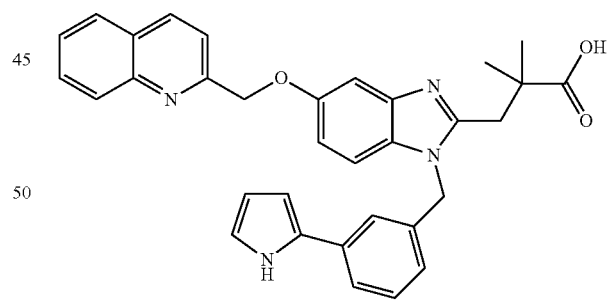

The title compound was prepared with similar methods to those in Example 33 by using 1-bromo-3-(bromomethyl)benzene in Step A and as in Example 147 using (1H-pyrrol-2-yl)boronic acid. MS (ESI): mass calcd. for $C_{33}H_{30}N_4O_3$, 530.23; m/z found, 531.2 [M+H]$^+$. $^1$H NMR (500 MHz, DMSO-d$_6$) δ 11.39 (s, 1H), 8.53 (d, J=8.5, 1H), 8.11 (d, J=8.6, 1H), 8.05 (d, J=8.0, 1H), 7.85 (t, J=7.6, 1H), 7.75 (d, J=8.5, 1H), 7.67 (t, J=7.5, 1H), 7.63-7.52 (m, 3H), 7.40 (d, J=2.0, 1H), 7.36-7.20 (m, 2H), 7.01 (d, J=7.8, 1H), 6.83 (s, 1H), 6.48 (s, 1H), 6.09 (s, 1H), 5.76 (s, 2H), 5.54 (s, 2H), 3.56 (s, 2H), 1.32 (s, 6H).

Example 167

2,2-Dimethyl-3-{5-(quinolin-2-ylmethoxy)-1-[3-(1,3-thiazol-5-yl)benzyl]-1H-benzimidazol-2-yl}propanoic acid

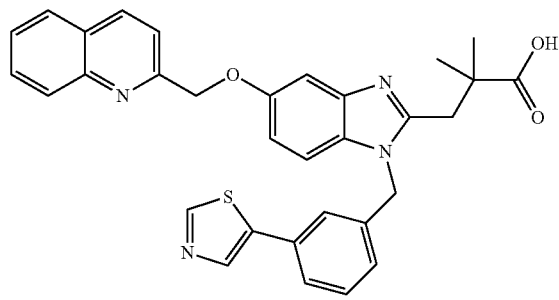 [SMILES: CC(C)(Cc1nc2cc(OCc3ccc4ccccc4n3)ccc2n1Cc1cccc(-c2cncs2)c1)C(=O)O]

The title compound was prepared with similar methods to those in Example 147 using 2,2-dimethyl-3-(5-(quinolin-2-ylmethoxy)-1-(3-(4,4,5,5-tetramethyl-1,3,2-dioxaborolan-2-yl)benzyl)-1H-benzo[d]imidazol-2-yl)propanoic acid and 5-bromothiazole. MS (ESI): mass calcd. for $C_{32}H_{28}N_4O_3S$, 548.19; m/z found, 549.2 [M+H]$^+$. $^1$H NMR (500 MHz, DMSO-$d_6$) δ 9.12 (s, 1H), 8.71 (d, J=8.4, 1H), 8.32 (s, 1H), 8.24 (d, J=8.7, 1H), 8.13 (d, J=8.1, 1H), 7.94 (t, J=7.7, 1H), 7.88 (d, J=8.5, 1H), 7.80-7.69 (m, 2H), 7.66-7.61 (m, 2H), 7.48-7.36 (m, 2H), 7.32 (dd, J=9.1, 2.3, 1H), 7.16 (d, J=7.6, 1H), 5.85 (s, 2H), 5.64 (s, 2H), 3.56 (s, 2H), 1.32 (s, 6H).

Example 168

2,2-Dimethyl-3-[1-({4'-[(methylsulfonyl)amino]biphenyl-3-yl}methyl)-5-(quinolin-2-ylmethoxy)-1H-benzimidazol-2-yl]propanoic acid

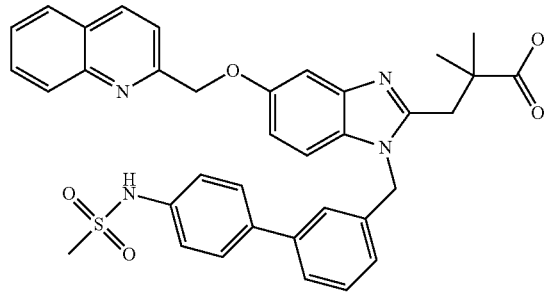

The title compound was prepared with similar methods to those in Example 33 by using 1-bromo-3-(bromomethyl)benzene in Step A and as in Example 147 using (4-(methylsulfonamido)phenyl)boronic acid. MS (ESI): mass calcd. for $C_{36}H_{34}N_4O_5S$, 634.22; m/z found, 635.1 [M+H]$^+$. $^1$H NMR (500 MHz, DMSO-$d_6$) δ 9.84 (s, 1H), 8.39 (d, J=8.7, 1H), 8.02 (d, J=8.6, 1H), 7.97 (d, J=8.1, 1H), 7.78 (t, J=6.9, 1H), 7.71-7.49 (m, 6H), 7.44-7.35 (m, 3H), 7.31-7.19 (m, 3H), 7.01 (d, J=7.9, 2H), 5.60 (s, 2H), 5.39 (s, 2H), 3.20 (s, 2H), 3.01 (s, 3H), 1.27 (s, 6H).

Example 169

2,2-Dimethyl-3-[1-{[4'-(methylsulfonyl)biphenyl-3-yl]methyl}-5-(quinolin-2-ylmethoxy)-1H-benzimidazol-2-yl]propanoic acid

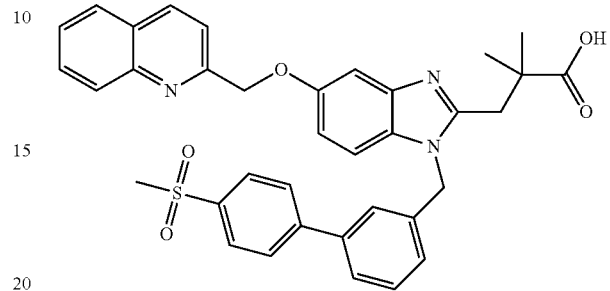

The title compound was prepared with similar methods to those in Example 33 by using 1-bromo-3-(bromomethyl)benzene in Step A and as in Example 147 using (4-(methylsulfonyl)phenyl)boronic acid. MS (ESI): mass calcd. for $C_{36}H_{33}N_3O_5S$, 619.21; m/z found, 620.2 [M+H]$^+$. $^1$H NMR (500 MHz, DMSO-$d_6$) δ 8.52 (brs, 1H), 8.22-7.96 (m, 4H), 7.95-7.60 (m, 8H), 7.56-7.38 (m, 2H), 7.32-7.26 (m, 2H), 5.87 (s, 2H), 5.53 (brs, 2H), 3.56 (s, 2H), 3.25 (s, 3H), 1.32 (s, 6H).

Example 170

3-{1-[(4'-Methoxybiphenyl-4-yl)methyl]-5-(quinolin-2-ylmethoxy)-1H-benzimidazol-2-yl}-2,2-dimethylpropanoic acid

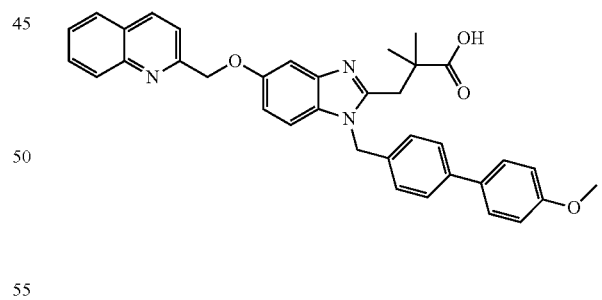

The title compound was prepared with similar methods to those in Example 33 by using 1-bromo-4-(bromomethyl)benzene in Step A and as in Example 147 using (4-methoxyphenyl)boronic acid MS (ESI): mass calcd. for $C_{36}H_{33}N_3O_4$, 571.25; m/z found, 572.2 [M+H]$^+$. $^1$H NMR (500 MHz, CD$_3$OD) δ 8.44 (d, J=8.1, 1H), 8.07 (d, J=8.0, 1H), 7.98 (d, J=8.9, 1H), 7.86-7.79 (m, 1H), 7.76 (d, J=8.5, 1H), 7.69-7.56 (m, 4H), 7.52 (d, J=8.9, 2H), 7.39 (d, J=2.0, 1H), 7.33 (dd, J=9.1, 2.4, 1H), 7.27 (d, J=8.4, 2H), 6.98 (d, J=8.8, 2H), 5.82 (s, 2H), 5.51 (s, 2H), 3.82 (s, 3H), 3.52 (s, 2H), 1.40 (s, 6H).

Example 171

2,2-Dimethyl-3-[1-({3'-[(methylsulfonyl)amino]
biphenyl-4-yl}methyl)-5-(quinolin-2-ylmethoxy)-
1H-benzimidazol-2-yl]propanoic acid

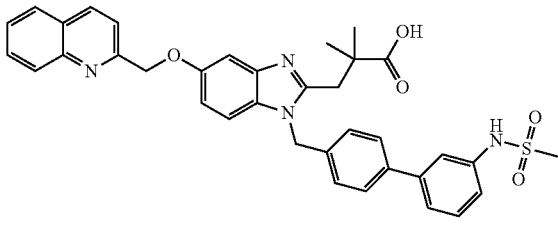 [SMILES: CC(C)(Cc1nc2cc(OCc3ccc4ccccc4n3)ccc2n1Cc1ccc(-c2cccc(NS(C)(=O)=O)c2)cc1)C(=O)O]

The title compound was prepared with similar methods to those in Example 33 by using 1-bromo-4-(bromomethyl)benzene in Step A and as in Example 147 using (3-(methylsulfonamido)phenyl)boronic acid. MS (ESI): mass calcd. for $C_{36}H_{34}N_4O_5S$, 634.23; m/z found, 635.2 [M+H]$^+$. $^1$H NMR (500 MHz, CD$_3$OD) δ 8.49 (s, 1H), 8.10 (d, J=8.7, 1H), 8.01 (d, J=7.7, 1H), 7.91-7.75 (m, 2H), 7.69 (d, J=7.3, 1H), 7.65-7.58 (m, 3H), 7.48 (s, 1H), 7.44-7.29 (m, 6H), 7.25-7.19 (m, 1H), 5.86 (s, 2H), 5.53 (s, 2H), 3.53 (s, 2H), 2.97 (s, 3H), 1.41 (s, 6H).

Example 172

2,2-Dimethyl-3-{5-(quinolin-2-ylmethoxy)-1-[(3'-sulfamoylbiphenyl-4-yl)methyl]-1H-benzimidazol-2-yl}propanoic acid

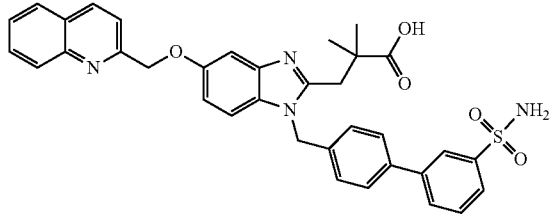 [SMILES: CC(C)(Cc1nc2cc(OCc3ccc4ccccc4n3)ccc2n1Cc1ccc(-c2cccc(S(N)(=O)=O)c2)cc1)C(=O)O]

The title compound was prepared with similar methods to those in Example 33 by using 1-bromo-4-(bromomethyl)benzene in Step A and as in Example 147 using (3-sulfamoylphenyl)boronic acid. MS (ESI): mass calcd. for $C_{35}H_{32}N_4O_5S$, 620.21; m/z found, 621.2 [M+H]$^+$. $^1$H NMR (500 MHz, CD$_3$OD) δ 8.48 (d, J=8.6, 1H), 8.11-8.07 (m, 2H), 7.99 (d, J=8.4, 1H), 7.92-7.75 (m, 4H), 7.72-7.55 (m, 5H), 7.42-7.30 (m, 4H), 5.88 (s, 2H), 5.53 (s, 2H), 3.53 (s, 2H), 1.41 (s, 6H).

Example 173

3-{1-[(3'-Carbamoylbiphenyl-4-yl)methyl]-5-(quinolin-2-ylmethoxy)-1H-benzimidazol-2-yl}-2,2-dimethylpropanoic acid

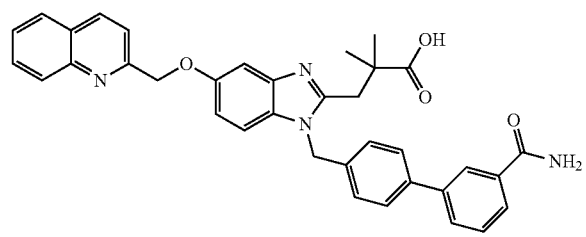 [SMILES: CC(C)(Cc1nc2cc(OCc3ccc4ccccc4n3)ccc2n1Cc1ccc(-c2cccc(C(N)=O)c2)cc1)C(=O)O]

The title compound was prepared with similar methods to those in Example 33 by using 1-bromo-4-(bromomethyl)benzene in Step A and as in Example 147 using (3-carbamoylphenyl)boronic acid. MS (ESI): mass calcd. for $C_{36}H_{32}N_4O_4$, 584.24; m/z found, 585.2 [M+H]$^+$. $^1$H NMR (500 MHz, CD$_3$OD) δ 8.54 (d, J=8.3, 1H), 8.12-8.10 (m, 2H), 8.02 (d, J=8.4, 1H), 7.90-7.77 (m, 4H), 7.71-7.66 (m, 3H), 7.60 (d, J=9.1, 1H), 7.53 (t, J=7.8, 1H), 7.42 (s, 1H), 7.36-7.32 (m, 3H), 5.87 (s, 2H), 5.55 (s, 2H), 3.54 (s, 2H), 1.41 (s, 6H).

Example 174

3-[1-{[3'-(Acetylamino)biphenyl-4-yl]methyl}-5-(quinolin-2-ylmethoxy)-1H-benzimidazol-2-yl]-2,2-dimethylpropanoic acid

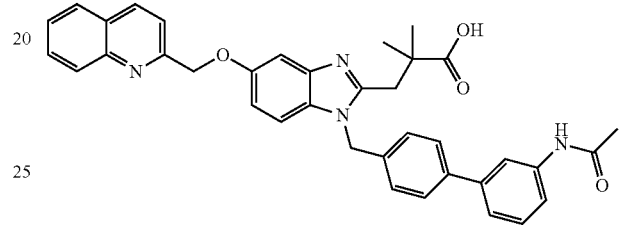

The title compound was prepared with similar methods to those in Example 33 by using 1-bromo-4-(bromomethyl)benzene in Step A and as in Example 147 using (3-acetamidophenyl)boronic acid. MS (ESI): mass calcd. for $C_{37}H_{34}N_4O_4$, 598.26; m/z found, 599.2 [M+H]$^+$. $^1$H NMR (500 MHz, CD$_3$OD) δ 8.35 (d, J=8.6, 1H), 8.22 (s, 1H), 8.04 (d, J=8.9, 1H), 7.92 (d, J=8.2, 1H), 7.80-7.72 (m, 3H), 7.62-7.48 (m, 4H), 7.38-7.24 (m, 4H), 7.12 (d, J=8.1, 2H), 7.04 (dd, J=8.9, 2.1, 1H), 5.56 (s, 2H), 5.40 (s, 2H), 3.16 (s, 2H), 2.13 (s, 3H), 1.32 (s, 6H).

Example 175

2,2-Dimethyl-3-[1-({2'-[(methylsulfonyl)amino]biphenyl-4-yl}methyl)-5-(quinolin-2-ylmethoxy)-1H-benzimidazol-2-yl]propanoic acid

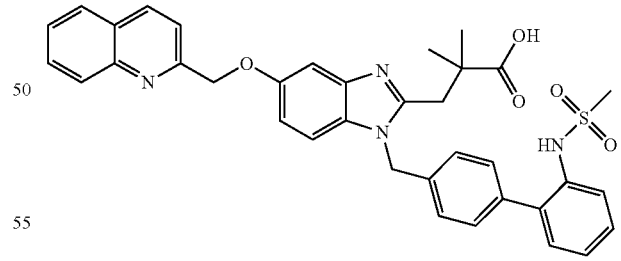

The title compound was prepared with similar methods to those in Example 33 by using 1-bromo-4-(bromomethyl)benzene in Step A and as in Example 147 using (2-(methylsulfonamido)phenyl)boronic acid. MS (ESI): mass calcd. for $C_{36}H_{34}N_4O_5S$, 634.23; m/z found, 635.2 [M+H]$^+$. $^1$H NMR (500 MHz, CD$_3$OD) δ 8.51 (d, J=8.5, 1H), 8.10 (d, J=8.5, 1H), 8.01 (d, J=8.3, 1H), 7.86 (t, J=7.7, 1H), 7.80 (d, J=8.6, 1H), 7.68 (t, J=7.6, 1H), 7.60 (d, J=9.2, 1H), 7.49-7.29 (m, 10H), 5.86 (s, 2H), 5.54 (s, 2H), 3.53 (s, 2H), 2.71 (s, 3H), 1.42 (s, 6H).

Example 176

3-{1-[(2'-Carbamoylbiphenyl-4-yl)methyl]-5-(quinolin-2-ylmethoxy)-1H-benzimidazol-2-yl}-2,2-dimethylpropanoic acid

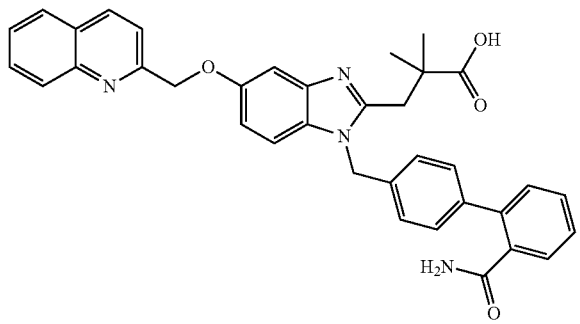 [SMILES: CC(C)(Cc1nc2cc(OCc3ccc4ccccc4n3)ccc2n1Cc1ccc(-c2ccccc2C(N)=O)cc1)C(=O)O]

The title compound was prepared with similar methods to those in Example 33 by using 1-bromo-4-(bromomethyl)benzene in Step A and as in Example 147 using (2-carbamoylphenyl)boronic acid. MS (ESI): mass calcd. for $C_{36}H_{32}N_4O_4$, 584.24; m/z found, 585.2 [M+H]$^+$. $^1$H NMR (500 MHz, CD$_3$OD) δ 8.54 (d, J=7.9, 1H), 8.12 (d, J=8.6, 1H), 8.07-7.98 (m, 1H), 7.91-7.77 (m, 2H), 7.72-7.31 (m, 10H), 7.27 (d, J=8.1, 2H), 5.85 (s, 2H), 5.56 (s, 2H), 3.52 (s, 2H), 1.41 (s, 6H).

Example 177

2,2-Dimethyl-3-{5-(quinolin-2-ylmethoxy)-1-[4-(1,3-thiazol-2-yl)benzyl]-1H-benzimidazol-2-yl}propanoic acid

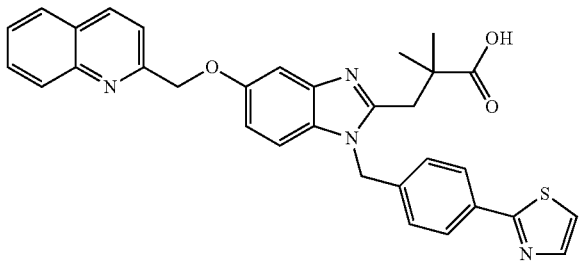 [SMILES: CC(C)(Cc1nc2cc(OCc3ccc4ccccc4n3)ccc2n1Cc1ccc(-c2nccs2)cc1)C(=O)O]

The title compound was prepared with similar methods to those in example 147 using 2,2-dimethyl-3-(5-(quinolin-2-ylmethoxy)-1-(4-(4,4,5,5-tetramethyl-1,3,2-dioxaborolan-2-yl)benzyl)-1H-benzo[d]imidazol-2-yl)propanoic acid and 2-bromothiazole. MS (ESI): mass calcd. for $C_{32}H_{28}N_4O_3S$, 548.19; m/z found, 549.1 [M+H]$^+$. $^1$H NMR (500 MHz, DMSO-d$_6$) δ 8.85 (d, J=8.5, 1H), 8.35 (d, J=8.6, 1H), 8.20 (d, J=8.0, 1H), 8.07-7.86 (m, 5H), 7.85-7.77 (m, 2H), 7.62 (d, J=9.1, 1H), 7.50 (d, J=2.3, 1H), 7.40 (d, J=8.3, 2H), 7.34 (dd, J=9.1, 2.3, 1H), 5.89 (s, 2H), 5.72 (s, 2H), 3.55 (s, 2H), 1.33 (s, 6H).

Example 178

2,2-Dimethyl-3-{1-[4-(1-methyl-1H-pyrazol-4-yl)benzyl]-5-(quinolin-2-ylmethoxy)-1H-benzimidazol-2-yl}propanoic acid

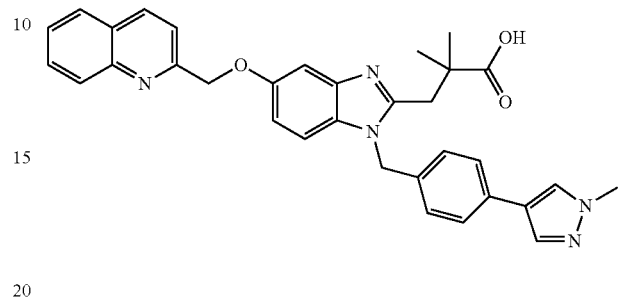

The title compound was prepared with similar methods to those in Example 147 using 2,2-dimethyl-3-(5-(quinolin-2-ylmethoxy)-1-(4-(4,4,5,5-tetramethyl-1,3,2-dioxaborolan-2-yl)benzyl)-1H-benzo[d]imidazol-2-yl)propanoic acid and 4-bromo-1-methyl-1H-pyrazole. MS (ESI): mass calcd. for $C_{33}H_{31}N_5O_3$, 545.24; m/z found, 546.2 [M+H]$^+$. $^1$H NMR (500 MHz, DMSO-d$_6$) δ 8.92 (d, J=8.6, 1H), 8.41 (d, J=8.5, 1H), 8.24 (d, J=8.1, 1H), 8.15 (s, 1H), 8.06-8.01 (m, 2H), 7.87-7.79 (m, 2H), 7.64 (d, J=9.1, 1H), 7.53 (d, J=8.2, 2H), 7.49 (d, J=2.3, 1H), 7.34 (dd, J=9.1, 2.3, 1H), 7.27 (d, J=8.3, 2H), 5.79 (s, 2H), 5.76 (s, 2H), 3.84 (s, 3H), 3.56 (s, 2H), 1.32 (s, 6H).

Example 179

2,2-Dimethyl-3-{1-[3-(1-methyl-1H-pyrazol-5-yl)benzyl]-5-(quinolin-2-ylmethoxy)-1H-benzimidazol-2-yl}propanoic acid

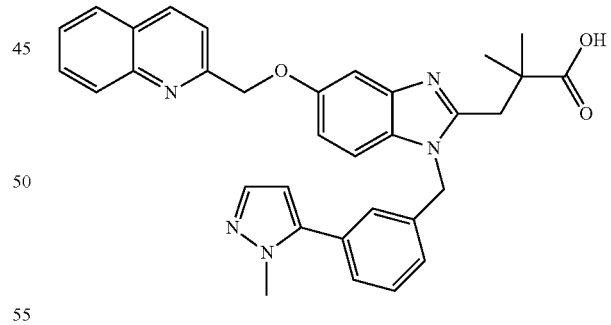

The title compound was prepared with similar methods to those in Example 33 by using 1-bromo-3-(bromomethyl)benzene in Step A and as in Example 147 using 5-bromo-1-methyl-1H-pyrazole. MS (ESI): mass calcd. for $C_{33}H_{31}N_5O_3$, 545.24; m/z found, 546.1 [M+H]$^+$. $^1$H NMR (500 MHz, DMSO-d$_6$) δ 8.38 (d, J=8.2, 1H), 8.02 (d, J=8.4, 1H), 7.97 (d, J=7.0, 1H), 7.77 (t, J=7.6, 1H), 7.68 (d, J=8.4, 1H), 7.60 (t, J=7.5, 1H), 7.44-7.36 (m, 3H), 7.33 (d, J=8.7, 1H), 7.19 (d, J=10.7, 2H), 7.03 (s, 1H), 6.90 (dd, J=8.6, 2.2, 1H), 6.31 (d, J=1.8, 1H), 5.62 (s, 2H), 5.36 (s, 2H), 3.72 (s, 3H), 2.96 (s, 2H), 1.14 (s, 6H).

Example 180

2,2-Dimethyl-3-{1-[(2'-methylbiphenyl-4-yl)methyl]-5-(quinolin-2-ylmethoxy)-1H-benzimidazol-2-yl}propanoic acid

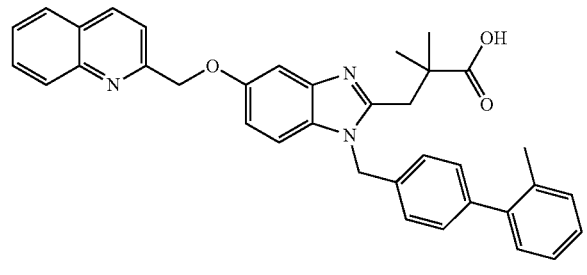 [SMILES: Cc1ccccc1-c1ccc(Cn2c(CC(C)(C)C(=O)O)nc3cc(OCc4ccc5ccccc5n4)ccc32)cc1]

The title compound was prepared with similar methods to those in Example 33 by using 1-bromo-4-(bromomethyl)benzene in Step A and as in Example 147 using o-tolylboronic acid. MS (ESI): mass calcd. for $C_{36}H_{33}N_3O_3$, 555.25; m/z found, 556.1 [M+H]$^+$. $^1$H NMR (500 MHz, CD$_3$OD) δ 8.70 (d, J=8.5, 1H), 8.13 (d, J=8.4, 1H), 8.06 (d, J=7.5, 1H), 7.95-7.85 (m, 2H), 7.71 (t, J=7.8, 1H), 7.58 (d, J=9.2, 1H), 7.40 (s, 1H), 7.31 (dd, J=8.8, 2.2, 1H), 7.25-7.18 (m, 4H), 7.16-6.99 (m, 4H), 5.78 (s, 2H), 5.58 (s, 2H), 3.46 (s, 2H), 2.09 (s, 3H), 1.31 (s, 6H).

Example 181

2,2-Dimethyl-3-[5-(quinolin-2-ylmethoxy)-1-{2-[6-(trifluoromethyl)pyridin-3-yl]benzyl}-1H-benzimidazol-2-yl]propanoic acid

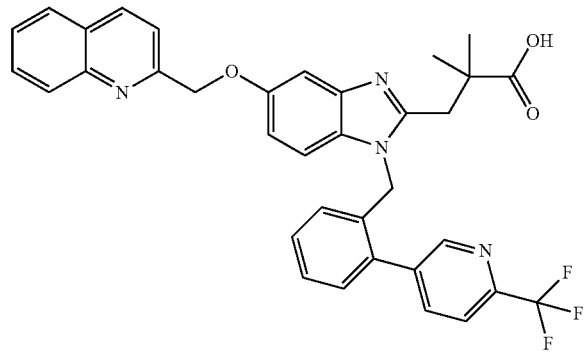 [SMILES: CC(C)(Cc1nc2cc(OCc3ccc4ccccc4n3)ccc2n1Cc1ccccc1-c1ccc(C(F)(F)F)nc1)C(=O)O]

The title compound was prepared with similar methods to those in example 33 by using 1-bromo-2-(bromomethyl)benzene in Step A and as in Example 147 using (6-(trifluoromethyl)pyridin-3-yl)boronic acid. MS (ESI): mass calcd. for $C_{36}H_{29}F_3N_4O_3$, 610.22; m/z found, 611.1 [M+H]$^+$. $^1$H NMR (500 MHz, CD$_3$OD) δ 8.79 (s, 1H), 8.66 (s, 1H), 8.23 (d, J=8.9, 1H), 8.16 (d, J=7.9, 1H), 8.05-7.92 (m, 3H), 7.87-7.76 (m, 2H), 7.55-7.44 (m, 2H), 7.42-7.35 (m, 2H), 7.31 (s, 2H), 7.20 (d, J=7.4, 1H), 5.85 (s, 2H), 5.65 (s, 2H), 3.18 (s, 2H), 1.32 (s, 6H).

Example 182

3-{1-[(2'-Cyanobiphenyl-4-yl)methyl]-5-(quinolin-2-ylmethoxy)-1H-benzimidazol-2-yl}-2,2-dimethylpropanoic acid

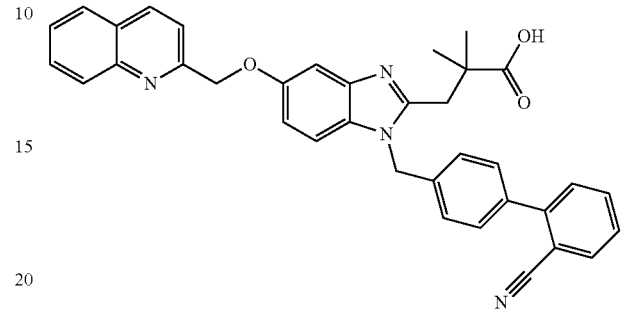

The title compound was prepared with similar methods to those in Example 33 by using 1-bromo-4-(bromomethyl)benzene in Step A and as in Example 147 using (2-cyanophenyl)boronic acid. MS (ESI): mass calcd. for $C_{36}H_{30}N_4O_3$, 566.23; m/z found, 567.2 [M+H]$^+$. $^1$H NMR (500 MHz, CD$_3$OD) δ 8.47 (s, 1H), 8.09 (d, J=9.2, 1H), 8.00 (d, J=8.2, 1H), 7.88-7.50 (m, 10H), 7.43-7.31 (m, 4H), 5.90 (s, 2H), 5.53 (s, 2H), 3.53 (s, 2H), 1.41 (s, 6H).

Example 183

2,2-Dimethyl-3-[1-{[3'-(methylsulfonyl)biphenyl-4-yl]methyl}-5-(quinolin-2-ylmethoxy)-1H-benzimidazol-2-yl]propanoic acid

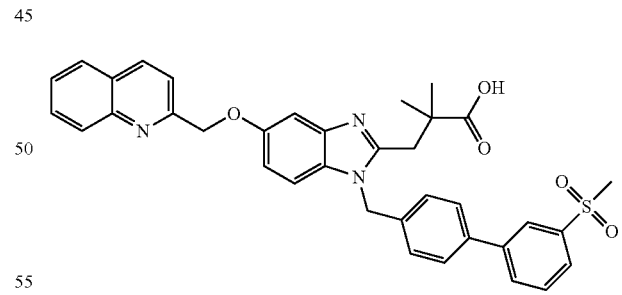

The title compound was prepared with similar methods to those in Example 33 by using 1-bromo-4-(bromomethyl)benzene in Step A and as in Example 147 using (3-(methylsulfonyl)phenyl)boronic acid. MS (ESI): mass calcd. for $C_{36}H_{33}N_3O_5S$, 619.21; m/z found, 620.1 [M+H]$^+$. $^1$H NMR (500 MHz, CD$_3$OD) δ 9.09 (d, J=8.4, 1H), 8.39-8.27 (m, 2H), 8.21-8.11 (m, 3H), 7.98-7.92 (m, 3H), 7.75-7.66 (m, 4H), 7.58 (d, J=2.3, 1H), 7.48-7.37 (m, 3H), 5.93 (s, 2H), 5.81 (s, 2H), 3.59 (s, 2H), 3.17 (s, 3H), 1.45 (s, 6H).

Example 184

2,2-Dimethyl-3-{1-[4-(1-methyl-1H-pyrazol-3-yl)benzyl]-5-(quinolin-2-ylmethoxy)-1H-benzimidazol-2-yl}propanoic acid

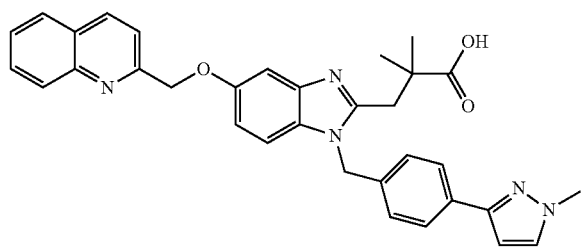 [SMILES: Cn1ccc(-c2ccc(Cn3c(CC(C)(C)C(=O)O)nc4cc(OCc5ccc6ccccc6n5)ccc43)cc2)n1]

The title compound was prepared with similar methods to those in Example 33 by using 1-bromo-4-(bromomethyl)benzene in Step A and as in Example 147 using (1-methyl-1H-pyrazol-3-yl)boronic acid. MS (ESI): mass calcd. for $C_{33}H_{31}N_5O_3$, 545.24; m/z found, 546.2 [M+H]$^+$. $^1$H NMR (500 MHz, DMSO-$d_6$) δ 8.81 (d, J=8.6, 1H), 8.29 (d, J=7.9, 1H), 8.18 (d, J=8.1, 1H), 8.01-7.93 (m, 2H), 7.84-7.67 (m, 4H), 7.62 (d, J=9.1, 1H), 7.48 (s, 1H), 7.35-7.28 (m, 3H), 6.66 (s, 1H), 5.81 (s, 2H), 5.69 (s, 2H), 3.85 (s, 3H), 3.55 (s, 2H), 1.31 (s, 6H).

Example 185

3-[1-(4-Isoxazol-4-ylbenzyl)-5-(quinolin-2-ylmethoxy)-1H-benzimidazol-2-yl]-2,2-dimethylpropanoic acid The title compound was prepared with similar methods to those in Example 147 using 2,2-dimethyl-3-(5-(quinolin-2-ylmethoxy)-1-(4-(4,4,5,5-tetramethyl-1,3,2-dioxaborolan-2-yl)benzyl)-1H-benzo[d]imidazol-2-yl)propanoic acid and 4-bromoisoxazole. MS (ESI): mass calcd. for $C_{32}H_{28}N_4O_4$, 532.21; m/z found, 533.2 [M+H]$^+$. $^1$H NMR (500 MHz, CD$_3$OD) δ 9.18 (d, J=7.8, 1H), 9.08 (s, 1H), 8.82 (s, 1H), 8.42 (d, J=8.6, 1H), 8.35 (d, J=8.2, 1H), 8.24-8.17 (m, 2H), 7.98 (t, J=7.4, 1H), 7.67-7.64 (m, 4H), 7.45 (d, J=8.0, 1H), 7.34 (d, J=7.0, 2H), 5.88 (s, 4H), 3.59 (s, 2H), 1.44 (s, 6H).

Example 186

2,2-Dimethyl-3-{5-(quinolin-2-ylmethoxy)-1-[4-(1,3-thiazol-5-yl)benzyl]-1H-benzimidazol-2-yl}propanoic acid

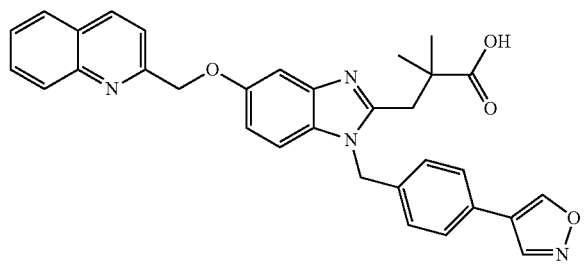 [SMILES: CC(C)(Cc1nc2cc(OCc3ccc4ccccc4n3)ccc2n1Cc1ccc(-c2cnoc2)cc1)C(=O)O]

The title compound was prepared with similar methods to those in Example 147 using 2,2-dimethyl-3-(5-(quinolin-2-ylmethoxy)-1-(4-(4,4,5,5-tetramethyl-1,3,2-dioxaborolan-2-yl)benzyl)-1H-benzo[d]imidazol-2-yl)propanoic acid and 5-bromothiazole. MS (ESI): mass calcd. for $C_{32}H_{28}N_4O_3S$, 548.19; m/z found, 549.1 [M+H]$^+$. $^1$H NMR (500 MHz, DMSO-$d_6$) δ 9.10 (s, 1H), 8.83 (d, J=9.1, 1H), 8.32-8.28 (m, 2H), 8.18 (d, J=8.8, 1H), 8.01-7.93 (m, 2H), 7.79 (t, J=7.5, 1H), 7.68-7.59 (m, 3H), 7.49 (s, 1H), 7.34 (d, J=7.8, 3H), 5.84 (s, 2H), 5.69 (s, 2H), 3.54 (s, 2H), 1.31 (s, 6H).

Example 187

2,2-Dimethyl-3-{5-(quinolin-2-ylmethoxy)-1-[4-(1,3-thiazol-4-yl)benzyl]-1H-benzimidazol-2-yl}propanoic acid The title compound was prepared with similar methods to those in Example 147 using 2,2-dimethyl-3-(5-(quinolin-2-ylmethoxy)-1-(4-(4,4,5,5-tetramethyl-1,3,2-dioxaborolan-2-yl)benzyl)-1H-benzo[d]imidazol-2-yl)propanoic acid and 4-bromothiazole. MS (ESI): mass calcd. for $C_{32}H_{28}N_4O_3S$, 548.18; m/z found, 549.1 [M+H]$^+$. $^1$H NMR (500 MHz, DMSO-$d_6$) δ 9.17 (d, J=1.6, 1H), 8.59 (d, J=8.5, 1H), 8.18-8.14 (m, 2H), 8.07 (d, J=8.1, 1H), 7.96 (d, J=8.2, 2H), 7.92-7.84 (m, 1H), 7.79 (d, J=8.4, 1H), 7.69 (t, J=7.4, 1H), 7.60 (d, J=9.4, 1H), 7.42 (s, 1H), 7.35 (d, J=8.3, 2H), 7.30 (d, J=9.4, 1H), 5.82 (s, 2H), 5.58 (s, 2H), 3.53 (s, 2H), 1.31 (s, 6H).

Example 188 racemic cis-2-[1-(4-Pyrimidin-2-ylbenzyl)-5-(quinolin-2-ylmethoxy)-1H-benzimidazol-2-yl]cyclohexanecarboxylic acid as the TFA salt

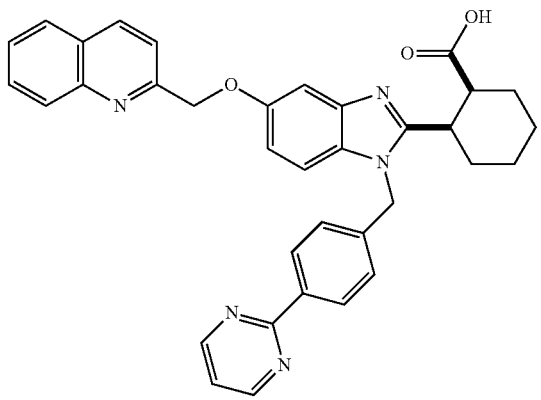

To a 5 mL microwave vial were added a stirbar, racemic cis-2-[1-(4-bromobenzyl)-5-(quinolin-2-ylmethoxy)-1H-benzimidazol-2-yl]cyclohexanecarboxylic acid (106 mg, 0.19 mmol), 2-tributylstannylpyrimidine (99 mg, 0.27 mmol), Pd(PPh$_3$)$_2$Cl$_2$ (8 mg, 0.01 mmol), cesium fluoride (58 mg, 0.38 mmol), and copper iodide (5 mg, 0.03 mmol). The vial was capped and flushed with nitrogen before adding 2 mL N$_2$ sparged DMF and heating at 80° C. After 12 h, the vial was cooled to RT and the reaction mixture was partitioned between pH 3 water (30 mL) and DCM (30 mL) The mixture was stirred vigorously. The organic layer was separated and the aqueous layer was further extracted with DCM (20 mL×2). The combined organic layers were dried with magnesium sulfate, filtered, and concentrated to dryness. The residue was subjected to reverse phase HPLC to give the title compound (35 mg, 28%). MS (ESI): mass calcd. for C$_{35}$H$_{31}$N$_5$O$_3$, 569.24; m/z found, 570.2 [M+H]$^+$. $^1$H NMR (500 MHz, CD$_3$OD) δ 8.83 (d, J=4.9, 2H), 8.49 (d, J=8.5, 1H), 8.41 (d, J=8.5, 2H), 8.10 (d, J=8.5, 1H), 8.00 (d, J=8.1, 1H), 7.89-7.82 (m, 1H), 7.80 (d, J=8.5, 1H), 7.70-7.63 (m, 1H), 7.57 (d, J=9.1, 1H), 7.41-7.32 (m, 3H), 7.28 (d, J=8.5, 2H), 5.91 (d, J=17.2, 1H), 5.84 (d, J=17.3, 1H), 5.54 (s, 2H), 3.71-3.61 (m, 1H), 3.02-2.94 (m, 1H), 2.38-2.26 (m, 1H), 2.24-2.12 (m, 1H), 2.12-2.04 (m, 1H), 2.00-1.93 (m, 1H), 1.85-1.75 (m, 1H), 1.72-1.66 (m, 1H), 1.60-1.45 (m, 2H).

Example 189 racemic cis-2-[1-(3-Pyrimidin-2-ylbenzyl)-5-(quinolin-2-ylmethoxy)-1H-benzimidazol-2-yl]cyclohexanecarboxylic acid as the TFA salt

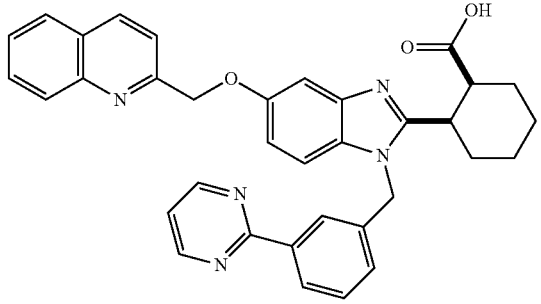

The title compound was prepared using analogous conditions to those described in Example 188 using racemic cis-2-[1-(3-bromobenzyl)-5-(quinolin-2-ylmethoxy)-1H-benzimidazol-2-yl]cyclohexanecarboxylic acid and 2-tributylstannylpyrimidine. MS (ESI): mass calcd. for C$_{35}$H$_{31}$N$_5$O$_3$, 569.24; m/z found, 570.2 [M+H]$^+$. $^1$H NMR (500 MHz, CD$_3$OD) δ 8.81 (d, J=4.9, 2H), 8.51 (d, J=8.6, 1H), 8.41 (d, J=7.9, 1H), 8.27 (s, 1H), 8.11 (d, J=8.5, 1H), 8.02 (d, J=8.2, 1H), 7.91-7.84 (m, 1H), 7.81 (d, J=8.5, 1H), 7.69 (t, J=7.5, 1H), 7.61 (d, J=9.1, 1H), 7.52 (t, J=7.7, 1H), 7.42-7.27 (m, 4H), 5.91 (d, J=17.0, 1H), 5.86 (d, J=16.8, 1H), 5.54 (s, 2H), 3.68 (dt, J=12.3, 3.7, 1H), 3.01-2.96 (m, 1H), 2.40-2.30 (m, 1H), 2.22-2.12 (m, 1H), 2.11-2.04 (m, 1H), 2.00-1.94 (m, 1H), 1.84-1.73 (m, 1H), 1.70-1.63 (m, 1H), 1.61-1.44 (m, 2H).

Example 190 racemic cis-2-[1-(4-Piperidin-1-ylbenzyl)-5-(quinolin-2-ylmethoxy)-1H-benzimidazol-2-yl]cyclohexanecarboxylic acid as the TFA salt

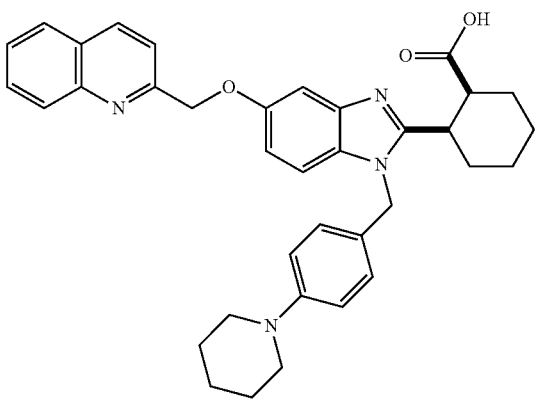

To a 5 mL microwave vial were added racemic cis-2-[1-(4-bromobenzyl)-5-(quinolin-2-ylmethoxy)-1H-benzimidazol-2-yl]cyclohexanecarboxylic acid (70 mg, 0.12 mmol), RuPhos (6 mg, 0.01 mmol), RuPhos pre-catalyst (9 mg, 0.01 mmol), piperidine (25 µL, 0.25 mmol) and THF (1.3 mL). The vial was flushed with N$_2$ and a solution of LiHMDS (0.37 mL, 1 M in THF) was added. The flask was capped and placed in a heating block at 80° C. After 3 h, the mixture was partitioned between pH 4 water (20 mL) and DCM (20 mL) and the mixture was stirred vigorously. The organic layer was separated and the aqueous layer was further extracted with DCM (20 mL×2). The combined organic layers were dried with magnesium sulfate, filtered, and concentrated to dryness. The residue was subjected to reverse phase HPLC to give the title compound (12 mg, 14%). MS (ESI): mass calcd. for C$_{36}$H$_{38}$N$_4$O$_3$, 574.29; m/z found, 575.2 [M+H]$^+$. $^1$H NMR (600 MHz, CD$_3$OD) δ 8.45 (d, J=8.5, 1H), 8.10-8.07 (m, J=8.0, 1H), 7.99 (d, J=7.7, 1H), 7.84 (ddd, J=8.5, 7.0, 1.4, 1H), 7.77 (d, J=8.5, 1H), 7.68-7.64 (m, 1H), 7.51 (d, J=9.1, 1H), 7.44 (d, J=8.6, 2H), 7.37 (d, J=2.3, 1H), 7.31 (dd, J=9.1, 2.4, 1H), 7.27 (d, J=8.7, 2H), 5.83 (d, J=17.2, 1H), 5.77 (d, J=17.2, 1H), 5.51 (s, 2H), 3.63 (dt, J=12.1, 3.7, 1H), 3.49-3.43 (m, 4H), 2.91-2.84 (m, 1H), 2.35-2.26 (m, 1H), 2.23-2.15 (m, 1H), 2.08-2.02 (m, 1H), 2.00-1.87 (m, 5H), 1.81-1.66 (m, 4H), 1.56-1.49 (m, 2H).

Example 191 racemic cis-2-[1-{1-(4,4-Difluoropiperidin-1-yl)-2-fluorobenzyl]-5-(quinolin-2-ylmethoxy)-1H-benzimidazol-2-yl}cyclohexanecarboxylic acid as the TFA salt

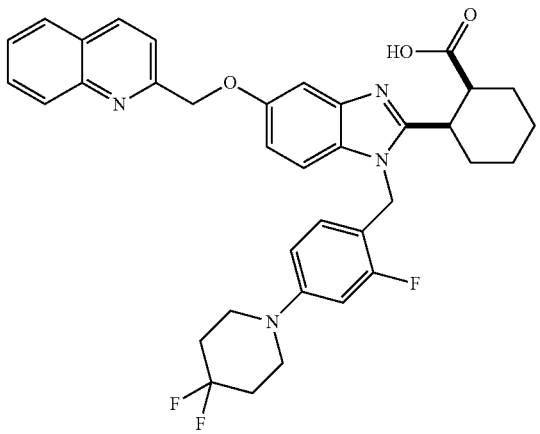

The title compound was prepared using analogous conditions to those described in Example 190 using racemic cis-2-(1-(4-bromo-2-fluorobenzyl)-5-(quinolin-2-ylmethoxy)-1H-benzo[d]imidazol-2-yl)cyclohexanecarboxylic acid and 4,4-difluoropiperidine. MS (ESI): mass calcd. for $C_{36}H_{35}F_3N_4O_3$, 628.27; m/z found, 629.1 [M+H]$^+$. $^1$H NMR (500 MHz, CD$_3$OD) δ 8.51 (d, J=8.4, 1H), 8.11 (dq, J=8.6, 0.8, 1H), 8.05-7.99 (m, 1H), 7.87 (ddd, J=8.4, 6.9, 1.4, 1H), 7.80 (d, J=8.5, 1H), 7.69 (ddd, J=8.2, 6.9, 1.1, 1H), 7.66-7.62 (m, 1H), 7.37-7.30 (m, 2H), 7.08 (t, J=8.8, 1H), 6.84-6.74 (m, 2H), 5.72 (d, J=16.3, 1H), 5.64 (d, J=16.3, 1H), 5.53 (s, 2H), 3.66 (dt, J=12.3, 3.6, 1H), 3.41 (dd, J=7.0, 4.6, 4H), 2.94 (q, J=4.2, 1H), 2.43-2.28 (m, 1H), 2.28-2.18 (m, 1H), 2.01 (dtt, J=19.2, 12.3, 6.9, 6H), 1.87-1.76 (m, 1H), 1.71 (d, J=10.7, 1H), 1.54 (td, J=13.0, 12.4, 6.7, 2H).

Example 192 racemic cis-2-{1-[4-(3,3-Difluoropiperidin-1-yl)-2-fluorobenzyl]-5-(quinolin-2-ylmethoxy)-1H-benzimidazol-2-yl}cyclohexanecarboxylic acid as the TFA salt

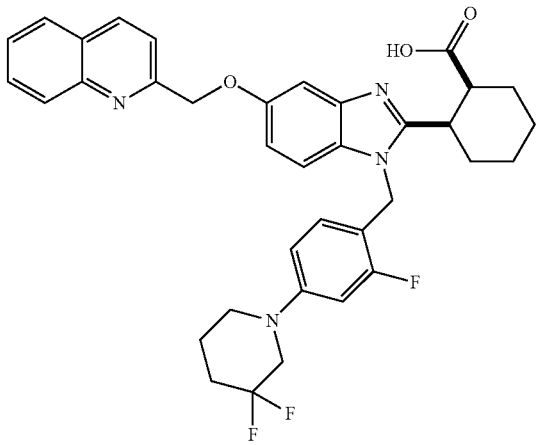

The title compound was prepared using analogous conditions to those described in Example 190 using racemic cis-2-(1-(4-bromo-2-fluorobenzyl)-5-(quinolin-2-ylmethoxy)-1H-benzo[d]imidazol-2-yl)cyclohexanecarboxylic acid and 3,3-difluoropiperidine. MS (ESI): mass calcd. for $C_{36}H_{35}F_3N_4O_3$, 628.27; m/z found, 629.1 [M+H]$^+$. $^1$H NMR (500 MHz, CD$_3$OD) δ 8.58 (dd, J=8.6, 0.7, 1H), 8.14 (dt, J=8.6, 0.9, 1H), 8.05 (dd, J=8.2, 1.4, 1H), 7.90 (ddd, J=8.5, 6.9, 1.4, 1H), 7.85 (d, J=8.5, 1H), 7.72 (ddd, J=8.2, 6.9, 1.2, 1H), 7.64 (d, J=9.1, 1H), 7.38-7.30 (m, 2H), 7.07 (t, J=8.7, 1H), 6.80-6.72 (m, 2H), 5.71 (d, J=16.3, 1H), 5.65 (d, J=16.3, 1H), 5.56 (s, 2H), 3.67 (dt, J=12.3, 3.7, 1H), 3.48 (t, J=11.6, 2H), 3.30 (s, 2H), 3.00 (q, J=4.2, 1H), 2.35 (d, J=12.1, 1H), 2.24 (dd, J=13.5, 3.3, 1H), 2.13-1.89 (m, 4H), 1.88-1.75 (m, 3H), 1.71 (d, J=9.7, 1H), 1.55 (s, 2H).

Example 193 racemic cis-2-{1-[4-(3,3-Difluoropyrrolidin-1-yl)-2-fluorobenzyl]-5-(quinolin-2-ylmethoxy)-1H-benzimidazol-2-yl}cyclohexanecarboxylic acid as the TFA salt

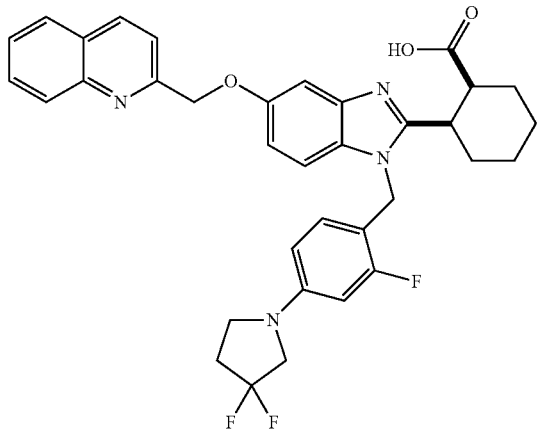

The title compound was prepared using analogous conditions to those described in Example 190 using racemic cis-2-(1-(4-bromo-2-fluorobenzyl)-5-(quinolin-2-ylmethoxy)-1H-benzo[d]imidazol-2-yl)cyclohexanecarboxylic acid and 3,3-difluoropyrrolidine. MS (ESI): mass calcd. for $C_{35}H_{33}F_3N_4O_3$, 614.25; m/z found, 615.1 [M+H]$^+$. $^1$H NMR (500 MHz, CD$_3$OD) δ 8.55 (dd, J=8.6, 0.8, 1H), 8.13 (dt, J=8.6, 1.0, 1H), 8.04 (dd, J=8.3, 1.4, 1H), 7.89 (ddd, J=8.5, 6.9, 1.4, 1H), 7.83 (d, J=8.5, 1H), 7.71 (ddd, J=8.1, 6.9, 1.2, 1H), 7.63 (d, J=9.1, 1H), 7.37-7.29 (m, 2H), 7.11 (app t, J=8.8, 1H), 6.45-6.36 (m, 2H), 5.70 (d, J=16.2, 1H), 5.63 (d, J=16.2, 1H), 5.55 (s, 2H), 3.71-3.60 (m, 3H), 3.50 (t, J=7.2, 2H), 3.03 (q, J=4.2, 1H), 2.50 (tt, J=14.0, 7.2, 2H), 2.42-2.28 (m, 1H), 2.25 (d, J=14.2, 1H), 2.04-1.94 (m, 2H), 1.89-1.77 (m, 1H), 1.71 (d, J=9.1, 1H), 1.60-1.49 (m, 2H).

Example 194 racemic cis-2-{1-[4-(3,3-Difluoroazetidin-1-yl)-2-fluorobenzyl]-5-(quinolin-2-ylmethoxy)-1H-benzimidazol-2-yl}cyclohexanecarboxylic acid as the TFA salt

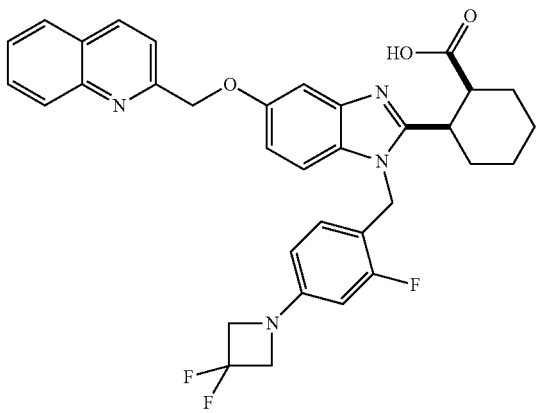

The title compound was prepared using analogous conditions to those described in Example 190 using racemic cis-2-(1-(4-bromo-2-fluorobenzyl)-5-(quinolin-2-ylmethoxy)-1H-benzo[d]imidazol-2-yl)cyclohexanecarboxylic acid and 3,3-difluoroazetidine. MS (ESI): mass calcd. for $C_{34}H_{31}F_3N_4O_3$, 600.23; m/z found, 601.1 [M+H]+. 1H NMR (500 MHz, CD3OD) δ 8.55 (d, J=8.5, 1H), 8.13 (dt, J=8.6, 1.0, 1H), 8.07-7.98 (m, 1H), 7.89 (ddd, J=8.5, 6.9, 1.4, 1H), 7.83 (d, J=8.5, 1H), 7.70 (ddd, J=8.1, 6.9, 1.2, 1H), 7.61 (d, J=9.1, 1H), 7.38-7.29 (m, 2H), 7.10 (t, J=8.4, 1H), 6.40 (dd, J=12.5, 2.3, 1H), 6.35 (dd, J=8.4, 2.4, 1H), 5.72 (d, J=16.3, 1H), 5.68 (s, OH), 5.55 (s, 2H), 4.23 (t, J=11.9, 4H), 3.68 (dt, J=12.1, 3.8, 1H), 3.01 (q, J=4.3, 1H), 2.36 (dd, J=11.8, 3.8, 1H), 2.29-2.17 (m, 1H), 2.04-1.94 (m, 3H), 1.83 (ddt, J=13.1, 8.5, 4.5, 1H), 1.71 (d, J=9.2, 1H), 1.55 (dq, J=12.5, 8.6, 6.8, 2H).

Example 195 racemic cis-2-[1-{2-Fluoro-4-[4-(trifluoromethyl)piperidin-1-yl]benzyl}-5-(quinolin-2-ylmethoxy)-1H-benzimidazol-2-yl]cyclohexanecarboxylic acid as the TFA salt

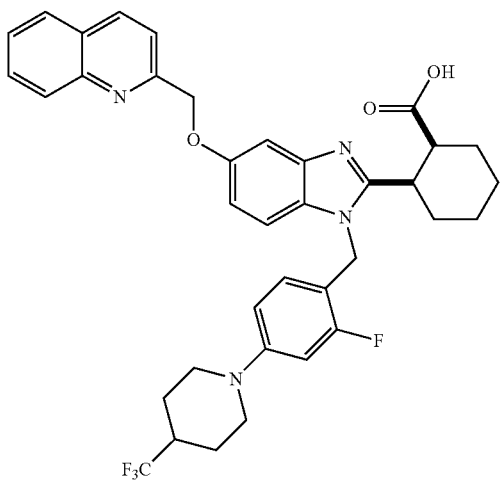

The title compound was prepared using analogous conditions to those described in Example 190 using racemic cis-2-(1-(4-bromo-2-fluorobenzyl)-5-(quinolin-2-ylmethoxy)-1H-benzo[d]imidazol-2-yl)cyclohexanecarboxylic acid and 4-(trifluoromethyl)piperidine. MS (ESI): mass calcd. for $C_{37}H_{36}F_4N_4O_3$, 660.27; m/z found, 661.1 [M+H]+. 1H NMR (500 MHz, CD3OD) δ 8.56 (d, J=8.5 Hz, 1H), 8.15-8.11 (m, 1H), 8.05-8.01 (m, 1H), 7.91-7.86 (m, 1H), 7.83 (d, J=8.5 Hz, 1H), 7.73-7.68 (m, 1H), 7.65 (d, J=8.9 Hz, 1H), 7.38-7.32 (m, 2H), 7.10-7.04 (m, 1H), 6.79-6.69 (m, 2H), 5.71 (d, J=16.3 Hz, 1H), 5.64 (d, J=16.3 Hz, 1H), 5.55 (s, 2H), 3.88-3.81 (m, 2H), 3.70-3.61 (m, 1H), 2.99-2.94 (m, 1H), 2.85-2.74 (m, 2H), 2.43-2.30 (m, 2H), 2.27-2.20 (m, 1H), 2.01-1.88 (m, 4H), 1.87-1.76 (m, 1H), 1.76-1.46 (m, 5H).

Example 196 racemic cis-2-(5-(((6-fluoroquinolin-2-yl)methoxy)-1-(4-(4-(trifluoromethyl)piperidin-1-yl)benzyl)-1H-benzo[d]imidazol-2-yl)cyclohexanecarboxylic acid

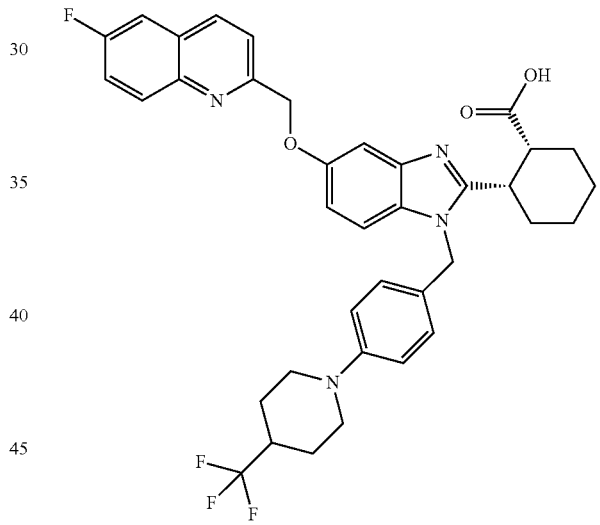

The title compound was prepared using analogous conditions to those described in Example 190 using racemic cis-2-(1-(4-bromobenzyl)-5-((6-fluoroquinolin-2-yl)methoxy)-1H-benzo[d]imidazol-2-yl)cyclohexanecarboxylic acid and 4-(trifluoromethyl)piperidine. MS (ESI): mass calcd. for $C_{37}H_{36}F_4N_4O_3$, 660.27; m/z found, 661.2 [M+H]+. 1H NMR (500 MHz, CD3OD) δ 8.40 (d, J=8.6, 1H), 8.15-8.08 (m, 1H), 7.78 (d, J=8.6, 1H), 7.69-7.60 (m, 2H), 7.57 (d, J=9.1, 1H), 7.37-7.28 (m, 2H), 7.13-7.02 (m, 4H), 5.68 (d, J=3.9, 2H), 5.49 (s, 2H), 3.82-3.76 (m, 2H), 3.65-3.57 (m, 1H), 2.92-2.88 (m, 1H), 2.88-2.80 (m, 2H), 2.43-2.25 (m, 2H), 2.22-2.15 (m, 1H), 2.05-1.93 (m, 4H), 1.82-1.63 (m, 4H), 1.57-1.47 (m, 2H).

Example 197

1-{[1-(4-Morpholin-4-ylbenzyl)-5-(quinolin-2-yl-methoxy)-1H-benzimidazol-2-yl]methyl}cyclopentanecarboxylic acid

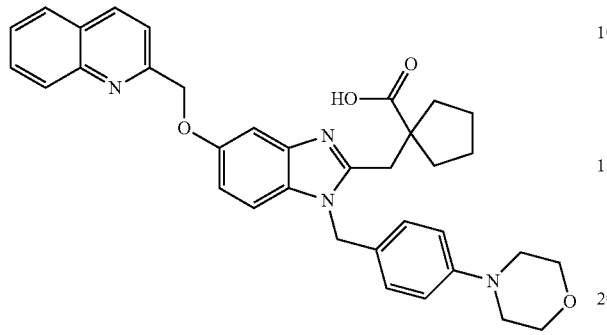

Step A. Ethyl 1-((1-(4-morpholinobenzyl)-5-(quinolin-2-ylmethoxy)-1H-benzo[d]imidazol-2-yl)methyl)cyclopentanecarboxylate To a 5 mL microwave vial were added ethyl 1-((1-(4-bromobenzyl)-5-(quinolin-2-ylmethoxy)-1H-benzo[d]imidazol-2-yl)methyl)cyclopentanecarboxylate (50 mg, 0.08 mmol), RuPhos (4.0 mg, 0.008 mmol), RuPhos pre-catalyst (6.2 mg, 0.008 mmol), morpholine (10.3 µL, 0.12 mmol), NaOt-Bu (11 mg, 0.12 mmol) and toluene (0.85 mL). The vial was flushed with $N_2$ then capped and placed in a heating block at 85° C. After 1.5 h, the mixture was cooled to RT. The mixture was diluted with EtOAc (10 mL) and washed with water (10 mL). The organic layer was dried with $Na_2SO_4$, filtered and concentrated to dryness. The residue was purified by reverse phase HPLC to afford the title compound. MS (ESI): mass calcd. for $C_{37}H_{40}N_4O_4$, 604.3; m/z found 605.1 [M+H]$^+$.

Step B. 1-{[1-(4-Morpholin-4-ylbenzyl)-5-(quinolin-2-ylmethoxy)-1H-benzimidazol-2-yl]methyl}cyclopentanecarboxylic acid To a 20 mL vial were added ethyl 1-((1-(4-morpholinobenzyl)-5-(quinolin-2-ylmethoxy)-1H-benzo[d]imidazol-2-yl)methyl)cyclopentanecarboxylate (28 mg, 0.046 mmol), THF (1.1 mL) and MeOH (1.1 mL) followed by LiOH (0.65 mL, 1 M). The reaction mixture was capped and heated to 80° C. for 3 h. The mixture was cooled to RT and the solvent was concentrated to dryness. Water (1 mL) and acetonitrile (1 mL) were added and the pH was adjusted to ~5-6 using 1 M HCl and then the mixture was concentrated to dryness. The resulting residue was purified using FCC to provide the title compound. MS (ESI): mass calcd. for $C_{35}H_{36}N_4O_4$, 576.27; m/z found, 577.2 [M+H]$^+$. $^1$H NMR (400 MHz, CDCl$_3$) δ 8.20 (d, J=8.5, 1H), 8.11 (d, J=8.4, 1H), 7.83 (d, J=8.1, 1H), 7.77-7.72 (m, 1H), 7.69 (d, J=8.5, 1H), 7.58-7.53 (m, 1H), 7.33-7.31 (m, 1H), 7.22 (d, J=8.9, 1H), 7.10-7.05 (m, 1H), 6.97-6.93 (m, 2H), 6.85-6.80 (m, 2H), 5.43 (s, 2H), 5.22 (s, 2H), 3.86-3.81 (m, 4H), 3.14-3.09 (m, 4H), 3.05 (s, 2H), 2.41-2.33 (m, 2H), 1.75-1.66 (m, 2H), 1.47-1.39 (m, 4H).

Example 198

1-{[1-(4-Piperidin-1-ylbenzyl)-5-(quinolin-2-yl-methoxy)-1H-benzimidazol-2-yl]methyl}cyclopentanecarboxylic acid as the TFA salt

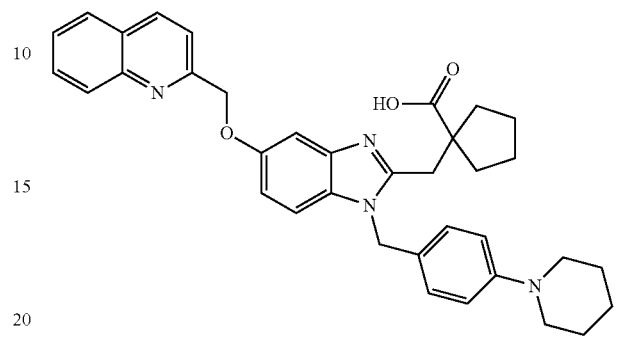

The title compound was prepared using similar methods to those in Example 197 using piperidine in Step A. MS (ESI): mass calcd. for $C_{36}H_{38}N_4O_3$, 574.29; m/z found, 575.1 [M+H]$^+$. $^1$H NMR (500 MHz, CDCl$_3$) δ 8.38-8.32 (m, 1H), 8.19-8.12 (m, 1H), 7.94-7.87 (m, 1H), 7.84-7.79 (m, 1H), 7.78-7.72 (m, 1H), 7.66-7.60 (m, 1H), 7.55-7.49 (m, 1H), 7.30-7.28 (m, 1H), 7.25-7.19 (m, 3H), 7.13-7.06 (m, 2H), 5.55 (s, 2H), 5.48 (s, 2H), 3.32-3.28 (m, 4H), 2.30-2.20 (m, 2H), 1.90-1.84 (m, 4H), 1.83-1.69 (m, 8H), 1.68-1.61 (m, 2H).

Example 199

1-{[1-(3-Pyrrolidin-1-ylbenzyl)-5-(quinolin-2-yl-methoxy)-1H-benzimidazol-2-yl]methyl}cyclopentanecarboxylic acid

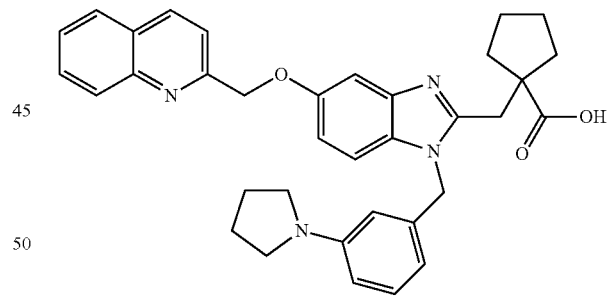

Step A. Methyl 1-((1-(3-(pyrrolidin-1-yl)benzyl)-5-(quinolin-2-ylmethoxy)-1H-benzo[d]imidazol-2-yl)methyl)cyclopentanecarboxylate To a 5 mL microwave vial were added methyl 1-{[1-(3-bromobenzyl)-5-(quinolin-2-ylmethoxy)-1H-benzimidazol-2-yl]methyl}cyclopentanecarboxylate (50.5 mg, 0.08 mmol), RuPhos (4.1 mgs, 0.008 mmol), RuPhos pre-catalyst (7.1 mg, 0.009 mmol), pyrrolidine (15 µL, 0.17 mmol) and toluene (1.5 mL). The vial was flushed with $N_2$, NaOt-Bu was added (16.2 mg, 0.17 mmol) then capped and placed in a heating block at 100° C. After 6 h the mixture was cooled to RT, transferred to a round-bottomed flask and concentrated to dryness. The resulting residue was purified using FCC to provide 21 mg of the title compound. MS (ESI): mass calcd. for $C_{36}H_{38}N_4O_3$, 574.71; m/z found 575.2 [M+H]$^+$.

Step B. 1-{[1-(3-Pyrrolidin-1-ylbenzyl)-5-(quinolin-2-ylmethoxy)-1H-benzimidazol-2-yl]methyl}cyclopentanecarboxylic acid To a 20 mL vial were added methyl 1-((1-(3-(pyrrolidin-1-yl)benzyl)-5-(quinolin-2-ylmethoxy)-1H-benzo[d]imidazol-2-yl)methyl)cyclopentanecarboxylate (20.7 mg, 0.04 mmol), THF (1 mL) and MeOH (1 mL) followed by treatment with LiOH (1 mL, 1 M). The reaction mixture was capped and heated to 80° C. for 3 h. The mixture was cooled to RT, water (5 mL) was added and the pH was adjusted to ~4 using 1 M HCl. To the mixture was added DCM (5 mL) and the mixture was stirred for 1 h at RT. The organic layer was separated then concentrated to dryness. The resulting residue was purified using FCC to provide the title compound. MS (ESI): mass calcd. for $C_{35}H_{36}N_4O_3$, 560.28; m/z found, 561.1 [M+H]$^+$.

Example 200

3-[1-(4-Azetidin-1-ylbenzyl)-5-(quinolin-2-ylmethoxy)-1H-benzimidazol-2-yl]-2,2-dimethylpropanoic acid

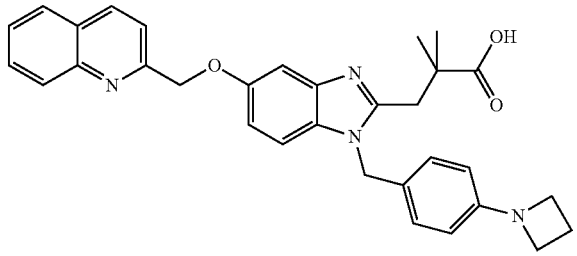 [SMILES: CC(C)(Cc1nc2cc(OCc3ccc4ccccc4n3)ccc2n1Cc1ccc(N2CCC2)cc1)C(=O)O]

To a 5 mL microwave vial were added a stirbar, ethyl 3-(1-(4-bromobenzyl)-5-(quinolin-2-ylmethoxy)-1H-benzo[d]imidazol-2-yl)-2,2-dimethylpropanoate (100 mg, 0.2 mmol), azetidine (20 mg, 0.4 mmol), JohnPhos (32 mg, 0.12 mmol), t-BuOK (35 mg, 0.4 mmol), and Pd$_2$(dba)$_3$ (60 mg, 0.07 mmol). The vial was capped and flushed with N$_2$ before adding 3 mL of N$_2$ sparged toluene. The resulting mixture was heated at 95° C. for 18 hours. The vial was cooled to RT and concentrated to dryness. The resulting residue was dissolved in MeOH (9 mL) and THF (9 mL). To the solution was added 5% aqueous NaOH (2 mL) and the mixture was stirred at 40° C. overnight. The mixture was cooled to RT and acidified to ~pH=4-5 with 6 N HCl, then extracted with EtOAc (3×20 mL). The combined organic layers were dried over Na$_2$SO$_4$, filtered, concentrated to dryness and purified by prep-HPLC to give the title compound (50 mg, 30%). MS (ESI): mass calcd. for $C_{32}H_{32}N_4O_3$, 520.25; m/z found, 521.2 [M+H]$^+$. $^1$H NMR (500 MHz, CD$_3$OD) δ 8.35 (d, J=8.9, 1H), 8.05 (d, J=8.6, 1H), 7.93 (d, J=7.8, 1H), 7.82-7.69 (m, 2H), 7.60 (t, J=7.6, 1H), 7.33-7.20 (m, 3H), 7.08-6.97 (m, 2H), 6.92 (d, J=8.3, 1H), 6.38 (d, J=8.3, 1H), 5.50-5.36 (m, 4H), 3.79 (t, J=7.2, 2H), 3.35-3.32 (m, 2H), 3.14 (s, 2H), 2.40-2.25 (m, 2H), 1.28 (s, 6H).

Example 201

3-{1-[4-(3,3-Difluoropiperidin-1-yl)benzyl]-5-(quinolin-2-ylmethoxy)-1H-benzimidazol-2-yl}-2,2-dimethylpropanoic acid

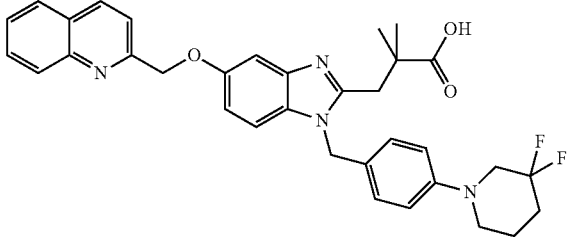 [SMILES: CC(C)(Cc1nc2cc(OCc3ccc4ccccc4n3)ccc2n1Cc1ccc(N2CCCC(F)(F)C2)cc1)C(=O)O]

The title compound was prepared with similar methods to those in Example 200 using 3,3-difluoropiperidine. MS (ESI): mass calcd. for $C_{34}H_{34}F_2N_4O_3$, 584.26; m/z found, 585.3 [M+H]$^+$. $^1$H NMR (500 MHz, CD$_3$OD) δ 9.23 (d, J=8.5, 1H), 8.44 (d, J=8.6, 1H), 8.38 (d, J=8.3, 1H), 8.29-8.18 (m, 2H), 8.01 (t, J=7.5, 1H), 7.68 (d, J=9.1, 1H), 7.63 (d, J=2.0, 1H), 7.46 (d, J=9.2, 1H), 7.23 (d, J=8.6, 2H), 7.09 (d, J=8.6, 2H), 5.88 (s, 2H), 5.77 (s, 2H), 3.64-3.44 (m, 4H), 3.34 (brs, 2H), 2.16-1.84 (m, 4H), 1.42 (s, 6H).

Example 202

2,2-Dimethyl-3-[1-(4-morpholin-4-ylbenzyl)-5-(quinolin-2-ylmethoxy)-1H-benzimidazol-2-yl]propanoic acid

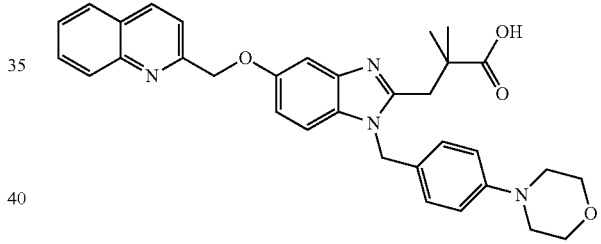

The title compound was prepared with similar methods to those in Example 200 using morpholine. MS (ESI): mass calcd. for $C_{33}H_{34}N_4O_4$, 550.25; m/z found, 551.3 [M+H]$^+$. $^1$H NMR (500 MHz, CD$_3$OD) δ 9.20 (d, J=8.6, 1H), 8.41 (d, J=9.1, 1H), 8.37 (d, J=7.9, 1H), 8.24-8.18 (m, 2H), 8.00 (t, J=7.6, 1H), 7.65 (d, J=9.2, 1H), 7.62 (d, J=2.3, 1H), 7.52-7.42 (m, 3H), 7.39 (d, J=8.7, 2H), 5.88 (s, 2H), 5.86 (s, 2H), 4.06-3.95 (m, 4H), 3.56 (s, 2H), 3.53-3.44 (m, 4H), 1.44 (s, 6H).

Example 203

2,2-Dimethyl-3-[1-(4-piperidin-1-ylbenzyl)-5-(quinolin-2-ylmethoxy)-1H-benzimidazol-2-yl]propanoic acid

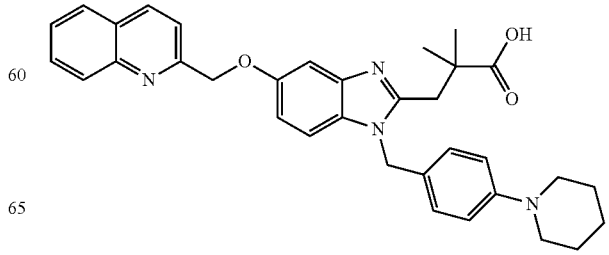

The title compound was prepared with similar methods to those in Example 200 using piperidine. MS (ESI): mass calcd. for $C_{34}H_{36}N_4O_3$, 548.27; m/z found, 549.2 [M+H]$^+$. $^1$H NMR (500 MHz, CD$_3$OD) δ 9.04 (d, J=8.6, 1H), 8.34 (d, J=8.6, 1H), 8.29 (d, J=8.1, 1H), 8.16-8.10 (m, 2H), 7.93 (t, J=7.6, 1H), 7.75 (d, J=8.8, 2H), 7.62-7.58 (m, 2H), 7.50 (d, J=8.7, 2H), 7.42 (dd, J=9.2, 2.4, 1H), 5.95 (s, 2H), 5.79 (s, 2H), 3.77-3.57 (m, 4H), 3.54 (s, 2H), 2.12-1.98 (m, 4H), 1.80 (s, 2H), 1.44 (s, 6H).

Example 204

2,2-Dimethyl-3-[1-(4-pyrrolidin-1-ylbenzyl)-5-(quinolin-2-ylmethoxy)-1H-benzimidazol-2-yl]propanoic acid

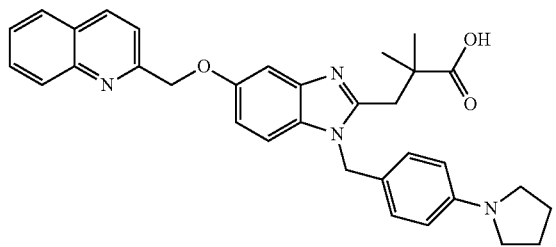 [SMILES: CC(C)(Cc1nc2cc(OCc3ccc4ccccc4n3)ccc2n1Cc1ccc(N2CCCC2)cc1)C(=O)O]

The title compound was prepared with similar methods to those in Example 200 using pyrrolidine. MS (ESI): mass calcd. for $C_{33}H_{34}N_4O_3$, 534.26; m/z found, 535.2 [M+H]$^+$. $^1$H NMR (500 MHz, CD$_3$OD) δ 9.24 (d, J=8.3, 1H), 8.45 (d, J=8.6, 1H), 8.39 (d, J=8.0, 1H), 8.29-8.19 (m, 2H), 8.06-7.98 (m, 1H), 7.69-7.56 (m, 4H), 7.53-7.40 (m, 3H), 5.94 (s, 2H), 5.89 (s, 2H), 3.74 (t, J=6.6, 4H), 3.57 (s, 2H), 2.37-2.20 (m, 4H), 1.45 (s, 6H).

Example 205

2,2-Dimethyl-3-{1-[4-(1H-pyrazol-1-yl)benzyl]-5-(quinolin-2-ylmethoxy)-1H-benzimidazol-2-yl}propanoic acid

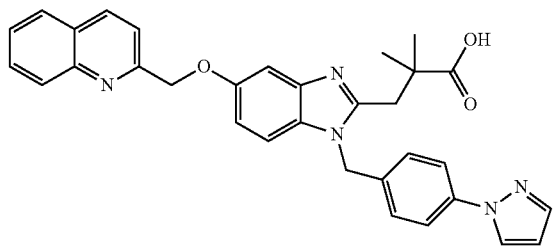 [SMILES: CC(C)(Cc1nc2cc(OCc3ccc4ccccc4n3)ccc2n1Cc1ccc(-n2cccn2)cc1)C(=O)O]

The title compound was prepared with similar methods to those in Example 200 using pyrazole. MS (ESI): mass calcd. for $C_{32}H_{29}N_5O_3$, 531.23; m/z found, 532.2 [M+H]$^+$. $^1$H NMR (500 MHz, CD$_3$OD) δ 9.21 (d, J=8.7, 1H), 8.41 (d, J=8.7, 1H), 8.37 (d, J=7.8, 1H), 8.27-8.17 (m, 3H), 8.05-7.96 (m, 1H), 7.78 (d, J=8.7, 2H), 7.72 (d, J=1.4, 1H), 7.68 (d, J=9.2, 1H), 7.63 (d, J=2.3, 1H), 7.45 (dd, J=9.2, 2.4, 1H), 7.41 (d, J=8.7, 2H), 6.53 (dd, J=2.5, 1.9, 1H), 5.91 (s, 2H), 5.87 (s, 2H), 3.59 (s, 2H), 1.45 (s, 6H).

Example 206

2,2-Dimethyl-3-{5-(quinolin-2-ylmethoxy)-1-[4-(1H-1,2,3-triazol-1-yl)benzyl]-1H-benzimidazol-2-yl}propanoic acid

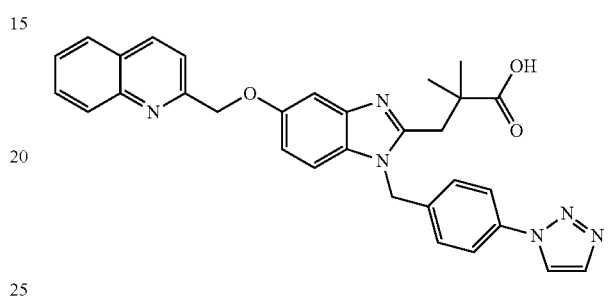

The title compound was prepared with similar methods to those in Example 200 using 1,2,3-triazole. MS (ESI): mass calcd. for $C_{31}H_{28}N_6O_3$, 532.22; m/z found, 533.2 [M+H]$^+$. $^1$H NMR (500 MHz, CD$_3$OD) δ 8.53 (d, J=1.1, 1H), 8.47 (d, J=8.6, 1H), 8.09 (d, J=8.8, 1H), 7.99 (d, J=9.2, 1H), 7.91-7.81 (m, 4H), 7.77 (d, J=8.4, 1H), 7.70-7.63 (m, 1H), 7.57 (d, J=9.0, 1H), 7.46 (d, J=8.5, 2H), 7.41 (d, J=2.1, 1H), 7.33 (dd, J=9.1, 2.4, 1H), 5.91 (s, 2H), 5.52 (s, 2H), 3.53 (s, 2H), 1.42 (s, 6H).

Example 207

2,2-Dimethyl-3-{5-(quinolin-2-ylmethoxy)-1-[4-(2H-1,2,3-triazol-2-yl)benzyl]-1H-benzimidazol-2-yl}propanoic acid

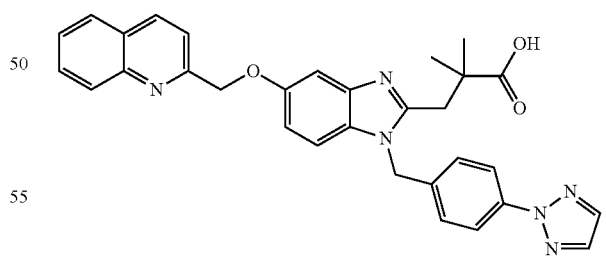

The title compound was prepared with similar methods to those in Example 200 using 1,2,3-triazole. MS (ESI): mass calcd. for $C_{31}H_{28}N_6O_3$, 532.22; m/z found, 533.2 [M+H]$^+$. $^1$H NMR (500 MHz, CD$_3$OD) δ 8.45 (d, J=8.9, 1H), 8.12-8.05 (m, 3H), 7.98 (d, J=7.8, 1H), 7.91 (s, 2H), 7.87-7.79 (m, 1H), 7.76 (d, J=8.6, 1H), 7.65 (t, J=7.5, 1H), 7.58 (d, J=9.0, 1H), 7.43-7.37 (m, 3H), 7.33 (dd, J=9.1, 2.3, 1H), 5.87 (s, 2H), 5.51 (s, 2H), 3.52 (s, 2H), 1.41 (s, 6H).

Example 208 racemic cis-2-(5-(Benzo[d]thiazol-2-ylmethoxy)-1-(4-bromobenzyl)-1H-benzo[d]imidazol-2-yl)cyclohexanecarboxylic acid

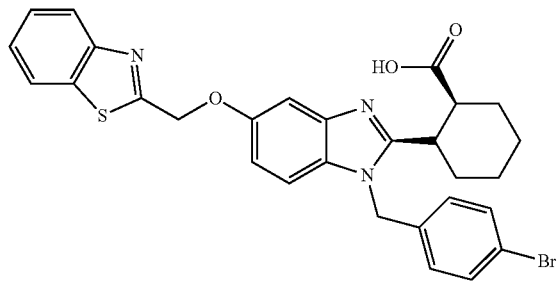

Step A: 2-((4-Fluoro-3-nitrophenoxy)methyl)benzo[d]thiazole

A solution of 4-fluoro-3-nitrophenol (2.1 g, 13 mmol), potassium carbonate (2.2 g, 16 mmol), 2-(chloromethyl)benzo[d]thiazole (2.4 g, 13 mmol) and DMF (15 mL) was stirred at 80° C. for 6 h. The reaction mixture was cooled to RT and poured onto ice water (300 mL). Solid precipitate was collected by vacuum filtration and dried in a vacuum oven at 60° C. to provide the title product, which was used without purification. MS (ESI): mass calcd. for $C_{14}H_9FN_2O_3S$, 304.1; m/z found, 305.1 $[M+H]^+$. $^1$H-NMR (500 MHz, DMSO-$d_6$) δ 8.15 (t, J=6.7, 1H), 8.08-8.01 (m, 1H), 7.90-7.84 (m, 1H), 7.63-7.53 (m, 3H), 7.52-7.45 (m, 1H), 5.75 (s, 2H).

Step B: 4-(Benzo[d]thiazol-2-ylmethoxy)-N-(4-bromobenzyl)-2-nitroaniline

A solution of 2-((4-fluoro-3-nitrophenoxy)methyl)benzo[d]thiazole (1.9 g, 6.4 mmol), 4-bromobenzylamine hydrochloride (2.1 g, 9.6 mmol), DIPEA (5.5 mL, 31.9 mmol) and acetonitrile (10 mL) was added to a sealed tube and heated to reflux for 16 h. The reaction was cooled to 0° C. and solid product precipitated. Solids were collected by vacuum filtration, washed with cold acetonitrile (10 mL) and dried in vacuum oven at 60° C. This material was used without purification. MS (ESI): mass calcd. for $C_{21}H_{16}BrN_3O_3S$, 469.10; m/z found, 470.1 $[M+H]^+$. $^1$H-NMR (500 MHz, DMSO-$d_6$) δ 8.67-8.53 (m, 1H), 8.12 (d, J=7.9, 1H), 8.02 (d, J=8.1, 1H), 7.74 (d, J=3.1, 1H), 7.56-7.52 (m, 2H), 7.48-7.43 (m, 1H), 7.37-7.34 (m, 1H), 7.31 (d, J=8.4, 2H), 6.89 (d, J=9.5, 1H), 5.58 (s, 2H), 4.60 (d, J=6.2, 2H).

Step C: 4-(Benzo[d]thiazol-2-ylmethoxy)-N1-(4-bromobenzyl)benzene-1,2-diamine as the hydrochloride salt Zinc dust (10.8 g, 164 mmol) was added to a stirred solution of 4-(benzo[d]thiazol-2-ylmethoxy)-N-(4-bromobenzyl)-2-nitroaniline (7.7 g, 16.4 mmol), acetone (80 mL) and saturated aqueous ammonium chloride (16 mL) at 0° C. The mixture was warmed to RT and stirred for 1 h. The reaction mixture was diluted with EtOAc (600 mL) and filtered through Celite. The organic layer was washed with brine, dried with sodium sulfate and concentrated to dryness. The residue was purified using FCC to provide an oil that was dissolved in EtOH (100 mL) and acidified with HCl (4 N in dioxane) to pH 2. The mixture was concentrated to dryness to provide the title compound. MS (ESI): mass calcd. for $C_{21}H_{18}BrN_3OS$, 439.1; m/z found, 440.1 $[M+H]^+$. $^1$H NMR (400 MHz, DMSO-$d_6$) δ 8.12 (d, J=7.9, 1H), 8.01 (d, J=7.8, 1H), 7.59-7.50 (m, 3H), 7.49-7.41 (m, 1H), 7.37 (d, J=8.4, 2H), 6.74 (s, 2H), 6.60 (s, 1H), 5.50 (s, 2H), 4.32 (s, 2H), 4.22-3.22 (m, 1H).

Step D: racemic cis-2-(5-(Benzo[d]thiazol-2-ylmethoxy)-1-(4-bromobenzyl)-1H-benzo[d]imidazol-2-yl)cyclohexanecarboxylic acid To a 4 mL microwave vial were added 4-(benzo[d]thiazol-2-ylmethoxy)-N1-(4-bromobenzyl)benzene-1,2-diamine hydrochloride (100 mg, 0.21 mmol), cis-hexahydroisobenzofuran-1,3-dione (34 mg, 0.21 mmol), DIPEA (27 mg, 0.21 mmol), and acetonitrile (2 mL). The mixture was irradiated for 1 h at 82° C. in a microwave reactor. The reaction was cooled to RT, HCl (1 mL, 6 N) was added and the reaction was irradiated for 1 h at 82° C. in a microwave reactor. The reaction was cooled to RT and the solid byproducts were removed by filtration and filtrate was purified using reverse phase HPLC to provide the title compound. MS (ESI): mass calcd. for $C_{29}H_{26}BrN_3O_3S$, 575.10; m/z found, 576.1 $[M+H]^+$. $^1$H-NMR (500 MHz, CDCl$_3$) δ 8.03 (d, J=8.0, 1H), 7.89 (d, J=8.0, 1H), 7.56-7.48 (m, 4H), 7.45-7.38 (m, 2H), 7.19-7.16 (m, 1H), 7.16-7.11 (m, 1H), 6.97 (d, J=8.4, 2H), 5.59-5.49 (m, 1H), 5.46 (s, 2H), 3.40-3.24 (m, 1H), 2.93 (d, J=4.5, 1H), 2.39-2.19 (m, 2H), 1.96-1.83 (m, 2H), 1.82-1.69 (m, 1H), 1.65-1.50 (m, 2H), 1.35 (d, J=13.0, 1H).

Example 209

(1R*,2S*)-2-(5-(benzo[d]thiazol-2-ylmethoxy)-1-(4-bromobenzyl)-1H-benzo[d]imidazol-2-yl)cyclohexanecarboxylic acid

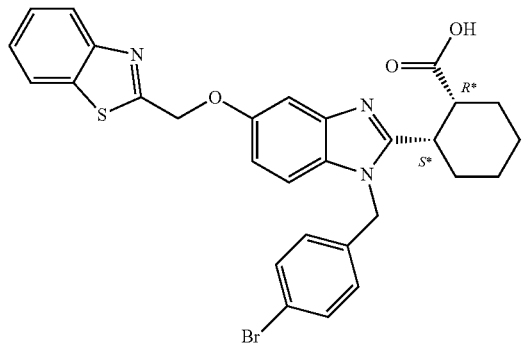 [SMILES: O=C(O)[C@@H]1CCCC[C@@H]1c1nc2cc(OCc3nc4ccccc4s3)ccc2n1Cc1ccc(Br)cc1]

Racemic-cis-2-(5-(benzo[d]thiazol-2-ylmethoxy)-1-(4-bromobenzyl)-1H-benzo[d]imidazol-2-yl)cyclohexanecarboxylic acid was purified by chiral SFC on (CHIRALPAK AD-H 5 μm 250×20 mm). Mobile phase (55% CO$_2$, 45% MeOH) to yield the title compound as the first eluting isomer. MS (ESI): mass calcd. for $C_{29}H_{26}BrN_3O_3S$, 576.52; m/z found, 577.95 $[M+H]^+$.

Example 210

(1S*,2R*)-2-(5-(benzo[d]thiazol-2-ylmethoxy)-1-(4-bromobenzyl)-1H-benzo[d]imidazol-2-yl)cyclohexanecarboxylic acid

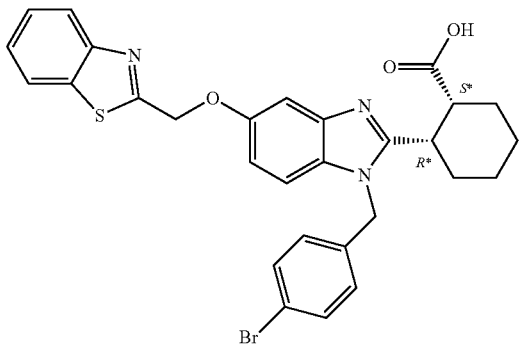 [SMILES: O=C(O)[C@@H]1CCCC[C@@H]1c1nc2cc(OCc3nc4ccccc4s3)ccc2n1Cc1ccc(Br)cc1]

Racemic-cis-2-(5-(benzo[d]thiazol-2-ylmethoxy)-1-(4-bromobenzyl)-1H-benzo[d]imidazol-2-yl)cyclohexanecarboxylic acid was purified by chiral SFC on (CHIRALPAK AD-H 5 µm 250×20 mm). Mobile phase (55% CO$_2$, 45% MeOH) to yield the ttile compound as the second eluting isomer. MS (ESI): mass calcd. for C$_{29}$H$_{26}$BrN$_3$O$_3$S, 576.52; m/z found, 578.1 [M+H]$^+$. $^1$H NMR (500 MHz, CD$_3$OD) δ 8.01-7.95 (m, 2H), 7.56-7.49 (ddd, J=8.4, 7.2, 1.2, 1H), 7.49-7.40 (m, 3H), 7.38-7.31 (d, J=2.3, 1H), 7.23-7.18 (d, J=8.9, 1H), 7.09-7.03 (d, J=8.5, 2H), 7.03-6.97 (dd, J=8.8, 2.4, 1H), 5.57-5.53 (s, 2H), 5.53-5.40 (m, 2H), 3.62-3.52 (dt, J=8.3, 4.0, 1H), 2.87-2.77 (dt, J=7.9, 4.4, 1H), 2.50-2.30 (m, 1H), 2.00-1.94 (m, 1H), 1.93-1.80 (m, 2H), 1.80-1.70 (d, J=8.4, 2H), 1.51-1.37 (m, 2H).

Example 211 racemic cis-3-(5-(Benzo[d]thiazol-2-ylmethoxy)-1-(4-bromobenzyl)-1H-benzo[d]imidazol-2-yl)-2,2-dimethylcyclopropanecarboxylic acid

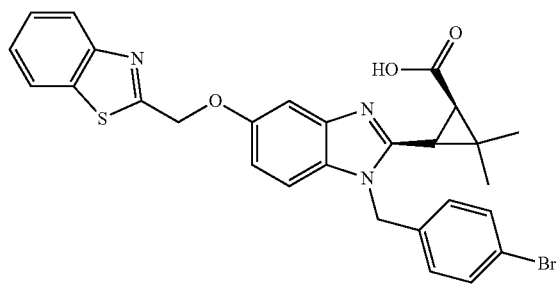

The title compound was prepared in a manner analogous to Example 208 using cis-6,6-dimethyl-3-oxabicyclo[3.1.0]hexane-2,4-dione in step D. MS (ESI): mass calcd. for C$_{28}$H$_{24}$BrN$_3$O$_3$S, 561.07; m/z found, 562.1 [M+H]$^+$. $^1$H-NMR (500 MHz, DMSO-d$_6$) δ 8.12 (d, J=7.9, 1H), 8.07-8.00 (m, 1H), 7.58-7.52 (m, 4H), 7.41 (s, 1H), 7.26-7.19 (m, 3H), 5.71 (s, 2H), 5.64-5.48 (m, 2H), 2.64 (d, J=8.3, 1H), 2.30 (d, J=8.3, 1H), 1.31 (s, 3H), 1.22 (s, 3H).

Example 212 racemic trans-2-(5-(benzo[d]thiazol-2-ylmethoxy)-1-(4-bromobenzyl)-1H-benzo[d]imidazol-2-yl)cyclohexanecarboxylic acid

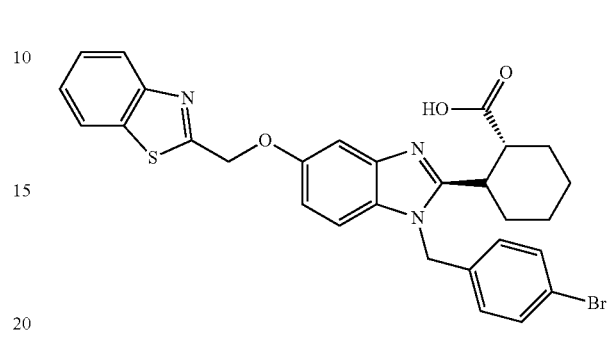

The title compound was prepared in a manner analogous to Example 208 using trans-hexahydroisobenzofuran-1,3-dione in step D. MS (ESI): mass calcd. for C$_{29}$H$_{26}$BrN$_3$O$_3$S, 575.09; m/z found, 576.1 [M+H]$^+$. $^1$H-NMR (500 MHz, CDCl$_3$) δ 8.15-8.07 (m, 1H), 8.06-8.00 (m, 1H), 7.57-7.49 (m, 3H), 7.50-7.44 (m, 1H), 7.42 (d, J=8.3 Hz, 1H), 7.36 (d, J=2.4 Hz, 1H), 7.18-7.08 (m, 3H), 5.72-5.57 (m, 4H), 3.69-3.63 (m, 1H), 2.86-2.80 (m, 1H), 2.33-2.18 (m, 1H), 2.04-1.91 (m, 1H), 1.90-1.66 (m, 3H), 1.64-1.53 (m, 1H), 1.53-1.43 (m, 1H), 1.43-1.33 (m, 1H).

Example 213

2-((5-(benzo[d]thiazol-2-ylmethoxy)-1-(4-bromobenzyl)-1H-benzo[d]imidazol-2-yl)methyl)-2-ethylbutanoic acid

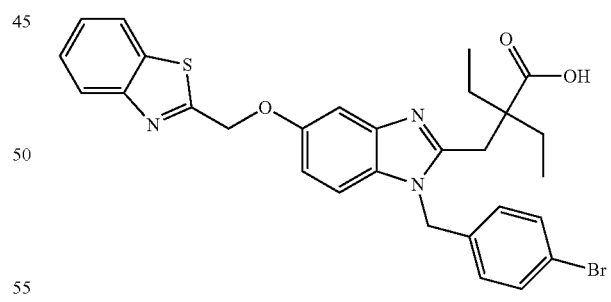

The title compound was prepared in a manner analogous to Example 208 using 3,3-diethyldihydrofuran-2,5-dione in step D using conventional heating. MS (ESI): mass calcd. for C$_{29}$H$_{28}$BrN$_3$O$_3$S, 578.53; m/z found, 579.2 [M+H]$^+$. $^1$H NMR (500 MHz, CDCl$_3$) δ 8.09-8.02 (d, J=8.2, 1H), 7.93-7.87 (dd, J=7.8, 1.0, 1H), 7.53-7.49 (m, 1H), 7.49-7.44 (m, 3H), 7.44-7.39 (m, 1H), 7.20-7.15 (m, 1H), 7.13-7.08 (m, 1H), 6.94-6.88 (d, J=8.4, 2H), 5.58-5.49 (s, 2H), 5.40-5.32 (s, 2H), 3.12-3.03 (s, 2H), 1.76-1.66 (dt, J=14.6, 7.3, 2H), 1.66-1.57 (dt, J=14.2, 7.4, 2H), 0.85-0.80 (t, J=7.4, 6H).

Example 214 racemic 2-(5-(benzo[d]thiazol-2-ylmethoxy)-1-(4-(2-methoxypyrimidin-5-yl)benzyl)-1H-benzo[d]imidazol-2-yl)cyclohexanecarboxylic acid

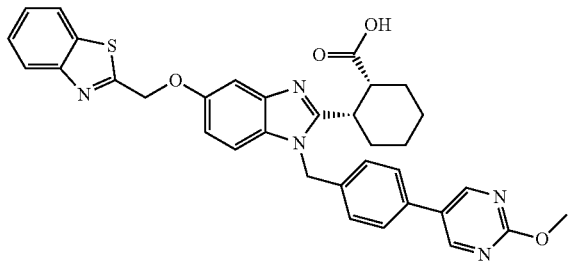

The title compound was prepared using analogous conditions described in Step A of Example 97 using racemic cis-2-(5-(benzo[d]thiazol-2-ylmethoxy)-1-(4-bromobenzyl)-1H-benzo[d]imidazol-2-yl)cyclohexanecarboxylic acid and (2-methoxypyrimidin-5-yl)boronic acid. MS (ESI): mass calcd. for $C_{34}H_{31}N_5O_4S$, 605.72; m/z found, 606.2 [M+H]$^+$. $^1$H NMR (500 MHz, CD$_3$OD) δ 8.77-8.72 (s, 2H), 8.01-7.91 (m, 2H), 7.60-7.53 (d, J=8.3, 2H), 7.53-7.48 (m, 1H), 7.45-7.39 (ddd, J=8.2, 7.2, 1.2, 1H), 7.36-7.30 (d, J=2.4, 1H), 7.28-7.23 (d, J=8.3, 2H), 7.23-7.19 (d, J=8.9, 1H), 7.02-6.95 (dd, J=8.8, 2.4, 1H), 5.62-5.47 (m, 4H), 4.03-4.00 (s, 3H), 3.64-3.57 (m, 1H), 2.90-2.81 (dt, J=7.3, 4.1, 1H), 2.45-2.31 (qd, J=7.6, 3.6, 1H), 2.08-2.02 (m, 1H), 1.93-1.81 (m, 2H), 1.81-1.71 (m, 2H), 1.51-1.41 (d, J=14.1, 2H).

Example 215 racemic cis-2-(5-(benzo[d]thiazol-2-ylmethoxy)-1-(4-(pyrimidin-5-yl)benzyl)-1H-benzo[d]imidazol-2-yl)cyclohexanecarboxylic acid

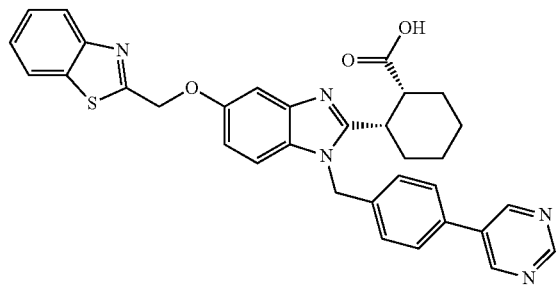 [SMILES: O=C(O)[C@@H]1CCCC[C@@H]1c1nc2cc(OCc3nc4ccccc4s3)ccc2n1Cc1ccc(-c2cncnc2)cc1]

The title compound was prepared using analogous conditions described in Step A of Example 97 using racemic cis-2-(5-(benzo[d]thiazol-2-ylmethoxy)-1-(4-bromobenzyl)-1H-benzo[d]imidazol-2-yl)cyclohexanecarboxylic acid and pyrimidin-5-ylboronic acid. MS (ESI): mass calcd. for $C_{33}H_{29}N_5O_3S$, 575.69; m/z found, 576.2 [M+H]$^+$. $^1$H NMR (400 MHz, CD$_3$OD) δ 9.20-9.10 (s, 1H), 9.10-9.00 (s, 2H), 8.11-7.94 (m, 2H), 7.77-7.69 (d, J=8.3, 2H), 7.60-7.51 (m, 2H), 7.51-7.42 (m, 2H), 7.38-7.30 (m, 3H), 6.01-5.78 (q, J=17.2, 2H), 5.71-5.65 (s, 2H), 3.74-3.60 (dt, J=12.1, 3.6, 1H), 3.05-2.92 (q, J=4.1, 1H), 2.44-2.26 (m, 1H), 2.24-2.15 (m, 1H), 2.13-2.04 (m, 1H), 2.02-1.93 (m, 1H), 1.88-1.74 (m, 1H), 1.75-1.62 (m, 1H), 1.63-1.40 (m, 2H).

Example 216 racemic cis-2-(5-(Benzo[d]thiazol-2-ylmethoxy)-1-(4-(6-(trifluoromethyl)pyridin-3-yl)benzyl)-1H-benzo[d]imidazol-2-yl)cyclohexanecarboxylic acid

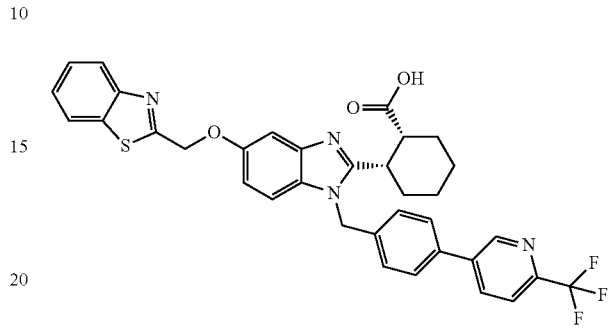

The title compound was prepared using analogous conditions described in Step A of Example 97 using racemic cis-2-(5-(benzo[d]thiazol-2-ylmethoxy)-1-(4-bromobenzyl)-1H-benzo[d]imidazol-2-yl)cyclohexanecarboxylic acid and (6-(trifluoromethyl)pyridin-3-yl)boronic acid. MS (ESI): mass calcd. for $C_{35}H_{29}F_3N_4O_3S$, 642.71; m/z found, 643.1 [M+H]$^+$. $^1$H NMR (400 MHz, CD$_3$OD) δ 9.00-8.88 (d, J=2.2, 1H), 8.29-8.22 (dd, J=8.2, 2.2, 1H), 8.05-7.94 (m, 2H), 7.92-7.84 (d, J=8.2, 1H), 7.79-7.71 (m, 2H), 7.62-7.51 (m, 2H), 7.51-7.41 (m, 2H), 7.38-7.26 (m, 3H), 6.01-5.75 (q, J=17.2, 2H), 5.75-5.62 (d, J=1.3, 2H), 3.83-3.57 (m, 1H), 3.03-2.90 (d, J=4.5, 1H), 2.42-2.27 (td, J=13.8, 13.3, 9.5, 1H), 2.27-2.16 (m, 1H), 2.13-2.05 (d, J=12.7, 1H), 2.01-1.93 (m, 1H), 1.88-1.74 (dd, J=15.2, 10.3, 1H), 1.74-1.64 (s, 1H), 1.64-1.45 (q, J=11.0, 2H).

Example 217 racemic cis-2-(5-(Benzo[d]thiazol-2-ylmethoxy)-1-(4-(6-methoxypyridin-3-yl)benzyl)-1H-benzo[d]imidazol-2-yl)cyclohexanecarboxylic acid

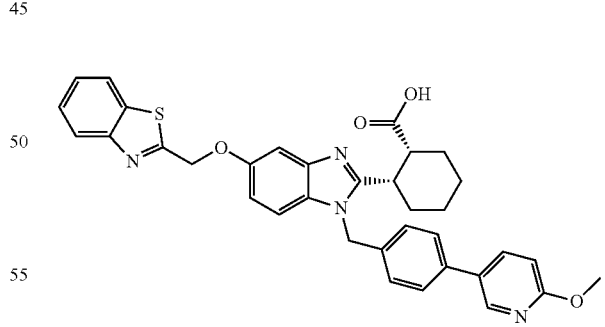

The title compound was prepared using analogous conditions described in Step A of Example 97 using racemic cis-2-(5-(benzo[d]thiazol-2-ylmethoxy)-1-(4-bromobenzyl)-1H-benzo[d]imidazol-2-yl)cyclohexanecarboxylic acid and (6-methoxypyridin-3-yl)boronic acid. MS (ESI): mass calcd. for $C_{35}H_{32}N_4O_4S$, 604.73; m/z found, 605.1 [M+H]$^+$. $^1$H NMR (400 MHz, CD$_3$OD) δ 8.38-8.28 (dd, J=2.6, 0.8, 1H), 8.06-7.96 (m, 2H), 7.96-7.88 (dd, J=8.7, 2.6, 1H), 7.63-7.57 (m, 2H), 7.57-7.52 (m, 2H), 7.49-7.43 (m, 1H), 7.43-7.42 (d, J=2.3, 1H), 7.37-7.28 (dd, J=9.2, 2.4, 1H), 7.27-7.18 (d, J=8.4, 2H), 6.91-6.82 (dd, J=8.7, 0.7, 1H), 5.92-5.73 (m, 2H), 5.72-5.63 (s, 2H), 3.97-3.90 (s, 3H), 3.71-3.60 (m, 1H), 3.03-2.94 (q, J=4.1, 1H), 2.41-2.26 (td, J=12.8, 9.2, 1H), 2.25-2.16 (d, J=13.7, 1H), 2.13-2.04 (d, J=12.6, 1H), 2.02-1.92 (d, J=9.7, 1H), 1.86-1.76 (m, 1H), 1.74-1.64 (d, J=10.0, 1H), 1.60-1.47 (m, 2H).

Example 218 racemic cis-2-(5-(Benzo[d]thiazol-2-ylmethoxy)-1-(4-(pyrimidin-2-yl)benzyl)-1H-benzo[d]imidazol-2-yl)cyclohexanecarboxylic acid

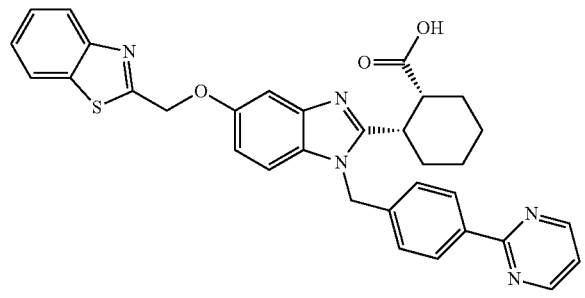 [SMILES: O=C(O)[C@@H]1CCCC[C@@H]1c1nc2cc(OCc3nc4ccccc4s3)ccc2n1Cc1ccc(-c2ncccn2)cc1]

The title compound was prepared using analogous conditions described in Example 208 using (4-(pyrimidin-2-yl)phenyl)methanamine and 2-((4-fluoro-3-nitrophenoxy)methyl)benzo[d]thiazole in step B and cis-1,2-cyclohexanedicarboxylic anhydride in step D. MS (ESI): mass calcd. for $C_{33}H_{29}N_5O_3S$, 575.69; m/z found, 576.2 [M+H]$^+$. $^1$H NMR (500 MHz, CD$_3$OD) δ 8.91-8.78 (d, J=4.9, 2H), 8.50-8.29 (d, J=8.4, 2H), 8.17-7.89 (d, J=8.0, 2H), 7.59-7.57 (d, J=9.2, 1H), 7.57-7.52 (m, 1H), 7.49-7.44 (ddd, J=8.2, 7.2, 1.2, 1H), 7.44-7.43 (d, J=2.4, 1H), 7.39-7.35 (m, 1H), 7.35-7.31 (dd, J=9.1, 2.4, 1H), 7.29-7.26 (d, J=8.5, 2H), 5.95-5.80 (m, 2H), 5.71-5.63 (s, 2H), 3.71-3.62 (dt, J=12.1, 3.9, 1H), 3.04-2.94 (q, J=3.7, 1H), 2.40-2.26 (m, 1H), 2.25-2.14 (m, 1H), 2.11-2.04 (m, 1H), 2.01-1.94 (m, 1H), 1.88-1.73 (m, 1H), 1.73-1.64 (m, 1H), 1.61-1.47 (m, 2H).

Example 219

2-((5-(Benzo[d]thiazol-2-ylmethoxy)-1-(4-(pyrimidin-2-yl)benzyl)-1H-benzo[d]imidazol-2-yl)methyl)-2-ethylbutanoic acid

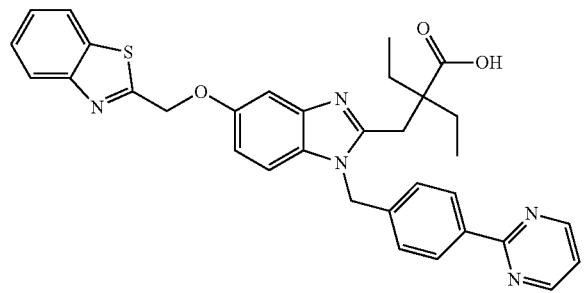 [SMILES: CCC(CC)(Cc1nc2cc(OCc3nc4ccccc4s3)ccc2n1Cc1ccc(-c2ncccn2)cc1)C(=O)O]

The title compound was prepared using analogous conditions described in Example 208 using (4-(pyrimidin-2-yl)phenyl)methanamine and 2-((4-fluoro-3-nitrophenoxy)methyl)benzo[d]thiazole in step B and 3,3-diethyldihydrofuran-2,5-dione in step D using conventional heating. MS (ESI): mass calcd. for $C_{33}H_{31}N_5O_3S$, 577.71; m/z found, 578.1 [M+H]$^+$. $^1$H NMR (500 MHz, CD$_3$OD) δ 8.87-8.78 (d, J=4.9, 2H), 8.43-8.36 (d, J=8.5, 2H), 8.05-7.96 (m, 2H), 7.61-7.57 (d, J=9.1, 1H), 7.57-7.51 (ddd, J=8.4, 7.2, 1.2, 1H), 7.48-7.42 (m, 2H), 7.39-7.35 (m, 1H), 7.35-7.32 (d, J=8.3, 2H), 7.30-7.24 (dd, J=9.1, 2.4, 1H), 5.89-5.76 (s, 2H), 5.70-5.61 (s, 2H), 3.40-3.37 (s, 2H), 1.92-1.71 (m, 4H), 0.93-0.82 (t, J=7.4, 6H).

Example 220 racemic cis-2-(5-(Benzo[d]thiazol-2-ylmethoxy)-1-(4-(piperidin-1-yl)benzyl)-1H-benzo[d]imidazol-2-yl)cyclohexanecarboxylic acid

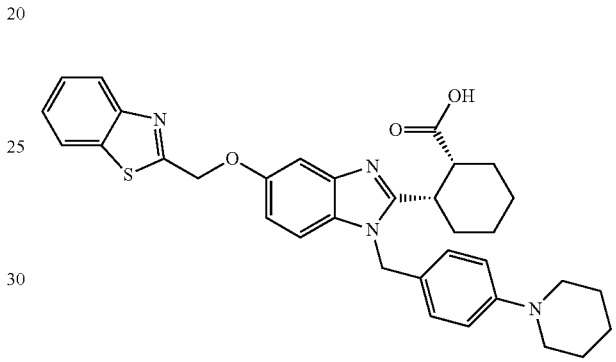

The title compound was prepared using analogous conditions described in Example 208 using (4-(piperidin-1-yl)phenyl)methanamine and 2-((4-fluoro-3-nitrophenoxy)methyl)benzo[d]thiazole in step B and cis-1,2-cyclohexanedicarboxylic anhydride in step D using conventional heating. MS (ESI): mass calcd. for $C_{34}H_{36}N_4O_3S$, 580.76; m/z found, 581.3 [M+H]$^+$. $^1$H NMR (500 MHz, CD$_3$OD) δ 8.21 (s, 1H), 7.99-7.94 (m, 2H), 7.55-7.48 (m, 1H), 7.45-7.39 (m, 1H), 7.34-7.28 (m, 2H), 7.04 (dd, J=8.9, 2.4 Hz, 2H), 6.92-6.87 (m, 2H), 5.54 (s, 2H), 5.45 (d, J=16.6 Hz, 1H), 5.38 (d, J=16.6 Hz, 1H), 3.59-3.51 (m, 1H), 3.11-3.04 (m, 4H), 2.89-2.82 (m, 1H), 2.38-2.26 (m, 1H), 2.10-1.99 (m, 1H), 1.86-1.70 (m, 4H), 1.70-1.60 (m, 4H), 1.60-1.35 (m, 4H).

D) GENERAL ADMINISTRATION, FORMULATION, AND DOSAGES

The present invention provides substituted heteroaryl ketone compounds which are useful as FLAP modulators.

The invention features a method for treating a subject in need thereof with an FLAP-mediated disease and/or disorder, said method comprising administering to the subject a therapeutically effective amount of a compound of the invention. In particular, the invention also provides a method for treating or inhibiting the progression of an FLAP-mediated disease and/or disorder, or associated symptoms or complications thereof in a subject afflicted with such a disease and/or disorder, wherein the method comprises administering to the subject a therapeutically effective amount of a compound of the invention.

Embodiments of the present invention include a method wherein the compound of Formula (I) is a FLAP modulator.

Embodiments of the present invention include a use of the compound of Formula (I) in the manufacture of a medicament for treating an FLAP-mediated disease and/or disorder.

Embodiments of the present invention include a use of the compound of Formula (I) as a medicine.

The compounds of Formula (I) have an FLAP-modulating effect and are useful as therapeutic agents for various FLAP-mediated disorders and/or disorders, or associated symptoms or complications, for example, respiratory disorders, cardiac and cardiovascular diseases, autoimmune disorders, carcinogenesis, and associated symptoms or complications thereof.

The compounds of Formula (I) may be administered orally or parenterally, and after formulation into preparations suitable for the intended administration route, they can be used as therapeutic agents for treating an FLAP-mediated disease and/or disorder. FLAP-mediated diseases and/or disorders include, but are not limited, diseases and/or disorders that are related to leukotriene synthesis pathway, and therefore may be treated, controlled or in some cases prevented, by treatment with the compounds of this invention.

One aspect of the present invention provides a method for the treatment of diseases and/or disorders, or associated symptoms or complications thereof, responsive to the modulation of FLAP in a subject in need thereof which comprises administering to the subject a therapeutically or prophylactically effective amount of a compound of Formula (I) or a form thereof.

Another aspect of the present invention provides a method for the treatment of a disease and/or disorder selected from the group consisting of respiratory diseases and/or disorders, cardiac and cardiovascular diseases and/or disorders, autoimmune diseases and/or disorders, carcinogenesis, and associated symptoms or complications thereof, in a subject in need thereof which comprises administering to the subject a therapeutically or prophylactically effective amount of a compound of Formula (I) or a form thereof.

More specifically, this invention is directed to a method of treating exacerbations, non-allergic asthma, aspirin exacerbated respiratory disease, pulmonary arterial hypertension, fibrotic lung diseases, acute respiratory distress syndrome, obstructive sleep apnea and chronic obstructive pulmonary disease, or associated symptoms or complications thereof, in a subject afflicted with such a disease and/or disorder, wherein the method comprises administering to the subject a therapeutically or prophylactically effective amount of a compound of Formula (I) or a form thereof.

Furthermore, this invention is directed to a method of treating myocardial infarction, atherosclerosis and coronary artery disease, stroke, aortic aneurisms, atherosclerosis, or associated symptoms or complications thereof, in a subject afflicted with such a disease and/or disorder, wherein the method comprises administering to the subject a therapeutically or prophylactically effective amount of a compound of Formula (I) or a form thereof.

Yet, this invention is also directed to a method of treating rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, chronic sinusitis, allergic dermatitis and asthma, wherein the method comprises administering to the subject a therapeutically or prophylactically effective amount of a compound of Formula (I) or a form thereof.

Finally, this invention is also directed to a method of treating tumor cell proliferation, differentiation, apoptosis, tumor-associated angiogenesis, as well as the migration and invasion of carcinoma cells, wherein the method comprises administering to the subject a therapeutically or prophylactically effective amount of a compound of Formula (I) or a form thereof.

Another aspect of the present invention provides a pharmaceutical composition comprising at least one compound of Formula (I) or a form thereof, and a pharmaceutically acceptable carrier.

The invention also features a method for treating a subject in need thereof with an FLAP-mediated disease and/or disorder, said method comprising administering to the subject a therapeutically effective amount of a pharmaceutical composition comprising at least one compound of the invention.

Yet another aspect of the present invention relates to the use of a compound of Formula (I) or a form thereof, for the manufacture of a medicament useful for the treatment of an FLAP-mediated disease and/or disorder in a subject in need thereof.

In a clinical use of the compounds of the invention, pharmaceutically-acceptable additives may be added thereto to formulate various preparations in accordance with the intended administration route thereof, and the preparations may be administered.

Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals, including humans and other mammals. Any ordinary physician, veterinarian or clinician may readily determine the necessity, if any, of treatment with an instant compound.

Those of skill in the treatment of diseases and/or disorders, or associated symptoms or complications thereof, mediated by FLAP can determine the effective daily amount from the test results presented hereinafter and other information. The exact dosage and frequency of administration depends on the particular compound of invention used, the particular disease and/or disorder, or associated symptoms or complications thereof, being treated, the severity of the disease and/or disorder, or associated symptoms or complications thereof, being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the FLAP diseases and/or disorders described in the present invention using any of the compounds as defined herein, the dosage form will contain a pharmaceutically acceptable carrier containing between from about 1 mg to about 1000 mg; particularly from about 0.5 mg to about 500 mg of the compound, and may be constituted into any form suitable for the mode of administration selected. The dosages, however, may be varied depending upon the requirement of the subjects, the severity of the disease and/or disorder, or associated symptoms or complications thereof, being treated and the compound being employed. The use of either daily administration or post-periodic dosing may be employed.

When the compound of the invention is, for example, put into clinical use, then its dose and its administration frequency may vary depending on the sex, the age, the body weight and the condition of the patient and on the type and the range of the necessary treatment with the compound. For oral administration, in general, the dose of the compound may be in a range of from about 0.01 mg/kg/day to about 100 mg/kg of body weight/day or in a range of from about 0.03 mg/kg/day to about 1 mg/kg/day. The oral administration frequency is preferably from one to a few times per day. For parenteral administration, the dose may be in a range of from about 0.001 mg/kg/day to about 10 mg/kg/day, in a range of from about 0.001 mg/kg/day to about 0.1 mg/kg/day or, in a range of from about 0.01 mg/kg/day to about 0.1 mg/kg/day. The parenteral administration frequency is preferably from one to a few times per day. For oral administration, the compositions are preferably provided in the form of tablets containing from about 1.0 mg to about 1000 mg of the active ingredient, particularly 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds may be administered on a regimen of 1 to 4 times per day, preferably once or twice per day.

Ordinary physicians, veterinarians and clinicians may readily determine the effective dose of the pharmaceutical compound necessary to treat, prevent, inhibit, retard or stop the intended disease, and may readily treat the diseased patient with the compound.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for 1 to 4 times per day, preferably once or twice per day administration; for example, an insoluble salt of the active compound, such as the decanoate salt, may be adapted to provide a depot preparation for intramuscular injection.

The preparation may contain the compound of the invention in an amount in a range of from about 1.0 to about 100% by weight or, in a range of from about 1.0 to about 60% by weight of the preparation. The preparation may contain any other therapeutically-effective compound.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) USE

Dosages

For preparing pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agents include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms; however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions.

Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as FLAP modulators is required for a subject in need thereof.

In their use, the compounds of the invention may be combined with any other therapeutic agents that are useful for the treatment of an FLAP-mediated disorder.

The combination includes not only the composition of compounds of the invention and one other active substance but also the composition of compounds of the invention and two or more other active substances or non-drug therapy. The scope of possible combinations of a compound of the invention and one, two or more active substances are within the knowledge of one skilled in the art for the treatment of an FLAP-mediated disorder.

Specifically, the combination of a FLAP modulator with prostaglandin modulators, cyclooxygenase-1 modulators, or cyclooxygenase-2 modulators might be used to treat inflammatory and autoimmune diseases and/or disorders as well as cardiovascular diseases and/or disorders, or vascular injury (Z. Yu et al., "Disruption of the 5-lipoxygenase pathway attenuates atherogenesis consequent to COX-2 deletion in mice," *Proc. Natl. Acad. Sci. USA,* 2012, 109(17), 6727-32; Z. Yu et al., "Myeloid Cell 5-Lipoxygenase Activating Protein Modulates the Response to Vascular Injury," *Circ. Res.,* 2012, Epub December 18). Due to the synergy of histamine and leukotrienes, the combination of a FLAP modulator and a histamine receptor 1 or 4 antagonist might have utility in treating respiratory, allergic, dermatological and autoimmune disorders (A. Reicin et al., "Montelukast, a leukotriene receptor antagonist, in combination with loratadine, a histamine receptor antagonist, in the treatment of chronic asthma," *Arch. Intern. Med.,* 2000, 160(16), 2418-88; S. Sanada et al., "The effectiveness of montelukast for the treatment of anti-histamine-resistant chronic urticaria," *Arch. Dermatol. Res.,* 2005, 297(3), 134-38).

Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

F) BIOLOGICAL EXAMPLES

The ability of the compounds of the present invention to treat a FLAP-mediated disease and/or disorder, or associated symptoms or complications thereof, was determined using the following procedures. Binding assay data represent the average value obtained from two different assay plates, with samples run in duplicate on each plate. Human whole blood assay data represent a single replicate on an assay plate using whole blood from at least one healthy donor. Certain FLAP binding and human whole blood assay data is presented in Table 2.

FLAP Binding Assay

The assay below is used to test the modulatory activity of compounds against FLAP. Human and mouse FLAP-encoding DNA was amplified by polymerase chain reaction and cloned into pFastBac1 (Invitrogen) with a NH2-terminal 6-His tag for expression in *Spodoptera frugiperda* (Sf-9) cells. FLAP-containing membranes were prepared as was a FITC-labeled FLAP modulator (3-(3-(tert-butylthio)-1-(4-chlorobenzyl)-5-(quinolin-2-ylmethoxy)-1H-indol-2-yl)-2, 2-dimethylpropanoic acid). The FLAP binding assay is performed in HTRF format (homogeneous time resolved fluorescence). FLAP-containing membranes (1 µg/well final for human) are incubated in the presence of the HTRF ligand, [5-[({[2-(2-{3-[3-(tert-butylsulfanyl)-1-(4-chlorobenzyl)-5-(quinolin-2-ylmethoxy)-1H-indol-2-yl]-2,2-dimethylpropanoyl}hydrazino)-2-oxoethyl]sulfanyl}acetyl)amino]-2-(6-hydroxy-3-oxo-3H-xanthen-9-yl)benzoic acid] (25 nM final), a terbium labeled anti-His tag antibody (0.5 ng/well final, from Cisbio) and compounds. The reaction is allowed to proceed for two hours after which the plate is read on an Envision plate reader in HTRF mode. Data are expressed as a HTRF ratio.

For human FLAP binding assays, data are analyzed with 3DX Explorer software. A ratio is calculated with the relative light units at 520 nm over the relative light units at 495 nm. For analysis, data from multiple runs are averaged and each compound may be tested in 2 to 20 runs. Each run comprises two plates and each plate includes duplicates. Data from each plate is averaged and data are imported into 3DX. The data from multiple runs are aggregated as the average of duplicates of the calculated ratios in order to calculate Ki and 1050 values. Numbers in parentheses are the number of runs for the assay.

Human Whole Blood Assay

An in vitro cellular assay was performed using human whole blood collected in heparin-containing tubes, which was used to test the ability of compounds to modulate the leukotriene pathway in human whole blood. The blood was diluted 1:1 in RPMI medium, pre-incubated for 15 min at 37° C. with test compounds at various concentrations, and then stimulated with calcium ionophore, A23187 (7 µg/mL), for 30 min at 37° C. The samples were then centrifuged and plasma was removed. The plasma was diluted in assay buffer and $LTB_4$ levels were measured using a commercial kit (Enzo Life Sciences). The concentration of each compound that was required for half-maximal inhibition (modulation) of recombinant enzyme activity ($IC_{50}$) was calculated by a 4-parameter equation using the program GraphPad Prism (GraphPad software). Where duplicate assays were performed by the same team, the values were averaged. Numbers in parentheses are the number of runs for the assay.

TABLE 2

FLAP binding and Human Whole Blood assay data

| Cmp No. | FLAP Binding wild type HTRF $K_i$ (µM) | Human Whole Blood $LTB_4$ $IC_{50}$ (µM) |
|---|---|---|
| 1 | 0.0078 (4) | 2.46 (2) |
| 2 | 0.51 (4) | nt |
| 3 | 0.0016 (5) | 0.98 (3) |
| 4 | 0.016 (3) | >10 (1) |
| 5 | 0.45 (3) | 0.38 (2) |
| 6 | 0.45 (3) | >30 (1) |
| 7 | 0.35 (3) | >30 (1) |
| 8 | 0.003 (2) | >1 (1) |
| 9 | 0.055 (2) | 13.57 (1) |
| 10 | 0.07 (2) | >30 (1) |
| 11 | 0.079 (2) | 10.59 (1) |
| 12 | 0.078 (2) | ~8 (1) |
| 13 | 0.037 (2) | 2.55 (1) |
| 14 | 0.0027 (2) | 0.41 (2) |
| 15 | 0.007 (3) | 1.74 (2) |
| 16 | 0.012 (3) | 3.35 (1) |
| 17 | 0.0092 (2) | 3.47 (1) |
| 18 | 0.017 (2) | 3.57 (1) |
| 19 | 0.076 (2) | >10 (1) |
| 20 | 0.12 (3) | ~5 (1) |
| 21 | 0.0036 (2) | 3.53 (3) |
| 22 | 0.027 (2) | ~7 (1) |
| 23 | 0.014 (3) | 2.54 (1) |
| 24 | 0.014 (2) | 2.85 (2) |
| 25 | 0.28 (2) | ~27 (1) |
| 26 | 0.055 (8) | 17.22 (2) |
| 27 | 0.047 (2) | 10.13 (1) |

TABLE 2-continued

FLAP binding and Human Whole Blood assay data

| Cmp No. | FLAP Binding wild type HTRF $K_i$ (µM) | Human Whole Blood $LTB_4$ $IC_{50}$ (µM) |
|---|---|---|
| 28 | 0.075 (3) | ~30 (1) |
| 29 | 0.011 (5) | 3.95 (5) |
| 30 | 0.066 (1) | >30 (1) |
| 31 | 0.02 (3) | 2.98 (5) |
| 32 | 1.01 (2) | nt |
| 33 | 0.15 (2) | >30 (2) |
| 34 | 0.1 (4) | >30 (1) |
| 35 | 0.0048 (3) | 5.1 (1) |
| 36 | 0.009 (3) | 9.98 (1) |
| 37 | 0.053 (3) | 8.72 (1) |
| 38 | 0.0058 (4) | 3.22 (3) |
| 39 | 0.2 (3) | 10.54 (1) |
| 40 | 0.019 (4) | 3.35 (1) |
| 41 | 0.0063 (4) | 1.58 (2) |
| 42 | 0.63 (4) | nt |
| 43 | 0.0042 (3) | 0.83 (1) |
| 44 | 0.0084 (3) | 1.21 (1) |
| 45 | 0.0056 (3) | 3.01 (1) |
| 46 | 0.011 (3) | 3.59 (1) |
| 47 | 0.043 (3) | 26.42 (1) |
| 48 | 0.054 (3) | 1128.6 (1) |
| 49 | 0.0097 (3) | 17.01 (1) |
| 50 | 0.03 (3) | 10.75 (1) |
| 51 | 0.48 (3) | >10 (1) |
| 52 | 0.0057 (3) | 1.44 (1) |
| 53 | 0.07 (3) | 539.62 (1) |
| 54 | 0.044 (3) | 2.41 (1) |
| 55 | 0.32 (3) | >10 (1) |
| 56 | 0.072 (3) | >10 (1) |
| 57 | 0.022 (2) | ~20 (1) |
| 58 | 0.0093 (2) | 18.92 (1) |
| 59 | 0.037 (2) | 3.88 (1) |
| 60 | 0.017 (2) | 3.51 (1) |
| 61 | ~2 (2) | nt |
| 62 | ~0.83 (2) | nt |
| 63 | 0.0093 (6) | 3.43 (1) |
| 64 | 1.17 (2) | nt |
| 65 | 0.15 (3) | >30 (1) |
| 66 | 0.025 (3) | >30 (1) |
| 67 | 0.13 (3) | >30 (1) |
| 68 | 0.11 (3) | >30 (1) |
| 69 | 0.16 (3) | >30 (1) |
| 70 | 0.65 (2) | nt |
| 71 | 0.17 (3) | 11.46 (1) |
| 72 | 0.94 (1) | nt |
| 73 | 0.044 (2) | 21.08 (1) |
| 74 | 0.14 (2) | >30 (1) |
| 75 | 0.048 (2) | >30 (1) |
| 76 | 0.17 (2) | nt |
| 77 | 0.48 (6) | 6.36 (1) |
| 78 | 1.09 (1) | nt |
| 79 | 0.92 (2) | nt |
| 80 | 0.2 (2) | 10.37 (1) |
| 81 | ~0.75 (2) | nt |
| 82 | ~1.5 (4) | nt |
| 83 | ~2.5 (2) | nt |
| 84 | ~0.81 (2) | nt |
| 85 | ~2.5 (2) | nt |
| 86 | ~2.25 (2) | nt |
| 87 | 0.074 (2) | 2.84 (2) |
| 88 | 0.039 (2) | 5.1 (1) |
| 89 | 0.014 (2) | >30 (1) |
| 90 | 0.096 (2) | 12.48 (1) |
| 91 | 0.013 (2) | 3.09 (1) |
| 92 | 0.027 (2) | 6.02 (1) |
| 93 | 0.013 (2) | 3.64 (1) |
| 94 | 0.012 (2) | 2.5 (1) |
| 95 | 0.014 (2) | 2.64 (1) |
| 96 | 0.02 (2) | 5.02 (1) |
| 97 | 0.0051 (4) | 9.07 (1) |
| 98 | 0.013 (2) | 6.99 (1) |
| 99 | 0.0075 (4) | 2.28 (2) |
| 100 | 0.015 (2) | 4.78 (1) |
| 101 | 0.044 (2) | ~24 (1) |
| 102 | 0.41 (2) | 6.99 (1) |

TABLE 2-continued

FLAP binding and Human Whole Blood assay data

| Cmp No. | FLAP Binding wild type HTRF $K_i$ (μM) | Human Whole Blood LTB$_4$ IC$_{50}$ (μM) |
|---|---|---|
| 103 | 0.12 (2) | 1.6 (2) |
| 104 | 0.077 (2) | 1.4 (2) |
| 105 | 0.049 (2) | 8.53 (1) |
| 106 | 0.035 (2) | 2.9 (1) |
| 107 | 0.32 (2) | ~12 (1) |
| 108 | 0.098 (2) | 4.56 (1) |
| 109 | 0.078 (2) | 2.44 (1) |
| 110 | 0.04 (2) | 3.02 (1) |
| 111 | 0.17 (2) | 6.22 (1) |
| 112 | ~0.2 (2) | 4.52 (2) |
| 113 | 0.089 (4) | 2.86 (2) |
| 114 | 0.13 (2) | 3.84 (2) |
| 115 | 0.17 (2) | 6.6 (2) |
| 116 | 0.042 (2) | 1.23 (2) |
| 117 | 0.18 (2) | 4.81 (2) |
| 118 | 0.11 (2) | 3.01 (2) |
| 119 | 0.16 (2) | 2.99 (1) |
| 120 | 0.045 (2) | 10.83 (1) |
| 121 | 0.076 (2) | 3.52 (1) |
| 122 | 0.11 (2) | ~10 (1) |
| 123 | 0.21 (2) | nt |
| 124 | 0.3 (2) | 14.74 (1) |
| 125 | ~0.83 (2) | nt |
| 126 | 0.096 (2) | ~12 (1) |
| 127 | 0.37 (2) | ~22 (1) |
| 128 | 0.16 (2) | 3.43 (1) |
| 129 | 0.055 (2) | 1.55 (2) |
| 130 | 0.06 (2) | 4.06 (1) |
| 131 | 0.082 (2) | 2.84 (1) |
| 132 | 0.085 (2) | 3.35 (1) |
| 133 | 0.11 (2) | 3.7 (1) |
| 134 | 0.12 (2) | >10 (1) |
| 135 | 0.041 (4) | 3.32 (8) |
| 136 | 0.034 (2) | 1.03 (1) |
| 137 | 0.06 (4) | 3.15 (1) |
| 138 | 0.0043 (2) | ~5 (1) |
| 139 | 0.04 (2) | 2.19 (1) |
| 140 | 0.018 (2) | 0.59 (3) |
| 141 | 0.045 (4) | 0.66 (1) |
| 142 | 0.012 (2) | 9.93 (1) |
| 143 | ~0.22 (2) | >30 (1) |
| 144 | 0.17 (2) | nt |
| 145 | 0.31 (3) | nt |
| 146 | 0.31 (2) | nt |
| 147 | 0.05 (1) | 10.01 (2) |
| 148 | ~0.62 (1) | nt |
| 149 | 0.12 (1) | >30 (1) |
| 150 | 0.21 (1) | 1.1 (1) |
| 151 | ~0.62 (1) | nt |
| 152 | ~0.62 (1) | nt |
| 153 | ~2.08 (3) | nt |
| 154 | ~0.83 (3) | nt |
| 155 | ~0.75 (2) | nt |
| 156 | 0.14 (2) | >30 (1) |
| 157 | 0.26 (2) | 8.03 (1) |
| 158 | 0.34 (3) | 10.41 (1) |
| 159 | 0.58 (2) | >30 (1) |
| 160 | ~0.25 (2) | nt |
| 161 | 0.33 (2) | >10 (1) |
| 162 | ~0.83 (2) | nt |
| 163 | ~0.83 (2) | nt |
| 164 | ~0.75 (2) | nt |
| 165 | 0.016 (2) | >30 (1) |
| 166 | 0.064 (2) | >30 (1) |
| 167 | 0.017 (2) | >30 (1) |
| 168 | 0.0056 (2) | >30 (1) |
| 169 | 0.024 (2) | 7.57 (1) |
| 170 | 0.67 (2) | nt |
| 171 | 0.16 (2) | nt |
| 172 | 0.53 (2) | nt |
| 173 | 0.23 (2) | nt |
| 174 | 0.16 (2) | nt |
| 175 | ~2.5 (2) | nt |
| 176 | ~2.5 (2) | nt |
| 177 | 0.14 (3) | 8.21 (1) |
| 178 | ~1 (2) | nt |
| 179 | 0.089 (2) | nt |
| 180 | ~2.5 (1) | nt |
| 181 | 1.27 (1) | nt |
| 182 | ~0.83 (2) | nt |
| 183 | ~0.75 (2) | nt |
| 184 | 0.15 (2) | >30 (1) |
| 185 | 0.22 (7) | 3.58 (3) |
| 186 | 0.21 (3) | 3.25 (1) |
| 187 | 0.096 (3) | 2.37 (1) |
| 188 | 0.021 (2) | 2.18 (1) |
| 189 | 0.0041 (2) | 2.26 (1) |
| 190 | 0.03 (2) | 3.77 (2) |
| 191 | 0.029 (2) | 0.56 (2) |
| 192 | 0.023 (4) | 0.57 (2) |
| 193 | 0.031 (2) | 0.92 (2) |
| 194 | 0.027 (2) | 0.94 (2) |
| 195 | 0.029 (4) | 0.48 (3) |
| 196 | 0.067 (2) | 1.97 (1) |
| 197 | 0.11 (2) | 3.27 (1) |
| 198 | 0.19 (2) | nt |
| 199 | 0.014 (2) | 5.77 (2) |
| 200 | 0.65 (2) | nt |
| 201 | ~0.75 (2) | nt |
| 202 | 1.34 (2) | nt |
| 203 | 0.34 (3) | 5.16 (1) |
| 204 | 0.46 (2) | nt |
| 205 | 0.16 (2) | >30 (1) |
| 206 | ~2.5 (2) | nt |
| 207 | ~0.62 (2) | nt |
| 208 | 0.013 (3) | 1.38 (2) |
| 209 | 0.6 (2) | nt |
| 210 | 0.0035 (3) | 1.88 (1) |
| 211 | 0.028 (2) | 2.56 (2) |
| 212 | 0.013 (6) | 3.32 (2) |
| 213 | 0.024 (3) | 3.72 (1) |
| 214 | 0.16 (2) | >10 (1) |
| 215 | 0.043 (2) | >10 (1) |
| 216 | 0.051 (2) | >10 (1) |
| 217 | 0.043 (2) | >10 (1) |
| 218 | 0.034 (2) | 3.69 (5) |
| 219 | ~0.25 (2) | nt |
| 220 | 0.096 (2) | 4.96 (1) |

Numbers in parentheses are the number of runs for the assay
nt means not tested

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and modifications as come within the scope of the following claims and their equivalents.

We claim:

1. A compound of Formula (I)

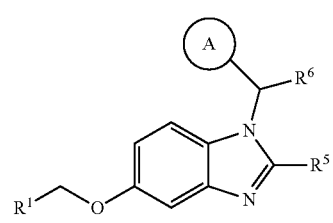

wherein:

R¹ is

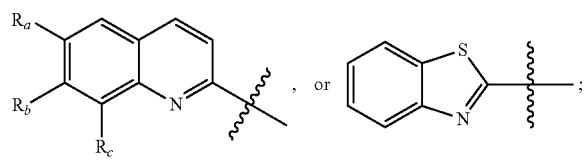, or

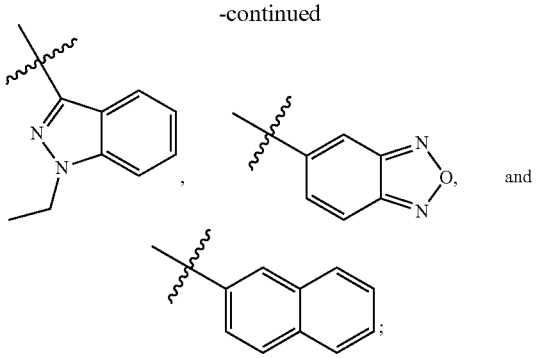, and

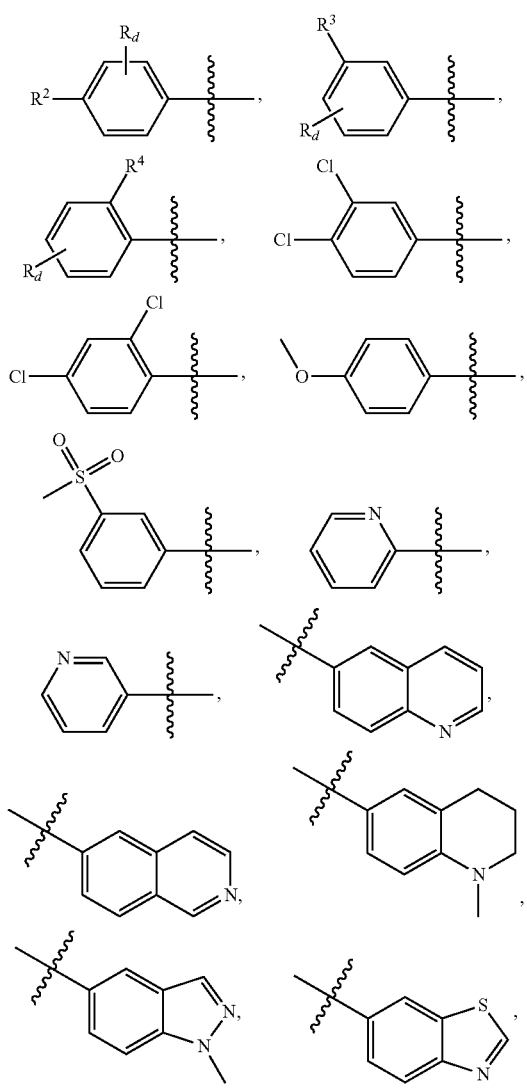

$R_a$ is H, F, or Cl;
$R_b$ is H, F, or Cl;
$R_c$ is H, or F;

Ⓐ is a ring selected from the group consisting of

R² is H, Br, Cl, F, —CN, —CH₂CN, OCF₃, CF₃, CH₃, pyrrolyl, pyridyl, pyrazolyl, pyrimidyl, pyridyl, thiazolyl, isoxazolyl, 1,2,3-triazolyl, furanyl, 3,5-dimethylisoxazol-4-yl, 5-methyl-1,2,4-oxadiazol-3-yl, —CH₂-(3,3-difluoropiperidin-1-yl), azetidin-1-yl, 3,3-difluoroazetidin-1-yl, pyrrolidinyl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluoro-phen-4-yl or phenyl, wherein said phenyl is optionally substituted with one substituent selected from the group consisting of F, CH₃, CF₃, CH(CH₃)₂, —CN, CH₃SO₂—, CH₃SO₂NH—, NH₂SO₂—, NH₂C(O)—, CH₃C(O)NH, and CH₃O—; and said pyrazolyl is optionally substituted with methyl, and said pyrimidyl and said pyridyl are optionally substituted with one or two substituents selected from the group consisting of —OC₍₁₋₂₎alkyl, —N(CH₃)₂, and CF₃;

R³ is H, Br, Cl, F, —CN, —CH₂CN, OCF₃, CF₃, CH₃, pyrrolyl, pyridyl, pyrazolyl, pyrimidyl, pyridyl, thiazolyl, isoxazolyl, 1,2,3-triazolyl, furanyl, 3,5-dimethylisoxazol-4-yl, 5-methyl-1,2,4-oxadiazol-3-yl, —CH₂-(3,3-difluoropiperidin-1-yl), azetidin-1-yl, 3,3-difluoroazetidin-1-yl, pyrrolidinyl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluoro-phen-4-yl or phenyl, wherein said phenyl is optionally substituted with one substituent selected from the group consisting of F, CH₃, CF₃, CH(CH₃)₂, —CN, CH₃SO₂—, CH₃SO₂NH—, NH₂SO₂—, NH₂C(O)—, CH₃C(O)NH, and CH₃O—; and said pyrazolyl is optionally substituted with methyl, and said pyrimidyl and said pyridyl are optionally substituted with one or two substituents selected from the group consisting of —OC₍₁₋₂₎alkyl, —N(CH₃)₂, and CF₃;

R⁴ is H, F, CF₃, OCF₃, Cl, Br, —CN, HO₂C-phen-3-yl, 2-trifluoromethyl-pyrid-5-yl, 2-methoxy-pyrid-5-yl, or CH₃;

$R_d$ is H, or F;

R⁵ is

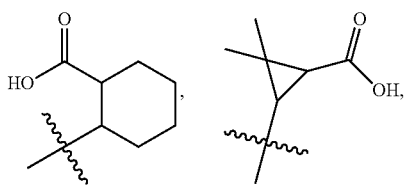

195

-continued

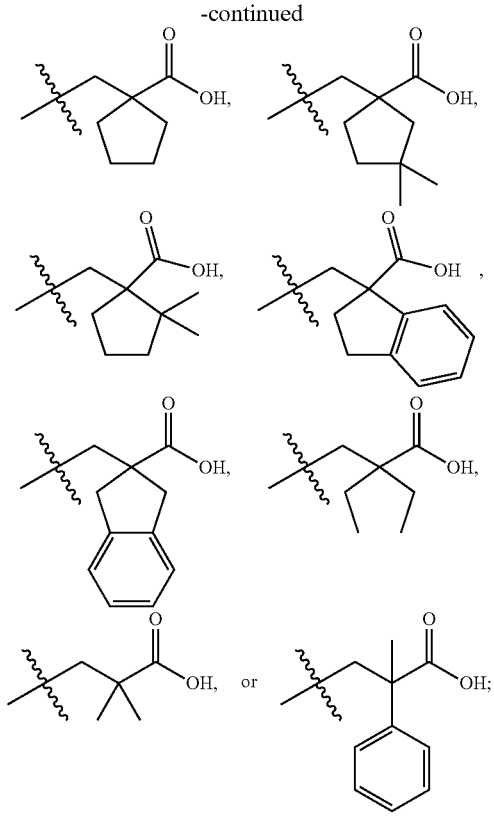

$R^6$ is H, $CH_3$, or $CH_2CH_3$;
and solvates, hydrates, and pharmaceutically acceptable salts thereof.

2. The compound of claim 1, wherein
$R^2$ is H, Br, Cl, F, —CN, —$CH_2CN$, $OCF_3$, $CF_3$, $CH_3$, pyrrole-2-yl, pyrid-3-yl, pyrid-2-yl, pyrimid-2-yl, pyrimid-5-yl, 2-methoxy pyrimid-5-yl, 2-dimethyl-amino-pyrimid-5-yl, 2-methoxy-pyrid-5-yl, 2-methoxy-3-trifluoromethyl-pyrid-5-yl, 2-ethoxy pyrid-5-yl, 2-trifluoromethyl-pyrid-5-yl, 2-dimethyl-amino-pyrid-5-yl, pyrazol-1-yl, 1-methyl-pyrazol-4-yl, 1-methyl pyrazol-5-yl, 1-H-pyrazol-4-yl, thiazolyl, isoxazol-4yl, 1,2,3-triazol-1-yl, 1,2,3-triazol-2-yl, furan-3-yl, 3,5-dimethylisoxazol-4-yl, 5-methyl-1,2,4-oxadiazol-3-yl, —$CH_2$-(3,3-difluoropiperidin-1-yl), azetidin-1-yl, 3,3-difluoroazetidin-1-yl, pyrrolidin-2-yl, 3,3-difluoropyrrolidin-1-yl, piperidin-1-yl, 4-trifluoromethylpiperidin-1-yl, 3,3-difluoropiperidin-1-yl, 4,4-difluoropiperidin-1-yl, morpholin-1-yl, 1,2-difluoro-phen-4-yl or phenyl, wherein said phenyl is optionally substituted with one substituent selected from the group consisting of F, $CH_3$, $CF_3$, $CH(CH_3)_2$, —CN, $CH_3SO_2$—, $CH_3SO_2NH$—, $NH_2SO_2$—, $NH_2C(O)$—, $CH_3C(O)NH$, and $CH_3O$—;
$R^3$ is H, Br, Cl, —CN, —$CH_2CN$, $OCF_3$, $CF_3$, $CH_3$, pyrrol-2-yl, thiazol-5-yl, thiazol-4-yl, 2-methoxy pyrid-5-yl, 2-trifluoromethyl-pyrid-5-yl, pyrimid-2-yl, 2-methoxy pyrimid-5-yl, 1-methyl-pyrazolyl, 1-H-pyrazol-5-yl, furan-3-yl, 3,5-dimethylisoxazol-4-yl, pyrrolidin-2-yl, 1,2-difluoro-phen-4-yl, or phenyl; wherein said phenyl is optionally substituted with one substituent selected from the group consisting of F, $CF_3$, $NH_2SO_2$—, $CH_3SO_2NH$—, and $CH_3SO_2$—;

196 and solvates, hydrates, and pharmaceutically acceptable salts thereof.

3. The compound of claim 1, wherein

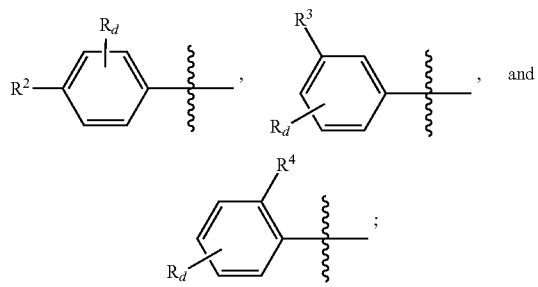

is a ring selected from the group consisting of $R^5$ is

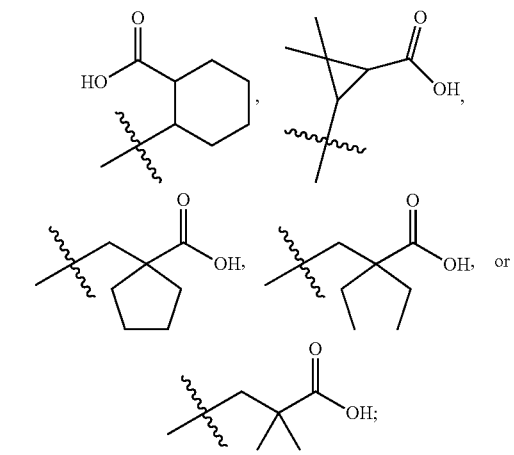

$R^6$ is H;
and solvates, hydrates, and pharmaceutically acceptable salts thereof.

4. The compound of claim 1, wherein
$R_a$ is H;
$R_b$ is H;
$R_c$ is H;
$R^5$ is

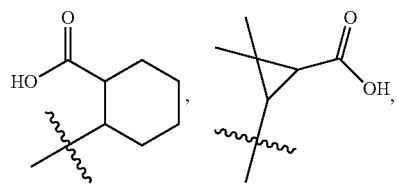

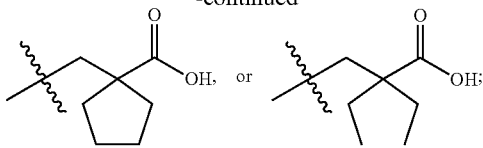

and solvates, hydrates, and pharmaceutically acceptable salts thereof.

5. A pharmaceutical composition comprising a therapeutically effective amount of at least one compound of claim 1 and at least one pharmaceutically acceptable carrier.

6. A method of treating a subject suffering from or diagnosed with a disease and/or disorder mediated by FLAP activity, comprising administering to the subject a therapeutically effective amount of at least one compound of claim 1.

7. A method according to claim 6, wherein the disease and/or disorder is selected from the group consisting of respiratory, cardiac and cardiovascular, autoimmune and allergic, carcinogenesis disease and/or disorder, and associated symptoms or complications thereof.

8. A method according to claim 7, wherein the respiratory disease and/or disorder is selected from the group consisting of exacerbations, non-allergic asthma, fibrotic lung diseases, acute respiratory distress syndrome and chronic obstructive pulmonary disease, or associated symptoms or complications thereof.

9. A method according to claim 7, wherein the cardiac and cardiovascular disease and/or disorder is selected from the group consisting of myocardial infarction, atherosclerosis, atherosclerosis and stroke aortic aneurisms, or associated symptoms or complications thereof.

10. A method according to claim 7, wherein the autoimmune and allergic disease and/or disorder is selected from the group consisting of rheumatoid arthritis, inflammatory bowel disease, nephritis, spondyloarthritis, polymyositis, dermatomyositis, gouty effusions, systemic lupus erythematosus, systemic sclerosis, Alzheimer's disease, multiple sclerosis, allergic rhinitis, allergic dermatitis and asthma, or associated symptoms or complications thereof.

11. A method according to claim 7, wherein the carcinogenesis disease and/or disorder is selected from the group consisting of tumor cell proliferation, differentiation, apoptosis, tumor-associated angiogenesis, and the migration or invasion of carcinoma cells.

12. The method of claim 6, wherein the therapeutically effective amount of the compound of Formula (I) is from about 0.1 mg/dose to about 5 g/dose.

13. A process for making a pharmaceutical composition comprising admixing a therapeutically effective amount of any of the compounds according to claim 1 and a pharmaceutically acceptable carrier.

* * * * *